United States Patent
Zabriskie et al.

(10) Patent No.: US 11,447,530 B2
(45) Date of Patent: Sep. 20, 2022

(54) COMPOSITIONS AND METHODS FOR ENHANCED PRODUCTION OF ENDURACIDIN IN A GENETICALLY ENGINEERED STRAIN OF STREPTOMYCES FUNGICIDICUS

(71) Applicant: Oregon State University, Corvallis, OR (US)

(72) Inventors: T. Mark Zabriskie, Corvallis, OR (US); Xihou Yin, Corvallis, OR (US)

(73) Assignee: OREGON STATE UNIVERSITY, Corvallis, OR (US)

( * ) Notice: Subject to any disclaimer, the term of this patent is extended or adjusted under 35 U.S.C. 154(b) by 620 days.

(21) Appl. No.: 16/465,444

(22) PCT Filed: Dec. 1, 2017

(86) PCT No.: PCT/US2017/064328
§ 371 (c)(1),
(2) Date: May 30, 2019

(87) PCT Pub. No.: WO2018/106545
PCT Pub. Date: Jun. 14, 2018

(65) Prior Publication Data
US 2019/0359659 A1    Nov. 28, 2019

Related U.S. Application Data

(60) Provisional application No. 62/430,838, filed on Dec. 6, 2016, provisional application No. 62/479,087, filed on Mar. 30, 2017.

(51) Int. Cl.
| | | |
|---|---|---|
| *C07K 14/36* | (2006.01) | |
| *C12P 21/02* | (2006.01) | |
| *C12N 15/76* | (2006.01) | |
| *C12N 1/20* | (2006.01) | |
| *C12R 1/465* | (2006.01) | |

(52) U.S. Cl.
CPC ............. *C07K 14/36* (2013.01); *C12N 15/76* (2013.01); *C12P 21/02* (2013.01); *C12N 1/205* (2021.05); *C12R 2001/465* (2021.05)

(58) Field of Classification Search
CPC .... C07K 14/36; C12N 15/76; C12R 2001/465
See application file for complete search history.

(56) References Cited

U.S. PATENT DOCUMENTS

| | | |
|---|---|---|
| 3,786,142 A | 1/1974 | Shibata et al. |
| 4,465,771 A | 8/1984 | Nogami et al. |

FOREIGN PATENT DOCUMENTS

| | | |
|---|---|---|
| CN | 104131054 A | 11/2014 |
| CN | 103374537 B | 1/2015 |
| CN | 105039382 A | 11/2015 |
| WO | 2008054945 A2 | 5/2008 |
| WO | 2018103905 A1 | 6/2018 |

OTHER PUBLICATIONS

Yin, X et al., "The Enduracidin Biosynthetic Gene Cluster from Streptomyces Fungicidicus"; Microbiology (2006); vol. 152, pp. 2969-2983.
Baltz, R. H. "Genetic Manipulation of Secondary Metabolite Biosynthesis for Improved Production in Streptomyces and other Actinomycetes"; J. Ind. Microbiol. Biotechnol (2016); vol. 43, pp. 343-370.
Yin, X. et al., "Enduracidin Analogues with Altered Halogenation Patterns Produced by Genetically Engineered Strains of Streptomyces Fungicidicus"; J. Nat. Prod. (2010); vol. 73; pp. 583-589.
Ostash, B. et al., "Identification and Characterization of the Streptomyces Globisporus 1912 Regulatory Gene IndYR that Affects Sporulation and Antibiotic Production"; Microbiology (2011); vol. 157; pp. 1240-1249.
Yuan, T. et al., Improvement of Antibiotic Productivity by Knock-Out of dauW in Streptomyces Coeruleobidus; Microbiology Research (2011); vol. 166; pp. 539-547.
Yepes, A. et al., "Novel Two-Component Systems Implied in Antibiotic Production in Streptomyces Coelicolor"; PLoSOne (2011); vol. 6:5; 10 pgs.
Kim, S. et al., "Transcriptome Analysis of an Antibiotic Downregulator Mutant and Synergistic Actinorhodin Stimulation via Disruption of a Precursor Flux Regulator in Streptomyces Coelicolor"; Applied and Environmental Microbiology (2011); vol. 77:5; pp. 1872-1877.

*Primary Examiner* — Maryam Monshipouri
(74) *Attorney, Agent, or Firm* — Fox Rothschild LLP

(57) ABSTRACT

This disclosure describes compositions and methods for enhanced production of enduracidin in genetically engineered strains of *Streptomyces fungicidicus*. In particular, the present disclosure describes the genetic manipulation of regulatory genes orf24 and orf18 associated with the enduracidin (enramycin) biosynthesis gene cluster from *Streptomyces fungicidicus* to generate vector constructs and recombinant strains producing greater yields of enduracidin.

17 Claims, 12 Drawing Sheets

Specification includes a Sequence Listing.

```
Score     Expect    Method                                        Identities      Positives     Gaps
281 bits(720) 3e-97  Compositional matrix adjust. 167/311(54%)  212/311(68%)  8/311(2%)

StrR    16    IELSRLSSASSPRTSGEDPEHVETLLSAEGELPPILVERPTMQVLDGLHRLKVAPVRGDT    75
              +E+S LS+ SPR   GE PEHVB L +A+  LPPI+VHR T +V+DG+HRL+ A + G T
Orf24   1     VEISSLSTDGSPRIDGESPRHVEMLAAADTALPPIMVHRRTGRVTDGMHPLRAAMLTGRT    60

StrR    76    KILARLVDATESDAFVLAVEANIRHGLPLSLADRKRAAVQIIGTRPQWSDPRVASATGIS    135
              I   R  D TE DAFVLAV++NI HGLPLS ADR+RAR +I+ THP+WSDR +AS  G S
Orf24   61    TIAVRFHDGTEEDAFVLAVKSNIAHGLPLSAADRRRAAGRIMATHPRWSDRMIASVVGTS    120

StrR    136   AGTVADLRRRAGEDGT--EARIGRDGRVRPSDGSERPRLAAELIRSDPGLSLRQVAKQVG    193
              A  VA++RR AG  G     RIGR DGRVRP D SE RRLA ++I  DPGLSLRQVA+ G
Orf24   121   ARTVAEIRRDAGAAGAGEPTRIGRDGRVRPVDVSEGRRLAHDMIVRDPGLSLRQVARAAG    180

StrR    194   ISPETVRDVRGRLERGESPTPDGTRRLPAKPHPLRLSEPDEGRA------VDQDRLALLER    248
              ISPETVRDVR R+ RGE P R  R     +   R +EP G+A +          +++R
Orf24   181   ISPETVRDVRHRMLRGEDPVPAPRPRTLVERGADRKARP-AGKAAAPCGTERPPAVVMKR    239

StrR    249   LKSDPALRLNEVGRILLRMLTMHSMDGQEWERILQGVPPHLHGVIAGHARDHARVWAEFA    308
              L++DPALRLNE GR LLR+L +H++   ++W RI++ VPPH   +A  AR A  W+E A
Orf24   240   LRADPALRLNENGRLLLRLLDIHTVRLEDWNRILESVPPHRIETVAQLARSCADKWSEIA    299

StrR    309   DHLESRATELA    319
              +ES A+ LA
Orf24   300   SRIESNASHLA    310
```

Fig. 9

```
Bbr      MDPTR--------VDIFALPA--------------VEIELSRLSSASSPRT
KasT     MAETVRADSPLKSSYRNVPAAEVQGSGLSVGQRTTRIAISSLLAADSPRS
NovG     MTNSG--------DEEIT-P------ASLKATRKGERVSIGSLLPPSELVR
SgcR1    MKSDS--------AQRAVER------------SRRVVRIDELIPADSPRL
StrR     MDPTR--------VDIFALPA--------------VEIELSRLSSASSPRT
Tei15*   MTPDE--------EALNRQPI--------------MEMEISSLSLGGSPRL
Orf24    ---------------------------------VEISSLSTDGSPRI
                                                : :. *   ..

Bbr      SGEDPEHVETLLSAEGELPPILVHRPTMQVLDGLHRLKVARVRGDTKILA
KasT     AGENAEHIRLLADSGAPLPPIVVQRSTMRVIDGMHRLRAAALRGETEIEV
NovG     SGESTEHIRVLAETDEDLPPIVVHRGTRRVVDGMHRLWAARFRGDESIEV
SgcR1    NGIDRSHVQRLATVYASLPPVLVHRPTMRVVDGMHRIGAARLKGLDTVEV
StrR     SGEDPEHVETLLSAEGELPPILVHRPTMQVLDGLHRLKVARVKGDTKILA
Tei15*   AGGDEVHLEAMVAAQGELPPIVVHRPTMRVIDGSHRIQAALRRGETTIAG
Orf24    DGESPEHVEMLAAADTALPPIMVHRRTGRVIDGMHRLRAAMLTGRTTIAV
          *  *:. :        ***::*:*  * :*:** **:  .*    *  :

Bbr      RLVDATESDAFVLAVEANIRHGLPLSLADRKRAAVQIIGTRPQWSDRRVA
KasT     RFFDGAEEDSFLLAVRSNIAHGLPLSQEERAAAAQRIIRSHAQWSNQAIG
NovG     VFVDGSPADVFVLAVELNRAHGLPLTLDERKSAAAQIMDSRPHWSDRRIA
SgcR1    TFFEGAEEQVFLRSVAANITNGLPLSVADRKTAAARILASHPTLSDPAVA
StrR     RLVDATESDAFVLAVEANIRHGLPLSLADRKRAAVQIIGTRPQWSDRRVA

Tei15*   RFFDGSDDEAFVMSVWLNVSHGLPLALADRKRAAERIAVSHPQWSDRRVA
Orf24    RFFDGTEKDAFVLAVKSNIAHGLPLSAADRREAAGRIMATHPRWSDRMIA
          :.:.:  :  *:  :*   *  :****:   :* ** :* :*.  *:. :.

Bbr      SATGISAGTVADLRRRA-GEDG-TEARIGRDGRVRPSDGSERRRLAAELI
KasT     EVTGLDAKTIAALRRDAKDV--FQLDARIGRDGRVRPVDGAQGRRLAGELM
NovG     RTTGLAASTVASLRSSST-AG--TVGRRTGQDGRSRPNDGTDGEQRAAALL
SgcR1    AHVGLDAKTVAGVRTCSAAGSPLLNMRTGADGRVRPLDRTAERLHAAALL
StrR     SATGISAGTVADLRRRA-GEDG-TEARIGRDGRVRPSDGSERRRLAAELI
Tei15*   AVTGISPSTVADIRRRVAGTSAPEASRIGQDGRVRPLDCSAGRLLAGRLM
Orf24    SVVGTSARTVAEIRRDAGAAGAGEPTRIGRDGRVRPVDVSEGRRLAHDMI
          .*  . *:* :*        * * *** :* *   *    *   ::

Bbr      RSDPGLSLRQVAKQVGISPETVRDVRGRLERGESPTPDGTRRLP-AKPH-
KasT     AEQPDAPLRKIAHAAGVSLGTASDVRRRIRNGQDPVPAGRQKAD-PQPP-
NovG     ARNPNASLREVTRAAGISVGTASDVRAKLRRGEPALTARQQAVMKLRPA-
SgcR1    TQDPGLPLRSVVEQTGLSLGTAHDVPRRLLRGEDPVPQNRQSAM-LEPGL
StrR     RSDPGLSLEQVAKQVGISPETVEDVRGRLERGESPTPDGTRRLP-AKPH-
Tei15*   AENPALSLRQVAKAAAISPETARDVENRLLSGAELVPNRPRDA-A-PV-
Orf24    VRDPGLSLRQVARAAGISPETVEDVRHRMLRGEDPVPAPRPRTL-VERG-
          :*  .**.:..:..:*   *. *** :*                :
                     Helix-Turn-Helix motif Bbr      -PL--RLSEP----DFGRA------------------V--DQDRLALLERL
KasT     -AR--YAASED----R-SGTTA------------FR--TG--EQNRRVLLQKL
NovG     -AA--QRSGP-----------------------------DYGRVLENL
SgcR1    APQKKATAKP-----PVGPAARPVPKVPPAVAGRPPVSPRSRAPLEALRKL
StrR     -PL--RLSEP----DFGRA------------------V--PQDRLALLERL
Tei15*   -GV--KGGRDPRPLNLIRSGD-----------KP--EP--VPCHAVVINRL
Orf24    -AD--RRAEP-----A-GKAAA-----------PC---GT---EPPPAVVMKRL
                                                      :..*

Bbr      DHARVWAEFADHLESRATEL------------AAG
KasT     GCSGVWQDFAAQLERPG--R------------RSA
NovG     ECAAAWQHLADQLADRD--------------TA
SgcR1    HCSDAWHRFAEEMVRPRHSAAADGSGLRTTQPTRR
StrR     DHARVWAEFADHLESRATEL------------AAG
Tei15'   QFADLWADFASRVGPEE---R------------MAS
Orf24    SCADKWSEIASRIESNAS--H-----------LAG
          :  *  :* .:   .
```

Fig. 11

```
SCO1745/AbrA2    MT---------------IRLLIVDDQELIRTGFRLFLQTQNDLEVVGE
SCO3226/AbsA2    M----------------IRVLLADDETIIRAGVRSILTTEPSIEVVAE
SCO3818          MPE--------------DGKIRVFLLDDHEVVRRGVHDLLSGEAOIEVVGE
Orf18            VSVLLEQPASLVAYRPNKPTAMVVV-ADPRVRSTVTRHLWA-LGVRDVIE
                   :          :.:    ,  :*  .   *    .:. * *

SCO1745/AbrA2    ADDGHGALAQAAALRPDVVLMDIRMPRMDGVEATSRLTASDSPPRVLILT
SCO3226/AbsA2    ASDGREAVELARKHRPDVALLDIRMPEMDGLTAAGEMRTTNPDTAVVVLT
SCO3818          AGTAAEAQARVTATRPDVAVLDVRLPDGSGVSVCRDIRSRDESVRCLMLT
Orf18            ASSVAEARPRIGNPR-DICVAEVHLPDGSGLTLLSETRAAGW-PNGLALS
                  *       *:  :  :::::*   ,*:             :  *:

SCO1745/AbrA2    TYDLDEYVFGALRAGASGFLLKDASRDRLLEAIRVVHAGEALLSPSITER
SCO3226/AbsA2    TFGEDRYIERALDQGVAGFLLKASPPRDLISGVRAVASGGSCLSPLVARR
SCO3818          SFADDSALFDAIMAGASGYVLKDIRGAELLGAVREVAAGKSLLDPAATAR
Orf18            AADDIGAVRNALAGGVKGYVVTGTPTNLGL-PTRPGAA----PI-GAAAAR
                  :       *:  *.  *::: .    :       *            :  *

SCO1745/AbrA2    LIEDYATRAAPV-RPR--EAVLAGLTPREREILLLVARGLSNPEIAARLV
SCO3226/AbsA2    LMTELR---RAPSPRSEVSGERTTLLTKREQEVLGMLGAGLSNAEIAQRLH
SCO3818          VLEFLR--GGGA----PF--DDRLARLTEQERRILELIGEGLTNRAIGERLH
Orf18            LHRRPP--GAPS----NPG-G-YRELSGREVEVLRLVAEGQSNKAIGVSMG
                  :        .        .           *.:*  .:   :. * :*  *.  :

SCO1745/AbrA2    VTEATVKSHVGSMFAKLHLRDRAQAVVFAYENAIVLP-GGTG
SCO3226/AbsA2    LVEGTIKTYVSAIFTQLEVRNRVQAAIIAYEAGLVKDADLNR
SCO3818          LAEKTIKNYVSSLLGKLGMQRRSQAAAFVAR----LE-AENR
Orf18            LSALTVKSHLARIARKLGTGDRAGMVAVALRTGII-------H
                  :   *:*  ::, :  :*         *   , ..
```

Fig. 12

COMPOSITIONS AND METHODS FOR ENHANCED PRODUCTION OF ENDURACIDIN IN A GENETICALLY ENGINEERED STRAIN OF STREPTOMYCES FUNGICIDICUS

CROSS-REFERENCE TO RELATED APPLICATIONS

This application claims the priority benefit of the earlier filing dates of U.S. Provisional Patent Nos. 62/430,838, filed Dec. 6, 2016 and 62/479,087, filed Mar. 30, 2017, each of which is hereby incorporated herein by reference in its entirety.

FIELD

This disclosure relates to antibiotic biosynthesis, in particular, to the compositions and methods for enhanced production of enduracidin.

BACKGROUND

The global emergence of multidrug-resistant bacterial infections has resulted in enormous healthcare costs and has become a major threat to public health. To stay ahead of the development of antibacterial drug resistances, there is a need to identify new antibiotics as well as methods of producing such antibiotics in a more cost-efficient manner.

SUMMARY

The present disclosure overcomes problems associated with limited production of enduracidin (enramycin) in wild type strains of Streptomyces fungicidicus, as well as production limits in industrial strains developed through conventional radiation and chemical-mediated mutagenesis of the chromosome and successive multiple rounds of selection of mutants for production of increased levels of the desired enduracidin peptide antibiotics. Disclosed herein is the genetic manipulation of regulatory genes orf24 and orf18 associated with the enduracidin (enramycin) biosynthesis gene cluster from Streptomyces fungicidicus to generate recombinant vectors and strains producing greater yields of this peptide antibiotic. Recombinant strains were constructed in both the wild-type producer, Streptomyces fungicidicus B-5477 (ATCC 21013), and Streptomyces fungicidicus BM38-2 (ATCC PTA-122342), which is derived from the wild-type strain and currently used for the industrial production of enduracidin. In the wild-type organism, site-specific integration of plasmid pXY152-endorf24, which drives the overexpression of a second copy of orf24, generated the strain SfpXY152endorf24. The integration of mutagenized fosmid pXYF24D3 into the wild-type chromosome replaced the native orf18 with a disrupted copy of the gene and created the mutant SfpXYF24D3. Working in the commercial producer Streptomyces fungicidicus BM38-2 (ATCC PTA-122342), integration of plasmid pXY152-endorf24 generated the recombinant strain Streptomyces fungicidicus BM38-2.24116. To create a BM38-2 (ATCC PTA-122342)-derived strain lacking a functional orf18, plasmid pKS-T-orf18pfrd-AmR was constructed to delete orf18 and its flanking regions, replacing this region with an apramycin resistance marker and generating the recombinant strain Streptomyces fungicidicus BM38-2.18pfrd-AmR. The genetically manipulated strains were demonstrated to produce yields of enduracidin ranging from 1.2 to 4.6-fold higher than the respective parent strains. The elevated enduracidin yields from the recombinant strains provide a more cost-effective production of enduracidin.

The foregoing and other features and advantages of the disclosure will become more apparent from the following detailed description, which proceeds with reference to the accompanying figures.

BRIEF DESCRIPTION OF THE DRAWINGS

FIG. 9 provides an alignment of streptomycin activator StrR protein (SEQ ID NO: 25) with Orf24 (SEQ ID NO: 26).

FIG. 11 Alignment of Orf24 with six functionally characterized StrR-like pathway specific activator ortholog proteins from actinomycetes. Orf24 (GenBank accession no. DQ403252; SEQ ID NO: 26) from S. fungicidicus enduracidin biosynthetic gene cluster; StrR (GenBank accession no. Y00459; SEQ ID NO: 25) from S. griseus streptomycin biosynthetic gene cluster; Tei15* (GenBank accession no. AJ632270; SEQ ID NO: 32) from Actinoplanes teichomyceticus teicoplanin gene cluster; Bbr (GenBank accession no. Y16952; SEQ ID NO: 28) from Amycolatopsis strain DSM 5908 balhimycina biosynthetic gene cluster; KasT (GenBank accession no. BAF79690; SEQ ID NO: 29) from S. kasugaensis kasugamycin gene cluster; NovG (GenBank accession no. AF170880; SEQ ID NO: 30) from S. niveus strain NCIMB 9219 novobiocin biosynthetic gene cluster; SgcR1 (GenBank accession no. AY048670; SEQ ID NO: 31) from S. globisporus C-1027 biosynthetic gene cluster. Identical amino acids (*), conservative amino acids (.) and highly conservative amino acids substitutions (:). The conserved helix-turn-helix (HTH) motif characteristic of DNA-binding proteins like StrR is underlined.

FIG. 12 Alignment of Orf18 (SEQ ID NO: 36) with other functionally characterized response regulator orthologs. SCO1745/AbrA2: S. coelicolor A3(2) two-component response regulator (GenBank Accession No. CAB50960; SEQ ID NO: 33). SCO3226/AbsA2: S. coelicolor A3(2) two-component response regulator (GenBank Accession No. AAB08053; SEQ ID NO: 34). SCO3818: S. coelicolor A3(2) two-component system response transcriptional regulator (GenBank Accession No. CAB46941; SEQ ID NO: 35).

SEQUENCE LISTING

Figure 1:
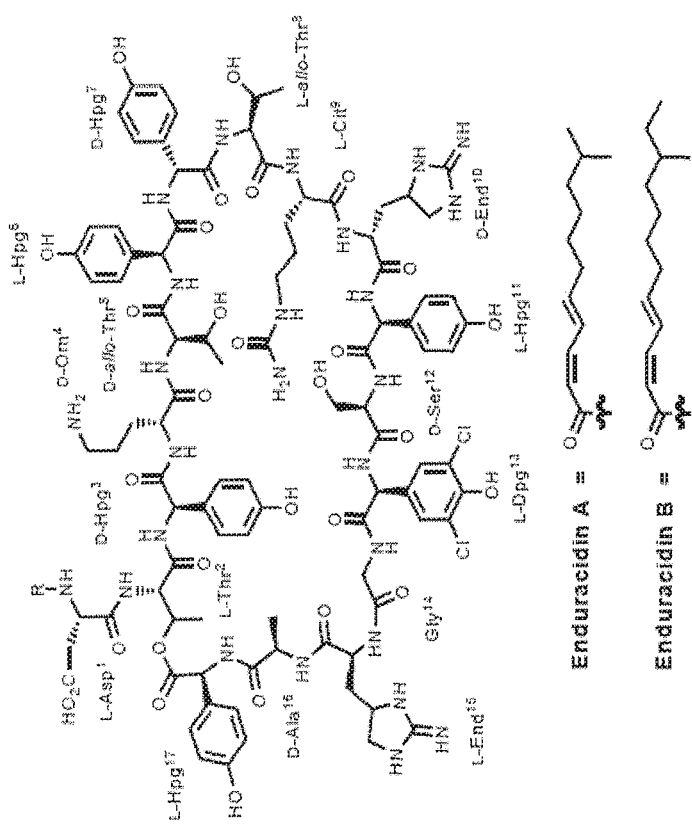
FIG. 1 provides the chemical structure of enduracidins A and B.

The nucleic and amino acid sequences listed herein and in the accompanying sequence listing are shown using standard letter abbreviations for nucleotide bases, and three letter code for amino acids, as defined in 37 C.F.R. 1.822. Only one strand of the nucleic acid sequence is shown, but the complementary strand is understood as included by any reference to the displayed strand. In the accompanying sequence listing:

SEQ ID NOs: 1 and 2 are oligonucleotide primers used to generate the insert of plasmid pXY152-endorf24.

SEQ ID NO: 3 is the nucleic acid sequence of plasmid pXY152-endorf24.

SEQ ID NOs: 4-7 are oligonucleotide primers used to generate the insert of plasmid pXY300-orf18ifd.

SEQ ID NO: 8 is the nucleic acid sequence of plasmid pXY300-orf18ifd.

SEQ ID NOs: 9 and 10 are oligonucleotide primers used to generate the oriT fragment of plasmid pKS-T-orf18pfrd.

SEQ ID NO: 11 is the nucleic acid sequence of plasmid pKS-T-orf18pfrd.

SEQ ID NOs: 12 and 13 are oligonucleotide primers used to generate the amR fragment of plasmid pKS-T-orf18pfrd-AmR.

SEQ ID NO: 14 is the nucleic acid sequence of plasmid pKS-T-orf18pfrd-AmR.

SEQ ID NOs: 15-18 are oligonucleotide primers used to generate the oriT and amR fragments of plasmid pKS-orf18ifd-T-AmR(NS).

SEQ ID NO: 19 is the nucleic acid sequence of plasmid pKS-orf18ifd-T-AmR(NS).

SEQ ID NO: 20 is the nucleic acid sequence of plasmid pXY152-endorf24-camtsr.

SEQ ID NOs: 21 and 22 are oligonucleotide primers used to generate the bla fragment of plasmid pXY152-endorf24-blatsr.

SEQ ID NO: 23 is the nucleic acid sequence of plasmid pXY152-endorf24-blatsr.

SEQ ID NO: 24 is an oligonucleotide primer which corresponds to a region of a apramycin resistance gene.

SEQ ID NO: 25 is the amino acid sequence of streptomycin activator StrR protein.

SEQ ID NO: 26 is the amino acid sequence encoded by ORF24.

SEQ ID NO: 27 is the nucleic acid sequence illustrating an in-frame deletion in orf18.

SEQ ID NO: 28 is the amino acid sequence of Bbr insert.

SEQ ID NO: 29 is the amino acid sequence of KasT insert.

SEQ ID NO: 30 is the amino acid sequence of NovG insert.

SEQ ID NO: 31 is the amino acid sequence of SgcR1 insert.

SEQ ID NO: 32 is the amino acid sequence of Teil5* insert.

SEQ ID NO: 33 is the amino acid sequence of response regulator ortholog SCO1745/AbrA2 from *S. coelicolor* A3(2) (GenBank Accession No. CAB50960).

SEQ ID NO: 34 is the amino acid sequence of response regulator ortholog SCO/3226/AbsA2 from *S. coelicolor* A3(2) (GenBank Accession No. AAB08053).

SEQ ID NO: 35 is the amino acid sequence of response regulator ortholog SCO3818 from *S. coelicolor* A3(2) (GenBank Accession No. CAB46941).

SEQ ID NO: 36 is the amino acid sequence encoded by ORF18.

SEQ ID NO: 37 is the nucleic acid sequence of orf18.

SEQ ID NO: 38 is the nucleic acid sequence of orf24.

SEQ ID NO: 39 is the nucleic acid sequence of the fosmid pXYF148 with the orf24 located at nucleotide position 23109 through 24044).

SEQ ID NO: 40 is the nucleic acid sequence of fosmid pXYF24 with the orf18 located at nucleotide position 31091-31753).

DETAILED DESCRIPTION OF SEVERAL EMBODIMENTS

I. Introduction

Enduracidin (FIG. 1), also called enramycin, is a 17 amino acid lipodepsipeptide antibiotic produced by the soil bacterium *S. fungicidicus* B-5477 (ATCC 21013). The peptide is isolated from the fermentation broth and mycelia primarily as a mixture of enduracidins A and B, which differ by one carbon in the length of the attached lipid chain. Structurally, the enduracidins are distinguished by a $C_{12}$ or $C_{13}$ 2Z,4E branched fatty acid moiety attached by an amide linkage to an aspartic acid residue, and the presence of numerous nonproteinogenic amino acid residues such as enduracididine (End), 4-hydroxyphenylglycine (Hpg), 3,5-dichloro-4-hydroxyphenylglycine (Dpg), citrulline (Cit) and ornithine (Orn) (cf. FIG. 1). Seven of the 17 amino acids have the D configuration and six of the residues are Hpg or the chlorinated derivative Dpg.

Enduracidin (for simplicity, the peptides will be referred to singularly) exhibits potent in vitro and in vivo antibacterial activity against a wide spectrum of Gram-positive organisms, including methicillin-resistant *Staphylococcus aureus* (MRSA) and vancomycin-resistant *Enterococcus* (VRE). Minimum inhibitory concentrations (MICs) are as low as 0.05 µg/mL and the effect is bactericidal. A study with 100 strains of *S. aureus* collected from various pathological products, and including 40% MRSA, established MICs ranging from 0.09 to 0.56 µg/mL with no strain able to survive exposure to 1 µg/mL. For comparison, typical MICs for vancomycin toward sensitive strains of *S. aureus* range from 0.5 to 2 µg/mL. In addition, enduracidin has an excellent toxicological profile. In a study in mice, rabbits, dogs and monkeys the acute LD50s were: intravenous, 30-125 mg/kg; intraperitoneal, 750-910 mg/kg; subcutaneous, intramuscular (i.m.) or oral, >5-10 g/kg. In the same study, monkeys receiving enduracidin i.m. for 6 months and rats that were similarly dosed for 12 months were found to only have localized inflammation at the injections site. In humans, enduracidin was administered i.m. (100 mg every 12 hours) to 20 hospitalized adult patients infected with MRSA. The peptide was reported to be free of side effects and also highly effective for treating urinary tract and skin infections caused by MRSA, but not chronic bone infections (Peromet et al., *Chemotherapy* 19:53-61, 1973).

Enduracidin inhibits bacterial peptidoglycan cell wall biosynthesis by complexing with extracellular Lipid II, a precursor to the bacterial cell wall structure. The site of Lipid II complexation is distinct from that recognized by vancomycin and accounts for the action of enduracidin against vancomycin-resistant organisms. To date, there is no documented cross-resistance of enduracidin with any clinically-used antibiotic and no evidence of developed, acquired or transferable resistance. The absence of any known form of transferable resistance mechanism, the lack of oral bioavailability, its low toxicity, and excellent activity towards *Clostridium* spp. have made enduracidin a key commercial peptide antibiotic used as a poultry feed additive for controlling clostridial enteritis.

To derive a strain of the producing organism that could supply the quantities of the peptides required for commercial uses, Japan Takeda Animal Health (now part of Intervet/Merck Animal Health) subjected *S. fungicidicus* B-5477 to various traditional strain improvement methods and selected for mutants that produced higher yields of enduracidin. An increasing worldwide market for enduracidin has driven efforts to further improve the yield of this antibiotic in BM38-2 (ATCC PTA-122342). With the genetic sequence of the enduracidin biosynthesis gene cluster available (GenBank accession no. DQ403252 which is hereby incorporated by reference as available on the world wide web on Oct. 3, 2006, BM38-2 (ATCC PTA-122342) served as the starting strain for the targeted genetic manipulation of regulatory genes associated with the gene cluster and constitutes the basis for this disclosure. Herein, it is disclosed that the product of orf18 has a negative effect on enduracidin production and the orf24 gene product has a positive effect on enduracidin production and that recombinant strains derived from both the *S. fungicidicus* wild-type and BM38-2 (ATCC PTA-122342) organisms that exploit these regulatory effects produce elevated yields of enduracidin. In addition, disclosed herein are new gene replacement and integrative expression vectors based on pBluescript II KS and pSET152, respectively.

II. Abbreviations and Terms a. Abbreviations

AA: amino acid
Am: apramycin
AmR: apramycin resistance marker
amRp: native apramycin resistance promoter
ATCC: American Type Culture Collection
bla: ampicillin resistance gene
BLAST: Basic Local Alignment Search Tool
cam: chloramphenicol resistance gene
CFU colony forming units
CTAB: Cetyl Trimethyl Ammonium Bromide
Cit: L-citrulline
Dpg: 3,5-dichloro-L-4-hydroxyphenylglycine
EDTA: disodium EthyleneDiamineTetra-Acetate
End: enduracididine
Enradin: Enduracidin, Enramycin
EPM: Enduracidin Production Medium
Hpg: D- and L-4-hydroxyphenylglycine
HPLC: High Performance Liquid Chromatography
HTH: Helix-Turn-Helix
IM: Intramuscular
ISP2: International *Streptomyces* Project Medium 2
ISP4: International *Streptomyces* Project Medium 4
LB: Luria-Bertani Broth
LD50: Lethal Dosage, an LD50 represents the individual dose required to kill 50 percent of a population of test animals
MAH: Intervet/Merck Animal Health
MeOH: Methanol
MICs: Minimum Inhibitory Concentrations,
MRSA: methicillin-resistant *Staphylococcus aureus* nm: Nanometer
NRPS: non-ribosomal peptide synthetase
ORF: open reading frame
Orn: D-ornithine
PCP: peptidyl carrier protein
PCR: Polymerase Chain Reaction
Pfrd: Plus Flanking Region Deletion
SDS: Sodium Dodecyl Sulfate
SNP: single nucleotide polymorphism
SPD: Spectrophotodiode
TFA: TriFluoroacetic Acid
TSB: Tryptic Soy Broth
tsr: Thiostrepton resistance gene
UV: ultraviolet
VRE: vancomycin-resistant enterococci b. Terms Unless otherwise noted, technical terms are used according to conventional usage. Definitions of common terms in molecular biology may be found in Benjamin Lewin *Genes V* published by Oxford University Press, 1994 (ISBN 0-19-854287-9); Kendrew et al. (eds.) *The Encyclopedia of Molecular Biology*, published by Blackwell Science Ltd., 1994 (ISBN 0-632-02182-9); and Robert A. Meyers (ed.) *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administering: Administration by any route to the animal. As used herein, administration typically refers to oral administration.

Allelic variant: An alternate form of a polypeptide that is characterized as having a substitution, deletion, or addition of one or more amino acids. In one example, the variant does not alter the biological function of the polypeptide.

Amplification: When used in reference to nucleic acids, techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, and/or a change in ionization. Structural analogs are often found using quantitative structure activity relationships (QSAR), with techniques such as those disclosed in Remington (*The Science and Practice of Pharmacology*, 19th Edition (1995), chapter 28). When the changes to the original compound are substantial; or many incremental changes are combined, the compound is no longer an analog. For example, ramoplanin is not considered herein to be an analog of enduracidin; ramoplanin does not have either enduracididine amino acid, includes different amino acids; and though it has a lipid side chain, the chain length is substantially shorter. Analogs of enduracidin may be prepared by addition or deletion of functional groups on the amino acids that constitute the lipodepsipeptides, by substitution of one amino acid for another (excepting the enduracididine amino acids) or a combination of functional group modification and amino acid substitution. Exemplary enduracidin analogs include tetrahydroenduracidin A, tetrahydroenduracidin B, deschloroenduracidin A, and deschloroenduracidin B.

A derivative is a biologically active molecule derived from the base structure. A mimetic is a molecule that mimics the activity of another molecule by mimicking the structure of such a molecule, such as a biologically active molecule. Thus, the term "mimetic" indicates a definite structure related to activity.

Antibiotic: A substance, for example enduracidin, penicillin or streptomycin, often produced by or derived from certain fungi, bacteria, and other organisms, that can destroy or inhibit the growth of other microorganisms.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T). Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits transcription of the target mRNA.

Binding or stable binding: A molecule, such as an oligonucleotide or protein, binds or stably binds to a target molecule, such as a target nucleic acid or protein, if binding is detectable. In one example, an oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target: oligonucleotide complex. Binding between a target and an oligonucleotide can be detected by any procedure known to one of ordinary skill in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

The binding between a protein and its target protein, such as an antibody for an antigen is frequently characterized by determining the binding affinity. In one embodiment, affinity is calculated by a modification of the Scatchard method described by Frankel et al., *Mol. Immunol.*, 16:101-106, 1979. In another embodiment, binding affinity is measured by a specific binding agent receptor dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Biological function: The function(s) of a polypeptide in the cells in which it naturally occurs. A polypeptide can have more than one biological function.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Conservative substitution: Amino acid substitutions that do not substantially alter the activity (specificity or binding affinity) of the molecule. Typically conservative amino acid substitutions involve substitutions of one amino acid for another amino acid with similar chemical properties (e.g., charge or hydrophobicity). The following table shows exemplar conservative amino acid substitutions:

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |

-continued

| Original Residue | Conservative Substitutions |
|---|---|
| Tyr | Trp; Phe |
| Val | Ile; Leu |

Control *Streptomyces fungicidicus* strain: The naturally-occurring wild-type strain, *Streptomyces fungicidicus* ATCC21013.

DNA (deoxyribonucleic acid): A long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Domain: A portion of a molecule such as proteins or nucleic acids that is structurally and/or functionally distinct from another portion of the molecule.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Enduracidin: Enduracidins A and B are 17 amino acid lipodepsipeptides discovered in the late 1960s from fermentations of the soil bacterium *Streptomyces fungicidicus* B-5477 (ATCC 21013). The A and B peptides are homologs that differ by one carbon in the length of the attached lipid chain. Structurally, the enduracidins are distinguished by $C_{12}$ or $C_{13}$ 2 Z,4E branched fatty acid moiety and the presence of numerous nonproteinogenic amino acid residues such as enduracididine (End), 4-hydroxyphenylglycine (Hpg), 3,5-dichloro-4-hydroxyphenylglycine (Dpg), citrulline (Cit) and ornithine (Orn). Seven of the 17 amino acids have the D configuration and six of the residues are Hpg or the chlorinated analog Dpg.

Functional fragments and variants of a polypeptide: Included are those fragments and variants that maintain one or more functions of the parent polypeptide. It is recognized that the gene or cDNA encoding a polypeptide can be considerably mutated without materially altering one or more the polypeptide's functions. First, the genetic code is degenerate, and thus different codons encode the same amino acids. Second, even where an amino acid substitution is introduced, the mutation can be conservative and have no material impact on the essential function(s) of a protein. See Stryer *Biochemistry* 3rd Ed., (c) 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. *J. Immunol.* 159(5): 2502-12, 1997). Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by those well skilled in the art, A variety of methods for labeling polypeptides, and labels useful for such purposes, include radioactive isotopes such as $^{32}P$, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, 200, or even more amino acid residues.

Effective amount: A quantity or concentration of a specified compound or composition sufficient to achieve a desired effect in a subject. The effective amount may depend at least in part on the species of animal being treated, the size of the animal, and/or the nature of the desired effect.

Gene Cluster: A set of genetic elements grouped together on the chromosome, the protein products of which have a related function, such as forming a natural product biosynthetic pathway.

Heterologous: As it relates to nucleic acid sequences such as coding sequences and control sequences, "heterologous" denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature, Another example of a heterologous coding sequence is a construct where the coding sequence itself is not found in nature (e.g., synthetic sequences having codons different than the native gene). Similarly, a host cell transformed with a construct which is not normally present in the host cell would be considered heterologous for purposes of this disclosure.

Homologous amino acid sequence: Any polypeptide which is encoded, in whole or in part, by a nucleic acid sequence that hybridizes to any portion of the coding region nucleic acid sequences. A homologous amino acid sequence is one that differs from an amino acid sequence shown in the sequence listing by one or more conservative amino acid substitutions. Such a sequence also encompasses allelic variants (defined above) as well as sequences containing deletions or insertions which retain the functional characteristics of the polypeptide. Preferably, such a sequence is at least 75%, more preferably 80%, more preferably 85%, more preferably 90%, more preferably 95%, and most preferably 98% identical to any one of the amino acid sequences.

Homologous amino acid sequences include sequences that are identical or substantially identical to the amino acid sequences of the sequence listing. By "amino acid sequence substantially identical" it is meant a sequence that is at least 90%, preferably 95%, more preferably 97%, and most preferably 99% identical to an amino acid sequence of reference and that preferably differs from the sequence of reference by a majority of conservative amino acid substitutions. Consistent with this aspect of the invention, polypeptides having a sequence homologous to any one of the amino acid sequences of the sequence listing include naturally-occurring allelic variants, as well as mutants or any other non-naturally occurring variants that retain the inherent characteristics of any polypeptide of the sequences disclosed herein. Homology can be measured using sequence analysis software such as Sequence Analysis Software Package of the Genetics Computer Group, University of Wisconsin Biotechnology Center, 1710 University Avenue, Madison, Wis. 53705. Amino acid sequences can be aligned to maximize identity. Gaps can also be artificially introduced into the sequence to attain optimal alignment. Once the optimal alignment has been set up, the degree of homology is established by recording all of the positions in which the amino acids of both sequences are identical, relative to the total number of positions. Homologous polynucleotide sequences are defined in a similar way. Preferably, a homologous sequence is one that is at least 45%, 50%, 60%, 70%, 75%, 80%, 85%, 86%, 87%, 88%, 89%, 90%, 91%, 92%, 93%, 94%, 95%, 96%, 97%, 98%, 99% or identical to any one of the coding sequences.

Hybridization: Oligonucleotides and other nucleic acids hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)), These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between two distinct nucleic acid sequences or two distinct regions of the same nucleic acid sequence.

Specifically hybridizable and specifically complementary are terms that indicate a sufficient degree of complementarity such that stable and specific binding occurs between a first nucleic acid (such as, an oligonucleotide) and a DNA or RNA target. The first nucleic acid (such as, an oligonucleotide) need not be 100% complementary to its target sequence to be specifically hybridizable. A first nucleic acid (such as, an oligonucleotide) is specifically hybridizable when there is a sufficient degree of complementarity to avoid non-specific binding of the first nucleic acid (such as, an oligonucleotide) to non-target sequences under conditions where specific binding is desired. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though wash times also influence stringency. Calculations regarding hybridization conditions required for attaining particular degrees of stringency are discussed by Sambrook et al, (ed.) *Molecular Cloning: A Laboratory Manual*, 2nd ed., vol. 1-3, Cold Spring Harbor Laboratory Press, Cold Spring Harbor, N.Y., 1989, chapters 9 and 11.

The following are exemplary sets of hybridization conditions and are not meant to be limiting.

Very High Stringency (Detects Sequences that Share 90% Sequence Identity)
  Hybridization: 5×SSC at 65 EC for 16 hours
  Wash twice: 2×SSC at room temperature (RT) for 15 minutes each
  Wash twice: 0.5×SSC at 65 EC for 20 minutes each
High Stringency (Detects Sequences that Share 80% Sequence Identity or Greater)
  Hybridization: 5×-6×SSC at 65 EC-70 EC for 16-20 hours
  Wash twice: 2×SSC at RT for 5-20 minutes each
  Wash twice: 1×SSC at 55 EC-70 EC for 30 minutes each
Low Stringency (Detects Sequences that Share Greater than 50% Sequence Identity)
  Hybridization: 6×SSC at RT to 55 EC for 16-20 hours
  Wash at least twice: 2×-3×SSC at RT to 55 EC for 20-30 minutes each.

Isolated: An isolated biological component (such as a nucleic acid molecule or protein) is one that has been substantially separated or purified away from other biological components in the cell of the organism in which the component naturally occurs, such as other chromosomal and extra-chromosomal DNA and RNA, proteins and organelles. With respect to nucleic acids and/or polypeptides, the term can refer to nucleic acids or polypeptides that are no longer flanked by the sequences typically flanking them in nature. Nucleic acids and proteins that have been isolated include nucleic acids and proteins purified by standard purification methods. The term also embraces nucleic acids and proteins prepared by recombinant expression in a host cell as well as chemically synthesized nucleic acids.

Mutate: The process of causing a change in the sequence of a genetic material (usually DNA or RNA) of a cell or organism. Mutations can be intentionally introduced into genetic material using molecular techniques well known in the art (e.g., site-directed mutagenesis, PCR mutagenesis and others).

Nonribosomal peptide (NRP): A class of secondary metabolites, usually produced by microorganisms, such as bacteria and fungi. Unlike polypeptides synthesized on the ribosome, these peptides are synthesized by nonribosomal peptide synthetases (NRPS) from amino acids.

Nonribosomal peptide backbone assembly: The second step in nonribosomal peptide biosynthesis, which includes amide bond formation (condensation) of the peptide sequence.

Nonribosomal peptide synthetase (NRPS): A large multifunctional protein that synthesizes polypeptides by a nonribosomal mechanism, often known as thiotemplate synthesis (Kleinkauf and von Doehren *Ann. Rev. Microbiol.* 41: 259-289, 1987). Such nonribosomal polypeptides can have a linear, cyclic, or branched cyclic structure and often contain amino acids not present in proteins or amino acids modified through methylation or epimerization. In particular examples, NRPS produce dipeptides.

Nonribosomal peptide tailoring: The third step in nonribosomal peptide biosynthesis. There are numerous novel precursor amino acids found in nonribosomal peptides and many of these building blocks are formed or modified while attached to PCP domains of specialized proteins or the NRPS. This post-synthetic modification can occur after amide bond formation of the peptide backbone. Exemplary modifications include α-carbon epimerization, N-methylation, heterocyclization of Cys or Ser/Thr residues to thiazolines and oxazolines, and side chain halogenation or hydroxylation. Other modifications such as oxidation, alkylation, acylation and glycosylation can occur after release of the nascent peptide from the NRPS complex and are often needed for full biological activity.

Nonribosomal precursor amino acid biosynthesis: The first step in nonribosomal peptide biosynthesis. Nonribosomal peptides often possess amino acids not found in peptides and proteins that are assembled on ribosomes. These nonproteinogenic amino acids contribute to the diversity of these peptides and often have roles in their biological activity. Biosynthesis of these amino acids can occur via protein-bound intermediates or as free, soluble species.

Nucleic Acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Nucleotide: This term includes, but is not limited to, a monomer that includes a base linked to a sugar, such as a pyrimidine, purine or synthetic analogs thereof, or a base linked to an amino acid, as in a peptide nucleic acid. A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15, or 20 bases.

Open reading frame (ORF): A series of nucleotide triplets (codons) coding for amino acids without any internal termination codons. These sequences are usually translatable into a peptide. For example, ORF, open reading frame, and enduracidin ORF refer to an open reading frame in the enduracidin biosynthetic gene cluster as isolated from *Streptomyces fungicidicus*. The term also embraces the same ORFs as present in other enduracidin-synthesizing organisms. The term encompasses allelic variants and single nucleotide polymorphisms (SNPs). In certain instances the term enduracidin ORF is used synonymously with the polypeptide encoded by the enduracidin ORF and may include conservative substitutions in that polypeptide. The particular usage will be clear from context.

An open Reading Frame that has been nulled is an open reading frame that has been rendered non-functional through the deletion, insertion or mutation of one of more nucleotides in the coding sequence.

A *Streptomyces fungicidicus* comprising a diminished open reading frame-18 (orf18) is an organism that has a decrease in, such as a 2-fold decrease, or even complete loss of the biological function of the gene product of orf18, relative to a wild type *Streptomyces fungicidicus* e.g., through genetic modification of orf18, including the orf18 being nulled as exemplified below, and/or through regulatory manipulation, e.g., modifying, inserting into, removing, and/or replacing non-coding regions of the gene encoding ORF18 that result in a decrease in the expression of the orf18 gene product. For example, the wild type promoter of orf18 could be modified so as to substantially decrease the transcription of orf18.

A *Streptomyces fungicidicus* comprising an augmented open reading frame-24 (orf24) is an organism that has an increase, such as a 2-fold increase or more, in the biological function of the gene product of orf24, relative to a wild type *Streptomyces fungicidicus*, e.g., through genetic modification of orf24 to enhance biological function of the gene product of orf24 and/or by regulatory manipulation, e.g., modifying, inserting into, removing, and/or replacing non-coding regions of the gene encoding ORF24 that result in an increase in the expression of the orf24 gene product. For example, the wild type promoter for orf24 was replaced with a strong constitutive promoter which enhanced the transcription of orf24, as exemplified below.

Modified gene: A gene sequence which contains a modification as compared to that found in the naturally occurring (wild-type) gene.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ortholog: Two nucleic acid or amino acid sequences are orthologs of each other if they share a common ancestral sequence and diverged when a species carrying that ancestral sequence split into two species. Orthologous sequences are also homologous sequences.

Polypeptide: A polymer in which the monomers are amino acid residues which are joined together through amide bonds. When the amino acids are alpha-amino acids, either the L-optical isomer or the D-optical isomer can be used, the L-isomers being preferred in some instances. The term polypeptide or protein as used herein encompasses any amino acid sequence and includes modified sequences such as glycoproteins. The term polypeptide is specifically intended to cover naturally occurring proteins (whether produced by ribosomal or nonribosomal mechanisms), as well as those that are recombinantly or synthetically produced.

The term polypeptide fragment refers to a portion of a polypeptide that exhibits at least one useful epitope. The phrase functional fragment of a polypeptide refers to all fragments of a polypeptide that retain an activity (such as a biological activity), or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell.

The term substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Probes and primers: Nucleic acid probes and primers can be readily prepared based on the nucleic acid molecules provided in this disclosure. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides, 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (FOR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al, (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). The specificity of a particular probe or primer increases with its length. Thus, in order to obtain greater specificity, probes and primers can be selected that comprise at least 17, 20, 23, 25, 30, 35, 40, 45, 50 or more consecutive nucleotides of desired nucleotide sequence.

Protein: A biological molecule expressed by a gene and comprised of amino acids.

Purified: The term purified does not require absolute purity; rather, it is intended as a relative term. Thus, for example, a purified protein preparation is one in which the protein referred to is more pure than the protein in its natural environment within a cell.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. "Recombinant" also is used to describe nucleic acid molecules that have been artificially manipulated, but contain the same control sequences and coding regions that are found in the organism from which the gene was isolated.

Regulating antibiotic production: To cause an alteration, such as an increase or decrease, in the amount, type or quality of antibiotic production. Disclosed herein are recombinant strains of *Streptomyces fungicidicus* with enhanced enduracidin production.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=-3]; reward for a match [default=1]; expectation value (E) [default=10.0]; word size [default=3]; number of one-line descriptions (V) [default=100]; number of alignments to show (B) [default=100]), When aligning short peptides (fewer than around 30 amino acids), the alignment should be performed using the Blast 2 sequences function, employing the PAM30 matrix set to default parameters (open gap 9, extension gap 1 penalties). Proteins (or nucleic acids) with even greater similarity to the reference sequences will show increasing percentage identities when assessed by this method, such as at least 50%, at least 60%, at least 70%, at least 80%, at least 85%, at least 90%, or at least 95% sequence identity.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity.

An alternative indication that two nucleic acid molecules are closely related is that the two molecules hybridize to each other under stringent conditions (see "Hybridization" above).

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Transfected: A process by which a nucleic acid molecule is introduced into cell, for instance by molecular biology techniques, resulting in a transfected (or transformed) cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Transformed: A transformed cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Transposon: A mobile genetic element having nearly identical repeating sequences at either end, and containing at least a gene encoding a transposase (the enzyme needed to insert the transposon in the DNA sequence). Transposons can be integrated into different positions in the genome of a cell, or over an isolated plasmid, cosmid, or fosmid DNA template in vitro, Transposons may also contain genes other than those needed for insertion.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses, A plasmid is a vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

Suitable methods and materials for the practice of the disclosed embodiments are described below. In addition, any appropriate method or technique well known to the ordinarily skilled artisan can be used in the performance of the disclosed embodiments. Some conventional methods and techniques applicable to the present disclosure are described, for example, in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; Harlow and Lane, *Using Antibodies: A Laboratory Manual*, Cold Spring Harbor Laboratory Press, 1999; and Kieser, T., Bibb, M. J., Buttner, M. J., Chater, K. F., and Hopwood, D. A.: Practical *Streptomyces* genetics, John Innes Centre, Norwich Research Park, Colney, Norwich NR4 &UH, England, 2000.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Engineered Recombinant Expression Vectors of *Streptomyces fungicidicus*

Disclosed herein are engineered recombinant *Streptomyces fungicidicus* expression plasmid vectors. In some embodiments, an engineered recombinant *Streptomyces fungicidicus* vector comprises at least one selected open reading frame of *Streptomyces fungicidicus*. In some embodiments, an engineered recombinant *Streptomyces fungicidicus* vector comprises at least one selected open reading frame of *Streptomyces fungicidicus* expressed under the control of a promoter. In some examples, the promoter is a strong constitutive *Streptomyces* promoter that results in the enhanced production of enduracidin when the vector is expressed in a strain of *Streptomyces fungicidicus*. In some embodiments, the open reading frame is operatively linked to a heterologous promoter instead of its own native promoter. For example, it may be operatively linked to a constitutive promoter, such as a strong constitutive expression promoter or an inducible promoter. In some examples, the strong constitutive promoter is ermE*p from the erythromycin producer. In some examples, the inducible promoter is tipA. In some examples, the P(nitA)-NitR system (Herai S, Hashimoto Y, Higashibata H, Maseda H, Ikeda H, Omura S, Kobayashi M, Proc Natl Acad Sci USA. 2004. 101(39):14031-5) or the streptomycete promoter SF14 is employed. In some examples, a native promoter of the apramycin resistant gene (amRp) is employed. In some examples, $P_{hrdB}$, $P_{tcp830}$, $P_{SF14}$, $P_{ermE*}$ and/or Pneos are employed.

In some embodiments, the engineered recombinant vector comprises an open reading frame orf24 (SEQ ID NO: 38) and/or open reading frame orf18 (SEQ ID NO: 37) which has been nulled. In some examples, the open reading frame orf18 (SEQ ID NO: 37) is nulled by an in-frame-deletion, frame-shifting and/or point mutation.

In some embodiments, the engineered recombinant vector comprises an open reading frame orf24 from the enduracidin gene cluster of *Streptomyces fungicidicus*. In some examples, the open reading frame orf24 (SEQ ID NO: 38) is operatively linked to a heterologous promoter. For example, it is linked to a strong constitutive promoter such as ermE*p. In other examples, the open reading frame orf24 is operatively linked to promoter tipA, SF14, amRp, $P_{hrdB}$, $P_{tcp830}$, $P_{SF14}$, $P_{ermE*}$ and/or Pneos.

In another embodiment, an engineered recombinant vector comprises an open reading frame orf18 that resides in the upstream region of the enduracidin gene cluster. The open reading frame orf18 (SEQ ID NO: 37) is nulled by insertional disruption, in-frame deletion, frame-shifting and/or point mutation. In some examples, the open reading frame orf18 is nulled by an in-frame deletion, such as an in-frame deletion as illustrated in FIG. 96. In one example, the open reading frame orf18 (SEQ ID NO: 37) is nulled by an in-frame deletion. For example, the open reading frame orf18 (SEQ ID NO: 37) is nulled by an in-frame deletion of nucleic acids 5 through 660 of orf18 (SEQ ID NO: 37). In general, any internal in-frame deletion over orf18 results in a nulled function of Orf18 due to its incompleteness. In some examples, the in-frame deletion includes deletion of at least 3 nucleic acids in orf18 (SEQ ID NO: 37), such as at least 3 nucleic acids, including 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 204, 207, 210, 213, 216, 219, 221, 224, 227, 230, 233, 236, 239, 242, 245, 248, 251, 254, 257, 260, 263, 266, 269, 272, 275, 278, 281, 284, 287, 290, 293, 296, 299, 302, 305, 308, 311, 314, 317, 320, 323, 326, 329, 332, 335, 338, 341, 344, 347, 350, 353, 356, 359, 362, 365, 368, 371, 374, 377, 380, 383, 386, 389, 392, 395, 398, 401, 404, 407, 410, 413, 416, 419, 421, 424, 427, 430, 433, 436, 439, 442, 445, 448, 451, 454, 457, 460, 463, 466, 469, 472, 475, 478, 481, 484, 487, 490, 493, 496, 499, 502, 505, 508, 511, 514, 517, 520, 523, 526, 529, 532, 535, 538, 541, 544, 547, 550, 553, 556, 559, 562, 565, 568, 571, 574, 577, 580, 583, 586, 589, 592, 595, 598, 601, 604, 607, 610, 613, 616, 619, 621, 624, 627, 630, 633, 636, 639, 642, 645, 648, 651, or 654 nucleic acids between nucleic acids 5 through 660 of orf18 (SEQ ID NO: 37).

In related embodiments, an engineered recombinant plasmid vector involves two or more open reading frames from the enduracidin gene cluster and/or the regions flanking the gene cluster or from other actinomycete strains. The two or more open reading frames may be linked to a single promoter. Alternatively, they may be operatively linked to two different promoters. The two promoters may be the same type of promoter. Alternatively, they may be two different types of promoters.

In further embodiments, additional or alternative open reading frames that may enhance enduracidin production may be introduced, or inactivated, in the engineered strain of *Streptomyces fungicidicus*.

In some examples, the recombinant plasmid is pXY152-endorf24 (SEQ ID NO:3). In some examples, the recombinant plasmid is pXY300-orf18ifd (SEQ ID NO: 8). In some examples, the recombinant plasmid is pKS-T-orf18ifd (SEQ ID NO: 11). In some examples, the recombinant plasmid is pKS-T-orf18pfrd-AmR (SEQ ID NO: 14). In some examples, the recombinant plasmid is pKS-orf18ifd-T-AmR (NS)(SEQ ID NO: 19). In some examples, the recombinant plasmid is pXY152-endorf24-camtsr (SEQ ID NO: 20). In some examples, the recombinant plasmid is pXY152-endorf24-blatsr (SEQ ID NO: 23).

IV. Engineered Recombinant Strains of *Streptomyces fungicidicus*

Disclosed herein are engineered recombinant *Streptomyces fungicidicus* strains capable of producing enhanced enduracidin as compared to a control strain (such as a wild-type *Streptomyces fungicidicus* strain or industrial parent strain). In some embodiments, an engineered recombinant *Streptomyces fungicidicus* strain comprises at least one selected open reading frame from *Streptomyces fungicidicus* introduced onto the chromosome and expressed under the control of a promoter, such as a strong constitutive *Streptomyces* promoter, that results in the enhanced production of enduracidin in the engineered strain. In some embodiments, the expression of the introduced open reading frame in the *Streptomyces fungicidicus* is driven by a heterologous promoter instead of its own native promoter. For example, it may be operatively linked to a constitutive promoter, such as a strong constitutive expression promoter or an inducible promoter. In some examples, the strong constitutive promoter is ermE*p from the erythromycin producer. In some examples, the inducible promoter is tipA. In some examples, the P(nitA)-NitR system (see Herai S, Hashimoto Y, Higashibata H, Maseda H, Ikeda H, Omura 5, Kobayashi M, Proc Natl Acad Sci USA., 2004. 101(39):14031-5) or the streptomycete promoter SF14 is employed. In some examples, the constitutive expression promoter is amRp. In some examples, $P_{hrdB}$, $P_{tcp830}$, $P_{SF14}$, $P_{ermE*}$ and/or Pneos promoters are employed.

In some embodiments, the engineered strain comprises an open reading frame orf24 from the enduracidin gene cluster of *Streptomyces fungicidicus*. In some examples, the open reading frame orf24 is operatively linked to a heterologous promoter. For example, it is linked to a strong constitutive promoter such as ermE*p. In other examples, the open reading frame orf24 is operatively linked to promoter tipA, SF14, amRp, $P_{hrdB}$, $P_{tcp830}$, $P_{SF14}$, $P_{ermE*}$ and/or Pneos.

In another embodiment, the engineered strain is related to an open reading frame orf18 that resides in the upstream region of the enduracidin gene cluster. The open reading frame orf18 is nulled by insertional disruption, in-frame deletion, frame-shifting and/or point mutation. In some examples, the open reading frame orf18 is nulled by an in-frame deletion, such as an in-frame deletion as illustrated in FIG. 9B. In one example, the open reading frame orf18 (SEQ ID NO: 37) is nulled by an in-frame deletion. For example, the open reading frame orf18 (SEQ ID NO: 37) is nulled by an in-frame deletion of nucleic acids 5 through 660 of (SEQ ID NO: 37). In general, any internal in-frame deletion over orf18 should result in a nulled function of Orf18 due to its incompleteness.

In related embodiments, the engineered strain involves two or more open reading frames from the enduracidin gene cluster and/or the regions flanking the gene cluster or from other actinomycete strains. The two or more open reading frames may be linked to a single promoter. Alternatively, they may be operatively linked to two different promoters. The two promoters may be the same type of promoter. Alternatively, they may be two different types of promoters.

In further embodiments, additional or alternative open reading frames that may enhance enduracidin production may be introduced, or inactivated, in the engineered strain of *Streptomyces fungicidicus*.

In some embodiments, the engineered strain of *Streptomyces fungicidicus* is derived from a wild type parent strain, such as, but not limited to, *Streptomyces fungicidicus* American Tissue Culture Company (ATCC) 21013. In other embodiments, the engineered strain of *Streptomyces fungicidicus* is derived from an industrial parent strain, such as, but not limited to BM38-2 (ATCC PTA-122342), In other embodiments, the engineered strain of *Streptomyces fungicidicus* is derived from the conventional mutant strains, such as, but not limited to *Streptomyces fungicidicus* ATCC 31729, *Streptomyces fungicidicus* ATCC 31730 and *Streptomyces fungicidicus* ATCC 31731.

In some embodiments, enhanced production of enduracidin is an at least 1.2 fold increase, such as at least 1.5 fold, at least 2 fold, at least 2.5 fold, at least a 3 fold, at least a 3.5 fold, at least a 4 fold, at least a 4.5 fold increase, including, but not limited to a 1.2 to 10 fold increase, a 1.2 to 4.6 fold increase, a 2 to 5 fold increase, such as 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5 and 10 fold increase in enduracidin production as compared to the control *Streptomyces fungicidicus* strain. In some embodiments, the control *Streptomyces fungicidicus* strain is a wild-type *Streptomyces fungicidicus* strain, including, but not limited to, *Streptomyces fungicidicus* American Tissue Culture Company (ATCC) 21013 or an industrial parent strain, such as, but not limited to, BM38-2 (ATCC PTA-122342), or the conventional mutant strain, such as, but not limited to *Streptomyces fungicidicus* ATCC 31729, *Streptomyces fungicidicus* ATCC 31730 and *Streptomyces fungicidicus* ATCC 31731. In one example, the control is *Streptomyces fungicidicus* ATCC 21013 and the increase in enhanced enduracidin production is at least a 1.2 fold increase, such as a 1.2 to 4.6 fold increase. In one example, the control is *Streptomyces fungicidicus* BM38-2 (ATCC PTA-122342) and the increase in enhanced enduracidin productions is at least a 1.2 fold increase, such as a 1.2 to 4.6 fold increase.

V. Construction of Engineered Recombinant Strains of *Streptomyces fungicidicus*

In embodiments, recombinant strains of *Streptomyces fungicidicus* may be constructed by integration of a recombinant plasmid comprising at least one enduracidin production enhancing open reading frame into the chromosome of a parent strain of *Streptomyces fungicidicus*. The integrative conjugal vector may have, or may be engineered to have, a strong constitutive *Streptomyces* promoter. In some embodiments, the plasmid may lack a streptomycete replicon and may be integrated into the chromosome by site-specific single crossover homologous recombination. In other embodiments, the plasmid may be present as a free plasmid. In some embodiments, an conjugal vector may be engineered in which the plasmid insert carries a partially or completely deleted gene of interest, and its flanking regions, that may be integrated into the chromosome after double crossover homologous recombination to generate an in-frame deletion mutant.

VI. Production of Enduracidin from Engineered Recombinant Strains of *Streptomyces fungicidicus*

The engineered recombinant strains of *Streptomyces fungicidicus* provided by the present disclosure provide for methods of producing enhanced levels of enduracidin. This technical advance in the art allows for significant cost savings associated with the production of enduracidin. In some examples, methods of producing enduracidin comprises culturing a disclosed recombinant strain of *Streptomyces fungicidicus* under conditions sufficient for producing enduracidin. In some examples, the method further comprises isolating the enduracidin from the culture medium following culturing. In some examples, the method further comprising determining the antibacterial activity of the produced enduracidin, such as by HPLC analysis or bioassay using the S, *aureus* ATCC 29213 or *Bacillis subtilis* ATCC 6633 as indicating microorganisms.

In some examples, enduracidin is produced by a disclosed *Streptomyces fungicidicus* strain by utilizing fermentation conditions as previously described for the production of enduracidin (Higashide et al. *J. Antibiot.* 21: 126-137, 1968). After production, the compounds can be purified and/or analyzed including HPLC analysis as described in Example 1. Methods of producing enduracidin and harvesting this compound from growth medium can be found in U.S. Pat. No. 4,465,771, which is hereby incorporated by reference in its entirety.

In some examples, a disclosed *Streptomyces fungicidicus* strain is cultured in tryptic soy broth (TSB) on a shaker (such as at 225 rpm and 30° C. for 48 hours) and then transferred to a enduracidin production medium (EPM, Table 1 below) for a period of time for continuous fermentation, such as for at least five days and up to eleven days, including 5, 6, 7, 8, 9, 10 or 11 days of continuous fermentation. In some examples, production of enduracidin by the wild-type and derivative strains is conducted in automatic fermenters.

TABLE 1

| Enduracidin Production Medium (EPM) Composition (pH 6.7) | |
|---|---|
| Ingredient | Concentration (%) |
| Soluble starch | 1.5 |
| Glucose | 1.0 |
| Corn flour | 2.5 |
| Corn gluten meal | 2.0 |
| Corn steep liquor | 0.25 |
| Sodium chloride | 0.25 |
| NaH2PO4 | 1.3 |
| KH2PO4 | 0.05 |
| (NH4)2SO4 | 0.15 |
| CaCO3 | 0.5 |
| Lactose | 0.5 |
| ZnCl2 | 0.005 |
| Chicken oil | 0.7 |

In some examples, *Streptomyces fungicidicus* biomass is produced by a fermentation process in deep tank sanitary design industrial fermenters with systems to monitor and control pH, temperature, oxygen, aeration, agitation. For example, each fermented batch of *S. fungicidicus* is initiated from a characterized and controlled working seed stock of the production seed stored in a secure location and held in low temperature environment.

In some examples, the fermentation process occurs in one or more stages, such as following three stages and can optionally be followed by further processing downstream:

Stage I:

Characterized established working seed cultures are used to start a fermentation batch. One-to-five vials of frozen seed vials are retrieved from low temperature storage and thawed either naturally or placed in a water bath at 28° C.-32° C. until the contents are thawed. The thawed culture(s) are aseptically transferred into sterile water held at room temperature and gently mixed to re-suspend the culture.

Stage II:

The re-suspended culture is aseptically transferred into 0.005 m3-0.05 m3 seed medium. The seed medium is composed of glucose (0.1-1.0 g/L), Dextrin (0.1-3 g/L), corn steep liquor (0-5.0 mL/L), soybean powder (1-5.0 g/L), ammonium sulfate (0.1-0-0.5 g/L), mono-potassium phosphate (0.13-0.54 g/L), ferrous sulfate (0.00-0.5 g/L), potassium hydroxide (0.13 mL/L), calcium carbonate (1-2 g/L), silicone-based de-foaming agent (0.1 mL/L), water, q. s. The medium is sterilized at 125° C.-128° C. for 30-45 minutes and then cooled to 28° C.-32° C. The volume of medium is adjusted using sterile water to the desired working volume. The pH is adjusted to 6.5-7.0.

The operating parameters of the seed scale up cycle include: Incubation temperature of 28° C.±2° C., an internal pressure of 1.0±0.5 kg/cm2, an aeration rate of 3±2 Nm3/min, and agitation rate of approximately 80 rpm, depending upon size and configuration of the vessel. The pH, oxygen consumption and viscosity is monitored but not controlled. The culture is grown for 40-80 hours before transfer into the main production fermenter. The viscosity at the time of transfer should range from 200-600 cps, and the pH should be ≤6.0, and there should be an increase in oxygen consumption. The seed culture is aseptically transferred into the main fermentation medium to complete the fermentation cycle.

Stage III:

Production Fermenter medium (10 m3-250 m3) composition includes natural and chemical components such as corn flour (13.0-15.0 w/v %), corn gluten meal (3.0-6.0 w/v %), cotton seed flour (0.1-0.3 w/v %), corn steep liquor (0.1-0.6 v/v %), sodium chloride (0.3 w/v %), ammonium sulfate (0.25-0.6 w/v %), lactic acid (0-0.5 v/v %), zinc chloride (0.01 w/v %), ferrous sulfate (0.0-0.02 w/v %), potassium hydroxide (0.20-0.5 v/v %), calcium sulfate (0.0-0.5 w/v %), calcium carbonate (0.5 w/v %), amylase (0.02-0.06 w/v %), potassium hydroxide (0.05 v/v %), vegetable oil (0.5-2.0 v/v %), de-foaming agent, and water, q. s. The ingredients are added according to the order listed. Add water to the ingredients then heat to 70-90° C. to allow the enzyme to break down the complex carbohydrates for 15 minutes at temperature. Add remaining ingredients, adjust pH to 6.6-6.8, and add water q. s., sterilize at 125° C.-128° C. for 25-50 minutes to sterilize the media. Cool the media to 25° C.-32° C., and add water to q. s., working volume.

Transfer the contents from the seed fermenter into the main fermentation medium and set the fermenter to the following conditions: Temperature 28° C.±3° C., aeration rate 20-60 Nm3/min, internal pressure 0.1-1.0 kg/cm2, agitation rate equivalent to about 1.85 kW/m3. The aeration rate, internal pressure and agitation rates are adjusted a needed to ensure that the dissolved oxygen is not a rate limiting determinate. Carefully control foaming throughout the cycle to prevent contamination or outflow. Start controlling pH after oxygen demand increases. The following parameters are controlled and/or monitored throughout the fermentation cycle: pH, aeration, dissolved oxygen, CO2, viscosity, purity, agitation speed, internal pressure, and residual sugar. Maintain pH at 6.8 until the bacteria growth ceases, then allow pH to change naturally until harvest. The typical fermentation cycle is 210-300 hours. The culture is ready to be harvested when potency is greater than 5,000 µl/L, pH rises to 7.5 or higher, viscosity decreases, and oxygen demand ceases.

The fermentation is harvested by heating the culture to 70° C. for 30 minutes to inactivate the bacteria, and then cool the harvest fluids to 25° C.-32° C.

In some examples, downstream processing includes removing water from the biomass, drying the biomass and formulating the dried biomass into a premix.

Deposits of Biological Material

The following biological materials have been deposited under the terms of the Budapest Treaty with The American Type Culture Collection, and given the following accession numbers:

| Deposit | Accession Number | Date of Deposit |
| --- | --- | --- |
| BM38-2-18pfrd | PTA-124007 | Mar. 2, 2017 |
| BM38-2-24/16 | PTA-124006 | Mar. 2, 2017 |

The above strains have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposits represent substantially pure culture of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The following non-liming examples are provided to illustrate certain particular features and/or embodiments. These examples should not be construed to limit the disclosure to the particular features or embodiments described.

EXAMPLES

Example 1

Materials and Methods for Enhanced Enduracidin Production

This example provides representative methods for enhanced enduracidin production.

Bacterial Strains, Plasmids, Fosmids and Culture Conditions.

*Streptomyces fungicidicus* B-5477 (ATCC 21013) and *Escherichia coli* S17-1 (ATCC 47055) were purchased from ATCC. The *S. fungicidicus* strain BM38-2 (ATCC PTA-122342) and standards of enduracidins A and B were provided by Intervet/Merck Animal Health (MAH). *E. coli* strains DH5a (Life Technologies, Inc.), EPI300 (Epicentre) and XL10-Gold (Stratagene) were used as hosts for E, coil plasmids, fosmids and *E. coli-Streptomyces* shuttle vectors. Plasmids pSET152 (Bierman et al., Gene 116: 43-49, 1992, which is hereby incorporated by reference in its entirety) and pIJ773 were provided by Professor Keith Chater (JIC, Norwich, UK). Plasmid pWHM860 harboring ermE*p promoter was provided by Professor Bradley Moore (UCSD, San Diego). ISP2 (Difco™ ISP Medium 2), ISP4 and TSB (Bacto™ Tryptic Soy Broth) were purchased from VWR. Primers used for PCR and DNA sequencing were synthesized from Fisher and Sigma-Aldrich. Media and culture conditions for growing *S. fungicidicus* were described by Higashide et al. (*Journal of Antibiotics*, 21:126-137, 1968). All *E. coli* procedures were performed according to standard protocols.

DNA Isolation and Manipulations.

To prepare genomic DNA from *S. fungicidicus* B-5477, BM38-2 (ATCC PTA-122342) and derivative recombinant and mutant strains for sequencing, fosmid library construction, subcloning and FOR, freshly harvested spores from the individual strains were inoculated and grown in 100 mL TSB liquid medium supplemented with 5 mM $MgCl_2$ and 0.5% glycine. The representative culture was conducted in 500 mL Erlenmeyer flasks on a rotary shaking incubator at 225 rpm and 30° C. for 48 to 72 hours. Mycelial cells were harvested by centrifugation at 4000 rpm and 4° C. for 15 minutes. The supernatant was discarded and the pellet was successively washed once with 10.3% sucrose and twice with 10 mM Tris-HCl and 1 mM disodium ethylenediaminetetra-acetate (EDTA), pH 8.0 (TE buffer). The wet cells, equivalent to the volume of 80 μL water were distributed into 1.5 mL sterile micro-centrifuge tubes. After adding 300 μL of the lysis solution containing 200 μL of 10 mM Tris-HCl and 1 mM EDTA, pH 8.0 and 0.3 M sucrose (TES buffer), 50 μL of 0.5 M EDTA, 50 μL of lysozyme (50 mg/mL), the tubes were incubated at 37° C. for 30 to 60 minutes until the solution became viscous. Next, 5 μL of proteinase K (20 mg/mL) and 180 μL of 10% sodium dodecyl sulfate (SDS) were added to each tube. After gentle but thorough mixing, the solutions were incubated at 37° C. for 90 minutes. Then, 80 μL of 10% Cetyl Trimethyl Ammonium Bromide (CTAB) was added. After thorough mixing, the tubes were incubated at 65° C. for 10 minutes. The solutions were extracted twice with 600 μL of phenol/chloroform/isoamyl alcohol (25/24/1). The genomic DNA in the upper aqueous phases were recovered and precipitated with 0.6 volume of isopropanol. The harvested genomic DNA was washed twice with 70% ethanol. After drying at room temperature for 10 minutes, the genomic DNA was dissolved in 50 to 100 μL of sterile water. The high quality of the genomic DNA preparation was confirmed by digestion with HindIII and Sau3AI which showed complete digestion and no degradation of undigested genomic DNA by 0.8% agarose gel electrophoresis. Pooled genomic DNA was further digested with RNase to remove RNA contamination. The purity and quantity of the genomic DNA were determined with a Nanodrop spectrophotometer. General streptomycete DNA manipulations including agarose gel electrophoresis were performed and QIAprep Spin Miniprep kits (Qiagen) were used to prepare plasmids and fosmids from E. coli strains. Restriction endonucleases, DNA ligase, DNA polymerase, transposase, Klenow enzyme, alkaline phosphatase and ligase were purchased from Biolabs, Invitrogen, Epicentre and Roche, and used according to the manufacturers' recommendations. DNA fragments were purified using QIAquick Gel Extraction kits.
PCR.

The colony FOR was conducted as follows: spores from independent mutant candidate colonies were inoculated in TSB liquid culture. After growing for 48 to 72 hours, mycelia were harvested by centrifugation and washed twice with TE buffer (10 mM Tris, 1 mM EDTA), pH 8.0. Mycelia were re-suspended in sterile H$_2$O and used as template in FOR reaction mixture in a final volume of 100 μL containing 60 μL of mycelia, 150 pmol of each primer, 20 μL of 5× AccuPrime GC-rich buffer A (Invitrogen), and 1 μL of Polymix (added at 80° C.) from the Expand long template FOR system (Roche). FOR was performed as follows: 1 cycle at 95° C. for 3 minutes, 30 cycles at 95° C. for 1 minute, at 55° C. for 1 minute, and at 72° C. for 2 minutes. The reaction was terminated with one extension cycle at 72° C. for 10 minutes. FOR products were gel-purified and sequenced. General PCR was similarly conducted as described above except that the isolated genomic DNA, plasmid/fosmid DNA was used as template instead of the direct use of DNA released from mycelial colonies without prior purification.

Construction of the Integrative Expression Plasmid pXY152-endorf24

Figure 2:
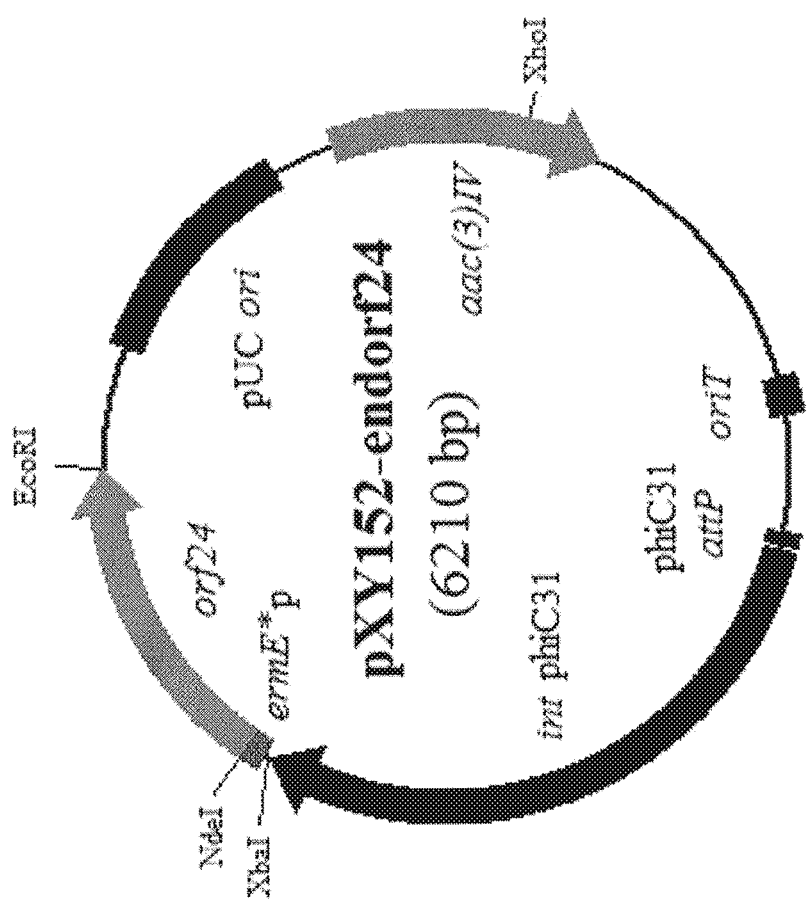
FIG. 2 is a map of the integrative expression plasmid pXY152-endorf24.

In order to ectopically express the putative regulatory gene orf24 from the enduracidin gene cluster in S. fungicidicus wild-type and BM38-2 (ATCC PTA-122342) strains, orf24 was cloned into the integrative plasmid pXY152 derived from pXY152aR20 (Yin et al., J. Natural Products, 73: 583-589, 2010 which is hereby incorporated by reference in its entirety) orf24 was FOR-amplified from S. fungicidicus genomic DNA using the forward primer (End24Ndpf: 5'-CCACCACATATG-GAAATAAGTTCGCTCTCCA-3' (SEQ ID NO:1, NdeI site is in bold) and the reverse primer (End24ERpr: 5'-GTGTGT-GAATTCCTCGTTCACCCGGCCAGATG-3' (SEQ ID NO: 2, EcoRI site is in bold). The FOR product was digested with NdeI and EcoRI. The gel-purified orf24 fragment was then ligated with the similarly restricted vector pXY152. The resulting plasmid was designated pXY152-endorf24 (FIG. 2; SEQ ID NO: 3). The orf24 insert was confirmed to be error free by sequencing.

Figure 3:
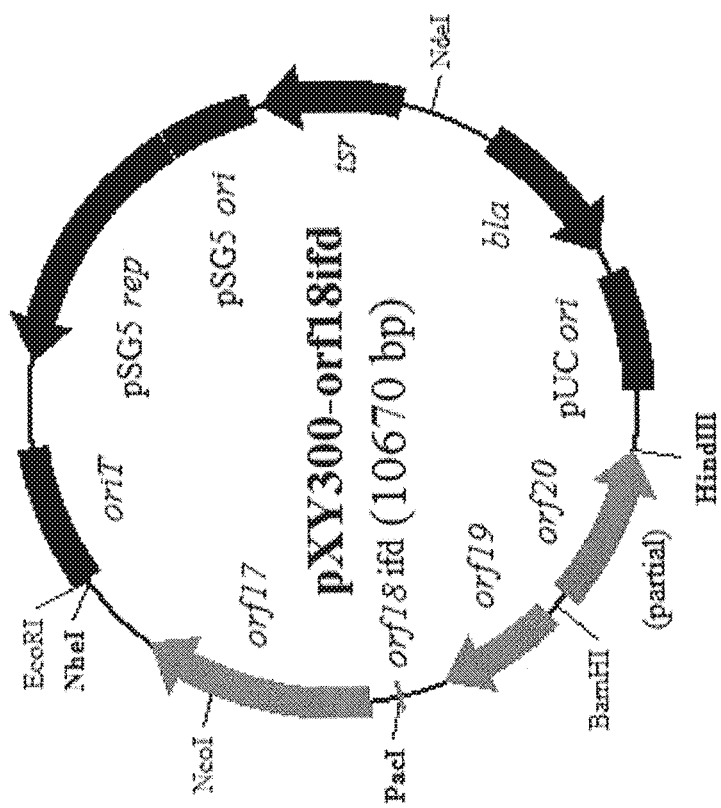
FIG. 3 is a map of the gene deletion plasmid pXY300-orf18ifd.

Construction of Plasmid pXY300-orf18ifd for in-Frame Deletion of Orf18 pXY300-orf18ifd was constructed by cloning two fragments that flank orf18 and are destined for deletion into pXY300, an E. coli-Streptomyces shuttle conjugal temperature-sensitive vector containing the thiostrepton resistance gene (tsr) for selection in S. fungicidicus. An "upstream" 2 kb and a "downstream" 2 kb flanking sequence, designated orf18ifdNP and orf18ifdPH, respectively, that flank orf18 were generated by FOR using S. fungicidicus genomic DNA as the template and two sets of primers. Fragment orf18ifdPH was amplified by using the forward and reverse primers (Ifdenorf18pf1, 5'-TTATT-GAAGCTTGCCGGGGCCGACGCGGCGGGCGGCCT-3' (SEQ ID NO: 4), Ifdendorf18pr1, 5'-GTTGTTTTAAT-TAAACACCAGGCCTCCTGGGGTG-3' (SEQ ID NO: 5), HindIII and PacI sites are in bold). Fragment orf18ifdNP was amplified by using the forward and reverse primers (Ifdendorf18pf2, 5'-TTTATATTAAT-TAATGACCCTTCCGTCCCGCCCCCGAT-3' (SEQ ID NO: 6), Ifdendorf18pr2, 5'-TTTGGTGCTAGCTGGTCGTGGCGCTGTTCC-3' (SEQ ID NO: 7), PacI and NheI sites are in bold). These two PCR fragments were appropriately restricted and simultaneously ligated with the pXY300 vector prepared by digestion with NheI and HindIII, to yield plasmid pXY300-orf18ifd (FIG. 3; SEQ ID NO: 8). The error-free in-frame deletion insert of pXY300-orf18ifd was confirmed by sequencing.

Construction of Plasmid pKS-T-orf18pfrd-AmR for Deletion of Orf18 and its Flanking Regions.

Figure 4:
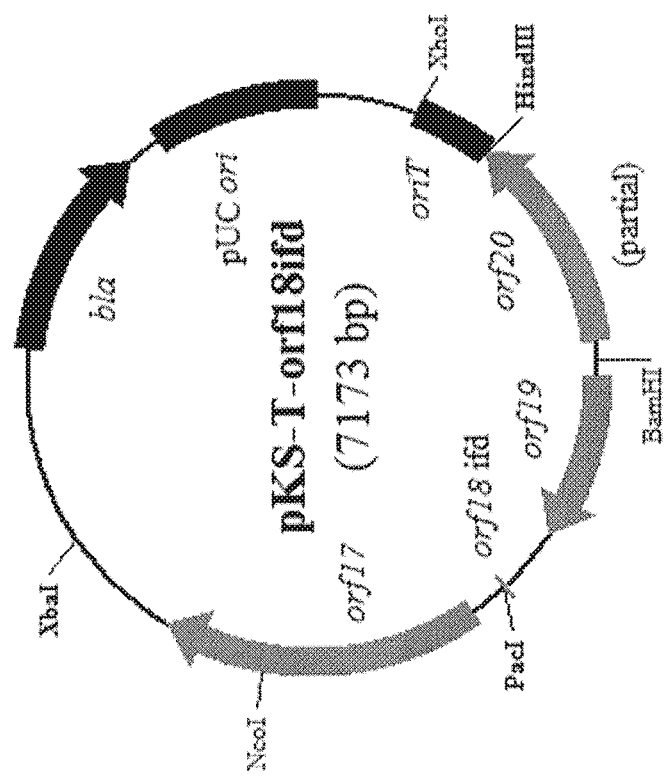
FIG. 4 is a map of the gene deletion plasmid pKS-T-orf18ifd.

The oriT fragment was amplified by PCR from plasmid pIJ773 using the forward primer (Oritnhexband3f, 5'-AGCACAGCTAGCTTCTAGAAGCTTCATT-CAAAGGCCGGCA-3' (SEQ ID NO: 9) HindIII site is in bold) and the reverse primer (Oriter1pstxhor, 5'-GCCAGT-GAATTCTGCAGCTCGAGCAGAGCAGGAT-TCCCGTTGA-3' (SEQ ID NO: 10), XhoI site is in bold). The oriT fragment was digested with HindIII and XhoI, gel-purified and then ligated into the similarly restricted vector pBluescript II KS derivative to yield plasmid pKS-T (Alting-Mees and Short, Nucleic acids Research, 17: 9494, 1989). The insert of plasmid pXY300-orf18ifd was excised by digestion with NheI and HindIII, gel-purified and then ligated with NheI and HindIII linearized plasmid pKS-T to afford the plasmid pKS-T-orf18ifd (FIG. 4; SEQ ID NO: 11). A 1 kb fragment carrying aac(3)IV, the apramycin resistance gene (amR), was amplified from pIJ773 using forward primer (ApraNcoIpf, 5'-GAATGGCCATGGTT-CATGTGCAGCTCCAT-3' (SEQ ID NO: 12), NcoI site is in bold) and reverse primer (ApraBamHIpr, 5'-TCTCGAG-GATCCGAATAGGAACTTCGGAAT-3' (SEQ ID NO: 13), BamHI site is in bold). Digestion of the fragment AmR and plasmid pKS-T-orf18ifd with NcoI and BamHI prepared both the insert and vector for ligation. The resulting plasmid was designated pKS-T-orf18pfrd-AmR (FIG. 5; SEQ ID NO: 14).

Construction of Plasmid pKS-T-orf18ifd-AmR(NS) for in-Frame-Deletion of orf18.

Figure 6:
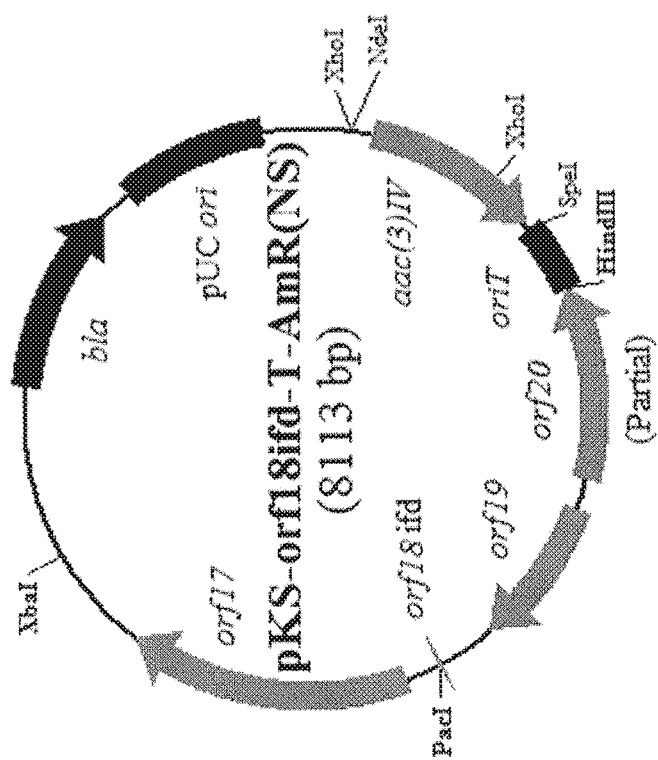
FIG. 6 is a map of the gene deletion plasmid pKS-orf18ifd-T-AmR(NS).

The insert of pXY300-orf18ifd was excised by digestion with NheI and HindIII, gel-purified and then ligated with SpeI and HindIII linearized vector pBluescript II KS to produce a plasmid pKS-orf18ifd. The oriT fragment was amplified by FOR using the forward primer (Oritnhexband3f,
5'-AGCACAGCTAGCTTCTAGAAGCTTCATT-CAAAGGCCGGCA-3' (SEQ ID NO: 15), HindIII site is in bold) and the reverse primer (oriTXhNdSpr, 5'-AGGCAGCTCGAGCATATGACTAGTCAGAGCAG-GATTCCCGTTGA-3'(SEQ ID NO: 16), XhoI, NdeI and SpeI sites are in bold). The oriT fragment was digested with XhoI and HindIII, gel-purified and then ligated with the similarly restricted plasmid pKS-orf18ifd to obtain a plasmid pKS-orf18ifd-T. A 1 kb fragment carrying aac(3)IV gene conferring apramycin resistance (AmR) was amplified from pIJ773 by PCR using the forward primer (ApraNdpf, 5'-GAATGGCATATGGTTCATGTGCAGCTCCAT-3' (SEQ ID NO: 17), NdeI site is in bold) and the reverse primer (ApraSpeIpr, 5'-TCTAGAACTAGTGAATAG-GAACTTCGGAAT-3' (SEQ ID NO: 18), SpeI site is in bold). Plasmid pKS-orf18ifd-T was linearized by digestion with NdeI and SpeI and then ligated with the similarly restricted fragment AmR to generate the plasmid pKS-orf18ifd-T-AmR(NS) (FIG. 6; SEQ ID NO: 19).

Intergeneric Conjugation, pXY300-Based and pKS-Based Gene Disruption Procedures.

The gene disruption plasmids were individually introduced into *E. coli* S17-1 by transformation and then transferred to *S. fungicidicus* or its derivatives via conjugation. Briefly, freshly harvested *S. fungicidicus* spores were pre-germinated and E, coil S17-1 cells were grown overnight at 37° C. in Terrific broth. Serial dilutions of the germinated spore suspension were made and 100 mL of each dilution was mixed with an equal volume of *E. coli* S17-1 harboring the pXY300-based disruption plasmids. The solutions were plated onto ISP4 agar plates with addition of 10 mM $MgCl_2$ and incubated for 22 hours at either 30 or 37° C. Each plate was overlaid with 3 mL soft nutrient agar containing sodium nalidixate and apramycin (0.5 mg/mL) and further incubated at 30° C. for about one week. Isolated exconjugants that survived antibiotic selection were purified by streaking onto ISP4 agar plates supplemented with sodium nalidixate and apramycin (50 µg/mL each).

To conduct the gene disruption studies with the pXY300-based plasmids, exconjugants were first cultured in TSB liquid medium containing apramycin (5 µg/mL) at 30° C. for 24 hours at which time the mycelia were harvested, homogenized and used to inoculate TSB liquid media supplemented with apramycin (5 µg/mL). After 3-6 days incubation at 40° C., the mycelia were homogenized and plated onto ISP4 agar plates containing apramycin (50 µg mL) and incubated at 30° C. for one week. Genomic DNA was isolated from randomly selected individual surviving colonies and analyzed by either FOR or Southern blot to confirm that single- or double crossover disruption had occurred. For pKS-based gene disruption and in-frame-deletion plasmids, exconjugants were passed through three successive rounds of incubations on ISP4 agar plates for sporulation without addition of any antibiotic selection in order to stimulate the conversion to double crossover recombinants. The pKS-based exconjugants were not passed through the 40° C. temperature selection. The correct construction of all mutants was confirmed by FOR and/or Southern blot analysis.

Construction of the Integrative Expression Plasmids pXY152-endorf24-camtsr and pXY152-endorf24-blatsr.

Figure 7:
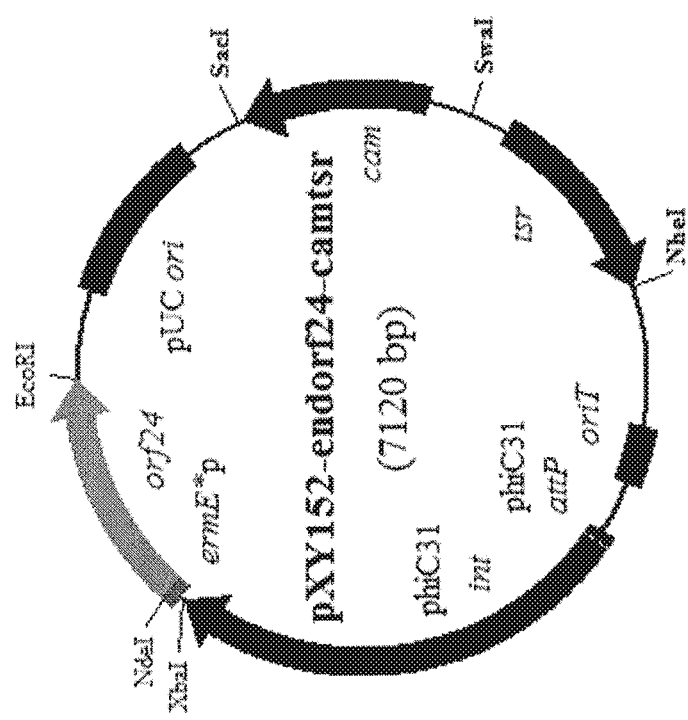
FIG. 7 is a map of the integrative expression plasmid pXY152-endorf24-camtsr.
Figure 8:
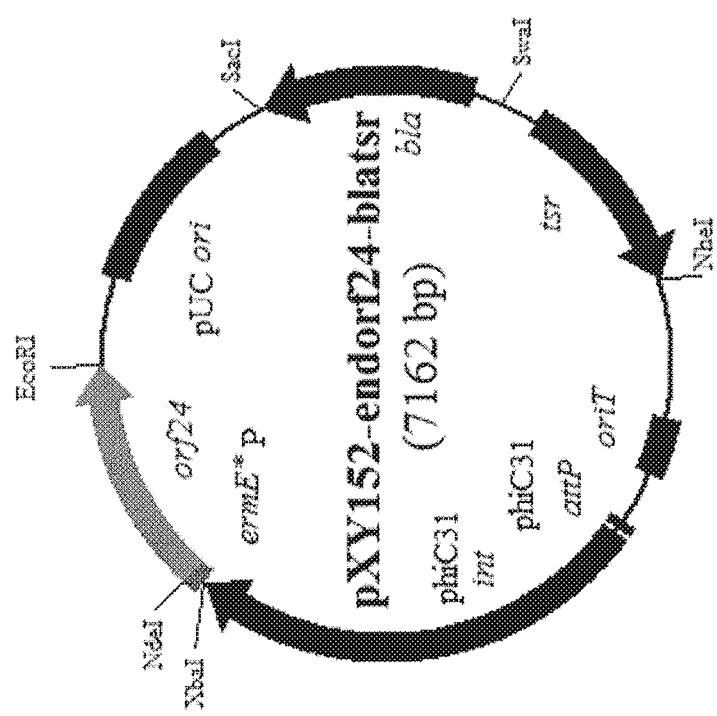
FIG. 8 is a map of the integrative expression plasmid pXY152-endorf24-blatsr.

To ectopically express orf24 in the apramycin resistant mutant carrying the deletion of orf18 and its flanking regions, the integrative expression plasmid pXY152-endorf24-blatsr was designed. To construct this plasmid, a cassette (camtsr) harboring the chloramphenicol resistance gene and thiostrepton resistance gene (tsr) was excised from a plasmid pUC57 derivative by digestion with SacI and NheI. The camtsr cassette was then ligated with SacI and NheI linearized plasmid pXY152-endorf24 to yield a new construct pXY152-endorf24-camtsr (FIG. 7; SEQ ID NO: 20). An ampicillin resistance gene (bla) was FOR-amplified from pBluescript KS using the forward primer (amp2956SwaIpf, 5'-GTGGCAATTTAAATG-GAAATGTGCGCGGAA-3' (SEQ ID NO: 21), SwaI site is in bold) and reverse primer (amp1973SacIpr, 5'-TATATAGAGCTCAACTTGGTCTGACAGTTAC-3' (SEQ ID NO: 22), SacI site is in bold). bla was then cloned into the SacI and SwaI sites of pXY152-endorf24-camtsr to replace the cassette camtsr with blatsr. The resulting conjugal expression plasmid was designated pXY152-endorf24-blatsr (FIG. 8; SEQ ID NO: 23).

Construction of the Tn5AT Cassette for In Vitro Transposon Mutation

The Tn5AT cassette was designed to combine three genetic elements: the transposon Tn5, oriT and aac3(IV). Tn5 is specifically and uniquely recognized by Tn5 transposase (Epicentre) and readily inserts into high G+C *Streptomyces* DNA cloned into *E. coli* plasmids and fosmids (also referred to in U.S. Pat. No. 8,188,245 which his hereby incorporated by reference), oriT is required for the conjugal transfer of DNA from *E. coli* S17-1 to *Streptomyces* and aac(3)IV is an *E. coli*-*Streptomyces* bifunctional selection marker conferring apramycin resistance. Both oriT and aac3(10 were excised from plasmid pIJ773 as a XbaI fragment and then cloned into the transposon donor plasmid pMOD™-2(MCS) (Epicentre), previously linearized with XbaI. The resulting plasmids pXYTn5ATa and pXYTn5ATb only differ by the orientation of XbaI fragment and were used to prepare the Tn5AT cassette by digestion with PvuII according to the manufacturer's specification.

In Vitro Transposon Mutation and Selection of Mutagenized Fosmid pXYF24D3 and pXYF148D12

To generate a library of random mutagenized fosmids carrying segments of the enduracidin biosynthesis cluster for gene replacement studies, in vitro transposon insertional mutation studies of fosmids pXYF24 and pXYF148 were performed. Two putative enduracidin biosynthesis regulatory genes, orf18 and orf24, reside on the inserts of fosmids pXYF24 and pXYF148, respectively (GenBank accession no. D0403252). The in vitro transposon reaction was performed at 37° C. for 2 hours after mixing 10 µL (0.5 µg) fosmid template DNA, 2 µL (20 ng) Tn5AT cassette DNA, 2 µL 10× reaction buffer, 1 µL Tn5 transposase and 5 µL sterile water. Transformation of *E. coli* competent cells EPI300™-T1® (Epicentre) with the transposon reaction mixture was performed by electroporation. Mutagenized fosmids were selected on LB agar plates supplemented with 100 µg/mL apramycin. Plates were incubated overnight at 37° C. and surviving colonies were randomly picked and grown in LB liquid culture with addition of 100 µg/mL apramycin. The mutagenized fosmid DNA from these colonies and control fosmid pXYF24 or pXYF148 were digested with HindIII and analyzed by electrophoresis on 1% agarose gels. The Tn5AT cassette contains a single HindIII site that is useful when screening for single versus multiple disruption events over the fosmid insert. No HindIII sites are present in the fosmid inserts of pXYF24 or pXYF148, and only one HindIII site is present in the fosmid vector. Hence, digestion with HindIII readily identifies fosmids with a single insertion of Tn5AT by the presence of two bands in the gel. Colonies carrying mutagenized fosmids with a single transposon insertion were randomly selected and grown in LB liquid culture to permit fosmid isolation and identification of the disrupted gene. Screening was conducted by sequence analysis using the primer 5'-AAGGAGAAGAGCCTTCAGAAGGAA-3' (SEQ ID NO: 24), which corresponds to a region of the apramycin resistance gene. In this manner, fosmid pXYF24D3 and pXYF148D12 were found to have Tn5AT inserted into orf18 at the nucleotide position 26386 and orf24 at the nucleotide position 34333 (GenBank accession no. D0403252), respectively.

Insertional Disruption of Orf18 and Orf24 in the Wild-Type S. fungicidicus ATCC 21013.

The gene replacement fosmids pXYF24D3 and pXYF148D12 were separately transformed into E. coli S17-1 by electroporation and then introduced into S. fungicidicus by intergeneric conjugation (Mazodier et al., J. Bacteriology 171: 3583-3585, 1989 which is hereby incorporated by reference in its entirety). Exconjugant colonies surviving apramycin selection were passed through three successive rounds of sporulation without antibiotic selection on ISP2 agar plates to create the stable mutant strain via double crossover homologous recombination. The resulting spores were pooled, diluted and plated on ISP2 agar plates supplemented with 50 μg/mL apramycin for confirmation of the apramycin resistance and for use in seed culture and enduracidin production fermentation. The mutant strain with the insertional disruption of orf18 in S. fungicidicus wild-type was designated SfpXYF24D3 and the mutant strain with the insertional disruption of orf24 in S. fungicidicus wild-type was designated SfpXYF148D12, Production of Enduracidin in Laboratory Scale and in 10-Liter Fermenter.

Laboratory shake flask fermentation conditions for the production of enduracidin in S. fungicidicus wild-type, BM38-2 (ATCC PTA-122342) and derivative strains were as described by Higashide et al, (J. Antibiotics, 21: 126-137, 1968) except for the enduracidin production media which was disclosed in a patent (U.S. Pat. No. 4,465,771). For laboratory scale fermentation, 5 mL TSB was used for inoculation of the seed culture with freshly harvested streptomycete spores. Typically 5 to 10 mL of the seed culture incubated on a rotary shaker at 225 rpm and 30° C. for 48 hours and was then transferred to a 50 mL enduracidin production medium for 10 days continuous fermentation. Production of enduracidin by the wild-type and derivative strains under closely controlled conditions was also conducted in 10-liter automatic fermenters.

TABLE 2

Comparison of enduracidin (enramycin) yields in wild-type, mutant and genetically engineered strains of Streptomyces fungicidicus

| S. fungicidicus Strain | Fermentation Conditions | Yield (HPLC) |
|---|---|---|
| Wild-type (ATCC21013) | Shake flask | 5-30 mg/L |
| BM38-2 | Shake flask | 60-90 mg/L |
| SfpXY52endorf24 | Shake flask | 60 mg/L |
| SfpXYF24D3 | Shake flask | 40 mg/L |
| BM38-2.orf18pfrd-AmR | Shake flask | 67 mg/L |
| BM38-2.24/16 | Shake flask | 30-130 mg/L |
| BM38-2 | 10 L fermentor | 80-145 mg/L |
| BM38-2.24/16 | 10 L fermentor | 375 mg/L |

Extraction of Enduracidin from Fermentation Products for HPLC Analysis.

To extract the metabolites for HPLC analysis of enduracidin production, the fresh mycelia was harvested by centrifugation and washed with deionized water and re-suspended in 5× volume (ratio of the aqueous methanol (mL) to the wet mycelial weight (g)) 70% aqueous methanol (pH was adjusted to 3.5 with 1 N HCl). The suspension was shaken at 200 rpm at room temperature overnight and then centrifuged at 4000 rpm and 4° C. for 20 minutes. Then 1.4 mL of supernatant from each sample was transferred to individual 1.5 mL microcentrifuge tubes and centrifuged at 13,000 rpm at room temperature for 10 minutes. The filtrate was passed through a 0.22 μm syringe filter and then analyzed by HPLC. Metabolite extraction from mycelia produced in 10 L fermenters was conducted on a small scale equivalent to laboratory fermentations.

HPLC Analysis and Enduracidin Yield Determination.

A 50 μL HPLC sample prepared as describe above was injected onto a Gemini $C_{18}$ column (5 μm, 4.6×150 mm, Phenomenex, Torrance, Calif.) attached to a Shimadzu HPLC. Separation was achieved using an 18 min stepwise linear gradients with solvent A: water+0.1% TFA and solvent B: acetonitrile. The flow rate was 1 mL/minute starting with 10% B, increasing to 40% B over 10 min, and then further increasing to 95% B over 8 minutes. The UV region from 200 to 300 nm was scanned with a SPD M20A photodiode array detector. Yields of enduracidins were calculated by comparison with a standard curve constructed from a stock solution of enduracidin standards in 70% methanol. A series of injections including 2, 4, 6, 8, 10 and 12 μg of enduracidin was used to construct the standard curve using the sum of the absorbance areas for enduracidins A and B at 230 nm. A regression equation was generated from the standard curve and used to calculate enduracidin yields.

Evaluation of Antibacterial Activity.

Staphylococcus aureus (ATCC 29213) was used as an indicating microorganism in the bioassay. Cells were used to inoculate LB broth, grown at 37° C. overnight, and then 100 μL of the culture was mixed with 5 mL of the top agar (mixture of equal volumes of nutrient agar and nutrient broth). The top agar was overlaid onto a nutrient agar plate in which appropriately spaced wells were made by cutting out the agar plugs. Enduracidin standards and aliquots of culture extractions were dissolved or diluted in 50% MeOH at a concentration of 20 μg/mL, and 100 μL of each solution was loaded into the wells, After incubating the plates at 37° C. for 16 hours, the zones of inhibition were observed and compared, and the plates photographed or stored at 4° C.

Example 2

Disruption of Orf18 and Orf24 in Wild-Type *S. fungicidicus* and Effect on Enduracidin Production This example describes the disruption of orf18 and orf24 in wild-type *S. fungicidicus* and the effect on enduracidin production.

A 116,000 bp DNA sequence from the wild-type *S. fungicidicus* ATCC 21013 that harbors the enduracidin biosynthetic gene cluster and its flanking regions (U.S. Pat. No. 8,188,245 which is hereby incorporated by reference in its entirety) was previously identified and is available in GenBank (accession No. D0403252). Among the 48 annotated orfs are eight putative regulatory genes: orf5, orf12, orf18, orf22, orf24, orf41, orf42 and orf43. To decipher the role of each of the gene products in enduracidin production, fosmid inserts carrying segments of the enduracidin cluster harboring these putative regulatory genes were randomly mutated using a transposon-mediated insertion of an apramycin resistance marker as described in Example 1.

The subsequent screening for apramycin resistance and insert location among *E. coli* colonies carrying mutagenized fosmids identified pXYF24D3 to carry the disrupted orf18 and pXYF148D12 to harbor the disrupted orf24. A single insertional mutation in each of these fosmids and the site of the insertion was confirmed by sequencing. These two mutagenized fosmids were then individually introduced by conjugation into the *S. fungicidicus* wild-type strain, Exconjugants showing apramycin resistance were then passed through three rounds of sporulation on ISP2 agar without addition of any antibiotic selection to promote conversion of the single crossover homologous recombination to double crossover mutation. The resulting stable mutant strains SfpXYF24D3 and SfpXYF148D12 were fermented in enduracidin production medium (EPM) on laboratory scale in shake flasks. HPLC analysis of the 70% methanol extraction of the mycelia from 10 days fermentation revealed an increase of 1.3-fold in enduracidin yield by the orf18-disrupted strain SfpXYF24D3 and the complete loss of enduracidin production by strain SfpXYF148D12 having a disrupted orf24. The mycelia extracts were also evaluated for activity towards *S. aureus*. The orf18 disruptant SfpXYF24D3 retained activity whereas the orf24 disruptant SfpXYF148D12 lost activity towards *S. aureus*.

Example 3

Construction of the Recombinant Strain SfpXY152-endorf24 and Effect on Enduracidin Production This example describes the construction of the recombinant strain SfpXY152-endorf24 and the ability of this strain to produce enduracidin.

The loss of enduracidin production in the mutant strain SfpXYF148D12 indicated a possible regulatory role for orf24. A BLAST search of the GenBank database using the Orf24 protein sequence revealed high sequence similarity with a pathway-specific regulatory protein, StrR, involved in streptomycin biosynthesis. A sequence alignment between Orf24 and StrR showed the proteins share a significant similarity (54% aa identity, FIG. 9). The loss of enduracidin production upon orf24 disruption and the similarity with StrR indicate that Orf24 may act as a pathway-specific activator in enduracidin production.

To explore the role of orf24 as a positive regulatory target for strain improvement, the integrative expression plasmid pXY152-endorf24 (FIG. 2) was constructed (Example 1). Plasmid pXY152-endorf24 was introduced into wild-type S, *fungicidicus* by conjugation and exconjugants were screened for the apramycin resistance phenotype, leading to the identification of the new recombinant strain SfpXY152-endorf24. At least ten independent exconjugant colonies from this strain were randomly selected and purified. These colony strains carry the pXY152-endorf24 plasmid integrated into an attB site on the *S. fungicidicus* chromosome by single crossover homologous recombination with the attP site on the plasmid.

To investigate the metabolites produced by the recombinant strains, spores from two colony strains were inoculated into TSB seed culture and then transferred to enduracidin production medium for laboratory scale fermentation. HPLC analysis of the 70% methanol extracts of the harvested mycelia revealed a 2-fold increase (60 mg/L) in the enduracidin production by both recombinant strains compared to the wild-type strain (30 mg/L). The elevated yields of enduracidin observed in these colony strains that are capable of overexpressing orf24 is further evidence of the positive regulatory role this gene has in enduracidin production and the results are consistent with those obtained from the disruption of orf24 that led to the loss of enduracidin production.

Example 4

Construction of the Strain BM38-2.24/16 Overexpressing Orf24 in *S. fungicidicus* BM38-2 (ATCC PTA-122342) and Effect on Enduracidin Production This example describes construction of the strain BM38-2.24/16 (ATCC Deposit No. PTA-124006), overexpressing orf24 in *S. fungicidicus* BM38-2 (ATCC PTA-122342) and effect on enduracidin production.

To further explore the positive regulatory role of Orf24, plasmid pXY152-endorf24 was incorporated into the chromosome of the commercial production strain *S. fungicidicus* BM38-2 (ATCC PTA-122342), as described above for the wild-type organism. Selection of exconjugants exhibiting the apramycin resistance phenotype yielded a number of recombinant colony strains, including *S. fungicidicus* BM38-2.24/16, capable of producing elevated enduracidin levels up to 200 mg/L (for a 3.3-fold increase over BM38-2 (ATCC PTA-122342)) in laboratory shake flask cultures. *S. fungicidicus* BM38-2-24/16 was selected for further evaluation of enduracidin production capacity based on yields during the preliminary screening.

Enduracidin production by recombinant strain *S. fungicidicus* BM38-2.24/16 in laboratory shake flask cultures showed clear potential for significant improvement over BM38-2 (ATCC PTA-122342) and yields were also observed to vary greatly. To more closely control culture conditions over the 10 day growth period, including pH and dissolved oxygen that are not easily managed in shake flasks, production was evaluated through multiple runs in 10 L fermenters. Under these more closely controlled conditions, the yields were more consistent and triplicate 10 L fermentations averaged 375 mg/mL (4.6-fold of BM38-2 (ATCC PTA-122342)). The increased enduracidin yields in the recombinant strain *S. fungicidicus* BM38-2.24/16

(ATCC Deposit No. PTA-124006) further support a positive upregulation role of Orf24 in enduracidin production.

Example 5

Figure 5:
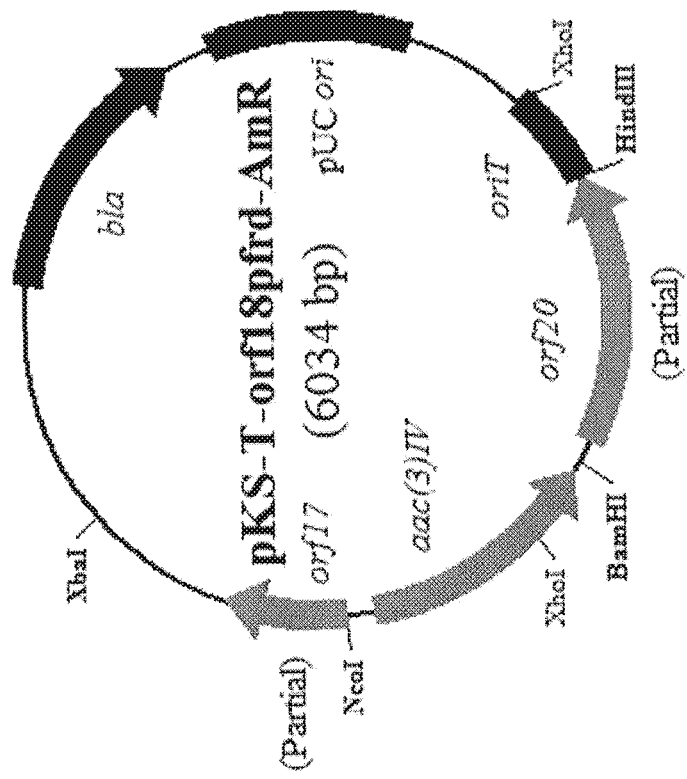
FIG. 5 is a map of the gene deletion plasmid pKS-T-orf18pfrd-AmR.
Figures 10A, 10B:
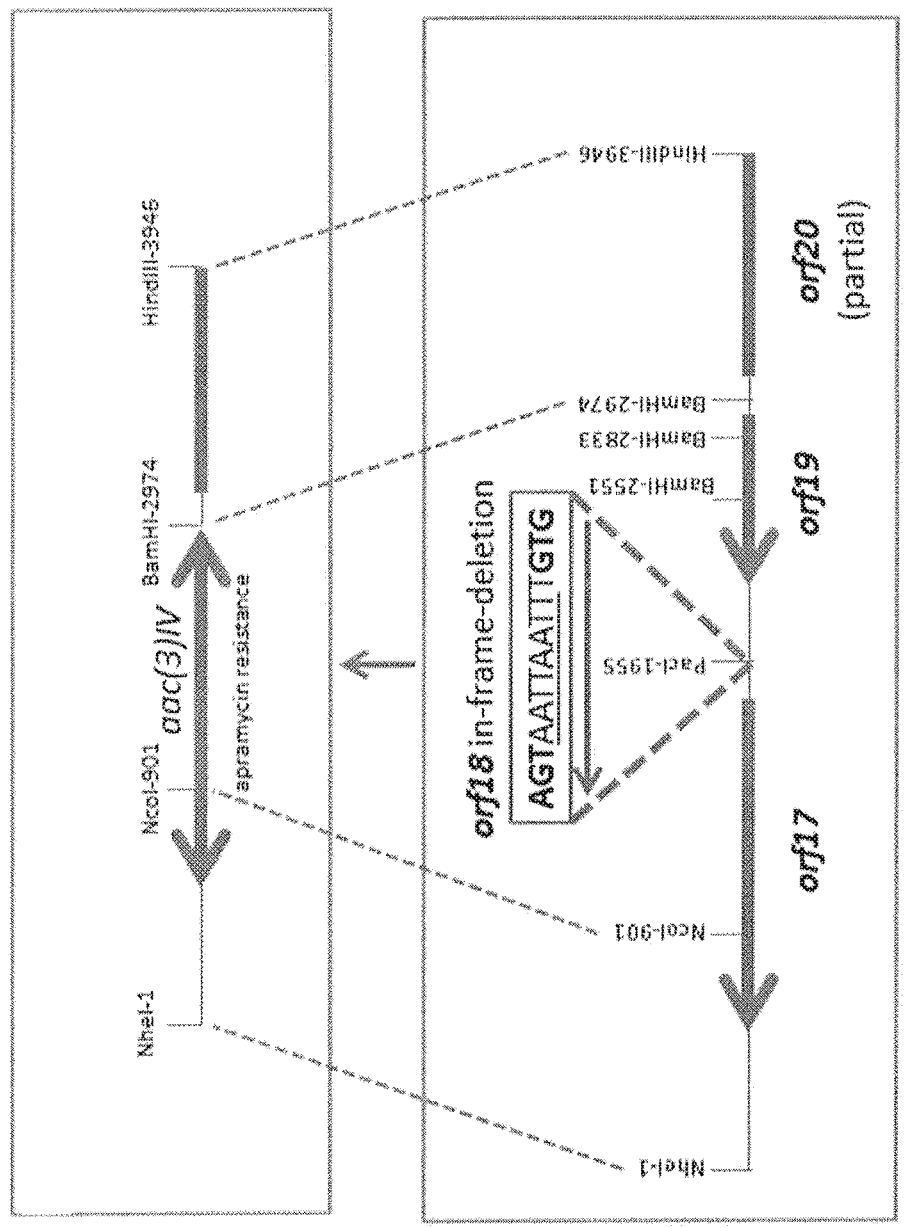
FIGS. 10A and 10B are maps of the inserts of plasmids pKS-T-orf18pfrd-AmR (a) and pXY300-orf18ifd (b). In the construct pXY30-orf18ifd, the internal sequence of off/8 from nucleotide position 25795 through 26450 (GenBank accession no. DQ403252) was deleted and replaced with a PacI restriction site (TTAATTAA, FIG. 10B). The resulting in-frame deleted orf18 (GTGTTTAATTAATGA (SEQ ID NO: 27)) could be translated into a three amino acid peptide (VFN). In general, any internal in-frame deletion over the length of orf18 should result in a nulled function of Orf18 due to its incompleteness.

Construction of the Deletion Mutant Strain BM38-1.18Pfrd-AmR and the Effect on Enduracidin Production This example describes construction of the deletion mutant strain BM38-2.18pfrd-AmR (ATCC Deposit No. PTA-124007) and the effect on enduracidin production.

orf18 is located in the upstream region of the enduracidin biosynthetic gene cluster (GenBank accession no, DQ403252). Orf18 appears to have a negative role in enduracidin production inasmuch as insertional disruption of the gene in the mutant strain SfpXYF24D3 elevated the yield of enduracidin. Based on this observation, constructs were designed for the deletion of orf18 alone and orf18 and portions of its flanking regions. For this purpose, plasmid pKS-T-orf18pfrd-AmR was constructed (FIG. 5). This pKS vector-derived plasmid possesses neither a streptomycete replicon nor an element for integration into the streptomycete chromosome. It can only exchange its insert with a defined segment of DNA in the host chromosome via double crossover homologous recombination. The insert map of this plasmid is shown in FIG. 10. orf18 and its flanking regions containing the entire orf19 and the region coding for the N-terminal portion of orf17 is deleted in plasmid pKS-T-orf18pfrd-AmR. The 1-kb left arm contains the region coding for the C-terminal portion of orf17 and its downstream region and the 1-kb right arm contains a partial segment of orf20 coding for the N-terminal region. Therefore the deletion after double crossover homologous recombination resulted in a recombinant strain where the entire orf18 plus orf19 and the region coding for the N-terminal portion of orf17 are deleted and replaced with the apramycin resistant gene.

Plasmid pKS-T-orf18pfrd-AmR was conjugally introduced into *S. fungicidicus* BM38-2 (ATCC PTA-122342) and single and double crossover homologous recombination was promoted on ISP4 agar plates without apramycin supplementation. Exconjugants that were able to survive subsequent apramycin selection were purified and this new recombinant strain was designated BM38-2.18pfrd-AmR (ATCC Deposit No. PTA-124007). Spores from this strain were inoculated into TSB medium for seed culture and then transferred into enduracidin production medium. After 10 days fermentation the mycelia were harvested, processed and analyzed by HPLC. Relative to the parent strain BM38-2 (ATCC PTA-122342), an increase of 1.2-fold in enduracidin production was observed from these laboratory scale fermentations. The relative increase in yield is similar to that observed with the wild-type derived strain SfpXYF24D3 and the results imply that orf19 and orf17, which flank orf18 and were affected in the construction of BM38-2.18pfrd-AmR, have little or no effect on enduracidin production. Therefore, the increased enduracidin production in the recombinant strain BM38-2.18pfrd-AmR is due to elimination of the negative regulatory role of Orf18.

Regarding the deletion of orf18 alone with the plasmid pXY300-orf18ifd in BM38-2 (ATCC PTA-122342), difficulties were encountered with positively selecting the exconjugants and single/double mutants with thiostrepton resistance marker. Therefore, alternative vector pBluescript KS II was used to construct the markerless gene replacement delivery plasmids such as pKS-T-orf18ifd (FIG. 4) or pKS-orf18ifd-T, pKS-orf18ifd-T-AmR(NS) (apramycin resistance gene is carried on the vector instead of insertion into orf18, see FIG. 6).

Example 6

Development of the pKS-Derived Gene Inactivation Vector pKS-T-orf18pfrd-AmR Series This example describes development of pKS-derived gene inactivation vector pKS-T-orf18pfrd-AmR series.

A series of pKS-derived gene inactivation vectors were developed (FIGS. 4, 5 and 6) that possess the conjugative function and do not require passing transformants through a high temperature selection to eliminate the plasmid as some other gene disruption vectors require. These pKS-derived vectors carry a non-streptomycete replicon allowing replication in E. coil and can maintain and be selected with the apramycin resistance marker in *Streptomyces* and *E. coli* or ampicillin in *E. coli*. They produced copious stable copies of recombinant plasmids in *E. coli* for conjugation and they have been designed with several rare and unique restriction sites found in streptomycete DNA, such as PacI, HindIII, NheI, and XbaI, that can be conveniently used to assembly the target DNA into the plasmid for insertional gene disruption and in-frame-deletion studies.

Example 7

Development of pSET152-Derived Integrative Gene Expression Vectors pXY152-Endorf24-Camtsr and pXY152-Endorf24-Blatsr This example describes development of pSET152-derived integrative gene expression vectors pXY152-endorf24-camtsr (SEQ ID NO: 20) and pXY152-endorf24-blatsr (SEQ ID NO: 23).

Two new vectors, pXY152-endorf24-camtsr (FIG. 7) and pXY152-endorf24-blatsr (FIG. 8) were developed. They possess conjugative and integrative functions like vector pSET152, the most widely used integrative vector for streptomycete gene expression and complementation. Both these vectors carry several restriction sites that are rare in *Streptomyces* DNA for convenient cloning and assembly of the expression construct. Vector pXY152-endorf24-camtsr can be maintained and selected in *E. coli* with chloramphenicol at 12.5 µg/mL and in *Streptomyces* with thiostrepton at 50 µg/mL. Vector pXY152-endorf24-blatsr can be maintained and selected in *E. coli* with ampicillin and in *Streptomyces* with thiostrepton.

Summary of Examples 1-6

Genetic Manipulation of *Streptomyces* Regulatory and Biosynthesis Genes for Strain Improvement Among the numerous microbial producers of natural products, approximately 75% of the known microbial antibiotics are produced by actinomycetes. *Streptomyces*, Gram-positive filamentous soil bacteria, are members of the actinomycete family and are known for their unrivaled ability to produce a versatile array of structurally diverse, pharmacologically and biologically active secondary metabolites. Polyketides produced by polyketide synthases (PKS) and peptide natural products made by nonribosomal peptide synthetases (NRPS) are representatives.

Research on natural product antibiotic biosynthesis has some common challenges: first, how to overcome the typical low production of the parent or structurally modified compounds produced by the wild-type or genetically engineered strains; second, how to activate the many cryptic or orphan secondary metabolite biosynthetic pathways identified from genome sequences so the biological function of the products can be studied. Advances in the study of natural product antibiotic biosynthesis over the past decades have indicated that production of secondary metabolites is regulated by many pathways. For example, the precursor and structural assembly biosynthetic genes (such as PKS and NRPS), regulatory genes and self-resistance genes can be clustered on the bacterial chromosome. Antibiotic production may be regulated by pathway specific regulatory genes, including activators and/or repressors, pleiotropic ectopic regulatory genes, and two-component regulatory systems. Mutations occurring in any of these regulatory genes or systems may increase, decrease or completely abolish antibiotic production. Cryptic biosynthetic pathway can be activated by an unpredicted mutation leading to the production of a previously unknown product.

Strain improvement may play an important role in the cost effective industrial scale production of antibiotics or other microbial secondary metabolites. Mutant strains able to produce increased yields of particular metabolites can be generated through random mutations or by targeted disruption of specific genes or by the introduction of gene(s) that eliminate bottlenecks in a biosynthesis pathway. Genetic manipulation of positive and negative regulatory genes, as well as biosynthetic genes, to generate hyper-production of a targeted secondary metabolites has been proven to be a powerful and highly successful strategy of actinomycete strain improvement.

In the current disclosure, the positive regulatory role of orf24 and the negative regulatory role of orf18 on enduracidin production was demonstrated. Targeted insertional inactivation of orf24 resulted in a complete loss of enduracidin production in the recombinant strain SfpXYF148D12. Subsequent overexpression of orf24 under the control of the strong constitutive promoter ermE*p in the recombinant strains SfpXY152-endorf24 and BM38-2.24/16 led to increases in enduracidin yields of approximately 2 to 4.6-fold. The deletion of orf18 and its flanking regions, including the entire orf19 and a portion of orf17, increased enduracidin yields by 1.2-fold. These results provided strong genetic evidence in support of the roles of orf24 and orf18 as positive activator and negative repressor, respectively, in enduracidin biosynthesis.

Orf24 Orthologs have been Functionally Confirmed from Other Antibiotic Biosynthesis Pathways A BLAST query with Orf24 protein sequence against GenBank database revealed hundreds of hits (Gen Bank accession no. DQ403252). Many show very high amino acid similarity (from 60% to 99% identities) and are annotated as transcriptional regulators in the biosynthesis of the aminoglycoside antibiotic streptomycin. However, none of this group of genes has had the function verified experimentally. Analysis of the BLAST results identified several related proteins that share a lower similarity (over 40% but below 60% aa identity) to Orf24 that were functionally characterized. These include the well-characterized protein StrR which shares a lower but significant similarity (54% aa identities in 311 aa overlap) with Orf24. StrR has been genetically and biochemically demonstrated to function as a pathway specific positive activator of the expression of the streptomycin biosynthesis genes in *Streptomyces griseus*. StrR represents a family of pathway-specific activators, a handful of which have been characterized by either genetic manipulation or biochemical studies. FIG. 11 shows the alignment of Orf24 with six functionally confirmed actinomycete StrR-like proteins. A typical and highly conserved helix-turn-helix (HTH) DNA-binding domain is present in all seven proteins as underlined in FIG. 11. Orf24 also shares a significant sequence similarity (54% aa identities) to Tei15*, a pathway specific activator governing biosynthesis of the nonribosomally generated glycopeptide antibiotic teicoplanin. Tei15* positively regulates the transcription of at least 17 genes in the teicoplanin cluster. The wild-type *Actinoplanes teichomyceticus* produces about 100 mg/L of teicoplanin whereas the genetic recombinant strains, derived from the parent *A. teichomyceticus* and carrying tei15* expressed under the control of different promoters, increased teicoplanin yield to 1 g/L in the case of ermE*p promoter and to 4 g/L in the case of the native apramycin resistance gene promoter.

As illustrated in FIG. 11, Orf24 also shares a significant sequence similarity (54% aa identities) to Bbr, from the balhimycin glycopeptide antibiotic biosynthesis cluster; to KasT (50% aa identities) governing the expression of aminoglycoside antibiotic kasugamycin biosynthesis genes; and NovG (45% aa identities) the pathway specific activator involved in novobiocin biosynthesis. The ΔnovG mutant produced only 2% as much novobiocin as wild-type and overexpression of novG from a multi-copy plasmid in the recombinant strain led to a three-fold increase in the novobiocin production. Orf24 also shares 42% aa identities with SgcR1, one of four regulator genes (sgcR1, sgcR2, sgcR3 and sgcR) experimentally confirmed to be involved in production of the antitumor antibiotic 0-1027 in *S. globisporus*. Overexpression of sgcR1 in *S. globisporus* SB1022 increased the C-1027 yield approximately seven-fold compared to the wild-type strain. Overexpression of the positive regulator sgcR3 in a recombinant strain resulted in a 30-40% increase in 0-1027 production. In contrast, inactivation of the negative regulator sgcR led to increases both C-1027 and heptaene production. Moreover, overexpression of sgcR1 in the ΔsgcR mutant strain led to about a seven-fold increase of 0-1027 production. sgcR3 occupies a higher level regulation by control of sgcR1 and sgcR2 in the hierarchy regulation of 0-1027 production. In conclusion, the disruption and expression effects of orf24 and the comparison of Orf24 with other functionally characterized orthologs indicate Orf24 acts as a pathway specific positive regulator/activator in enduracidin production.

Orf18 is a Putative Atypical Orphan Response Regulator and Aligns with Functionally Confirmed Orthologs Production of antibiotics in *Streptomyces* species is tightly regulated by complex genetic networks that limit the ability of many wild-type antibiotic producers from generating yields necessary for large-scale, cost-effective industrial production. One important regulatory mechanism is the two-component signal transduction systems. Two-component systems include a sensor kinase and a cognate response regulator. The sensor kinase responds to specific external environmental stimuli/signals such as stress, nutrition and chemicals, etc., and then relays the signal to a cytoplasmic response regulator that triggers and activates the transcription of target genes. A response regulator that is unpaired with a sensor kinase is designated an orphan response regulator.

Two-component systems and orphan response regulators are present in streptomycete genomes and can function to repress secondary metabolite production. In the enduracidin gene cluster from *S. fungicidicus*, orf18 encodes a putative orphan response regulator that shares a low to moderate sequence similarity to three other characterized *Streptomyces* response regulators including one orphan response regulator, SCO3818, from *S. coelicolor* (FIG. 12). Orf18 has a longer N-terminal sequence compared to the other aligned proteins and appears to be an atypical orphan response regulator because a highly conserved lysine at position 118 (relative to the common position 105) is absent in Orf18 and replaced with a threonine. The lysine is proposed to be required for forming the phosphorylation pocket.

Only a few streptomycete response regulators have been functionally characterized. The *S. coelicolor* genome contains a total of five atypical and seven typical orphan response regulators. Orf18 shares 26% aa identities in 191 aa overlap with AbsA2. The deletion of AbsA2 in *S. coelicolor* resulted in increased production of two antibiotics, actinorhodin and undecylprodigiosin. Orf18 shows 32% aa identities in 176 aa overlap with SCO3818. Deletion of sco3818 led to enhanced production of actinorhodin. Orf18 shares 29% aa identities in 166 overlap aa with SCO1745 (AbrA2). Deletion of the AbrA2-containing-response regulator operon resulted in 100% increase of the antitumor antibiotic oviedomycin in the recombinant strain *S. coelicolor* M145 compared to the wild-type producer. The observed negative regulatory role of Orf18 in enduracidin production is consistent with the demonstrated activities of the related negative regulators (FIG. 12). In addition, it is noticed that Orf18 shares the highest protein sequence similarity with the members of the LuxR family of transcriptional regulators in the BLAST search.

Absence of Polar Effects in the Mutant BM38-1.orf18pfrd-AmR

The deleted region in the mutant BM38-1.18pfrd-AmR strain involves three genes, orf18, the region coding for the N-terminal portion of orf17 located downstream of orf18, and the entire orf19 located upstream of orf18 (FIGS. 5 and 10). orf17 is predicted to encode a ribonuclease apparently having no function related to the biosynthesis or regulation of enduracidin. Also, the apramycin resistance gene replacing orf18 and its flanking region is transcribed divergently with orf17 and should not create any read-through events from the apramycin resistance gene promoter. Therefore, there should be no polar effects resulting from the partial deletion of orf17.

orf19 is transcribed and translated in the same direction as orf18. This gene is annotated to encode a protein of unknown function. The mutant strain SfpXYF24D3 carrying the disruption of orf18 alone and the mutant BM38-1.18pfrd-AmR carrying the deletion of orf18 and orf19 together have similarly enhanced effects on enduracidin production which implies orf19 has no role or a negligible role in enduracidin production. The gene orf20 is located upstream of orf19 and transcribed and translated in the same direction as the inserted apramycin resistance marker (FIG. 10) orf20 is still intact in BM38-1.18pfrd-AmR and the product apparently does not have a role in enduracidin production. Therefore any polar effects on the expression of orf20 are not believed to be responsible for the enhanced enduracidin production in BM38-1.18pfrd-AmR.

Example 7

Further Applications and Manipulations of Orf24 and/or Orf18 for Enhanced Enduracidin Producing Strains In addition to the examples provided above, there are other possible ways to utilize the regulatory roles of orf24 and orf18 to improve the enduracidin production.

i. Expression of Orf24 Under an Alternative, Constitutive or Inducible Overexpression Promoter pXY152-endorf24 (shown in FIG. 2) was constructed for the integrative ectopic expression of orf24 under the control of ermE*p, a widely used streptomycete strong constitutive expression promoter. The overexpression of orf24 may also be driven by other constitutive or inducible promoters. The tipA promoter is a thiostrepton inducible overexpression streptomycete promoter. A multicopy tipA promoter-containing *E. coli-Streptomyces* shuttle plasmid, pXY200, was developed that has been successfully used for overexpression of streptomycete genes. For applications relevant to this disclosure, the tipA promoter can be excised from pXY200 and cloned into pXY152 to replace ermE*p and drive the expression of orf24. Likewise, orf24 can be easily transferred from pXY152-endorf24 to pXY200 for plasmid-based expression. Other promoter options include, but are not limited to, the P(nitA)-NitR system and the streptomycete promoter SF14. Recently, the integrative plasmid pKC1139 and the native promoter of the apramycin resistant gene were successfully used to express regulatory genes for hyperproduction of the peptide antibiotic teicoplanin. The regulatory gene sanG encodes a pathway specific activator for nikkomycin production. The expression of an extra copy of sanG under the control of five different promoters ($P_{hrdB}$, $P_{tcp830}$, $P_{SF14}$, $P_{ermE*}$ and Pneos) led to increases in nikkomycin yields by 69%, 51%, 26%, 22%, and 13%, respectively (see Du et al., Applied Microbiology and Biotechnology 97: 6383-6396, 2013).

ii. Double Mutant Strains of *S. fungicidicus* with Deletion of Orf18 and Overexpression of Orf24

With both the orf18 deletion mutant and the orf24 overexpression strains exhibiting increased enduracidin production, a double mutant containing both can be generated and whether an additive effect on the yield of this peptide antibiotic is observed. The double mutant can be created by introducing the overexpression plasmid pXY152-endorf24-blatsr (FIG. 8) into the mutant BM38-2.18pfrd-AmR. pXY152-endorf24-blatsr is a conjugal integrative plasmid carrying a thiostrepton resistance gene (tsr) for selection in streptomycetes and ampicillin resistance gene (bla) for selection in *E. coli*. Because the *E. coli* strain S17-1 used for conjugation is naturally resistant to chloramphenicol (cam), the chloramphenicol resistance marker in pXY152-endorf24-camtsr (see above) has been replaced with ampicillin resistance (b/a) in order to select S17-1 transformants. Alternatively, pXY152-endorf24-camtsr and derivatives can be introduced into streptomycetes by using a different conjugal *E. coli* strain, ET12567/pUZ8002.

Using either plasmid pXY152-endorf24-blatsr or pXY152-endorf24-camtsr to introduce the second copy of orf24 into the orf18 deficient mutant, it is possible to select for the double mutant by thiostrepton resistance. To generate a null orf18 in-frame-deletion mutant in BM38-2 (ATCC PTA-122342), plasmids pXY300-orf18ifd (FIG. 3) and pKS-orf18ifd-T-AmR(NS) (FIG. 6) were constructed for this purpose. pXY300-orf18ifd allows for selection of the orf18 in-frame deletion mutant with thiostrepton while pKS-orf18ifd-T-AmR(NS) uses apramycin to select in-frame deletion mutants. Although mutant strains of wild-type *S. fungicidicus* are readily selected using the thiostrepton resistance marker, difficulties have been encountered using this resistance marker in the BM38-2 (ATCC PTA-122342) strain. Thus, two plasmids, pXY300-orf18ifd and pKS-orf18ifd-T-AmR(NS), were constructed for the same purpose.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A recombinant strain of *Streptomyces fungicidicus* comprising one or more modified genes selected from the group consisting of an augmented open reading frame-24 (orf24) that encodes the amino acid sequence of SEQ ID NO: 26, and a diminished open reading frame-18 (orf18), wherein an enhanced production of enduracidin is obtained with the recombinant strain of *Streptomyces fungicidicus* in comparison to that obtained with a control *Streptomyces fungicidicus* strain.

2. The recombinant strain of claim 1, wherein the diminished orf18 is diminished because it has been nulled.

3. The recombinant strain of claim 2, wherein the diminished orf18 has been nulled by a process selected from the group consisting of an in-frame-deletion, a frame-shift mutation, a point mutation, and any combination thereof.

4. The recombinant strain of claim 3, wherein the diminished orf18 has been nulled by an in-frame deletion.

5. The recombinant strain of claim 4, wherein the in-frame deletion is of nucleotides 5 through 660 of the orf18 (SEQ ID NO: 27).

6. The recombinant strain of claim 1, wherein the augmented orf24 is operatively linked to a heterologous promoter.

7. The recombinant strain of claim 6, wherein the heterologous promoter is a strong constitutive promoter.

8. The recombinant strain of claim 7, wherein the strong constitutive promoter is ermE*p.

9. The recombinant strain of claim 1, wherein the augmented ORF24 is augmented because it has been overexpressed.

10. The recombinant strain of claim 1, wherein the *Streptomyces fungicidicus* is *Streptomyces fungicidicus* ATCC 21013.

11. The recombinant strain of claim 1, wherein the *Streptomyces fungicidicus* is *Streptomyces fungicidicus* ATCC PTA-122342.

12. The recombinant of claim 1, wherein the production of enduracidin by the recombinant strain is at least 1.2 fold greater than the production of enduracidin by the control *Streptomyces fungicidicus*.

13. The recombinant strain of claim 12, wherein the production of enduracidin by the recombinant strain is 1.2 to 4.6 fold greater than the production of enduracidin by the control *Streptomyces fungicidicus*.

14. The recombinant strain of *Streptomyces fungicidicus* that is BM38-2.24/16 (ATCC Deposit No. PTA-124006).

15. A method of producing enduracidin, comprising culturing the recombinant strain of *Streptomyces fungicidicus* of claim 1, under conditions sufficient for producing enduracidin.

16. The method of claim 15, further comprising isolating the enduracidin from the culture medium.

17. An expression vector selected from the group consisting of pXY152-endorf24 (SEQ ID NO:3), pXY152-endorf24-camtsr (SEQ ID NO: 20), and pXY152-endorf24-blatsr (SEQ ID NO: 23).

* * * * *

SEQUENCE LISTING

```
<160> NUMBER OF SEQ ID NOS: 40

<210> SEQ ID NO 1
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 1
ccaccacata tggaaataag ttcgctctcc a                                  31

<210> SEQ ID NO 2
<211> LENGTH: 32
<212> TYPE: DNA
<213> ORGANISM: Artificial sequence
<220> FEATURE:
<223> OTHER INFORMATION: Synthetic oligonucleotide primer

<400> SEQUENCE: 2
gtgtgtgaat tcctcgttca cccggccaga tg                                 32

<210> SEQ ID NO 3
<211> LENGTH: 6210
<212> TYPE: DNA
<213> ORGANISM: Artificial sequence
<220> FEATURE:
<223> OTHER INFORMATION: Synthetic plasmid pXY152-endorf24

<400> SEQUENCE: 3
gaattcgtaa tcatgtcata gctgtttcct gtgtgaaatt gttatccgct cacaattcca    60
cacaacatac gagccggaag cataaagtgt aaagcctggg gtgcctaatg agtgagctaa   120
ctcacattaa ttgcgttgcg ctcactgccc gctttccagt cgggaaacct gtcgtgccag   180
ctgcattaat gaatcggcca acgcgcgggg agaggcggtt tgcgtattgg gcgctcttcc   240
gcttcctcgc tcactgactc gctgcgctcg gtcgttcggc tgcggcgagc ggtatcagct   300
cactcaaagg cggtaatacg gttatccaca gaatcagggg ataacgcagg aaagaacatg   360
tgagcaaaag gccagcaaaa ggccaggaac cgtaaaaagg ccgcgttgct ggcgtttttc   420
cataggctcc gcccccctga cgagcatcac aaaaatcgac gctcaagtca gaggtggcga   480
aacccgacag gactataaag ataccaggcg tttccccctg gaagctccct cgtgcgctct   540
cctgttccga ccctgccgct taccggatac ctgtccgcct ttctcccttc gggaagcgtg   600
gcgctttctc atagctcacg ctgtaggtat ctcagttcgg tgtaggtcgt tcgctccaag   660
ctgggctgtg tgcacgaacc ccccgttcag cccgaccgct gcgccttatc cggtaactat   720
cgtcttgagt ccaacccggt aagacacgac ttatcgccac tggcagcagc cactggtaac   780
aggattagca gagcgaggta tgtaggcggt gctacagagt tcttgaagtg gtggcctaac   840
tacggctaca ctagaagaac agtatttggt atctgcgctc tgctgaagcc agttaccttc   900
ggaaaaagag ttggtagctc ttgatccggc aaacaaacca ccgctggtag cggtggtttt   960
tttgtttgca agcagcagat tacgcgcaga aaaaaaggat ctcaagaaga tcctttgatc  1020
ttttctacgg ggtctgacgc tcagtggaac gaaaactcac gttaagggat tttggtcatg  1080
agattatcaa aaaggatctt cacctagatc cttttggttc atgtgcagct ccatcagcaa  1140
```

```
aaggggatga taagtttatc accaccgact atttgcaaca gtgccgttga tcgtgctatg    1200
atcgactgat gtcatcagcg gtggagtgca atgtcgtgca atacgaatgg cgaaaagccg    1260
agctcatcgg tcagcttctc aaccttgggg ttaccccggc cggtgtgctg ctggtccaca    1320
gctccttccg tagcgtccgg cccctcgaag atgggccact ggactgatc gaggccctgc     1380 gtgctgcgct gggtccggga gggacgctcg tcatgccctc gtggtcaggt ctggacgacg    1440
agccgttcga tcctgccacg tcgcccgtta caccggacct tggagttgtc tctgacacat    1500
tctggcgcct gccaaatgta aagcgcagcg cccatccatt tgcctttgcg gcagcggggc    1560
cacaggcaga gcagatcatc tctgatccat tgcccctgcc acctcactcg cctgcaagcc    1620
cggtcgcccg tgtccatgaa ctcgatgggc aggtacttct cctcggcgtg ggacacgatg    1680
ccaacacgac gctgcatctt gccgagttga tggcaaaggt tccctatggg gtgccgagac    1740
actgcaccat tcttcaggat ggcaagttgg tacgcgtcga ttatctcgag aatgaccact    1800
gctgtgagcg ctttgccttg gcggacaggt ggctcaagga gaagagcctt cagaaggaag    1860
gtccagtcgg tcatgccttt gctcggttga tccgctcccg cgacattgtg gcgacagccc    1920
tgggtcaact gggccgagat ccgttgatct tcctgcatcc gccagaggcg ggatgcgaag    1980
aatgcgatgc cgctcgccag tcgattggct gagctcatga gcggagaacg agatgacgtt    2040
ggaggggcaa ggtcgcgctg attgctgggg caacacgtgg agcggatcgg ggattgtctt    2100
tcttcagctc gctgatgata tgctgacgct caatgccgtt tggcctccga ctaacgaaaa    2160
tcccgcattt ggacggctga tccgattggc acggcggacg gcgaatggcg gagcagacgc    2220
tcgtccgggg gcaatgagat atgaaaaagc ctgaactcac cgcgacgtat cgggccctgg    2280
ccagctagct agagtcgacc tgcaggtccc cggggatcgg tcttgccttg ctcgtcggtg    2340
atgtacttca ccagctccgc gaagtcgctc ttcttgatgg agcgcatggg gacgtgcttg    2400
gcaatcacgc gcaccccccg gccgttttag cggctaaaaa agtcatggct ctgccctcgg    2460
gcggaccacg cccatcatga ccttgccaag ctcgtcctgc ttctcttcga tcttcgccag    2520
cagggcgagg atcgtggcat caccgaaccg cgccgtgcgc gggtcgtcgg tgagccagag    2580
tttcagcagg ccgcccaggc ggcccaggtc gccattgatg cgggccagct cgcggacgtg    2640
ctcatagtcc acgacgcccg tgattttgta gccctggccg acggccagca ggtaggccga    2700
caggctcatg ccggccgccg ccgccttttc ctcaatcgct cttcgttcgt ctggaaggca    2760
gtacaccttg ataggtgggc tgcccttcct ggttggcttg gtttcatcag ccatccgctt    2820
gccctcatct gttacgccgg cggtagccgg ccagcctcgc agagcaggat tcccgttgag    2880
caccgccagg tgcgaataag ggacagtgaa gaaggaacac ccgctcgcgg gtgggcctac    2940
ttcacctatc ctgcccggct gacgccgttg gatacaccaa ggaaagtcta cacgaaccct    3000
ttggcaaaat cctgtatatc gtgcgaaaaa ggatggatat accgaaaaaa tcgctataat    3060
gaccccgaag cagggttatg cagcggaaaa gatccgtcga cctgcaggca tgcaagctct    3120
agcgattcca gacgtcccga aggcgtggcg cggcttcccc gtgccggagc aatcgccctg    3180
ggtgggttac acgacgcccc tctatggccc gtactgacgg acacaccgaa gccccggcgg    3240
caaccctcag cggatgcccc ggggcttcac gttttcccag gtcagaagcg gttttcggga    3300
gtagtgcccc aactggggta acctttgagt tctctcagtt ggggggcgtag gtcgccgac    3360 atgacacaag gggttgtgac cggggtggac acgtacgcgg gtgcttacga ccgtcagtcg    3420
cgcgagcgcg agaactcgag cgcagcaagc ccagcgacac agcgtagcgc caacgaagac    3480
```

```
aaggcggccg accttcagcg cgaagtcgag cgcgacgggg gccggttcag gttcgtcggg    3540
catttcagcg aagcgccggg cacgtcggcg ttcgggacgg cggagcgccc ggagttcgaa    3600
cgcatcctga acgaatgccg cgccgggcgg ctcaacatga tcattgtcta tgacgtgtcg    3660
cgcttctcgc gcctgaaggt catggacgcg attccgattg tctcggaatt gctcgccctg    3720
ggcgtgacga ttgtttccac tcaggaaggc gtcttccggc agggaaacgt catggacctg    3780
attcacctga ttatgcggct cgacgcgtcg cacaaagaat cttcgctgaa gtcggcgaag    3840
attctcgaca cgaagaacct tcagcgcgaa ttgggcgggt acgtcggcgg aaggcgcct    3900 tacggcttcg agcttgtttc ggagacgaag gagatcacgc gcaacggccg aatggtcaat    3960
gtcgtcatca acaagcttgc gcactcgacc actcccctta ccggacccctt cgagttcgag    4020 cccgacgtaa tccggtggtg gtggcgtgag atcaagacgc acaaacacct tcccttcaag    4080
ccgggcagtc aagccgccat tcacccgggc agcatcacgg ggctttgtaa gcgcatggac    4140
gctgacgccg tgccgacccg gggcgagacg attgggaaga agaccgcttc aagcgcctgg    4200
gacccggcaa ccgttatgcg aatccttcgg gacccgcgta ttgcgggctt cgccgctgag    4260
gtgatctaca agaagaagcc ggacggcacg ccgaccacga agattgaggg ttaccgcatt    4320
cagcgcgacc cgatcacgct ccggccggtc gagcttgatt gcggaccgat catcgagccc    4380
gctgagtggt atgagcttca ggcgtggttg gacggcaggg ggcgcggcaa ggggctttcc    4440 cggggggcaag ccattctgtc cgccatggac aagctgtact gcgagtgtgg cgccgtcatg    4500
acttcgaagc gcggggaaga atcgatcaag gactcttacc gctgccgtcg ccggaaggtg    4560
gtcgacccgt ccgcacctgg gcagcacgaa ggcacgtgca acgtcagcat ggcggcactc    4620
gacaagttcg ttgcggaacg catcttcaac aagatcaggc acgccgaagg cgacgaagag    4680
acgttggcgc ttctgtggga agccgcccga cgcttcggca agctcactga ggcgcctgag    4740
aagagcggcg aacgggcgaa ccttgttgcg gagcgcgccg acgccctgaa cgcccttgaa    4800
gagctgtacg aagaccgcgc ggcaggcgcg tacgacggac ccgttggcag gaagcacttc    4860
cggaagcaac aggcagcgct gacgctccgg cagcaagggg cggaagagcg gcttgccgaa    4920
cttgaagccg ccgaagcccc gaagcttccc cttgaccaat ggttccccga agacgccgac    4980
gctgacccga ccggccctaa gtcgtggtgg gggcgcgcgt cagtagacga caagcgcgtg    5040
ttcgtcgggc tcttcgtaga caagatcgtt gtcacgaagt cgactacggg caggggggcag    5100 ggaacgccca tcgagaagcg cgcttcgatc acgtgggcga agccgccgac cgacgacgac    5160
gaagacgacg cccaggacgg cacggaagac gtagcgcgt aggtgagtga agatctagac    5220
gtggcaccgc gatgctgttg tgggcacaat cgtgccggtt ggtaggatcc acatatggaa    5280
ataagttcgc tctccaccga cggctccccg cggatcgacg gggagagtcc cgagcacgtg    5340
gaaatgctgg ccgccgccga caccgcgctt ccaccgatca tggtgcaccg ccgcaccggg    5400
cgggtcatcg acggcatgca ccggctgcgc gccgcgatgc tgacgggccg tacgacgatc    5460
gcggtgaggt tcttcgacgg caccgaggag gacgccttcg tcctcgccgt gaagtcgaac    5520
atcgcgcacg gactgccgct gtccgccgcc gaccgccggc gggccgccgg gcgcatcatg    5580
gccacccatc cccggtggtc ggaccggatg atcgcctcgg tggtcggcac ctccgccagg    5640
acggtcgccg agatccgccg cgacgccggc gccgccgggg cggggagcc cacccgcatc    5700 ggccgggacg gcagggtacg gcccgtcgac gtgagcgagg gccgcagact ggcccacgac    5760
atgatcgtcc gcgacccggg cctgtcgctg cgccaggtcg cccgcgccgc cgggatctcg    5820
ccggagaccg tcagggacgt cagacaccgg atgctccgcg gtgaggaccc ggtgcccgcg    5880
```

```
ccgcggccgc ggaccctggt ggagcgcggc gcggaccgcc gggcggagcc ggccgggaag    5940
gccgccgcgc cgtgcgggac ggagccgccg cccgccgtcg tgatgaagcg gctgagggcc    6000
gatccggcgc tgcgtctcaa cgagaacgga cgcgacctgc tgcggcttct ggatatccac    6060
acggtccggt tggaggactg gaaccgcatt atcgaaagcg tgccgccgca ccgtctggag    6120
acggtggcgc agctggcacg ctcctgcgcc gacaaatggt ccgagatcgc gtcacgcatc    6180
gaaagcaacg catcacatct ggccgggtga                                     6210
```

<210> SEQ ID NO 4
<211> LENGTH: 38
<212> TYPE: DNA
<213> ORGANISM: Artificial sequence
<220> FEATURE:
<223> OTHER INFORMATION: Synthetic oligonucleotide primer

<400> SEQUENCE: 4

```
ttattgaagc ttgccggggc cgacgcggcg ggcggcct                              38
```

<210> SEQ ID NO 5
<211> LENGTH: 34
<212> TYPE: DNA
<213> ORGANISM: Artificial sequence
<220> FEATURE:
<223> OTHER INFORMATION: Synthetic oligonucleotide primer

<400> SEQUENCE: 5

```
gttgttttaa ttaaacacca ggcctcctgg ggtg                                  34
```

<210> SEQ ID NO 6
<211> LENGTH: 38
<212> TYPE: DNA
<213> ORGANISM: Artificial sequence
<220> FEATURE:
<223> OTHER INFORMATION: Synthetic oligonucleotide primer

<400> SEQUENCE: 6

```
tttatattaa ttaatgaccc ttccgtcccg cccccgat                              38
```

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 7

```
tttggtgcta gctggtcgtg gcgctgttcc                                       30
```

<210> SEQ ID NO 8
<211> LENGTH: 10670
<212> TYPE: DNA
<213> ORGANISM: Artificial sequence
<220> FEATURE:
<223> OTHER INFORMATION: Synthetic plasmid pXY300-orf18ifd

<400> SEQUENCE: 8

```
ccgcggctcc tgcccgccga acgcgtcgtc gtcgacggcc tggtgctcat cgacgagcac     60
ccggagccag gtgaaaagcg ccggcggacg ctcggactgg gcgcgggatt ccagcagtaa    120
cccaggtccg ccggccacct cacgcaggc agacccctcgg ctttcgcgcc gggaccgcca    180
tgagaccgcc acccgatgt ccggggtggc ggtctcatgg cggtccctca gcggccctac    240
```

```
gcgaccgctg tgtcgacgcg gaggcagtct ccggggagcc ggccccaggg ctggagtacc    300
ggggcgagct tgcccttgca gcggcggcac acgggcgacg cggcgccggg cggggggagtc   360 ttgacgtcga cggtgaccgg cttcggcttc aggcgcttcc gaaggctgat cgtcgggcgg    420
atcgcctcct tcttcggctg acgcactcgg tcgagcgaag cggccagctc ctccgtgcgg    480
gcctcgttgg ccttccggcg cgcctcgcgg aaagcagctt cctcctcgga catgacctcg    540
aacctcatct ggtcagcgtc aaggtcgccc ggcgcggccg cgcgttccgg ggcgggcggg    600
tccaggacgt ccttgcccca ccaggcccc caggactcga cgagccgccg gacgcccggt     660
aggccgtacg tctcggcgac cttgatgagg tcgaggtcga ggcgacgtcc ggcgacgcgg    720
gcgatgtatc ggtaccagat gtaggccggg atgaccgcga tggcgaccag gccctcggtg    780
tcgtcggtga tctcctcctc ggtgcggacg tcctgctgga tgccgagttc cttgatcagc    840
cggttcaggt tctgcgaccg gtagtgcttg cggacctgga agacgccgaa ctcgcgctcg    900
cggtacttct cgacgaacgg gccgggccga cgaagccgct gcagctcggc ggccgccgcg    960
tcgcccaggt cgagcggtcc catgcggtcg tcgccgcgac cggccttgaa gttctgtccg   1020
gccagctcca ggccgatctt ggcgacgccg cccttggtct tgtcgccgtc cttgtagagg   1080
tagcgggcct gcttgcccgc atcgccgtca gcggcgtccg cgccgttgag tgggcgcacg   1140
tcggtgccgt ggcccttgcc ctcacaggag caaccgggcc ggtcgcacgt ctcgctgacg   1200
gtgtagccgc ccgcggattc gaccccggcg gcccaggctc cggcgagtgc gtcgcggaac   1260
gcctgggcgt ccgggccgag cacctcgcgg gtgacccaga gcgtgtgcca gtgcaggtgc   1320
cagccggagc cccagccgaa ggtgtcctcg aaggcccgct cgtagccgat gatcccgaag   1380
tcgtcgcgca tcgtgcgcac gcggcggccg gacgagccgt acgcgcccctt ccagccgtcg   1440 tgcaagaccg cgaccaggcc gtgccgcatt cccttgcgga cggtgccgaa cgccatgcgc   1500
tcgaagtggc gcaacgtgtt cgtgccaagg tgcagcccgt acccggcgtc cgcgagaccg   1560
tcggcggcga gctgcacgtt cgagcccgt acggccagga tgcggctcat gcaccacggg   1620
caggtgtgga cgttgttgca gcggcacgtg ttgccccacg tcgcctcgcc cggcttccac   1680
atcagctcgc ggtccggcag tgagccgggt cccgcagccc ttgaacgcct cgttcagcga   1740
caccgtctgg tgccggtccc gccgggcgaa ccgctcgtcg cggcgggtcc tcccgcccgc   1800
tgtcgcggca ccctcgtttg gggtagaacc cgttccagtt acagcgctct gacctgcagt   1860
ggacggagat tttcccttac tactaaagcc cgcgtccgga ttacccgctg tagtcgtgct   1920
tgctacgctg cgtgactggt ccgcaatgag acgctttgcg cgctttcggc aggcgtccga   1980
gcagtagatt ttggggcgct tcccggggat gtggacgatc ggggtgccgc agtggcactt   2040
cggtccggcg gggcgcggtg gtgtcgacgc gctgttctct cgtacgcctc gtcacagagc   2100
aaacgtcctc actcggcatg ctgcgccggt tcggggcgg cgagccggga ggccaatccc    2160
gggctcgtgc catttctggg tcctgttgat catcactgac gaatcgaggt cgaggaaccg   2220
agcgtccgag gaacagaggc gcttatcggt tggccgcgag attcctgtcg atcctctcgt   2280
gcagcgcgat tccgagggaa acggaaacgt tgagagactc ggtctggctc atcatgggga   2340
tggaaaccga ggcggaagac gcctcctcga acaggtcgga aggcccaccc ttttcgctgc   2400
cgaacagcaa ggccagccga tccggattgt ccccgagttc cttcacggaa atgtcgccat   2460
ccgccttgag cgtcatcagc tgcataccgc tgtcccgaat gaaggcgatg gcctcctcgc   2520
gaccggagag aacgacggga agggagaaga cgtaacctcg gctggccctt tggagacgcc   2580
ggtccgcgat gctggtgatg tcactgtcga ccaggatgat ccccgacgct ccgagcgcga   2640
```

```
gcgacgtgcg tactatcgcg ccgatgttcc cgacgatctt caccccgtcg agaacgacga   2700
cgtccccacg ccggctcgcg atatcgccga acctggccgg gcgagggacg cgggcgatgc   2760
cgaatgtctt ggccttccgc tccccttga acaactggtt gacgatcgag gagtcgatga   2820
ggcggaccgg tatgttctgc cgcccgcaca gatccagcaa ctcagatgga aaggactgc    2880 tgtcgctgcc gtagacctcg atgaactcca ccccggccgc gatgctgtgc atgaggggct   2940
cgacgtcctc gatcaacgtt gtctttatgt tggatcgcga cggcttggtg acatcgatga   3000
tccgctgcac cgcgggatcg gacggatttg cgatggtgtc caactcagtc atggtcgtcc   3060
taccggctgc tgtgttcagt gacgcgattc ctggggtgtg cacccctacg cgacgatggc   3120
ggatggctgc cctgaccggc aatcaccaac gcaaggggaa gtcgtcgctc tctggcaaag   3180
ctccccgctc ttcccgtcc gggacccgcg cggtcgatcc ccgcatatgg tgcactctca    3240
gtacaatctg ctctgatgcc gcatagttaa gccagccccg acacccgcca cacccgctg    3300 acgcgccctg acgggcttgt ctgctcccgg catccgctta cagacaagct gtgaccgtct   3360
ccgggagctg catgtgtcag aggttttcac cgtcatcacc gaaacgcgcg agacgaaagg   3420
gcctcgtgat acgcctatt ttataggtta atgtcatgat aataatggtt tcttagacgt    3480
caggtggcac ttttcgggga atgtgcgcg gaaccctat ttgtttattt ttctaaatac     3540
attcaaatat gtatccgctc atgagacaat aaccctgata aatgcttcaa taatattgaa   3600
aaaggaagag tatgagtatt caacatttcc gtgtcgccct tattccctt tttgcggcat    3660 tttgccttcc tgtttttgct cacccagaaa cgctggtgaa agtaaaagat gctgaagatc   3720
agttgggtgc acgagtgggt tacatcgaac tggatctcaa cagcggtaag atccttgaga   3780
gttttcgccc cgaagaacgt tttccaatga tgagcacttt taaagttctg ctatgtggcg   3840
cggtattatc ccgtattgac gccgggcaag agcaactcgg tcgccgcata cactattctc   3900
agaatgactt ggttgagtac tcaccagtca cagaaaagca tcttacggat ggcatgacag   3960
taagagaatt atgcagtgct gccataacca tgagtgataa cactgcggcc aacttacttc   4020
tgacaacgat cggaggaccg aaggagctaa ccgcttttt gcacaacatg ggggatcatg    4080
taactcgcct tgatcgttgg gaaccggagc tgaatgaagc cataccaaac gacgagcgtg   4140
acaccacgat gcctgtagca atggcaacaa cgttgcgcaa actattaact ggcgaactac   4200
ttactctagc ttcccggcaa caattaatag actggatgga ggcggataaa gttgcaggac   4260
cacttctgcg ctcggccctt ccggctggct ggtttattgc tgataaatct ggagccggtg   4320
agcgtgggtc tcgcggtatc attgcagcac tggggccaga tggtaagccc tcccgtatcg   4380
tagttatcta cacgacgggg agtcaggcaa ctatggatga acgaaataga cagatcgctg   4440
agataggtgc ctcactgatt aagcattggt aactgtcaga ccaagtttac tcatatatac   4500
tttagattga tttaaaactt catttttaat ttaaaaggat ctaggtgaag atccttttg    4560 ataatctcat gaccaaaatc ccttaacgtg agttttcgtt ccactgagcg tcagaccccg   4620
tagaaaagat caaaggatct tcttgagatc ctttttttct gcgcgtaatc tgctgcttgc   4680
aaacaaaaaa accaccgcta ccagcggtgg tttgtttgcc ggatcaagag ctaccaactc   4740 ttttccgaa ggtaactggc ttcagcagag cgcagatacc aaatactgtc cttctagtgt    4800
agccgtagtt aggccaccac ttcaagaact ctgtagcacc gcctacatac ctcgctctgc   4860
taatcctgtt accagtggct gctgccagtg gcgataagtc gtgtcttacc gggttggact   4920
caagacgata gttaccggat aaggcgcagc ggtcgggctg aacggggggt tcgtgcacac   4980
```

```
agcccagctt ggagcgaacg acctacaccg aactgagata cctacagcgt gagctatgag   5040
aaagcgccac gcttcccgaa gggagaaagg cggacaggta tccggtaagc ggcagggtcg   5100
gaacaggaga gcgcacgagg gagcttccag ggggaaacgc ctggtatctt tatagtcctg   5160
tcgggtttcg ccacctctga cttgagcgtc gattttttgtg atgctcgtca gggggggcgga  5220 gcctatggaa aaacgccagc aacgcggcct ttttacggtt cctggccttt tgctggcctt   5280
ttgctcacat gttctttcct gcgttatccc ctgattctgt ggataaccgt attaccgcct   5340
ttgagtgagc tgataccgct cgccgcagcc gaacgaccga gcgcagcgag tcagtgagcg   5400
aggaagcgga gagcgcccca atacgcaaac cgcctctccc cgcgcgttgg ccgattcatt   5460
aatgcagctg gcacgacagg tttcccgact ggaaagcggg cagtgagcgc aacgcaatta   5520
atgtgagtta gctcactcat taggcacccc aggctttaca ctttatgctt ccggctcgta   5580
tgttgtgtgg aattgtgagc ggataacaat ttcacacagg aaacagctat gaccatgatt   5640
acgccaagct tgccggggcc gacgcggcgg gcggcctcgt ccatcgggac gcgccagtcg   5700
acgccgacga tgtccgcgcc ggcctcgccc atgagcccca gcagctcgcc ggtgccgacg   5760
ccgaagtgga tgcgcgggac gccgtggccg gccaccgcgc ggaacacctt cgccgaggcg   5820
ggcagcaccg aacgccggta gtcggagggg gcgagcgcgc cggcccagga gtcgaagagc   5880
tgcacggccg aggcgccggc ccggatctgg acgtcgagga aggccgccgt gatgtcggcg   5940
aggcggtcga gcaggtcggc ccagagctcg ggtcgccgt acatcatcgc cttggcgttc   6000
tcgtacgtac gggacgggcc gccctcgacg aggtaactcg caagggtgaa cggggcgccc   6060
gcgaaaccga tcagcggggt ggacccgagc tcacgggtca gcatgccgat ggcctcggtg   6120
acgtaggaga cgtcctccgg ggtcaggtcg cgcagccggg cgaggtcggc gcgggtgcgc   6180
accggctgct cgacgaccgg gccgatgccg ggcttgatgt cgaggtcgat gccgatggcc   6240
ttgagcggga cgacgatgtc gctgaagtag atcgccgcgt cgacgtggtg gcggcgcacc   6300
ggctggaggg tgatctcggt gaccagctcg gccgcatgc aggagtcgag catcccgatg    6360
ccctcgcgca ccttgcggta ctccggcagt gagcgcccgg cctgccgcat gaaccacacc   6420
ggcgtgtgcg gcaccggctc gcgccggcac gccttgagga aggctgattc ccggacggcg   6480
tcgttcttga cggggtcggg ggtcgcggta ggcgtctggc ccttcgggct cgtgttggca   6540
ctcacaccgg ccagtctcgc acgacccgtc cgccgcccg gaccccaggg gcgtccggcg    6600
ggcggggccg cggtgcagga tccggacagc gccgggcggc gcgggtgtcc ctccctgcgc   6660
cgggggcccg ttccgcttaa tcttcccggc atggctgcgg ctcagggacg actgtcggac   6720
ggcgctggcg gaatggacga accgaaggag ggcgggggg atcccgggca cggaggtgcg    6780
cctccgccgc ccttccgggc cgctgtcgag gcgctgcaga gcgccggct gcggccgcag    6840 atcgaggtgg agacggtgcc cgccgcgaaa cggctcgccc cgtacgcgca cgcgctggag   6900
gcggcggtcg tcgacggcga ggaggatctg ccgacggcc ggctggtgct gctgtgcgac    6960
ccggccggac acgacgcctg gcgggggacc ttccgtctgg tgacgctggt gcgcgccgag   7020
ctggagccgg agatggcggc ggatccgctg ctgccggacg tgtgctggtc ctggctgacc   7080
ggcgcgctgg cggcgcgcgg cctgtcgtac ggcgagccga gcggcacggt gacgcgggcg   7140
agttcgcact acttcggcgg gctgtccgcg cggcccgccg cctcccagat cgagatccgt   7200
gcctcgtgga cgccgcgtga gggtctgggc ggggttccgg acacggccgc ccatctggtc   7260
gcgtggtccg atctgctggc gcaggtcgcg gggctgccgc cggccgctcc gggggacgcg   7320
tccgtggtga cgctgccgca gcggaggggg ccgcagtcgc gctgagcctc ccgctgcggg   7380
```

```
gtcccgacga ccggcctcct gcatctctct tgtcgatac ggccactttc ggaagcgttg    7440
cgacgcagac cgaaaccgtt cgatcttcga atgatcgatc gtgcgtccga attgcccgga    7500
ttgttactca tcacttcgtg atcattcgtt aaaggacacc aggtttgctg ccgaagacga    7560
ctgtgacctt gaaagcacgg ttcgtcccgc cttcaccccc acgagccggc ccgtcccgca    7620
ccccaggagg cctggtgttt aattaatgac ccttccgtcc cgcccccgat ccgcccgtcc    7680
ccgatccgcc cgcccacggc caagcgaaca cgttctttca ctcttctgac cggaatacga    7740
cccaccggcg cccgtcacgg agcacaaccg tcgacgggcg ccttcgcggc acggataccc    7800
ttgacaggtg accgacgccc acgacaccgc agcagacagt tcactgcgca ccaccggagg    7860
cgctcctccg gacgacggcg gatcttctgt tacggaggcg ccgaccccct tgctggaacc    7920
ccgcgagggc attccgcccg tgatagcgga cgaggccgcc ctcgccgagg cggtcgccgc    7980
cttcgcggcc ggcagcggac ccgtcgccgt ggacgccgag cgcgcctccg ggtaccgcta    8040
cggccagcgc gcctacctcg tccagctgcg ccgcgagggt gcgggtaccg cgctgatcga    8100
ccccgtggcc tgccccgacc tgtccgccct cggcgaggcg ctgtccggcg tcgagtgggt    8160
gctgcacgcc gccacccagg acctgccctg tctgcgcgag ataggcatgg tgccctcccg    8220
cctcttcgac accgagctgg ccggccgcct tgccgggttc ccccgcgtcg ggctcggcgc    8280
gatggtcgag aacgtgctcg gcttcgtcct ggagaagggc cactccgccg tcgactggtc    8340
cacccgtccg ctgcccgagc cctggctgcg gtacgccgcc ctcgacgtcg aactgctggt    8400
cgatctgcgg gacgccctgg agaaggagct ggaccgccag ggcaagctgg actgggcccg    8460
gcaggagttc gacgcgatcg cctcggcccc gccgccggag cccgcaagg accctggcg    8520 ccgcacctcc ggcatgcaca aggtgcgccg gcgccgccag atggcggtgg tgcgggagct    8580
gtgggagacc cgcgaccgga tcgcccggcg ccgtgacgtc tcccccggca aggtgctttc    8640
cgacgcggcg atcgtggagg ccgcgctcgc gctgcccgcc aacctgcacg ccatggccgc    8700
gctcaacggg ttcgggcagc gggtggggcg cgcgccagctg gagcagtggc aggcggccgt    8760
cgaccgcgcg aaggcgctga gcgaggccca gctgccgcag cccggccagc cggtgaccgg    8820
ccctccgccg ccgcgcgcct gggcggacaa ggaccccgtt gccgcggccc ggctgtcggc    8880
ggcccgcgcg ggggtcgccg aactcgccga gcggctgaac atgccgccgg agaacctgat    8940
cacccccgga cacggtgcgca gggtctgctg ggagccgccg gggcccgacg agcggtccgt    9000
cgccgcggcg ctgacggcgc acggggcacg cgcgtggcag gtcgaccagg tcactcccgt    9060
gctggtggcc gcgctggcta cttcgtcgcc cccgcatga acccgttgta gatgaagcgc    9120
tggaggaaca ggaagacgat caaggtgggc aggatgacca ggaccgcgcc cgccgagatc    9180
gtctcccagt gcgcgccgaa ggggcccttg aagcggaaca gggacgtcga gatgaccccc    9240
aggtcctcgg agggcatgta gaggaagggg atgtagaagt cgttgtagac gttgatcccc    9300
tttacgatca ccaccgtcgc gatcgccggc ttgagcagcg gaagatcac cttgcggtag    9360 acggtgaacg cgttggcgcc gtccaggcgc gccgcctcgt ccagggagac ggggatggag    9420
cggatgaact gcaggaagac gtagatcgag acgatgtccg tgcccatgta gagggcgatc    9480
ggcgcccaca ggctgtcgaa catgccgaag ctgttgacga tctggaaggt cgccacctgg    9540
gtggtcaccc cggggaccag cgcggccagc aggaacagcg ccacgaccag ctagcgaatt    9600
cctgcaggtc cccggggatc ggtccttgcct tgctcgtcgg tgatgtactt caccagctcc    9660
gcgaagtcgc tcttcttgat ggagcgcatg gggacgtgct tggcaatcac gcgcaccccc    9720
```

```
cggccgtttt agcggctaaa aaagtcatgg ctctgccctc gggcggacca cgcccatcat    9780
gaccttgcca agctcgtcct gcttctcttc gatcttcgcc agcagggcga ggatcgtggc    9840
atcaccgaac cgcgccgtgc gcgggtcgtc ggtgagccag agtttcagca ggccgcccag    9900
gcggcccagg tcgccattga tgcgggccag ctcgcggacg tgctcatagt ccacgacgcc    9960
cgtgattttg tagccctggc cgacggccag caggtaggcc gacaggctca tgccggccgc   10020
cgccgccttt tcctcaatcg ctcttcgttc gtctggaagg cagtacacct tgataggtgg   10080
gctgcccttc ctggttggct tggtttcatc agccatccgc ttgccctcat ctgttacgcc   10140
ggcggtagcc ggccagcctc gcagagcagg attcccgttg agcaccgcca ggtgcgaata   10200
agggacagtg aagaaggaac acccgctcgc gggtgggcct acttcaccta tcctgcccgg   10260
ctgacgccgt tggatacacc aaggaaagtc tacacgaacc ctttggcaaa atcctgtata   10320
tcgtgcgaaa aaggatggat ataccgaaaa aatcgctata atgaccccga agcagggtta   10380
tgcagcggaa aagatccgtc gacctgcagc ccggggatc cccgggtacc gagctcgggc     10440
tggggctcgg ggccgccggt gagctggtag acgaaggcgc ccgagtctcc ttcgttcact   10500
gcgtgccact cgtggtgcgg gtacttccgg cgcaacgtgc tgtcgtccat gggcggcatc   10560
atggcagagg cggagacgcc gttccgcgcc tttcgtcggg gcccgtaggg tttcggacat   10620
tcttgtgcgg ggtgggggg cgccggcgga cccggtgcgc ccggcgtcgc                10670
```

<210> SEQ ID NO 9
<211> LENGTH: 40
<212> TYPE: DNA
<213> ORGANISM: Artificial sequence
<220> FEATURE:
<223> OTHER INFORMATION: Synthetic oligonucleotide primer

<400> SEQUENCE: 9

```
agcacagcta gcttctagaa gcttcattca aaggccggca                                    40
```

<210> SEQ ID NO 10
<211> LENGTH: 43
<212> TYPE: DNA
<213> ORGANISM: Artificial sequence
<220> FEATURE:
<223> OTHER INFORMATION: Synthetic oligonucleotide primer

<400> SEQUENCE: 10

```
gccagtgaat tctgcagctc gagcagagca ggattcccgt tga                                 43
```

<210> SEQ ID NO 11
<211> LENGTH: 7173
<212> TYPE: DNA
<213> ORGANISM: Artificial sequence
<220> FEATURE:
<223> OTHER INFORMATION: Synthetic plasmid pKS-T-orf18pfrd

<400> SEQUENCE: 11

```
gtggcacttt tcggggaaat gtgcgcggaa cccctatttg tttatttttc taaatacatt      60
caaatatgta tccgctcatg agacaataac cctgataaat gcttcaataa tattgaaaaa     120
ggaagagtat gagtattcaa catttccgtg tcgcccttat tcccttttt gcggcatttt      180 gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttt ccaatgatga gcacttttaa agttctgcta tgtggcgcgg     360
tattatcccg tattgacgcc gggcaagagc aactcggtcg ccgcatacac tattctcaga     420
```

```
atgacttggt tgagtactca ccagtcacag aaaagcatct tacgatggc atgacagtaa    480 gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct aacgtgagt tttcgttcca ctgagcgtca gaccccgtag   1140
aaaagatcaa aggatcttct tgagatcctt ttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740 tatgaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccggg ccccccctcg   2220
agcagagcag gattccgtt gagcaccgcc aggtgcgaat aagggacagt gaagaaggaa   2280
cacccgctcg cgggtgggcc tacttcacct atcctgcccg gctgacgccg ttggatacac   2340
caaggaaagt ctacacgaac cctttggcaa atcctgtat atcgtgcgaa aaaggatgga   2400
tataccgaaa aaatcgctat aatgaccccg aagcagggtt atgcagcgga aaatgcagct   2460
cacggtaact gatgccgtat ttgcagtacc agcgtacggc ccacagaatg atgtcacgct   2520
gaaaatgccg gcctttgaat gaagcttgcc ggggccgacg cggcgggcgg cctcgtccat   2580
cgggacgcgc cagtcgacgc cgacgatgtc cgcgccggcc tcgcccatga gccccagcag   2640
ctcgccggtg ccgacgccga agtggatgcg cgggacgccg tggccggcca ccgcgcggaa   2700
caccttcgcc gaggcgggca gcaccgaacg ccggtagtcg gaggggggcga gcgcgccggc   2760
```

```
ccaggagtcg aagagctgca cggccgaggc gccggcccgg atctggacgt cgaggaaggc    2820
cgccgtgatg tcggcgaggc ggtcgagcag gtcggcccag agctcggggt cgccgtacat    2880
catcgccttg gcgttctcgt acgtacggga cgggccgccc tcgacgaggt aactcgcaag    2940
ggtgaacggg gcgcccgcga aaccgatcag cggggtggac ccgagctcac gggtcagcat    3000
gccgatggcc tcggtgacgt aggagacgtc ctccggggtc aggtcgcgca gccgggcgag    3060
gtcggcgcgg gtgcgcaccg gctgctcgac gaccgggccg atgccgggct tgatgtcgag    3120
gtcgatgccg atggccttga gcgggacgac gatgtcgctg aagtagatcg ccgcgtcgac    3180
gtggtggcgg cgcaccggct ggagggtgat ctcggtgacc agctcggggcc gcatgcagga    3240 gtcgagcatc ccgatgccct cgcgcacctt gcggtactcc ggcagtgagc gcccggcctg    3300
ccgcatgaac cacaccggcg tgtgcggcac cggctcgcgc cggcacgcct tgaggaaggc    3360
tgattcccgg acgcgtcgt tcttgacggg gtcgggggtc gcggtaggcg tctggccctt    3420
cgggctcgtg ttggcactca caccggccag tctcgcacga cccgtccgcc gccccggacc    3480
ccaggggcgt ccggcgggcg gggccgcggt gcaggatccg gacagcgccg ggcggcgcgg    3540
gtgtccctcc ctgcgccggg ggcccgttcc gcttaatctt cccggcatgg ctgcggctca    3600
gggacgactg tcggacggcg ctggcggaat ggacgaaccg aaggagggcg gggggatcc    3660 cgggcacgga ggtgcgcctc cgccgcccctt ccgggccgct gtcgaggcgc tgcagagcgc    3720
ccggctgcgg ccgcagatcg aggtggagac ggtgcccgcg ccgaaacggc tcgcccgta    3780 cgcgcacgcg ctggaggcgg cggtcgtcga cggcgaggag gatctggccg acggccggct    3840
ggtgctgctg tgcgacccgg ccggacacga cgcctggcgg gggaccttcc gtctggtgac    3900
gctggtgcgc gccgagctgg agccggagat ggcggcggat ccgctgctgc cggacgtgtg    3960
ctggtcctgg ctgaccggcg cgctggcggc gcgcggcctg tcgtacgcg agccgagcgg    4020 cacggtgacg cgggcgagtt cgcactactt cggcgggctg tccgcgcggc ccgccgcctc    4080
ccagatcgag atccgtgcct cgtggacgcc gcgtgagggt ctgggcgggg ttccggacac    4140
ggccgcccat ctggtcgcgt ggtccgatct gctggcgcag gtcgcggggc tgccgccggc    4200
cgctccgggg gacgcgtccg tggtgacgct gccgcagcgg aggggccgc agtcgcgctg    4260 agcctcccgc tgcggggtcc cgacgaccgg cctcctgcat ctctctttgt cgatacggcc    4320
actttcggaa gcgttgcgac gcagaccgaa accgttcgat cttcgaatga tcgatcgtgc    4380
gtccgaattg cccggattgt tactcatcac ttcgtgatca ttcgttaaag gacaccaggt    4440
ttgctgccga agacgactgt gaccttgaaa gcacggttcg tcccgccttc accccacga    4500 gccggcccgt cccgcacccc aggaggcctg gtgtttaatt aatgacccctt ccgtcccgcc    4560 cccgatccgc ccgtccccga tccgcccgcc cacggcaag cgaacacgtt ctttcactct    4620
tctgaccgga atacgaccca ccggcgcccg tcacggagca caaccgtcga cgggcgcctt    4680
cgcggcacgg ataccttga caggtgaccg acgcccacga caccgcagca gacagttcac    4740
tgcgcaccac cggaggcgct cctccggacg acggcggatc ttctgttacg gaggcgccga    4800 ccccttgct ggaacccgc gagggcattc cgcccgtgat agcggacgag gccgccctcg    4860
ccgaggcggt cgccgccttc gcggccggca cggacccgt cgccgtggac gccgagcgcg    4920
cctccgggta ccgctacggc cagcgcgcct acctcgtcca gctgcgccgc gagggtgcgg    4980
gtaccgcgct gatcgacccc gtggcctgcc ccgacctgtc cgccctcggc gaggcgctgt    5040
ccggcgtcga gtgggtgctg cacgccgcca cccaggacct gccctgtctg cgcgagatag    5100
gcatggtgcc ctcccgcctc ttcgacaccg agctggccgg ccgccttgcc gggttccccc    5160
```

```
gcgtcgggct cggcgcgatg gtcgagaacg tgctcggctt cgtcctggag aagggccact    5220
ccgccgtcga ctggtccacc cgtccgctgc ccgagccctg gctgcggtac gccgccctcg    5280
acgtcgaact gctggtcgat ctgcgggacg ccctggagaa ggagctggac cgccagggca    5340
agctggactg ggcccggcag gagttcgacg cgatcgcctc ggccccgccg ccggagcccc    5400
gcaaggaccc ctggcgccgc acctccggca tgcacaaggt gcgccggcgc cgccagatgg    5460
cggtggtgcg ggagctgtgg gagacccgcg accggatcgc ccggcgccgt gacgtctccc    5520
ccggcaaggt gctttccgac gcggcgatcg tggaggccgc gctcgcgctg cccgccaacc    5580
tgcacgccat ggccgcgctc aacgggttcg ggcagcgggt ggggcggcgc cagctggagc    5640
agtggcaggc ggccgtcgac cgcgcgaagg cgctgagcga ggcccagctg ccgcagcccg    5700
gccagccggt gaccggccct ccgccgccgc gcgcctgggc ggacaaggac cccgttgccg    5760
cggcccggct gtcggcggcc cgcgcggggg tcgccgaact cgccgagcgg ctgaacatgc    5820
cgccggagaa cctgatcacc ccggacacgt gcgcagggt ctgctgggag ccgccggggc    5880
ccgacgagcg gtccgtcgcc gcggcgctga cggcgcacgg ggcacgcgcg tggcaggtcg    5940
accaggtcac tcccgtgctg gtggccgcgc tggctacttc gtcgcccccc gcatgaaccc    6000
gttgtagatg aagcgctgga ggaacaggaa gacgatcaag gtgggcagga tgaccaggac    6060
cgcgcccgcc gagatcgtct cccagtgcgc gccgaagggg cccttgaagc ggaacaggga    6120
cgtcgagatg acccccaggt cctcggaggg catgtagagg aaggggatgt agaagtcgtt    6180
gtagacgttg atccccttta cgatcaccac cgtcgcgatc gccggcttga gcagcgggaa    6240
gatcaccttg cggtagacgg tgaacgcgtt ggcgccgtcc aggcgcgccg cctcgtccag    6300
ggagacgggg atggagcgga tgaactgcag gaagacgtag atcgagacga tgtccgtgcc    6360
catgtagagg gcgatcggcg cccacaggct gtcgaacatg ccgaagctgt tgacgatctg    6420
gaaggtcgcc acctgggtgg tcaccccggg gaccagcgcg ccagcagga acagcgccac    6480 gaccagctag ttctagagcg gccgccaccg cggtggagct ccaattcgcc ctatagtgag    6540
tcgtattacg cgcgctcact ggccgtcgtt ttacaacgtc gtgactggga aaaccctggc    6600
gttacccaac ttaatcgcct tgcagcacat cccccttcg ccagctggcg taatagcgaa    6660
gaggcccgca ccgatcgccc ttcccaacag ttgcgcagcc tgaatggcga atggaaattg    6720
taagcgttaa tattttgtta aaattcgcgt taaattttg ttaaatcagc tcattttta    6780 accaataggc cgaaatcggc aaaatcccttt ataaatcaaa agaatagacc gagatagggt    6840
tgagtgttgt tccagtttgg aacaagagtc cactattaaa gaacgtggac tccaacgtca    6900
aagggcgaaa aaccgtctat cagggcgatg gcccactacg tgaaccatca ccctaatcaa    6960
gttttttggg gtcgaggtgc cgtaaagcac taaatcggaa ccctaaaggg agcccccgat    7020
ttagagcttg acggggaaag ccggcgaacg tggcgagaaa ggaagggaag aaagcgaaag    7080
gagcgggcgc tagggcgctg gcaagtgtag cggtcacgct gcgcgtaacc accacacccg    7140
ccgcgcttaa tgcgccgcta cagggcgcgt cag                                 7173
```

<210> SEQ ID NO 12
<211> LENGTH: 29
<212> TYPE: DNA
<213> ORGANISM: Artificial sequence
<220> FEATURE:
<223> OTHER INFORMATION: Synthetic oligonucleotide primer

<400> SEQUENCE: 12

```
gaatggccat ggttcatgtg cagctccat                                  29

<210> SEQ ID NO 13
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 13
tctcgaggat ccgaatagga acttcggaat                                 30

<210> SEQ ID NO 14
<211> LENGTH: 6034
<212> TYPE: DNA
<213> ORGANISM: Artificial sequence
<220> FEATURE:
<223> OTHER INFORMATION: Synthetic plasmid pKS-T-orf18pfrd-AmR

<400> SEQUENCE: 14
gtggcacttt tcggggaaat gtgcgcggaa cccctatttg tttattttc taaatacatt     60 caaatatgta tccgctcatg agacaataac cctgataaat gcttcaataa tattgaaaaa   120
ggaagagtat gagtattcaa catttccgtg tcgcccttat ccctttttt gcggcatttt   180 gccttcctgt ttttgctcac ccagaaacgc tggtgaaagt aaaagatgct gaagatcagt   240
tgggtgcacg agtgggttac atcgaactgg atctcaacag cggtaagatc cttgagagtt   300
ttcgccccga agaacgtttt ccaatgatga gcacttttaa agttctgcta tgtggcgcgg   360
tattatcccg tattgacgcc gggcaagagc aactcggtcg ccgcatacac tattctcaga   420
atgacttggt tgagtactca ccagtcacag aaaagcatct tacggatggc atgacagtaa   480
gagaattatg cagtgctgcc ataaccatga gtgataacac tgcggccaac ttacttctga   540
caacgatcgg aggaccgaag gagctaaccg cttttttgca acatggggg atcatgtaa   600 ctcgccttga tcgttgggaa ccggagctga atgaagccat accaaacgac gagcgtgaca   660
ccacgatgcc tgtagcaatg gcaacaacgt tgcgcaaact attaactggc gaactactta   720
ctctagcttc ccggcaacaa ttaatagact ggatggaggc ggataaagtt gcaggaccac   780
ttctgcgctc ggcccttccg gctggctggt ttattgctga taaatctgga gccggtgagc   840
gtgggtctcg cggtatcatt gcagcactgg ggccagatgg taagccctcc cgtatcgtag   900
ttatctacac gacggggagt caggcaacta tggatgaacg aaatagacag atcgctgaga   960
taggtgcctc actgattaag cattggtaac tgtcagacca agtttactca tatatacttt  1020
agattgattt aaaacttcat ttttaattta aaaggatcta ggtgaagatc cttttgata  1080 atctcatgac caaaatccct aacgtgagt tttcgttcca ctgagcgtca gaccccgtag  1140
aaaagatcaa aggatcttct tgagatcctt ttttctgcg cgtaatctgc tgcttgcaaa  1200
caaaaaaacc accgctacca gcggtggttt gtttgccgga tcaagagcta ccaactcttt  1260
ttccgaaggt aactggcttc agcagagcgc agataccaaa tactgtcctt ctagtgtagc  1320
cgtagttagg ccaccacttc aagaactctg tagcaccgcc tacatacctc gctctgctaa  1380
tcctgttacc agtggctgct gccagtggcg ataagtcgtg tcttacccgg ttggactcaa  1440
gacgatagtt accggataag gcgcagcggt cgggctgaac ggggggttcg tgcacacagc  1500
ccagcttgga gcgaacgacc tacaccgaac tgagatacct acagcgtgag ctatgagaaa  1560
gcgccacgct tcccgaaggg agaaaggcgg acaggtatcc ggtaagcggc agggtcggaa  1620
caggagagcg cacgagggag cttccagggg gaaacgcctg gtatctttat agtcctgtcg  1680
```

```
ggtttcgcca cctctgactt gagcgtcgat ttttgtgatg ctcgtcaggg gggcggagcc   1740
tatggaaaaa cgccagcaac gcggccttt  tacggttcct ggccttttgc tggcttttg    1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga agcgggcag  tgagcgcaac gcaattaatg   2040
tgagttagct cactcattag gcaccccagg ctttacactt tatgcttccg ctcgtatgt    2100
tgtgtggaat tgtgagcgga taacaatttc acacaggaaa cagctatgac catgattacg   2160
ccaagcgcgc aattaaccct cactaaaggg aacaaaagct gggtaccggg ccccccctcg   2220
agcagagcag gattcccgtt gagcaccgcc aggtgcgaat aagggacagt gaagaaggaa   2280
cacccgctcg cgggtgggcc tacttcacct atcctgcccg gctgacgccg ttggatacac   2340
caaggaaagt ctacacgaac cctttggcaa atcctgtat  atcgtgcgaa aaaggatgga   2400
tataccgaaa aaatcgctat aatgaccccg aagcagggtt atgcagcgga aaatgcagct   2460
cacggtaact gatgccgtat ttgcagtacc agcgtacggc ccacagaatg atgtcacgct   2520
gaaaatgccg gcctttgaat gaagcttgcc ggggccgacg cggcgggcgg cctcgtccat   2580
cgggacgcgc cagtcgacgc cgacgatgtc cgcgccggcc tcgcccatga gccccagcag   2640
ctcgccggtg ccgacgccga agtggatgcg cgggacgccg tggccggcca ccgcgcggaa   2700
caccttcgcc gaggcgggca gcaccgaacg ccggtagtcg gaggggcga  gcgcgccggc   2760
ccaggagtcg aagagctgca cggccgaggc gccggcccgg atctggacgt cgaggaaggc   2820
cgccgtgatg tcggcgaggc ggtcgagcag gtcggcccag agctcggggt cgccgtacat   2880
catcgccttg gcgttctcgt acgtacggga cgggccgccc tcgacgaggt aactcgcaag   2940
ggtgaacggg gcgcccgcga aaccgatcag cggggtggac ccgagctcac gggtcagcat   3000
gccgatggcc tcggtgacgt aggagacgtc ctccggggtc aggtcgcgca gccgggcgag   3060
gtcggcgcgg gtgcgcaccg gctgctcgac gaccggccg  atgccgggct tgatgtcgag   3120
gtcgatgccg atggccttga gcgggacgac gatgtcgctg aagtagatcg ccgcgtcgac   3180
gtggtggcgg cgcaccggct ggagggtgat ctcggtgacc agctcgggcc gcatgcagga   3240
gtcgagcatc ccgatgccct cgcgcacctt gcggtactcc ggcagtgagc gcccggcctg   3300
ccgcatgaac cacaccggcg tgtgcggcac cggctcgcgc cggcacgcct tgaggaaggc   3360
tgattcccgg acgcgtcgt  tcttgacggg gtcggggtc  gcggtaggcg tctgcccctt   3420
cgggctcgtg ttggcactca caccggccag tctcgcacga cccgtccgcc gccccggacc   3480
ccaggggcgt ccgcgggcg  gggccgcggt gcaggatccg aataggaact cggaataggg   3540
aacttcatga gctcagccaa tcgactggcg agcggcatcg cattcttcgc atcccgcctc   3600
tggcggatgc aggaagatca acggatctcg gcccagttga cccagggctg tcgccacaat   3660
gtcgcgggag cggatcaacc gagcaaaggc atgaccgact ggaccttcct tctgaaggct   3720
cttctccttg agccacctgt ccgccaaggc aaagcgctca cagcagtggt cattctcgag   3780
ataatcgacg cgtaccaact tgccatcctg aagaatggtg cagtgtctcg caccccata    3840
gggaaccttt gccatcaact cggcaagatg cagcgtcgtg ttggcatcgt gtcccacgcc   3900
gaggagaagt acctgcccat cgagttcatg gacacgggcg accgggcttg caggcgagtg   3960
aggtggcagg ggcaatggat cagagatgat ctgctctgcc tgtggccccg ctgccgcaaa   4020
```

```
ggcaaatgga tgggcgctgc gctttacatt tggcaggcgc agaatgtgt cagagacaac    4080 tccaaggtcc ggtgtaacgg gcgacgtggc aggatcgaac ggctcgtcgt ccagacctga    4140
ccacgagggc atgacgagcg tccctcccgg acccagcgca gcacgcaggg cctcgatcag    4200
tccaagtggc ccatcttcga ggggccggac gctacggaag gagctgtgga ccagcagcac    4260
accgccgggg gtaaccccaa ggttgagaag ctgaccgatg agctcggctt ttcgccattc    4320
gtattgcacg acattgcact ccaccgctga tgacatcagt cgatcatagc acgatcaacg    4380
gcactgttgc aaatagtcgg tggtgataaa cttatcatcc ccttttgctg atggagctgc    4440
acatgaacca tggccgcgct caacgggttc gggcagcggg tggggcggcg ccagctggag    4500
cagtggcagg cggccgtcga ccgcgcgaag gcgctgagcg aggcccagct gccgcagccc    4560
ggccagccgg tgaccggccc tccgccgccg cgcgcctggg cggacaagga ccccgttgcc    4620
gcggcccggc tgtcggcggc ccgcgcgggg gtcgccgaac tcgccgagcg gctgaacatg    4680
ccgccggaga acctgatcac cccggacacg gtgcgcaggg tctgctggga gccgccgggg    4740
cccgacgagc ggtccgtcgc cgcggcgctg acggcgcacg gggcacgcgc gtggcaggtc    4800
gaccaggtca ctcccgtgct ggtggccgcg ctggctactt cgtcgccccc cgcatgaacc    4860
cgttgtagat gaagcgctgg aggaacagga agacgatcaa ggtgggcagg atgaccagga    4920
ccgcgcccgc cgagatcgtc tcccagtgcg cgccgaaggg gcccttgaag cggaacaggg    4980
acgtcgagat gaccccagg tcctcggagg gcatgtagag aaggggatg tagaagtcgt    5040 tgtagacgtt gatcccttt acgatcacca ccgtcgcgat cgccggcttg agcagcggga    5100
agatcacctt gcggtagacg gtgaacgcgt tggcgccgtc caggcgcgcc gcctcgtcca    5160
gggagacggg gatggagcgg atgaactgca ggaagacgta gatcgagacg atgtccgtgc    5220
ccatgtagag ggcgatcggc gcccacaggc tgtcgaacat gccgaagctg ttgacgatct    5280
ggaaggtcgc cacctgggtg gtcaccccgg ggaccagcgc ggccagcagg aacagcgcca    5340
cgaccagcta gttctagagc ggccgccacc gcggtggagc tccaattcgc cctatagtga    5400
gtcgtattac gcgcgctcac tggccgtcgt tttacaacgt cgtgactggg aaaaccctgg    5460
cgttacccaa cttaatcgcc ttgcagcaca tccccctttc gccagctggc gtaatagcga    5520
agaggcccgc accgatcgcc cttcccaaca gttgcgcagc ctgaatggcg aatggaaatt    5580
gtaagcgtta atattttgtt aaaattcgcg ttaaattttt gttaaatcag ctcattttt    5640 aaccaatagg ccgaaatcgg caaaatccct tataaatcaa agaatagac cgagataggg    5700 ttgagtgttg ttccagtttg gaacaagagt ccactattaa agaacgtgga ctccaacgtc    5760
aaagggcgaa aaaccgtcta tcagggcgat ggcccactac gtgaaccatc accctaatca    5820
agttttttgg ggtcgaggtg ccgtaaagca ctaaatcgga accctaaagg agcccccga    5880 tttagagctt gacggggaaa gccggcgaac gtggcgagaa aggaagggaa gaaagcgaaa    5940
ggagcgggcg ctagggcgct ggcaagtgta gcggtcacgc tgcgcgtaac caccacaccc    6000
gccgcgctta atgcgccgct acagggcgcg tcag                                6034
```

<210> SEQ ID NO 15
<211> LENGTH: 40
<212> TYPE: DNA
<213> ORGANISM: Artificial sequence
<220> FEATURE:
<223> OTHER INFORMATION: Synthetic oligonucleotide primer

<400> SEQUENCE: 15
agcacagcta gcttctagaa gcttcattca aaggccggca                          40

<210> SEQ ID NO 16
<211> LENGTH: 44
<212> TYPE: DNA
<213> ORGANISM: Artificial sequence
<220> FEATURE:
<223> OTHER INFORMATION: Synthetic oligonucleotide primer

<400> SEQUENCE: 16
aggcagctcg agcatatgac tagtcagagc aggattcccg ttga         44

<210> SEQ ID NO 17
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 17
gaatggcata tggttcatgt gcagctccat                         30

<210> SEQ ID NO 18
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 18
tctagaacta gtgaatagga acttcggaat                         30

<210> SEQ ID NO 19
<211> LENGTH: 8113
<212> TYPE: DNA
<213> ORGANISM: Artificial sequence
<220> FEATURE:
<223> OTHER INFORMATION: Synthetic plasmid pKS-orf18ifd-T-AmR(NS)

<400> SEQUENCE: 19
gtggcacttt tcggggaaat gtgcgcggaa cccctatttg tttatttttc taaatacatt    60
caaatatgta tccgctcatg agacaataac cctgataaat gcttcaataa tattgaaaaa   120
ggaagagtat gagtattcaa catttccgtg tcgcccttat tcccttttttt gcggcatttt   180 gccttcctgt ttttgctcac ccagaaacgc tggtgaaagt aaaagatgct gaagatcagt   240
tgggtgcacg agtgggttac atcgaactgg atctcaacag cggtaagatc cttgagagtt   300
ttcgccccga agaacgtttt ccaatgatga gcacttttaa agttctgcta tgtggcgcgg   360
tattatcccg tattgacgcc gggcaagagc aactcggtcg ccgcatacac tattctcaga   420
atgacttggt tgagtactca ccagtcacag aaaagcatct tacgatggc atgacagtaa    480 gagaattatg cagtgctgcc ataaccatga gtgataacac tgcggccaac ttacttctga   540
caacgatcgg aggaccgaag gagctaaccg cttttttgca caacatgggg gatcatgtaa   600
ctcgccttga tcgttgggaa ccggagctga atgaagccat accaaacgac gagcgtgaca   660
ccacgatgcc tgtagcaatg gcaacaacgt tgcgcaaact attaactggc gaactactta   720
ctctagcttc ccggcaacaa ttaatagact ggatggaggc ggataaagtt gcaggaccac   780
ttctgcgctc ggcccttccg gctggctggt ttattgctga taaatctgga gccggtgagc   840
gtgggtctcg cggtatcatt gcagcactgg ggccagatgg taagccctcc cgtatcgtag   900
ttatctacac gacggggagt caggcaacta tggatgaacg aaatagacag atcgctgaga   960

```
taggtgcctc actgattaag cattggtaac tgtcagacca agtttactca tatatacttt    1020
agattgattt aaaacttcat ttttaattta aaaggatcta ggtgaagatc cttttgata     1080
atctcatgac caaaatccct taacgtgagt tttcgttcca ctgagcgtca gaccccgtag    1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct cccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatgaaaaaa cgccagcaac gcggccttttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct gggtaccggg ccccccctcg    2220
agcatatgtt catgtgcagc tccatcagca aaggggatg ataagtttat caccaccgac    2280
tatttgcaac agtgccgttg atcgtgctat gatcgactga tgtcatcagc ggtggagtgc    2340
aatgtcgtgc aatacgaatg gcgaaaagcc gagctcatcg gtcagcttct caaccttggg    2400
gttaccccg gcgtgtgct gctggtccac agctccttcc gtagcgtccg gcccctcgaa    2460
gatgggccac ttggactgat cgaggccctg cgtgctgcgc tgggtccggg agggacgctc    2520
gtcatgccct cgtggtcagg tctggacgac gagccgttcg atcctgccac gtcgccgtt    2580
acaccggacc ttgagttgt ctctgacaca ttctggcgcc tgccaaatgt aaagcgcagc    2640
gcccatccat ttgcctttgc ggcagcgggg ccacaggcag agcagatcat ctctgatcca    2700
ttgcccctgc cacctcactc gcctgcaagc ccggtcgccc gtgtccatga actcgatggg    2760
caggtacttc tcctcggcgt gggacacgat gccaacacga cgctgcatct tgccgagttg    2820
atggcaaagg ttccctatgg ggtgccgaga cactgcacca ttcttcagga tggcaagttg    2880
gtacgcgtcg attatctcga gaatgaccac tgctgtgagc gctttgcctt gcggacagg    2940
tggctcaagg agaagagcct tcagaaggaa ggtccagtcg gtcatgcctt tgctcggttg    3000
atccgctccc gcgacattgt ggcgacagcc ctgggtcaac tgggccgaga tccgttgatc    3060
ttcctgcatc cgccagaggc gggatgcgaa gaatgcgatg ccgctcgcca gtcgattggc    3120
tgagctcatg aagttcctat tccgaagttc ctattcacta gtcagagcag gattcccgtt    3180
gagcaccgcc aggtgcgaat aagggacagt gaagaaggaa caccgctcg cgggtgggcc    3240
tacttcacct atcctgcccg gctgacgccg ttggatacac caaggaaagt ctacacgaac    3300
cctttggcaa aatcctgtat atcgtgcgaa aaaggatgga tataccgaaa aaatcgctat    3360
```

```
aatgacoccg aagcagggtt atgcagcgga aaatgcagct cacggtaact gatgccgtat      3420
ttgcagtacc agcgtacggc ccacagaatg atgtcacgct gaaaatgccg gcctttgaat      3480
gaagcttgcc ggggccgacg cggcgggcgg cctcgtccat cgggacgcgc cagtcgacgc      3540
cgacgatgtc cgcgccggcc tcgcccatga gccccagcag ctcgccggtg ccgacgccga      3600
agtggatgcg cgggacgccg tggccggcca ccgcgcggaa caccttcgcc gaggcgggca      3660
gcaccgaacg ccggtagtcg gaggggcga gcgcgccggc ccaggagtcg aagagctgca      3720
cggccgaggc gccggcccgg atctggacgt cgaggaaggc cgccgtgatg tcggcgaggc      3780
ggtcgagcag gtcggcccag agctcggggt cgccgtacat catcgccttg gcgttctcgt      3840
acgtacggga cgggccgccc tcgacgaggt aactcgcaag ggtgaacggg cgcccgcga      3900 aaccgatcag cggggtggac ccgagctcac gggtcagcat gccgatggcc tcggtgacgt      3960
aggagacgtc ctccggggtc aggtcgcgca gccgggcgag gtcggcgcgg gtgcgcaccg      4020
gctgctcgac gaccgggccg atgccgggct tgatgtcgag gtcgatgccg atggccttga      4080
gcgggacgac gatgtcgctg aagtagatcg ccgcgtcgac gtggtggcgg cgcaccggct      4140
ggagggtgat ctcggtgacc agctcggggcc gcatgcagga gtcgagcatc ccgatgccct      4200
cgcgcacctt gcggtactcc ggcagtgagc gcccggcctg ccgcatgaac cacaccggcg      4260
tgtgcggcac cggctcgcgc cggcacgcct tgaggaaggc tgattcccgg acggcgtcgt      4320
tcttgacggg gtcgggggtc gcggtaggcg tctggcccctt cgggctcgtg ttggcactca      4380
caccggccag tctcgcacga cccgtccgcc gccccggacc ccaggggcgt ccggcgggcg      4440
gggccgcggt gcaggatccg gacagcgccg ggcggcgcgg gtgtccctcc ctgcgccggg      4500
ggcccgttcc gcttaatctt cccggcatgg ctgcggctca gggacgactg tcggacggcg      4560
ctggcggaat ggacgaaccg aaggagggcg gggggatcc cgggcacgga ggtgcgcctc      4620
cgccgccctt ccgggccgct gtcgaggcgc tgcagagcgc ccggctgcgg ccgcagatcg      4680
aggtggagac ggtgcccgcg ccgaaacggc tcgccccgta cgcgcacgcg ctggaggcgg      4740
cggtcgtcga cggcgaggag gatctggccg acggccggct ggtgctgctg tgcgacccgg      4800
ccggacacga cgcctggcgg gggaccttcc gtctggtgac gctggtgcgc gccgagctgg      4860
agccggagat ggcggcggat ccgctgctgc cggacgtgtg ctggtcctgg ctgaccggcg      4920
cgctggcggc gcgcggcctg tcgtacgcg agccgagcgg cacggtgacg cgggcgagtt      4980
cgcactactt cggcgggctg tccgcgcggc ccgccgcctc ccagatcgag atccgtgcct      5040
cgtggacgcc gcgtgagggt ctgggcgggg ttccggacac ggccgcccat ctggtcgcgt      5100
ggtccgatct gctggcgcag gtcgcggggc tgccgccggc cgctccgggg gacgcgtccg      5160
tggtgacgct gccgcagcgg aggggccgc agtcgcgctg agcctcccgc tgcggggtcc      5220
cgacgaccgg cctcctgcat ctctctttgt cgatacggcc actttcggaa gcgttgcgac      5280
gcagaccgaa accgttcgat cttcgaatga tcgatcgtgc gtccgaattg cccggattgt      5340
tactcatcac ttcgtgatca ttcgttaaag gacaccaggt ttgctgccga agacgactgt      5400
gaccttgaaa gcacggttcg tcccgccttc accccacga gccggccgt cccgcacccc      5460 aggaggcctg gtgtttaatt aatgacccctt ccgtcccgcc ccgatccgc ccgtcccga      5520 tccgcccgcc cacggccaag cgaacacgtt ctttcactct tctgaccgga atacgaccca      5580
ccggcgcccg tcacggagca caaccgtcga cgggcgcctt cgcggacgg atacccttga      5640 caggtgaccg acgcccacga caccgcagca gacagttcac tgcgcaccac cggaggcgct      5700
```

```
cctccggacg acggcggatc ttctgttacg gaggcgccga ccccttgct ggaaccccgc    5760 gagggcattc cgcccgtgat agcggacgag gccgccctcg ccgaggcggt cgccgccttc   5820
gcggccggca gcggacccgt cgccgtggac gccgagcgcg cctccgggta ccgctacggc   5880
cagcgcgcct acctcgtcca gctgcgccga gaggtgcgg gtaccgcgct gatcgacccc    5940
gtggcctgcc ccgacctgtc cgccctcggc gaggcgctgt ccggcgtcga gtgggtgctg   6000
cacgccgcca cccaggacct gccctgtctg cgcgagatag gcatggtgcc ctcccgcctc    6060
ttcgacaccg agctggccgg ccgccttgcc gggttccccc gcgtcgggct cggcgcgatg   6120
gtcgagaacg tgctcggctt cgtcctggag aagggccact ccgccgtcga ctggtccacc   6180
cgtccgctgc ccgagccctg gctgcggtac gccgccctcg acgtcgaact gctggtcgat    6240
ctgcgggacg ccctggagaa ggagctggac cgccagggca gctggactg ggcccggcag    6300 gagttcgacg cgatcgcctc ggccccgccg ccggagcccc gcaaggaccc ctggcgccgc    6360
acctccggca tgcacaaggt gcgccggcgc cgccagatgg cggtggtgcg ggagctgtgg   6420
gagacccgcg accggatcgc ccggcgccgt gacgtctccc ccggcaaggt gctttccgac   6480
gcggcgatcg tggaggccgc gctcgcgctg cccgccaacc tgcacgccat ggccgcgctc    6540
aacgggttcg gcagcgggt ggggcggcgc cagctggagc agtggcaggc ggccgtcgac    6600
cgcgcgaagg cgctgagcga ggcccagctg ccgcagcccg ccagccggt gaccggccct    6660 ccgccgccgc gcgcctgggc ggacaaggac cccgttgccg cggcccggct gtcggcggcc    6720
cgcgcggggg tcgccgaact cgccgagcgg ctgaacatgc cgccggagaa cctgatcacc    6780
ccggacacgt tgctcaggggt ctgctgggag ccgccggggc ccgacgagcg gtccgtcgcc   6840
gcggcgctga cggcgcacgg ggcacgcgcg tggcaggtcg accaggtcac tcccgtgctg   6900
gtggccgcgc tggctacttc gtcgcccccc gcatgaaccc gttgtagatg aagcgctgga   6960
ggaacaggaa gacgatcaag gtgggcagga tgaccaggac cgcgcccgcc gagatcgtct   7020
cccagtgcgc gccgaagggg cccttgaagc ggaacaggga cgtcgagatg accccaggt    7080 cctcggaggg catgtagagg aaggggatgt agaagtcgtt gtagacgttg atccccttta    7140
cgatcaccac cgtcgcgatc gccggcttga gcagcgggaa gatcaccttg cggtagacgg    7200
tgaacgcgtt ggcgccgtcc aggcgcgccg cctcgtccag ggagacgggg atggagcgga    7260
tgaactgcag gaagacgtag atcgagacga tgtccgtgcc catgtagagg gcgatcggcg    7320
cccacaggct gtcgaacatg ccgaagctgt tgacgatctg gaaggtcgcc acctgggtgg    7380
tcaccccggg gaccagcgcg gccagcagga acagcgccac gaccagctag ttctagagcg   7440
gccgccaccg cggtggagct ccaattcgcc ctatagtgag tcgtattacg cgcgctcact    7500
ggccgtcgtt ttacaacgtc gtgactggga aaaccctggc gttacccaac ttaatcgcct    7560
tgcagcacat ccccctttcg ccagctggcg taatagcgaa gaggcccgca ccgatcgccc    7620
ttcccaacag ttgcgcagcc tgaatggcga atggaaattg taagcgttaa tattttgtta   7680
aaattcgcgt taaattttg ttaaatcagc tcatttttta accaataggc cgaaatcggc     7740
aaaatccctt ataaatcaaa agaatagacc gagatagggt tgagtgttgt tccagtttgg    7800
aacaagagtc cactattaaa gaacgtggac tccaacgtca aagggcgaaa aaccgtctat    7860
cagggcgatg gcccactacg tgaaccatca ccctaatcaa gtttttttggg gtcgaggtgc   7920 cgtaaagcac taaatcggaa ccctaaaggg agccccgat ttagagcttg acggggaaag    7980
ccggcgaacg tggcgagaaa ggaagggaag aaagcgaaag gagcgggcgc tagggcgctg    8040
gcaagtgtag cggtcacgct gcgcgtaacc accacacccg ccgcgcttaa tgcgccgcta    8100
```

-continued

```
cagggcgcgt cag                                                    8113

<210> SEQ ID NO 20
<211> LENGTH: 7120
<212> TYPE: DNA
<213> ORGANISM: Artificial sequence
<220> FEATURE:
<223> OTHER INFORMATION: Synthetic plasmid pXY152-endorf24-camtsr

<400> SEQUENCE: 20
gaattcgtaa tcatgtcata gctgtttcct gtgtgaaatt gttatccgct cacaattcca      60
cacaacatac gagccggaag cataaagtgt aaagcctggg gtgcctaatg agtgagctaa     120
ctcacattaa ttgcgttgcg ctcactgccc gctttccagt cgggaaacct gtcgtgccag     180
ctgcattaat gaatcggcca acgcgcgggg agaggcggtt tgcgtattgg gcgctcttcc     240
gcttcctcgc tcactgactc gctgcgctcg tcgttcggc tgcggcgagc ggtatcagct      300
cactcaaagg cggtaatacg gttatccaca gaatcagggg ataacgcagg aaagaacatg     360
tgagcaaaag gccagcaaaa ggccaggaac cgtaaaaagg ccgcgttgct ggcgtttttc     420
cataggctcc gccccctga cgagcatcac aaaaatcgac gctcaagtca gaggtggcga      480
aacccgacag gactataaag ataccaggcg tttccccctg gaagctccct cgtgcgctct     540
cctgttccga ccctgccgct taccggatac ctgtccgcct ttctccttc gggaagcgtg      600
gcgctttctc atagctcacg ctgtaggtat ctcagttcgg tgtaggtcgt tcgctccaag     660
ctgggctgtg tgcacgaacc ccccgttcag cccgaccgct gcgccttatc cggtaactat     720
cgtcttgagt ccaacccggt aagacacgac ttatcgccac tggcagcagc cactggtaac     780
aggattagca gagcgaggta tgtaggcggt gctacagagt tcttgaagtg gtggcctaac     840
tacggctaca ctagaagaac agtatttggt atctgcgctc tgctgaagcc agttaccttc     900
ggaaaaagag ttggtagctc ttgatccggc aaacaaacca ccgctggtag cggtggtttt     960
tttgtttgca agcagcagat tacgcgcaga aaaaaaggat ctcaagaaga tcctttgatc    1020
ttttctacgg ggtctgacgc tcagtggaac gaaaactcac gttaagggat tttggtcatg    1080
agattatcaa aaaggatctt cacctagatc cttttggttc atgtgcagct ccatcagcaa    1140
aaggggatga taagtttatc accaccgact atttgcaaca gtgccgttga tcgtgctatg    1200
atcgactgat gtcatcagcg gtggagtgca atgtcgtgca atacgaatgg cgaaaagccg    1260
agctcaataa ctgccttaaa aaaattacgc cccgccctgc cactcatcgc agtactgttg    1320
taattcatta agcattctgc cgacatggaa gccatcacaa acggcatgat gaacctgaat    1380
cgccagcggc atcagcacct tgtcgccttg cgtataatat ttgcccatcg tgaaaacggg    1440
ggcgaagaag ttgtccatat tggccacgtt taagtcaaaa ctggtgaaac tcacccaggg    1500
attggctgag acgaaaaaca tattctcaat aaacccttta gggaatagg ccaggttttc     1560
accgtaacac gccacatctt gcgaatatat gtgtagaaac tgccggaaat cgtcgtggta    1620
ttcactccag agcgatgaaa acgtttcagt ttgctcatgg aaaacggtgt aacaagggtg    1680
aacactatcc catatcacca gctcaccgtc tttcattgcc atacgaaatt ccggatgagc    1740
attcatcagg cgggcaagaa tgtgaataaa ggccggataa aacttgtgct tatttttctt    1800
tacggtcttt aagaaggccg taatatccag ttgaacggtc tggttatagg tacattgagc    1860
aactgactga aatgcctcaa aatgttcttt acgatgccat gggatatat caacggtggt     1920
atatccagtg atttttttct ccatttagc ttccttagct cctgaaaatc tcgataactc     1980
```

```
aaaaaatacg cccggtagtg atcttatttc attatggtga aagttggaac ctcttacgtg    2040
ccgatcaacg tctcattttc gccaaaagtt ggcccagggc ttcccggtat caacagggac    2100
accaggattt atttattctg cgaagtgatc ttccgtcaca ggtatttatt cgcgataagc    2160
tcatggagcg gcgtaaccgt cgcacaggaa ggacagagaa agcgcggaag cttatttaaa    2220
taccgcgcgg gtcccggacg gggaagagcg gggagctttg ccagagagcg acgacttccc    2280
cttgcgttgg tgattgccgg tcagggcagc catccgccat cgtcgcgtag ggtgtcacac    2340
cccaggaatc gcgtcactga acacagcagc cggtaggacg accatgactg agttggacac    2400
catcgcaaat ccgtccgatc cggcggtgca gcggatcatc gatgtcacca agccgtcgcg    2460
atccaacata aagacaacgt tgatcgagga cgtcgagccc ctcatgcaca gcatcgcggc    2520
cggggtggag ttcatcgagg tctacggcag cgacagcagt cctttccat ctgagttgct     2580 ggatctgtgc gggcggcaga acataccggt ccgcctcatc gactcctcga tcgtcaacca    2640
gttgttcaag gggagcggaa aggccaagac attcggcatc gcccgcgtcc ctcgcccggc    2700
caggttcggc gacatcgcga gccggcgtgg ggacgtcgtc gttctcgacg gggtgaagat    2760
cgtcgggaac atcggcgcga tagtacgcac gtcgctcgcg ctcggagcgt cggggatcat    2820
cctggtcgac agtgacatca ccagcatcgc ggaccggcgt ctccaaaggg ccagccgagg    2880
ttacgtcttc tcccttcccg tcgttctctc cggtcgcgag gaggccatcg ccttcattcg    2940
ggacagcggt atgcaactga tgacgctcaa ggcggatggc gacatttccg tgaaggaact    3000
cggggacaat ccggatcggc tggccttgct gttcggcagc gaaaagggtg gccttccga     3060 cctgttcgag gaggcgtctt ccgcctcggt ttccatcccc atgatgagcc agaccgagtc    3120
tctcaacgtt tccgtttccc tcggaatcgc gctgcacgag aggatcgaca ggaatctcgc    3180
ggccaaccga taagctagct agagtcgacc tgcaggtccc cggggatcgg tcttgccttg    3240
ctcgtcggtg atgtacttca ccagctccgc gaagtcgctc ttcttgatgg agcgcatggg    3300
gacgtgcttg gcaatcacgc gcaccccccg gccgttttag cggctaaaaa agtcatggct    3360
ctgccctcgg gcggaccacg cccatcatga ccttgccaag ctcgtcctgc ttctcttcga    3420
tcttcgccag cagggcgagg atcgtggcat caccgaaccg cgccgtgcgc gggtcgtcgg    3480
tgagccagag tttcagcagg ccgcccaggc ggcccaggtc gccattgatg cgggccagct    3540
cgcggacgtg ctcatagtcc acgacgcccg tgattttgta gccctggccg acggccagca    3600
ggtaggccga caggctcatg ccggccgccg ccgccttttc ctcaatcgct cttcgttcgt    3660
ctggaaggca gtacaccttg ataggtgggc tgcccttcct ggttggcttg gtttcatcag    3720
ccatccgctt gccctcatct gttacgccgg cggtagccgg ccagcctcgc agagcaggat    3780
tcccgttgag caccgccagg tgcgaataag ggacagtgaa gaaggaacac ccgctcgcgg    3840
gtgggcctac ttcacctatc ctgcccggct gacgccgttg gatacaccaa ggaaagtcta    3900 cacgaacccct ttggcaaaat cctgtatatc gtgcgaaaaa ggatggatat accgaaaaaa   3960
tcgctataat gaccccgaag cagggttatg cagcggaaaa gatccgtcga cctgcaggca    4020
tgcaagctct agcgattcca gacgtcccga aggcgtggcg cggcttcccc gtgccggagc    4080
aatcgccctg ggtgggttac acgacgcccc tctatggccc gtactgacgg acacaccgaa    4140
gccccggcgg caaccctcag cggatgcccc ggggcttcac gttttcccag gtcagaagcg    4200
gttttcggga gtagtgcccc aactggggta acctttgagt tctctcagtt ggggggcgtag   4260 ggtcgccgac atgacacaag gggttgtgac cggggtggac acgtacgcgg gtgcttacga    4320
ccgtcagtcg cgcgagcgcg agaactcgag cgcagcaagc ccagcgacac agcgtagcgc    4380
```

```
caacgaagac aaggcggccg accttcagcg cgaagtcgag cgcgacgggg gccggttcag    4440
gttcgtcggg catttcagcg aagcgccggg cacgtcggcg ttcgggacgg cggagcgccc    4500
ggagttcgaa cgcatcctga acgaatgccg cgccgggcgg ctcaacatga tcattgtcta    4560
tgacgtgtcg cgcttctcgc gcctgaaggt catggacgcg attccgattg tctcggaatt    4620
gctcgccctg ggcgtgacga ttgtttccac tcaggaaggc gtcttccggc agggaaacgt    4680
catggacctg attcacctga ttatgcggct cgacgcgtcg cacaaagaat cttcgctgaa    4740
gtcggcgaag attctcgaca cgaagaacct tcagcgcgaa ttgggcgggt acgtcggcgg    4800
gaaggcgcct tacggcttcg agcttgtttc ggagacgaag gagatcacgc gcaacggccg    4860
aatggtcaat gtcgtcatca acaagcttgc gcactcgacc actcccctta ccggacccct    4920
cgagttcgag cccgacgtaa tccggtggtg gtggcgtgag atcaagacgc acaaacacct    4980
tcccttcaag ccgggcagtc aagccgccat tcacccgggc agcatcacgg gctttgtaa    5040 gcgcatggac gctgacgccg tgccgacccg gggcgagacg attgggaaga agaccgcttc    5100
aagcgcctgg gacccggcaa ccgttatgcg aatccttcgg gacccgcgta ttgcgggctt    5160
cgccgctgag gtgatctaca agaagaagcc ggacggcacg ccgaccacga agattgaggg    5220
ttaccgcatt cagcgcgacc cgatcacgct ccggccggtc gagcttgatt gcggaccgat    5280
catcgagccc gctgagtggt atgagcttca ggcgtggttg gacggcaggg ggcgcggcaa    5340
ggggctttcc cggggcaag ccattctgtc cgccatggac aagctgtact gcgagtgtgg    5400
cgccgtcatg acttcgaagc gcggggaaga atcgatcaag gactcttacc gctgccgtcg    5460
ccggaaggtg gtcgacccgt ccgcacctgg gcagcacgaa ggcacgtgca acgtcagcat    5520
ggcggcactc gacaagttcg ttgcggaacg catcttcaac aagatcaggc acgccgaagg    5580
cgacgaagag acgttggcgc ttctgtggga agccgcccga cgcttcggca agctcactga    5640
ggcgcctgag aagagcggcg aacgggcgaa ccttgttgcg gagcgcgccg acgccctgaa    5700
cgcccttgaa gagctgtacg aagaccgcgc ggcaggcgcg tacgacggac ccgttggcag    5760
gaagcacttc cggaagcaac aggcagcgct gacgctccgg cagcaagggg cggaagagcg    5820
gcttgccgaa cttgaagccg ccgaagcccc gaagcttccc cttgaccaat ggttccccga    5880
agacgccgac gctgacccga ccggccctaa gtcgtggtgg gggcgcgcgt cagtagacga    5940
caagcgcgtg ttcgtcgggc tcttcgtaga caagatcgtt gtcacgaagt cgactacggg    6000 caggggggcag ggaacgccca tcgagaagcg cgcttcgatc acgtgggcga agccgccgac    6060
cgacgacgac gaagacgacg cccaggacgg cacggaagac gtagcggcgt aggtgagtga    6120
agatctagac gtggcaccgc gatgctgttg tgggcacaat cgtgccggtt ggtaggatcc    6180
acatatggaa ataagttcgc tctccaccga cggctcccg cggatcgacg gggagagtcc    6240
cgagcacgtg gaaatgctgg ccgccgccga caccgcgctt ccaccgatca tggtgcaccg    6300
ccgcaccggg cgggtcatcg acggcatgca ccggctgcgc gccgcgatgc tgacgggccg    6360
tacgacgatc gcggtgaggt tcttcgacgg caccgaggag gacgccttcg tcctcgccgt    6420
gaagtcgaac atcgcgcacg gactgccgct gtccgccgcc gaccgccggc gggccgccgg    6480
gcgcatcatg gccaccccatc cccggtggtc ggaccggatg atcgcctcgg tggtcggcac    6540
ctccgccagg acgtcgccg agatccgccg cgacgccggc gccgcggggg cggggagcc    6600 cacccgcatc ggccgggacg gcagggtacg gcccgtcgac gtgagcgagg gccgcagact    6660
ggcccacgac atgatcgtcc gcgacccggg cctgtcgctg cgccaggtcg cccgcgccgc    6720
```

```
cgggatctcg ccggagaccg tcaggacgt cagacaccgg atgctccgcg gtgaggaccc      6780
ggtgcccgcg ccgcggccgc ggaccctggt ggagcgcggc gcggaccgcc gggcggagcc      6840
ggccgggaag gccgccgcgc cgtgcgggac ggagccgccg cccgccgtcg tgatgaagcg      6900
gctgagggcc gatccggcgc tgcgtctcaa cgagaacgga cgcgacctgc tgcggcttct      6960
ggatatccac acggtccggc tggaggactg gaaccgcatt atcgaaagcg tgccgccgca      7020
ccgtctggag acggtggcgc agctggcacg ctcctgcgcc gacaaatggt ccgagatcgc      7080
gtcacgcatc gaaagcaacg catcacatct ggccgggtga                           7120
```

<210> SEQ ID NO 21
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 21

```
gtggcaattt aaatggaaat gtgcgcggaa                                        30
```

<210> SEQ ID NO 22
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 22

```
tatatagagc tcaacttggt ctgacagtta c                                      31
```

<210> SEQ ID NO 23
<211> LENGTH: 7162
<212> TYPE: DNA
<213> ORGANISM: Artificial sequence
<220> FEATURE:
<223> OTHER INFORMATION: Synthetic pXY152-endorf24-blatsr

<400> SEQUENCE: 23

```
gaattcgtaa tcatgtcata gctgtttcct gtgtgaaatt gttatccgct cacaattcca        60
cacaacatac gagccggaag cataaagtgt aaagcctggg gtgcctaatg agtgagctaa       120
ctcacattaa ttgcgttgcg ctcactgccc gctttccagt cgggaaacct gtcgtgccag       180
ctgcattaat gaatcggcca acgcgcgggg agaggcggtt tgcgtattgg gcgctcttcc       240
gcttcctcgc tcactgactc gctgcgctcg gtcgttcggc tgcggcgagc ggtatcagct       300
cactcaaagg cggtaatacg gttatccaca gaatcagggg ataacgcagg aaagaacatg       360
tgagcaaaag gccagcaaaa ggccaggaac cgtaaaaagg ccgcgttgct ggcgtttttc       420
cataggctcc gcccccctga cgagcatcac aaaaatcgac gctcaagtca gaggtggcga       480
aacccgacag gactataaag ataccaggcg tttccccctg gaagctccct cgtgcgctct       540
cctgttccga ccctgccgct taccggatac ctgtccgcct ttctcccttc gggaagcgtg       600
gcgctttctc atagctcacg ctgtaggtat ctcagttcgg tgtaggtcgt tcgctccaag       660
ctgggctgtg tgcacgaacc ccccgttcag cccgaccgct gcgccttatc cggtaactat       720
cgtcttgagt ccaacccggt aagacacgac ttatcgccac tggcagcagc cactggtaac       780
aggattagca gagcgaggta tgtaggcggt gctacagagt tcttgaagtg gtggcctaac       840
tacggctaca ctagaagaac agtatttggt atctgcgctc tgctgaagcc agttaccttc       900
ggaaaaagag ttggtagctc ttgatccggc aaacaaacca ccgctggtag cggtggtttt       960
```

```
tttgtttgca agcagcagat tacgcgcaga aaaaaaggat ctcaagaaga tcctttgatc    1020
ttttctacgg ggtctgacgc tcagtggaac gaaaactcac gttaagggat tttggtcatg    1080
agattatcaa aaaggatctt cacctagatc cttttggttc atgtgcagct ccatcagcaa    1140
aaggggatga taagtttatc accaccgact atttgcaaca gtgccgttga tcgtgctatg    1200
atcgactgat gtcatcagcg gtggagtgca atgtcgtgca atacgaatgg cgaaaagccg    1260
agctcaactt ggtctgacag ttaccaatgc ttaatcagtg aggcacctat ctcagcgatc    1320
tgtctatttc gttcatccat agttgcctga ctccccgtcg tgtagataac tacgatacgg    1380
gagggcttac catctggccc cagtgctgca atgataccgc gagacccacg ctcaccggct    1440
ccagatttat cagcaataaa ccagccagcc ggaagggccg agcgcagaag tggtcctgca    1500
actttatccg cctccatcca gtctattaat tgttgccggg aagctagagt aagtagttcg    1560
ccagttaata gtttgcgcaa cgttgttgcc attgctacag gcatcgtggt gtcacgctcg    1620
tcgtttggta tggcttcatt cagctccggt tcccaacgat caaggcgagt tacatgatcc    1680
cccatgttgt gcaaaaaagc ggttagctcc ttcggtcctc cgatcgttgt cagaagtaag    1740
ttggccgcag tgttatcact catggttatg gcagcactgc ataattctct tactgtcatg    1800
ccatccgtaa gatgcttttc tgtgactggt gagtactcaa ccaagtcatt ctgagaatag    1860
tgtatgcggc gaccgagttg ctcttgcccg gcgtcaatac gggataatac cgcgccacat    1920
agcagaactt taaaagtgct catcattgga aaacgttctt cggggcgaaa actctcaagg    1980
atcttaccgc tgttgagatc cagttcgatg taacccactc gtgcacccaa ctgatcttca    2040
gcatctttta ctttcaccag cgtttctggg tgagcaaaaa caggaaggca aaatgccgca    2100
aaaaagggaa taagggcgac acggaaatgt tgaatactca tactcttcct ttttcaatat    2160
tattgaagca tttatcaggg ttattgtctc atgagcggat acatatttga atgtatttag    2220
aaaaataaac aaataggggt tccgcgcaca tttccattta ataccgcgc gggtcccgga    2280 cggggaagag cggggagctt tgccagagag cgacgacttc cccttgcgtt ggtgattgcc    2340
ggtcagggca gccatccgcc atcgtcgcgt agggtgtcac accccaggaa tcgcgtcact    2400
gaacacagca gccggtagga cgaccatgac tgagttggac accatcgcaa atccgtccga    2460
tccggcggtg cagcggatca tcgatgtcac caagccgtcg cgatccaaca taaagacaac    2520
gttgatcgag gacgtcgagc ccctcatgca cagcatcgcg gccggggtgg agttcatcga    2580
ggtctacggc agcgacagca gtccttttcc atctgagttg ctggatctgt gcgggcggca    2640
gaacataccg gtccgcctca tcgactcctc gatcgtcaac cagttgttca ggggggagcg    2700
gaaggccaag acattcggca tcgcccgcgt ccctcgcccg gccaggttcg gcgacatcgc    2760
gagccggcgt ggggacgtcg tcgttctcga cggggtgaag atcgtcggga acatcggcgc    2820
gatagtacgc acgtcgctcg cgctcggagc gtcgggggatc atcctggtcg acagtgacat    2880
caccagcatc gcggaccggc gtctccaaag ggccagccga ggttacgtct tctcccttcc    2940
cgtcgttctc tccggtcgcg aggaggccat cgccttcatt cgggacagcg gtatgcaact    3000
gatgacgctc aaggcggatg gcgacatttc cgtgaaggaa ctcggggaca atccggatcg    3060
gctggccttg ctgttcggca gcgaaaaggg tgggccttcc gacctgttcg aggaggcgtc    3120
ttccgcctcg gtttccatcc ccatgatgag ccagaccgag tctctcaacg tttccgtttc    3180
cctcggaatc gcgctgcacg agaggatcga caggaatctc gcggccaacc gataagctag    3240
ctagagtcga cctgcaggtc cccggggatc ggtcttgcct tgctcgtcgg tgatgtactt    3300
```

```
caccagctcc gcgaagtcgc tcttcttgat ggagcgcatg gggacgtgct tggcaatcac    3360
gcgcaccccc cggccgtttt agcggctaaa aaagtcatgg ctctgccctc gggcggacca    3420
cgcccatcat gaccttgcca agctcgtcct gcttctcttc gatcttcgcc agcagggcga    3480
ggatcgtggc atcaccgaac cgcgccgtgc gcggtcgtc ggtgagccag agtttcagca    3540
ggccgcccag gcggcccagg tcgccattga tgcgggccag ctcgcggacg tgctcatagt    3600
ccacgacgcc cgtgattttg tagccctggc cgacggccag caggtaggcc gacaggctca    3660
tgccggccgc cgccgccttt tcctcaatcg ctcttcgttc gtctggaagg cagtacacct    3720
tgataggtgg gctgcccttc ctggttggct tggtttcatc agccatccgc ttgccctcat    3780
ctgttacgcc ggcggtagcc ggccagcctc gcagagcagg attcccgttg agcaccgcca    3840
ggtgcgaata agggacagtg aagaaggaac acccgctcgc gggtgggcct acttcaccta    3900
tcctgcccgg ctgacgccgt tggatacacc aaggaaagtc tacacgaacc ctttggcaaa    3960
atcctgtata tcgtgcgaaa aaggatggat ataccgaaaa aatcgctata atgaccccga    4020
agcagggtta tgcagcggaa aagatccgtc gacctgcagg catgcaagct ctagcgattc    4080
cagacgtccc gaaggcgtgg cgcggcttcc ccgtgccgga gcaatcgccc tgggtgggtt    4140
acacgacgcc cctctatggc ccgtactgac ggacacaccg aagccccggc ggcaaccctc    4200
agcggatgcc ccggggcttc acgttttccc aggtcagaag cggttttcgg gagtagtgcc    4260
ccaactgggg taacctttga gttctctcag ttggggcgt agggtcgccg acatgacaca    4320
aggggttgtg accggggtgg acacgtacgc gggtgcttac gaccgtcagt cgcgcgagcg    4380
cgagaactcg agcgcagcaa gcccagcgac acagcgtagc gccaacgaag acaaggcggc    4440
cgaccttcag cgcgaagtcg agcgcgacgg gggccggttc aggttcgtcg ggcatttcag    4500
cgaagcgccg ggcacgtcgg cgttcgggac ggcgagcgc ccggagttcg aacgcatcct    4560
gaacgaatgc cgcgccgggc ggctcaacat gatcattgtc tatgacgtgt cgcgcttctc    4620
gcgcctgaag gtcatggacg cgattccgat tgtctcggaa ttgctcgccc tgggcgtgac    4680
gattgtttcc actcaggaag gcgtcttccg gcagggaaac gtcatggacc tgattcacct    4740
gattatgcgc ctcgacgcgt cgcacaaaga atcttcgctg aagtcggcga agattctcga    4800
cacgaagaac cttcagcgcg aattgggcgg gtacgtcggc gggaaggcgc cttacggctt    4860
cgagcttgtt tcggagacga aggagatcac gcgcaacggc cgaatggtca atgtcgtcat    4920
caacaagctt gcgcactcga ccactcccct taccggaccc ttcgagttcg agcccgacgt    4980
aatccggtgg tggtggcgtg agatcaagac gcacaaacac cttcccttca agccgggcag    5040
tcaagccgcc attcacccgg gcagcatcac ggggctttgt aagcgcatgg acgctgacgc    5100
cgtgccgacc cggggcgaga cgattgggaa gaagaccgct tcaagcgcct gggacccggc    5160
aaccgttatg cgaatccttc gggacccgcg tattgcgggc ttcgccgctg aggtgatcta    5220
caagaagaag ccggacggca cgccgaccac gaagattgag ggttaccgca ttcagcgcga    5280
cccgatcacg ctccggccgg tcgagcttga ttgcggaccg atcatcgagc ccgctgagtg    5340
gtatgagctt caggcgtggt tggacggcag ggggcgcggc aaggggcttt ccgggggca    5400 agccattctg tccgccatgg acaagctgta ctgcgagtgt ggcgccgtca tgacttcgaa    5460
gcgcggggaa gaatcgatca aggactctta ccgctgccgt cgccggaagg tggtcgaccc    5520
gtccgcacct gggcagcacg aaggcacgtg caacgtcagc atggcggcac tcgacaagtt    5580
cgttgcggaa cgcatcttca acaagatcag gcacgccgaa ggcgacgaag agacgttggc    5640
gcttctgtgg gaagccgccc gacgcttcgg caagctcact gaggcgcctg agaagagcgg    5700
```

```
cgaacgggcg aaccttgttg cggagcgcgc cgacgccctg aacgcccttg aagagctgta    5760
cgaagaccgc gcggcaggcg cgtacgacgg acccgttggc aggaagcact tccggaagca    5820
acaggcagcg ctgacgctcc ggcagcaagg ggcggaagag cggcttgccg aacttgaagc    5880
cgccgaagcc ccgaagcttc cccttgacca atggttcccc gaagacgccg acgctgaccc    5940
gaccggccct aagtcgtggt ggggcgcgc gtcagtagac gacaagcgcg tgttcgtcgg    6000
gctcttcgta gacaagatcg ttgtcacgaa gtcgactacg ggcaggggc agggaacgcc    6060 catcgagaag cgcgcttcga tcacgtgggc gaagccgccg accgacgacg acgaagacga    6120
cgcccaggac ggcacggaag acgtagcggc gtaggtgagt gaagatctag acgtggcacc    6180
gcgatgctgt tgtgggcaca atcgtgccgg ttggtaggat ccacatatgg aaataagttc    6240
gctctccacc gacggctccc cgcggatcga cggggagagt cccgagcacg tggaaatgct    6300
ggccgccgcc gacaccgcgc ttccaccgat catggtgcac cgccgcaccg gcgggtcat    6360 cgacggcatg caccggctgc gcgccgcgat gctgacgggc cgtacgacga tcgcggtgag    6420
gttcttcgac ggcaccgagg aggacgcctt cgtcctcgcc gtgaagtcga acatcgcgca    6480
cggactgccg ctgtccgccg ccgaccgccg gcgggccgcc gggcgcatca tggccaccca    6540
tccccggtgg tcgaccgga tgatcgcctc ggtggtcggc acctccgcca ggacggtcgc    6600
cgagatccgc cgcgacgccg gcgcgccgg gcgggggag cccacccgca tcggccggga    6660
cggcagggta cggcccgtcg acgtgagcga gggccgcaga ctggcccacg acatgatcgt    6720
ccgcgacccg ggcctgtcgc tgcgccaggt cgcccgcgcc gccgggatct cgccggagac    6780
cgtcagggac gtcagacacc ggatgctccg cggtgaggac ccggtgcccg cgccgcggcc    6840
gcggaccctg gtggagcgcg gcgcggaccg ccgggcggag ccggccggga aggccgccgc    6900
gccgtgcggg acggagccgc cgcccgccgt cgtgatgaag cggctgaggg ccgatccggc    6960
gctgcgtctc aacgagaacg gacgcgacct gctgcggctt ctggatatcc acacggtccg    7020
gctggaggac tggaaccgca ttatcgaaag cgtgccgccg caccgtctgg agacggtggc    7080
gcagctggca cgctcctgcg ccgacaaatg gtccgagatc gcgtcacgca tcgaaagcaa    7140
cgcatcacat ctggccgggt ga                                             7162
```

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 24
aaggagaaga gccttcagaa ggaa                                              24

<210> SEQ ID NO 25
<211> LENGTH: 321
<212> TYPE: PRT
<213> ORGANISM: S. griseus

<400> SEQUENCE: 25

Met Asp Pro Thr Arg Val Asp Ile Phe Ala Leu Pro Ala Val Glu Ile
1               5                   10                  15

Glu Leu Ser Arg Leu Ser Ser Ala Ser Ser Pro Arg Thr Ser Gly Glu
            20                  25                  30

Asp Pro Glu His Val Glu Thr Leu Leu Ser Ala Glu Gly Glu Leu Pro
        35                  40                  45

```
Pro Ile Leu Val His Arg Pro Thr Met Gln Val Leu Asp Gly Leu His
    50                  55                  60

Arg Leu Lys Val Ala Arg Val Arg Gly Asp Thr Lys Ile Leu Ala Arg
65                  70                  75                  80

Leu Val Asp Ala Thr Glu Ser Asp Ala Phe Val Leu Ala Val Glu Ala
                85                  90                  95

Asn Ile Arg His Gly Leu Pro Leu Ser Leu Ala Asp Arg Lys Arg Ala
            100                 105                 110

Ala Val Gln Ile Ile Gly Thr His Pro Gln Trp Ser Asp Arg Arg Val
        115                 120                 125

Ala Ser Ala Thr Gly Ile Ser Ala Gly Thr Val Ala Asp Leu Arg Arg
    130                 135                 140

Arg Ala Gly Glu Asp Gly Thr Glu Ala Arg Ile Gly Arg Asp Gly Arg
145                 150                 155                 160

Val Arg Pro Ser Asp Gly Ser Glu Arg Arg Leu Ala Ala Glu Leu
                165                 170                 175

Ile Arg Ser Asp Pro Gly Leu Ser Leu Arg Gln Val Ala Lys Gln Val
            180                 185                 190

Gly Ile Ser Pro Glu Thr Val Arg Asp Val Arg Gly Arg Leu Glu Arg
        195                 200                 205

Gly Glu Ser Pro Thr Pro Asp Gly Thr Arg Arg Leu Pro Ala Lys Pro
    210                 215                 220

His Pro Leu Arg Leu Ser Glu Pro Asp Phe Gly Arg Ala Val Asp Gln
225                 230                 235                 240

Asp Arg Leu Ala Leu Leu Glu Arg Leu Lys Ser Asp Pro Ala Leu Arg
                245                 250                 255

Leu Asn Glu Val Gly Arg Ile Leu Leu Arg Met Leu Thr Met His Ser
            260                 265                 270

Met Asp Gly Gln Glu Trp Glu Arg Ile Leu Gln Gly Val Pro Pro His
        275                 280                 285

Leu His Gly Val Ile Ala Gly Phe Ala Arg Asp His Ala Arg Val Trp
    290                 295                 300

Ala Glu Phe Ala Asp His Leu Glu Ser Arg Ala Thr Glu Leu Ala Ala
305                 310                 315                 320

Gly

<210> SEQ ID NO 26
<211> LENGTH: 311
<212> TYPE: PRT
<213> ORGANISM: Streptomyces fungicidicus

<400> SEQUENCE: 26

Val Glu Ile Ser Ser Leu Ser Thr Asp Gly Ser Pro Arg Ile Asp Gly
1               5                   10                  15

Glu Ser Pro Glu His Val Glu Met Leu Ala Ala Asp Thr Ala Leu
            20                  25                  30

Pro Pro Ile Met Val His Arg Thr Gly Arg Val Ile Asp Gly Met
        35                  40                  45

His Arg Leu Arg Ala Ala Met Leu Thr Gly Arg Thr Thr Ile Ala Val
    50                  55                  60

Arg Phe Phe Asp Gly Thr Glu Glu Asp Ala Phe Val Leu Ala Val Lys
65                  70                  75                  80

Ser Asn Ile Ala His Gly Leu Pro Leu Ser Ala Ala Asp Arg Arg Arg
                85                  90                  95
```

```
Ala Ala Gly Arg Ile Met Ala Thr His Pro Arg Trp Ser Asp Arg Met
            100                 105                 110

Ile Ala Ser Val Val Gly Thr Ser Ala Arg Thr Val Ala Glu Ile Arg
            115                 120                 125

Arg Asp Ala Gly Ala Ala Gly Ala Gly Glu Pro Thr Arg Ile Gly Arg
130                 135                 140

Asp Gly Arg Val Arg Pro Val Asp Val Ser Glu Gly Arg Arg Leu Ala
145                 150                 155                 160

His Asp Met Ile Val Arg Asp Pro Gly Leu Ser Leu Arg Gln Val Ala
                165                 170                 175

Arg Ala Ala Gly Ile Ser Pro Glu Thr Val Arg Asp Val Arg His Arg
            180                 185                 190

Met Leu Arg Gly Glu Asp Pro Val Pro Ala Pro Arg Pro Arg Thr Leu
        195                 200                 205

Val Glu Arg Gly Ala Asp Arg Arg Ala Glu Pro Ala Gly Lys Ala Ala
    210                 215                 220

Ala Pro Cys Gly Thr Glu Pro Pro Ala Val Val Met Lys Arg Leu
225                 230                 235                 240

Arg Ala Asp Pro Ala Leu Arg Leu Asn Glu Asn Gly Arg Asp Leu Leu
                245                 250                 255

Arg Leu Leu Asp Ile His Thr Val Arg Leu Glu Asp Trp Asn Arg Ile
            260                 265                 270

Ile Glu Ser Val Pro Pro His Arg Leu Glu Thr Val Ala Gln Leu Ala
        275                 280                 285

Arg Ser Cys Ala Asp Lys Trp Ser Glu Ile Ala Ser Arg Ile Glu Ser
    290                 295                 300

Asn Ala Ser His Leu Ala Gly
305                 310

<210> SEQ ID NO 27
<211> LENGTH: 15
<212> TYPE: DNA
<213> ORGANISM: Artificial sequence
<220> FEATURE:
<223> OTHER INFORMATION: Synthetic oligonucleotide primer

<400> SEQUENCE: 27
gtgtttaatt aatga                                                         15

<210> SEQ ID NO 28
<211> LENGTH: 321
<212> TYPE: PRT
<213> ORGANISM: Amycolatopsis

<400> SEQUENCE: 28

Met Asp Pro Thr Arg Val Asp Ile Phe Ala Leu Pro Ala Val Glu Ile
1               5                   10                  15

Glu Leu Ser Arg Leu Ser Ser Ala Ser Ser Pro Arg Thr Ser Gly Glu
            20                  25                  30

Asp Pro Glu His Val Glu Thr Leu Leu Ser Ala Glu Gly Glu Leu Pro
        35                  40                  45

Pro Ile Leu Val His Arg Pro Thr Met Gln Val Leu Asp Gly Leu His
    50                  55                  60

Arg Leu Lys Val Ala Arg Val Arg Gly Asp Thr Lys Ile Leu Ala Arg
65                  70                  75                  80

Leu Val Asp Ala Thr Glu Ser Asp Ala Phe Val Leu Ala Val Glu Ala
```

```
                    85                  90                  95
Asn Ile Arg His Gly Leu Pro Leu Ser Leu Ala Asp Arg Lys Arg Ala
                100                 105                 110

Ala Val Gln Ile Ile Gly Thr His Pro Gln Trp Ser Asp Arg Arg Val
                115                 120                 125

Ala Ser Ala Thr Gly Ile Ser Ala Gly Thr Val Ala Asp Leu Arg Arg
130                 135                 140

Arg Ala Gly Glu Asp Gly Thr Glu Ala Arg Ile Gly Arg Asp Gly Arg
145                 150                 155                 160

Val Arg Pro Ser Asp Gly Ser Glu Arg Arg Leu Ala Ala Glu Leu
                165                 170                 175

Ile Arg Ser Asp Pro Gly Leu Ser Leu Arg Gln Val Ala Lys Gln Val
                180                 185                 190

Gly Ile Ser Pro Glu Thr Val Arg Asp Val Arg Gly Arg Leu Glu Arg
                195                 200                 205

Gly Glu Ser Pro Thr Pro Asp Gly Thr Arg Arg Leu Pro Ala Lys Pro
                210                 215                 220

His Pro Leu Arg Leu Ser Glu Pro Asp Phe Gly Arg Ala Val Asp Gln
225                 230                 235                 240

Asp Arg Leu Ala Leu Leu Glu Arg Leu Lys Ser Asp Pro Ala Leu Arg
                245                 250                 255

Leu Asn Glu Val Gly Arg Ile Leu Leu Arg Met Leu Thr Met His Ser
                260                 265                 270

Met Asp Gly Gln Glu Trp Glu Arg Ile Leu Gln Gly Val Pro Pro His
                275                 280                 285

Leu His Gly Val Ile Ala Gly Phe Ala Arg Asp His Ala Arg Val Trp
                290                 295                 300

Ala Glu Phe Ala Asp His Leu Glu Ser Arg Ala Thr Glu Leu Ala Ala
305                 310                 315                 320

Gly

<210> SEQ ID NO 29
<211> LENGTH: 395
<212> TYPE: PRT
<213> ORGANISM: S. kasugaensis

<400> SEQUENCE: 29

Met Ala Glu Thr Val Arg Ala Asp Ser Pro Leu Lys Ser Ser Tyr Arg
1               5                   10                  15

Asn Val Pro Ala Ala Glu Val Gln Gly Ser Gly Leu Ser Val Gly Gln
                20                  25                  30

Arg Thr Thr Arg Ile Ala Ile Ser Ser Leu Leu Ala Ala Asp Ser Pro
                35                  40                  45

Arg Ser Ala Gly Glu Asn Ala Glu His Ile Arg Leu Leu Ala Asp Ser
50                  55                  60

Gly Ala Arg Leu Pro Pro Ile Val Val Gln Arg Ser Thr Met Arg Val
65                  70                  75                  80

Ile Asp Gly Met His Arg Leu Arg Ala Ala Leu Arg Gly Glu Thr
                85                  90                  95

Glu Ile Glu Val Arg Phe Phe Asp Gly Ala Glu Asp Ser Phe Leu
                100                 105                 110

Leu Ala Val Arg Ser Asn Ile Ala His Gly Leu Pro Leu Ser Gln Glu
                115                 120                 125

Glu Arg Ala Ala Ala Ala Gln Arg Ile Ile Arg Ser His Ala Gln Trp
```

```
            130                 135                 140
Ser Asn Gln Ala Ile Gly Glu Val Thr Gly Leu Asp Ala Lys Thr Ile
145                 150                 155                 160

Ala Ala Leu Arg Arg Asp Ala Lys Asp Val Pro Gln Leu Asp Ala Arg
                165                 170                 175

Ile Gly Arg Asp Gly Arg Val Arg Pro Val Asp Gly Ala Gln Gly Arg
            180                 185                 190

Arg Leu Ala Gly Glu Leu Met Ala Glu Gln Pro Asp Ala Pro Leu Arg
        195                 200                 205

Lys Ile Ala His Ala Ala Gly Val Ser Leu Gly Thr Ala Ser Asp Val
    210                 215                 220

Arg Arg Arg Ile Arg Asn Gly Gln Asp Pro Val Pro Ala Gly Arg Gln
225                 230                 235                 240

Lys Ala Asp Pro Gln Pro Pro Ala Arg Tyr Ala Ala Ser Glu Asp Arg
                245                 250                 255

Ser Gly Thr Thr Ala Pro Arg Thr Gly Glu Gln Asn Arg Arg Val Leu
            260                 265                 270

Leu Gln Lys Leu Arg Lys Asp Pro Ser Leu Arg Cys Asn Glu Ala Gly
        275                 280                 285

Arg Ala Leu Leu Arg Trp Leu Glu Val Gln Ala Val Glu Gly Glu Asp
    290                 295                 300

Trp Glu Arg Leu Leu Asp Ser Val Pro Met His Cys Ala Ala Thr Ile
305                 310                 315                 320

Val Glu Leu Ala Arg Arg Lys Asp Pro Ser Leu Arg Cys Asn Glu Ala
                325                 330                 335

Gly Arg Ala Leu Leu Arg Trp Leu Glu Val Gln Ala Val Glu Gly Glu
            340                 345                 350

Asp Trp Glu Arg Leu Leu Asp Ser Val Pro Met His Cys Ala Ala Thr
        355                 360                 365

Ile Val Glu Leu Ala Arg Gly Cys Ser Gly Val Trp Gln Asp Phe Ala
    370                 375                 380

Ala Gln Leu Glu Arg Arg Gly Arg Ala Ser Ala
385                 390                 395

<210> SEQ ID NO 30
<211> LENGTH: 367
<212> TYPE: PRT
<213> ORGANISM: S. niveus

<400> SEQUENCE: 30

Met Thr Asn Ser Gly Asp Glu Glu Ile Thr Pro Ala Ser Leu Lys Ala
1               5                   10                  15

Thr Arg Lys Gly Glu Arg Val Ser Ile Gly Ser Leu Leu Pro Pro Ser
            20                  25                  30

Glu Leu Val Arg Ser Gly Glu Ser Thr Glu His Ile Arg Val Leu Ala
        35                  40                  45

Glu Thr Asp Glu Asp Leu Pro Pro Ile Val Val His Arg Gly Thr Arg
    50                  55                  60

Arg Val Val Asp Gly Met His Arg Leu Trp Ala Ala Arg Phe Arg Gly
65                  70                  75                  80

Asp Glu Ser Ile Glu Val Val Phe Val Asp Gly Ser Pro Ala Asp Val
                85                  90                  95

Phe Val Leu Ala Val Glu Leu Asn Arg Ala His Gly Leu Pro Leu Thr
            100                 105                 110
```

Leu Asp Glu Arg Lys Ser Ala Ala Gln Ile Met Asp Ser His Pro
            115                 120                 125

His Trp Ser Asp Arg Lys Ile Ala Arg Thr Thr Gly Leu Ala Ala Ser
130                 135                 140

Thr Val Ala Ser Leu Arg Ser Ser Ser Thr Ala Gly Thr Val Gly Arg
145                 150                 155                 160

Arg Thr Gly Gln Asp Gly Arg Ser Arg Pro Asn Asp Gly Thr Asp Gly
                165                 170                 175

Arg Gln Arg Ala Ala Leu Leu Ala Arg Asn Pro Asn Ala Ser Leu
            180                 185                 190

Arg Glu Val Thr Arg Ala Ala Gly Ile Ser Val Gly Thr Ala Ser Asp
            195                 200                 205

Val Arg Ala Arg Leu Arg Arg Gly Glu Pro Ala Leu Thr Ala Arg Gln
            210                 215                 220

Gln Ala Val Met Lys Leu Arg Pro Ala Ala Arg Asn Pro Asn Ala Ser
225                 230                 235                 240

Leu Arg Glu Val Thr Arg Ala Ala Gly Ile Ser Val Gly Thr Ala Ser
                245                 250                 255

Asp Val Arg Ala Arg Leu Arg Arg Gly Glu Pro Ala Leu Thr Ala Arg
            260                 265                 270

Gln Gln Ala Val Met Lys Leu Arg Pro Ala Ala Gln Arg Ser Gly
            275                 280                 285

Pro Asp Tyr Gly Arg Val Leu Glu Asn Leu Arg Lys Asp Pro Ser Leu
            290                 295                 300

Arg Phe Thr Asp Leu Gly Arg Arg Leu Leu Arg Leu Asp Gly Ser
305                 310                 315                 320

Val Pro Gly Ser Val Glu Gln Ile Ala Gln Ile Ala Asp Gly Val Pro
                325                 330                 335

Glu His Cys Arg Thr Val Val Asp Met Ala Arg Glu Cys Ala Ala
            340                 345                 350

Ala Trp Gln His Leu Ala Asp Gln Leu Ala Asp Arg Asp Thr Ala
            355                 360                 365

<210> SEQ ID NO 31
<211> LENGTH: 359
<212> TYPE: PRT
<213> ORGANISM: S. globisporus

<400> SEQUENCE: 31

Met Lys Ser Asp Ser Ala Gln Arg Ala Val Glu Arg Ser Arg Arg Val
1               5                   10                  15

Val Arg Ile Asp Glu Leu Ile Pro Ala Asp Ser Pro Arg Leu Asn Gly
            20                  25                  30

Ile Asp Arg Ser His Val Gln Arg Leu Ala Thr Val Tyr Ala Ser Leu
        35                  40                  45

Pro Pro Val Leu Val His Arg Pro Thr Met Arg Val Val Asp Gly Met
    50                  55                  60

His Arg Ile Gly Ala Ala Arg Leu Lys Gly Leu Asp Thr Val Glu Val
65                  70                  75                  80

Thr Phe Phe Glu Gly Ala Glu Glu Gln Val Phe Leu Arg Ser Val Ala
                85                  90                  95

Ala Asn Ile Thr Asn Gly Leu Pro Leu Ser Val Ala Asp Arg Lys Thr
            100                 105                 110

Ala Ala Ala Arg Ile Leu Ala Ser His Pro Thr Leu Ser Asp Arg Ala
        115                 120                 125

```
Val Ala Ala His Val Gly Leu Asp Ala Lys Thr Val Ala Gly Val Arg
            130                 135                 140

Thr Cys Ser Ala Ala Gly Ser Pro Leu Leu Asn Met Arg Thr Gly Ala
145                 150                 155                 160

Asp Gly Arg Val His Pro Leu Asp Arg Thr Ala Glu Arg Leu His Ala
                165                 170                 175

Ala Ala Leu Leu Thr Gln Asp Pro Gly Leu Pro Leu Arg Ser Val Val
            180                 185                 190

Glu Gln Thr Gly Leu Ser Leu Gly Thr Ala His Asp Val Arg Arg Arg
            195                 200                 205

Leu Leu Arg Gly Glu Asp Pro Val Pro Gln Asn Arg Gln Ser Ala Met
    210                 215                 220

Leu Glu Pro Gly Leu Ala Pro Gln Lys Lys Ala Thr Ala Lys Pro Pro
225                 230                 235                 240

Val Gly Pro Ala Ala Arg Pro Val Pro Lys Val Pro Ala Val Ala
                245                 250                 255

Gly Arg Pro Pro Val Ser Pro Arg Ser Arg Ala Pro Leu Glu Ala Leu
            260                 265                 270

Arg Lys Leu Ser Asn Asp Pro Ser Leu Arg His Ser Asp Gln Gly Arg
            275                 280                 285

Glu Leu Met Arg Trp Leu His Asn Arg Phe Val Asp Glu Ala Trp
    290                 295                 300

Arg Arg Arg Ala Asp Ala Val Pro Ala His Cys Val Asp Ser Met Ala
305                 310                 315                 320

Glu Leu Ala Gln His Cys Ser Asp Ala Trp His Arg Phe Ala Glu Glu
                325                 330                 335

Met Val Arg Arg Arg His Ser Ala Ala Ala Asp Gly Ser Gly Leu Arg
                340                 345                 350

Thr Thr Gln Pro Thr Arg Arg
            355
```

<210> SEQ ID NO 32
<211> LENGTH: 329
<212> TYPE: PRT
<213> ORGANISM: Actinoplanes teichomyceticus

<400> SEQUENCE: 32

```
Met Thr Pro Asp Glu Glu Ala Leu Asn Arg Gln Pro Ile Met Glu Met
1               5                   10                  15

Glu Ile Ser Ser Leu Ser Leu Gly Gly Ser Pro Arg Leu Ala Gly Gly
            20                  25                  30

Asp Pro Val His Leu Glu Ala Met Val Ala Ala Gln Gly Glu Leu Pro
            35                  40                  45

Pro Ile Val Val His Arg Pro Thr Met Arg Val Ile Asp Gly Ser His
    50                  55                  60

Arg Ile Gln Ala Ala Leu Arg Arg Gly Glu Thr Thr Ile Ala Gly Arg
65                  70                  75                  80

Phe Phe Asp Gly Ser Asp Asp Glu Ala Phe Val Met Ser Val Trp Leu
                85                  90                  95

Asn Val Ser His Gly Leu Pro Leu Ala Leu Ala Asp Arg Lys Arg Ala
                100                 105                 110

Ala Glu Arg Ile Ala Val Ser His Pro Gln Trp Ser Asp Arg Arg Val
            115                 120                 125

Ala Ala Val Thr Gly Ile Ser Pro Ser Thr Val Ala Asp Ile Arg Arg
```

```
            130                 135                 140
Arg Val Ala Gly Thr Ser Ala Pro Glu Ala Ser Arg Ile Gly Gln Asp
145                 150                 155                 160

Gly Arg Val Arg Pro Leu Asp Cys Ser Ala Gly Arg Leu Leu Ala Gly
                165                 170                 175

Arg Leu Met Ala Glu Asn Pro Ala Leu Ser Leu Arg Gln Val Ala Lys
            180                 185                 190

Ala Ala Ala Ile Ser Pro Glu Thr Ala Arg Asp Val Arg Asn Arg Leu
        195                 200                 205

Leu Ser Gly Ala Glu Leu Val Pro Asn Arg Arg Pro Arg Asp Ala Ala
    210                 215                 220

Pro Val Gly Val Lys Gly Arg Asp Arg Arg Pro Leu Asn Leu Ile
225                 230                 235                 240

Arg Ser Gly Asp Arg Pro Glu Pro Val Pro Asp His Ala Val Val Ile
                245                 250                 255

Asn Arg Leu Met Ser Asp Pro Ala Leu Arg Tyr Thr Asp Thr Gly Arg
            260                 265                 270

Asn Leu Leu Arg Leu Leu Ser Leu His Thr Arg Trp Ala Lys Glu Trp
        275                 280                 285

Glu Ala Ile Val Asp Asn Leu Pro Pro His Cys Ala Asp Ala Val Ala
    290                 295                 300

Asp Leu Ala Arg Gln Phe Ala Asp Leu Trp Ala Asp Phe Ala Ser Arg
305                 310                 315                 320

Val Gly Pro Glu Glu Arg Met Ala Ser
                325

<210> SEQ ID NO 33
<211> LENGTH: 221
<212> TYPE: PRT
<213> ORGANISM: S. coelicolor

<400> SEQUENCE: 33

Met Thr Ile Arg Leu Leu Ile Val Asp Asp Gln Glu Leu Ile Arg Thr
1               5                   10                  15

Gly Phe Arg Leu Phe Leu Gln Thr Gln Asn Asp Leu Glu Val Val Gly
            20                  25                  30

Glu Ala Asp Asp Gly His Gly Ala Leu Ala Gln Ala Ala Ala Leu Arg
        35                  40                  45

Pro Asp Val Val Leu Met Asp Ile Arg Met Pro Arg Met Asp Gly Val
    50                  55                  60

Glu Ala Thr Ser Arg Leu Thr Ala Ser Asp Ser Pro Pro Arg Val Leu
65                  70                  75                  80

Ile Leu Thr Thr Tyr Asp Leu Asp Glu Tyr Val Phe Gly Ala Leu Arg
                85                  90                  95

Ala Gly Ala Ser Gly Phe Leu Leu Lys Asp Ala Ser Arg Asp Arg Leu
            100                 105                 110

Leu Glu Ala Ile Arg Val Val His Ala Gly Glu Ala Leu Leu Ser Pro
        115                 120                 125

Ser Ile Thr Arg Arg Leu Ile Glu Asp Tyr Ala Thr Arg Ala Ala Pro
    130                 135                 140

Val Arg Pro Arg Glu Ala Val Leu Ala Gly Leu Thr Pro Arg Glu Arg
145                 150                 155                 160

Glu Ile Leu Leu Leu Val Ala Arg Gly Leu Ser Asn Pro Glu Ile Ala
                165                 170                 175
```

```
Ala Arg Leu Val Val Thr Glu Ala Thr Val Lys Ser His Val Gly Ser
            180                 185                 190

Met Phe Ala Lys Leu His Leu Arg Asp Arg Ala Gln Ala Val Val Phe
            195                 200                 205

Ala Tyr Glu Asn Ala Ile Val Leu Pro Gly Gly Thr Gly
            210                 215                 220

<210> SEQ ID NO 34
<211> LENGTH: 222
<212> TYPE: PRT
<213> ORGANISM: S. coelicolor

<400> SEQUENCE: 34

Met Ile Arg Val Leu Leu Ala Asp Asp Glu Thr Ile Ile Arg Ala Gly
1               5                   10                  15

Val Arg Ser Ile Leu Thr Thr Glu Pro Gly Ile Glu Val Val Ala Glu
            20                  25                  30

Ala Ser Asp Gly Arg Glu Ala Val Glu Leu Ala Arg Lys His Arg Pro
        35                  40                  45

Asp Val Ala Leu Leu Asp Ile Arg Met Pro Glu Met Asp Gly Leu Thr
    50                  55                  60

Ala Ala Gly Glu Met Arg Thr Thr Asn Pro Asp Thr Ala Val Val Val
65                  70                  75                  80

Leu Thr Thr Phe Gly Glu Asp Arg Tyr Ile Glu Arg Ala Leu Asp Gln
                85                  90                  95

Gly Val Ala Gly Phe Leu Leu Lys Ala Ser Asp Pro Arg Asp Leu Ile
            100                 105                 110

Ser Gly Val Arg Ala Val Ala Ser Gly Gly Ser Cys Leu Ser Pro Leu
        115                 120                 125

Val Ala Arg Arg Leu Met Thr Glu Leu Arg Arg Ala Pro Ser Pro Arg
    130                 135                 140

Ser Glu Val Ser Gly Glu Arg Thr Thr Leu Leu Thr Lys Arg Glu Gln
145                 150                 155                 160

Glu Val Leu Gly Met Leu Gly Ala Gly Leu Ser Asn Ala Glu Ile Ala
                165                 170                 175

Gln Arg Leu His Leu Val Glu Gly Thr Ile Lys Thr Tyr Val Ser Ala
            180                 185                 190

Ile Phe Thr Gln Leu Glu Val Arg Asn Arg Val Gln Ala Ala Ile Ile
        195                 200                 205

Ala Tyr Glu Ala Gly Leu Val Lys Asp Ala Asp Leu Asn Arg
    210                 215                 220

<210> SEQ ID NO 35
<211> LENGTH: 218
<212> TYPE: PRT
<213> ORGANISM: S. coelicolor

<400> SEQUENCE: 35

Met Arg Glu Asp Gly Lys Ile Arg Val Phe Leu Leu Asp Asp His Glu
1               5                   10                  15

Val Val Arg Arg Gly Val His Asp Leu Leu Ser Gly Glu Ala Asp Ile
            20                  25                  30

Glu Val Val Gly Glu Ala Gly Thr Ala Ala Glu Ala Gln Ala Arg Val
        35                  40                  45

Thr Ala Thr Arg Pro Asp Val Ala Val Leu Asp Val Arg Leu Pro Asp
    50                  55                  60
```

```
Gly Ser Gly Val Glu Val Cys Arg Asp Ile Arg Ser Arg Asp Glu Ser
65                  70                  75                  80

Val Arg Cys Leu Met Leu Thr Ser Phe Ala Asp Asp Glu Ala Leu Phe
                85                  90                  95

Asp Ala Ile Met Ala Gly Ala Ser Gly Tyr Val Leu Lys Asp Ile Arg
            100                 105                 110

Gly Ala Glu Leu Leu Gly Ala Val Arg Glu Val Ala Ala Gly Lys Ser
        115                 120                 125

Leu Leu Asp Pro Ala Ala Thr Ala Arg Val Leu Glu Arg Leu Arg Gly
    130                 135                 140

Gly Gly Ala Arg Pro Asp Asp Arg Leu Ala Arg Leu Thr Glu Gln Glu
145                 150                 155                 160

Arg Arg Ile Leu Glu Leu Ile Gly Glu Gly Leu Thr Asn Arg Ala Ile
                165                 170                 175

Gly Glu Arg Leu His Leu Ala Glu Lys Thr Ile Lys Asn Tyr Val Ser
            180                 185                 190

Ser Leu Leu Gly Lys Leu Gly Met Gln Arg Arg Ser Gln Ala Ala Ala
        195                 200                 205

Phe Val Ala Arg Leu Glu Ala Glu Asn Arg
    210                 215

<210> SEQ ID NO 36
<211> LENGTH: 220
<212> TYPE: PRT
<213> ORGANISM: Streptomyces fungicidicus

<400> SEQUENCE: 36

Val Ser Val Leu Leu Glu Gln Pro Ala Ser Leu Val Ala Tyr Arg Pro
1               5                   10                  15

Asn Lys Pro Thr Ala Met Val Val Ala Asp Pro Arg Val Arg Ser
            20                  25                  30

Thr Val Thr Arg His Leu Trp Ala Leu Gly Val Arg Asp Val Ile Glu
        35                  40                  45

Ala Ser Ser Val Ala Glu Ala Arg Pro Arg Ile Gly Asn Pro Arg Asp
    50                  55                  60

Ile Cys Val Ala Glu Val His Leu Pro Asp Gly Ser Gly Leu Thr Leu
65                  70                  75                  80

Leu Ser Glu Thr Arg Ala Ala Gly Trp Pro Asn Gly Leu Ala Leu Ser
                85                  90                  95

Ala Ala Asp Asp Ile Gly Ala Val Arg Asn Ala Leu Ala Gly Gly Val
            100                 105                 110

Lys Gly Tyr Val Val Thr Gly Thr Arg Thr Asn Leu Gly Leu Pro Thr
        115                 120                 125

Arg Pro Gly Ala Ala Pro Ile Gly Ala Ala Ala Arg Leu His Arg
    130                 135                 140

Arg Pro Pro Gly Ala Pro Ser His Pro Gly Gly Tyr Arg Glu Leu Ser
145                 150                 155                 160

Gly Arg Glu Val Glu Val Leu Arg Leu Val Ala Glu Gly Gln Ser Asn
                165                 170                 175

Lys Ala Ile Gly Val Ser Met Gly Leu Ser Ala Leu Thr Val Lys Ser
            180                 185                 190

His Leu Ala Arg Ile Ala Arg Lys Leu Gly Thr Gly Asp Arg Ala Gly
        195                 200                 205

Met Val Ala Val Ala Leu Arg Thr Gly Ile Ile His
    210                 215                 220
```

<210> SEQ ID NO 37
<211> LENGTH: 663
<212> TYPE: DNA
<213> ORGANISM: Streptomyces fungicidicus

<400> SEQUENCE: 37

```
gtgtccgttc tcctcgagca gcccgcaagc ctggtcgcct accgcccgaa caagccgacc      60
gccatggtgg tcgtggccga ccccgcgtc cgttcgaccg tcacccgcca cctgtgggcg     120
ctcggcgtac gcgacgtcat cgaggcctcg tccgtcgcgg aggctcgtcc ccgcatcggc     180
aaccccgcg acatctgcgt cgccgaagtc catctgccgg atggttccgg cctcaccctc     240
ctctccgaga cccgcgccgc gggctggccc aacggcctcg ccctctccgc ggcggacgac     300
atcggcgccg tgcgcaacgc cctcgcgggc ggagtcaagg gctacgtcgt caccggcacc     360
cgcaccaacc tcgggctccc caccggccg gtgccgctc ccatcggcgc cgccgccgcg     420
cgcctgcacc gccgcccccc gggtgccccg agccacccgg gcggctaccg cgagctgtcc     480
ggccgcgagg tggaggtgct gcggctggtg gcggaaggcc agtcgaacaa ggcgatcggc     540
gtctcgatgg gcctgtccgc actgaccgtc aagagccacc tggcccggat cgcccgcaag     600
ctcggcacgg gcgaccgcgc cggcatggtg gccgtggccc tgcgcaccgg catcatccac     660
tga                                                                   663
```

<210> SEQ ID NO 38
<211> LENGTH: 936
<212> TYPE: DNA
<213> ORGANISM: Streptomyces fungicidicus

<400> SEQUENCE: 38

```
gtggaaataa gttcgctctc caccgacggc tccccgcgga tcgacgggga gagtcccgag      60
cacgtggaaa tgctggccgc cgccgacacc gcgcttccac cgatcatggt gcaccgccgc     120
accgggcggg tcatcgacgg catgcaccgg ctgcgcgccg cgatgctgac gggccgtacg     180
acgatcgcgg tgaggttctt cgacggcacc gaggaggacg ccttcgtcct cgccgtgaag     240
tcgaacatcg cgcacggact gccgctgtcc gccgccgacc gccggcgggc cgccgggcgc     300
atcatggcca cccatccccg gtggtcggac cggatgatcg cctcggtggt cggcacctcc     360
gccaggacgg tcgccgagat ccgccgcgac gccggcgccg ccggggcggg ggagcccacc     420
cgcatcggcc gggacggcag ggtacggccc gtcgacgtga gcgagggccg cagactggcc     480
cacgacatga tcgtccgcga cccgggcctg tcgctgcgcc aggtcgcccg cgccgccggg     540
atctcgccgg agaccgtcag ggacgtcaga caccggatgc tccgcggtga ggacccggtg     600
cccgcgccgc ggccgcggac cctggtggag cgcggcgcgg accgccgggc ggagccggcc     660
gggaaggccg ccgcgccgtg cgggacggag ccgccgcccg ccgtcgtgat gaagcggctg     720
agggccgatc cggcgctgcg tctcaacgag aacggacgcg acctgctgcg gcttctggat     780
atccacacgg tccggctgga ggactggaac cgcattatcg aaagcgtgcc gccgcaccgt     840
ctggagacgg tggcgcagct ggcacgctcc tgcgccgaca atggtccga gatcgcgtca     900
cgcatcgaaa gcaacgcatc acatctggcc gggtga                              936
```

<210> SEQ ID NO 39
<211> LENGTH: 39331
<212> TYPE: DNA
<213> ORGANISM: Artificial sequence
<220> FEATURE:

<223> OTHER INFORMATION: Synthetic the fosmid pXYF148

<400> SEQUENCE: 39

```
atcgaatata acttcgtata atgtatgcta tacgaagtta ttagcgatga gctcggactt      60
ccattgttca ttccacggac aaaaacagag aaaggaaacg acagaggcca aaaagctcgc     120
tttcagcacc tgtcgtttcc tttcttttca gagggtattt taaataaaaa cattaagtta     180
tgacgaagaa gaacggaaac gccttaaacc ggaaaatttt cataaatagc gaaacccgc      240
gaggtcgccg ccccgtaacc tgtcggatca ccggaaagga cccgtaaagt gataatgatt     300
atcatctaca tatcacaacg tgcgtggagg ccatcaaacc acgtcaaata atcaattatg     360
acgcaggtat cgtattaatt gatctgcatc aacttaacgt aaaaacaact tcagacaata     420
caaatcagcg acactgaata cggggcaacc tcatgtccga gctcgcgagc tcgtcgacag     480
cgacacactt gcatcggatg cagcccggtt aacgtgccgg cacggcctgg gtaaccaggt     540
attttgtcca cataaccgtg cgcaaaatgt tgtggataag caggacacag cagcaatcca     600
cagcaggcat acaaccgcac accgaggtta ctccgttcta caggttacga cgacatgtca     660
atacttgccc ttgacaggca ttgatggaat cgtagtctca cgctgatagt ctgatcgaca     720
atacaagtgg gaccgtggtc ccagaccgat aatcagaccg acaacacgag tgggatcgtg     780
gtcccagact aataatcaga ccgacgatac gagtgggacc gtggtcccag actaataatc     840
agaccgacga tacgagtggg accgtggttc cagactaata atcagaccga cgatacgagt     900
gggaccgtgg tcccagacta ataatcagac cgacgatacg agtgggacca tggtcccaga     960
ctaataatca gaccgacgat acgagtggga ccgtggtccc agtctgatta tcagaccgac    1020
gatacgagtg gaccgtggt cccagactaa taatcagacc gacgatacga gtgggaccgt    1080
ggtcccagac taataatcag accgacgata cgagtgggac cgtggtccca gtctgattat    1140
cagaccgacg atacaagtgg aacagtgggc ccagagagaa tattcaggcc agttatgctt    1200
tctggcctgt aacaaaggac attaagtaaa gacagataaa cgtagactaa aacgtggtcg    1260
catcagggtg ctggcttttc aagttcctta agaatggcct caattttctc tatacactca    1320
gttggaacac gagacctgtc caggttaagc accatttat cgcccttata caatactgtc     1380
gctccaggag caaactgatg tcgtgagctt aaactagttc ttgatgcaga tgacgtttta    1440
agcacagaag ttaaaagagt gataacttct tcagcttcaa atatcacccc agcttttttc    1500
tgctcatgaa ggttagatgc ctgctgctta agtaattcct ctttatctgt aaaggctttt    1560
tgaagtgcat cacctgaccg ggcagatagt tcaccggggt gagaaaaaag agcaacaact    1620
gatttaggca atttggcggt gttgatacag cgggtaataa tcttacgtga aatattttcc    1680
gcatcagcca gcgcagaaat atttccagca aattcattct gcaatcggct tgcataacgc    1740
tgaccacgtt cataagcact tgttgggcga taatcgttac ccaatctgga taatgcagcc    1800
atctgctcat catccagctc gccaaccaga acacgataat cactttcggt aagtgcagca    1860
gctttacgac ggcgactccc atcggcaatt tctatgacac cagatactct tcgaccgaac    1920
gccggtgtct gttgaccagt cagtagaaaa gaagggatga gatcatccag tgcgtcctca    1980
gtaagcagct cctggtcacg ttcattacct gaccataccc gagaggtctt ctcaacacta    2040
tcaccccgga gcacttcaag agtaaacttc acatcccgac cacatacagg caaagtaatg    2100
gcattaccgc gagccattac tcctacgcgc gcaattaacg aatccaccat cggggcagct    2160
ggtgtcgata acgaagtatc ttcaaccggt tgagtattga gcgtatgttt tggaataaca    2220
ggcgcacgct tcattatcta atctcccagc gtggtttaat cagacgatcg aaaatttcat    2280
```

```
tgcagacagg ttcccaaata gaaagagcat ttctccaggc accagttgaa gagcgttgat   2340
caatggcctg ttcaaaaaca gttctcatcc ggatctgacc tttaccaact tcatccgttt   2400
cacgtacaac attttttaga accatgcttc cccaggcatc ccgaatttgc tcctccatcc   2460
acggggactg agagccatta ctattgctgt atttggtaag caaaatacgt acatcaggct   2520
cgaacccttt aagatcaacg ttcttgagca gatcacgaag catatcgaaa actgcagtg    2580 cggaggtgta gtcaaacaac tcagcaggcg tgggaacaat cagcacatca gcagcacata   2640
cgacattaat cgtgccgata cccaggttag gcgcgctgtc aataactatg acatcatagt   2700
catgagcaac agtttcaatg gccagtcgga gcatcaggtg tggatcggtg ggcagtttac   2760
cttcatcaaa tttgcccatt aactcagttt caatacggtg cagagccaga caggaaggaa   2820
taatgtcaag ccccggccag caagtgggct ttattgcata agtgacatcg tccttttccc   2880
caagatagaa aggcaggaga gtgtcttctg catgaatatg aagatctggt acccatccgt   2940
gatacattga ggctgttccc tggggggtcgt taccttccac gagcaaaaca cgtagcccct   3000
tcagagccag atcctgagca agatgaacag aaactgaggt tttgtaaacg ccacctttat   3060
gggcagcaac cccgatcacc ggtggaaata cgtcttcagc acgtcgcaat cgcgtaccaa   3120
acacatcacg catatgatta atttgttcaa ttgtataacc aacacgttgc tcaacccgtc   3180
ctcgaatttc catatccggg tgcggtagtc gccctgcttt ctcggcatct ctgatagcct   3240
gagaagaaac cccaactaaa tccgctgctt cacctattct ccagcgccgg ttatttttcc   3300
tcgcttccgg gctgtcatca ttaaactgtg caatggcgat agccttcgtc atttcatgac   3360
cagcgtttat gcactggtta agtgtttcca tgagtttcat tctgaacatc ctttaatcat   3420
tgctttgcgt ttttttatta aatcttgcaa tttactgcaa agcaacaaca aaatcgcaaa   3480
gtcatcaaaa aaccgcaaag ttgtttaaaa taagagcaac actacaaaag gagataagaa   3540
gagcacatac ctcagtcact tattatcact agcgctcgcc gcagccgtgt aaccgagcat   3600
agcgagcgaa ctggcgagga agcaaagaag aactgttctg tcagatagct cttacgctca   3660
gcgcaagaag aaatatccac cgtgggaaaa actccaggta gaggtacaca cgcggatagc   3720
caattcagag taataaactg tgataatcaa ccctcatcaa tgatgacgaa ctaacccccg   3780
atatcaggtc acatgacgaa gggaaagaga aggaaatcaa ctgtgacaaa ctgccctcaa   3840
atttggcttc cttaaaaatt acagttcaaa aagtatgaga aaatccatgc aggctgaagg   3900
aaacagcaaa actgtgacaa attaccctca gtaggtcaga acaaatgtga cgaaccaccc   3960
tcaaatctgt gacagataac cctcagacta tcctgtcgtc atggaagtga tatcgcggaa   4020
ggaaaatacg atatgagtcg tctggcggcc tttcttttc tcaatgtatg agaggcgcat   4080
tggagttctg ctgttgatct cattaacaca gacctgcagg aagcggcggc ggaagtcagg   4140
catacgctgg taactttgag gcagctggta acgctctatg atccagtcga ttttcagaga   4200
gacgatgcct gagccatccg gcttacgata ctgacacagg gattcgtata aacgcatggc   4260
atacggattg gtgatttctt ttgtttcact aagccgaaac tgcgtaaacc ggttctgtaa   4320
cccgataaag aagggaatga gatatgggtt gatatgtaca ctgtaaagcc ctctggatgg   4380
actgtgcgca cgtttgataa accaaggaaa agattcatag ccttttttcat cgccggcatc   4440 ctcttcaggg cgataaaaaa ccacttcctt ccccgcgaaa ctcttcaatg cctgccgtat   4500
atccttactg gcttccgcag aggtcaatcc gaatatttca gcatatttag caacatggat   4560
ctcgcagata ccgtcatgtt cctgtagggt gccatcagat tttctgatct ggtcaacgaa   4620
```

```
cagatacagc atacgttttt gatcccggga gagactatat gccgcctcag tgaggtcgtt    4680
tgactggacg attcgcgggc tatttttacg tttcttgtga ttgataaccg ctgtttccgc    4740
catgacagat ccatgtgaag tgtgacaagt ttttagattg tcacactaaa taaaaaagag    4800
tcaataagca gggataactt tgtgaaaaaa cagcttcttc tgagggcaat ttgtcacagg    4860
gttaagggca atttgtcaca gacaggactg tcatttgagg gtgatttgtc acactgaaag    4920
ggcaatttgt cacaacacct tctctagaac cagcatggat aaaggcctac aaggcgctct    4980 aaaaagaag atctaaaaac tataaaaaaa ataattataa aaatatcccc gtggataagt    5040
ggataacccc aagggaagtt ttttcaggca tcgtgtgtaa gcagaatata taagtgctgt    5100
tccctggtgc ttcctcgctc actcgaccgg gagggttcga aaggggggg cacccccctt    5160 cggcgtgcgc ggtcacgcgc acagggcgca gccctggtta aaaacaaggt ttataaatat    5220
tggtttaaaa gcaggttaaa agacaggtta gcggtggccg aaaaacgggc ggaaacccttt    5280 gcaaatgctg gattttctgc ctgtggacag cccctcaaat gtcaataggt gcgccctca    5340 tctgtcagca ctctgcccct caagtgtcaa ggatcgcgcc cctcatctgt cagtagtcgc    5400 gccctcaag tgtcaatacc gcagggcact tatccccagg cttgtccaca tcatctgtgg    5460
gaaactcgcg taaaatcagg cgttttcgcc gatttgcgag gctggccagc tccacgtcgc    5520
cggccgaaat cgagcctgcc cctcatctgt caacgccgcg ccgggtgagt cggcccctca    5580
agtgtcaacg tccgcccctc atctgtcagt gagggccaag ttttccgcga ggtatccaca    5640
acgccggcgg ccggccgcgg tgtctcgcac acggcttcga cggcgtttct ggcgcgtttg    5700
cagggccata gacggccgcc agcccagcgg cgagggcaac cagccgaggg cttcgccctg    5760
tcgctcgact gcggcgagca ctactggctg taaaaggaca gaccacatca tggttctgtg    5820
ttcattaggt tgttctgtcc attgctgaca taatccgctc cacttcaacg taacaccgca    5880
cgaagatttc tattgttcct gaaggcatat tcaaatcgtt ttcgttaccg cttgcaggca    5940
tcatgacaga acactacttc ctataaacgc tacacaggct cctgagatta ataatgcgga    6000
tctctacgat aatgggagat tttcccgact gtttcgttcg cttctcagtg ataacagcc    6060 agcttctctg tttaacagac aaaaacagca tatccactca gttccacatt tccatataaa    6120
ggccaaggca tttattctca ggataattgt ttcagcatcg caaccgcatc agactccggc    6180
atcgcaaact gcaccggtg ccgggcagcc acatccagcg caaaaacctt cgtgtagact    6240
tccgttgaac tgatggactt atgtcccatc aggctttgca gaactttcag cggtataccg    6300
gcatacagca tgtgcatcgc ataggaatgg cggaacgtat gtggtgtgac cggaacagag    6360
aacgtcacac cgtcagcagc agcggcggca accgcctccc caatccaggt cctgaccgtt    6420
ctgtccgtca cttcccagat ccgcgctttc tctgtccttc ctgtgcgacg gttacgccgc    6480
tccatgagct tatcgcgaat aaatacctgt gacggaagat cacttcgcag aataaataaa    6540
tcctggtgtc cctgttgata ccgggaagcc ctgggccaac ttttggcgaa atgagacgt    6600 tgatcggcac gtaagaggtt ccaactttca ccataatgaa ataagatcac taccgggcgt    6660
attttttgag ttatcgagat tttcaggagc taaggaagct aaaatggaga aaaaatcac    6720 tggatatacc accgttgata tatcccaatg gcatcgtaaa gaacattttg aggcatttca    6780
gtcagttgct caatgtacct ataaccagac cgttcagctg gatattacgg ccttttaaa    6840 gaccgtaaag aaaaataagc acaagtttta tccggccttt attcacattc ttgcccgcct    6900
gatgaatgct catccggaat ttcgtatggc aatgaaagac ggtgagctgg tgatatggga    6960
tagtgttcac ccttgttaca ccgttttcca tgagcaaact gaaacgtttt catcgctctg    7020
```

```
gagtgaatac cacgacgatt tccggcagtt tctacacata tattcgcaag atgtggcgtg   7080
ttacggtgaa aacctggcct atttccctaa agggtttatt gagaatatgt ttttcgtctc   7140
agccaatccc tgggtgagtt tcaccagttt tgatttaaac gtggccaata tggacaactt   7200
cttcgccccc gttttcacca tgggcaaata ttatacgcaa ggcgacaagg tgctgatgcc   7260
gctggcgatt caggttcatc atgccgtttg tgatggcttc catgtcggca gaatgcttaa   7320
tgaattacaa cagtactgcg atgagtggca gggcggggcg taatttttt aaggcagtta   7380 ttggtgccct taaacgcctg gttgctacgc ctgaataagt gataataagc ggatgaatgg   7440
cagaaattcg atgataagct gtcaaacatg agaattggtc gacggcccgg gcggccgcaa   7500
ggggttcgcg ttggccgatt cattaatgca gctggcacga caggtttccc gactggaaag   7560
cgggcagtga gcgcaacgca attaatgtga gttagctcac tcattaggca ccccaggctt   7620
tacactttat gcttccggct cgtatgttgt gtggaattgt gagcggataa caatttcaca   7680
caggaaacag ctatgaccat gattacgcca agctatttag gtgagactat agaatactca   7740
agcttgcatg cctgcaggtc gactctagag gatcccacca ccgccggacg ggggtcgccg   7800
gcccggaagt ccaccaggat cgagccgccg atctgccgcc cgcgccacca cgactccatc   7860
agcccgacct cctcctccgg gctgcgcacc agccgcagca gcagcgagca ggaccgctcc   7920
accaggacgc tctccacccc ggagatgaac tccatgtaga acggctccag gccgagcagc   7980
cgggcgggcc ggcagaccgc gagacccacc acgtccaccc gcgacccggc cagcgtgcgc   8040
gcggttcggc tcggcgccca ccccagctcc cgcgccgccc ggaagatgcg gtcccgggtc   8100
gcctccgaca gcccgggctt ccggttgaag gcgagggaca cggcgccctt ggacacgccg   8160
gcgcgcgcgg cgacgtccct gatggtgacg cgaggggtcg gcgttgccgt catcgagtgg   8220
gctccacgca gtacagggcg gaacgggcgg tgtccgggtc cggagtcttc cacccccgca   8280
ccccgatggt cacctgttcc ccggggagca gggtcaccag ccccggtcg gcccgcgccc   8340 cggggtccag ccggtcggcc tggagcagca ggtcccgtac gagggtgcgg gccgtgaccg   8400
tgatcccgtc cggcgcgagg gcgacctcga actccggcgg ggggtagggg atctcccggt   8460
ccggcgccgg gaagtgccac gcccgcaccc cgtccgcgtc ggcgaccagg aactcccggg   8520
ggccgtccgg cagcagttcg accgggacct cgaccacggc caccgtccgc ccccggcgt   8580 ccagcgccgg ggccgcctcc gcgatcgggg cgccgtcgac ggacatccgg cgcagccgca   8640
gcgttccccg ccagtcctcc gcggactggt tgaccgccgc caccaccaga ccgtcaccgt   8700
ccgcgcgcac ggtcagcagc cggtccgcgt acagccggcg cagctcgtgg tagagcggct   8760 tctccccgccc gtccccgtcg atcgcggccc acgacgtcac cggccagcag tcgttgagct   8820
gccagaccac cgtgccgcg cacaccggcc agtgcgagcg ccagtgctcg acaccggccg   8880
ccaccgcacg cgcctggttg acctgcgtca gatagtgcca gcggtcgaag tcgccctccg   8940
gcacggcgaa gtggcgggcg aggccgcgct ccagcttgcc gttgccgtcc tccgccttct   9000
ggtggtgcag catgccgggg gagtccggcg cggggtcctc cccgggcagc gcccgccgca   9060
gcgtggcgtg cgcgggaggc gcctgccagc cgaactcggc cacgaagcgc gggacgtcgc   9120
gccggtagtc ggcgtagtcg gcgcggttcc acacctccca ggagtggtgg gtgccgtgcg   9180
ccggatcgtt ggggtggtgc cgccaggaac cggaccaggg actgcccgcc gtgtacggcc   9240
gcgtcgggtc cagctccgcg accacccgcg gcaggacgcc gaggtagtag ccctcgcccc   9300
aggagtcccc ggcgagcccc tgctcccagt cccagtcccg gaaccccac aggttctcgt   9360
```

```
tgttgccgtt ccacagcacc agggaggggt gcggcatcag ccgtacgacg ttctcccggg    9420
cctccgcctc cacctccccg cgcagcggct gctcctcggg gtaggcggcg cacgcgaacg    9480
ggaagtcctg ccagaccagc agccccaact cgtcgcaggc gtcgtagaag tcctcgtcct    9540
cgtagatccc gccgcccag acccggacca ggtccacccc cgcgccggcc gcctgctcca    9600
gccggtgccg gtagcgctcc cgggtgatcc gggacgggaa cacgtcgtcc gggatccagt    9660
tgacgccccg cgcgaacagc cgctcaccgt tgacgaccag ggtgaacccg gtgccgtgcg    9720
cgtcggccga ggtgtccagc tcaaccgtcc ggaacccggt cctgcgccgc caggcgtcca    9780
gcgcctcgtc accgtgggac aacgtcagct cgacgtcgta cagcggctgt tcgccgtatc    9840
cgcgcggcca ccacaggcgg acgtccggca cccggagccg cacggtcccg gccgtcccat    9900
cgacccgcgc ccgggcgcgc acgccccgg cgctcgcctc cagggtgagc ggtgcctcga    9960
cccgggagcg ctccacgtcg accgccagct cgatctgccc caccccgtcc tcgacggtga   10020
ccagcgggcg cacccgggcg atccgcgccg tcgaccagcg ctccagccgc accggccgcc   10080
agatcccggc cgtcaccagc gtcggccccc agtcccagcc gaacgagcag gccatcttcc   10140
gcaggtactg gtacggctcg gcgtacgctc cggggcgctc gcccagcctg ccgcgcaccg   10200
cctccgcctc ggcgtacgcg gaggcgaacc gcaccgtgag ccggccgctc agtcccgtca   10260
cgtcgaagcg gtacgagcgg tgcatgttcc gcgtccggcc cagtggccgg ccgtcgagca   10320
ggatctcggc gacggtgtcg agaccgtcga agacgaggtc cgtctgctcg tgcgggcccg   10380
tcccggcggt cagctccgtc tcgtacgtcc actcccgccg gcccacccag gccacctcgg   10440
tctcgttgcg gccgaggaac ggatcgggga tcagcccggc cgccagcaga tcggtgtgca   10500
cacacccgg caccgaggcg gggagggcgt ccccgtgcc gtccgggtgt cgcaggatcc   10560
atccctcggt gagcggtgtg acctgacgca tgcacactcc ctaaaccggt tgagccttct   10620
ctgaagagtg gtctggcatc gttggcgcga ttgcgacttt accggttcag ttcagggctg   10680
ccagagtgcc gaatcagcca tcccactcgt gctcgtccgt cccgtgaacg gagccgtgat   10740
gcatctgaac cgccgtacga cactcaccgg atcgctcgcc ctgctcgccc tcctggcctc   10800
cgcctgcacg ggcacggggg gttcctcgaa gggcgcggac gccaaggctc ccgacgaccc   10860
gtcaaaggtc aaggggtccc tcacggtcct cacccaccgg accgatctgg tgcaggacgg   10920
gacgatgaag aagtacgccg ccgagttcaa cgagacctat cccggggtga aggtggagtt   10980
cgacggcctc accgactacg agggcgaggt caagatccgt atgaacacgg agaactacgg   11040
cgacgtcctc atgatcccgg cggtcgtcga gaagaaggac tacccgaagt tcttcgcctc   11100
cctgggcacc aaggccgaac gcgccgccaa gtaccggttc accgactact ccaccgtcga   11160
cggcaaggtc tacgggcaga gccccgtcgg cgtcgtcccc gggttcatct acaacaagcg   11220
ggtgtggagc gaggccggcg tcaccgactg gcccaccacc ccgccgagt tcctggacga   11280
cctgaaggcg atccggtcga agaccgacgc ggtgccgtac tacaccaact tcaaggacat   11340
gtggccgctg acccagtgga ccaacgtcaa cggctccgtc ggctgcgacc cgcacgccac   11400
cacgaagctc gccgagggcg accgtgggc cgagggggcc gacctgcgcg tgggcgacac   11460
cctgctccac gacatcgtgc gcggcggact cgccgagaag gacccgacca ccaccaactg   11520
ggagggctcc aagcccaagc tggccaaggg cgagatcgcc accatgtggc tgggctcctg   11580
ggccgtcgtg cagatgcggg acggcggcgaa gcaggccggc gccgaccccg ccgacatcgg   11640
cttcatgccc ttccccgcac agcgggacgg cacgttctgc gcggtgacct ccccggacta   11700
ccagcaggcg gtcaacgtca actccgacaa caaggaggcc gcccgcgcct ggatcgactg   11760
```

-continued

```
gttcaccgac aagtccggct acgccgaggc caacctcgcc ctatccccc tgaaggacgc   11820
cccgctgccc gccgtcctcg agccctacga gaaggccggc gtgaagctcc tggacctcga   11880
ggacagcaag ggcgccgagg tgaagtccct cgacaaccgc tccgaggtcg catctacaa   11940
gcccgactac cgccaggaac tcgtcgacct cgcccgcggc gcccgcaagg gcggcctgga   12000
cgactacctc ggcggcctcg gcgagcgctg ggccgaggcg cgcagcgcgc tggggggcctg   12060
atgacggaca ccacccgcaa ggcggcgcgg ccggttcccc cggccgcgcc cgccgggccg   12120
ggccgcgcgg cgccggcccc gcgccgcacc cggctgtcgc gccgcctcac cccgtggctg   12180
ttcctggccg caccgctggc cctgctcctg accttcacct acgcgcccga tcgccaacat   12240
ggtcgcgtac agcttcaccg actgggacgg cgtgagcccg gagctgaact ggacgggcac   12300
cgggaactac accgaactcc tcacccgctc cgagctgttc gaggtcttct tcgtcagcgg   12360
ctactacctc gtcgcctccg cggtgcagat cgtgctcgcc ctctacttcg ccacggtcct   12420
cagcttcgac gtccgcttcc ggaacttctt caagggcgtg ctgttcttcc cgtacctcat   12480
caacggggtg gccatcggct tcgtcttcct ctacttcttc caggacggcg gcaccctcga   12540
ctccgtactg ggcctgctcg gcgtcgagac cgaccacgcc tggctgggca cgccgttctc   12600
cgcgaacacc tcgctggccg gcgtctccgt ctggcgctac ctcggactga acttcgtcct   12660
cttcctcggc gcgatccagt ccatcccggg cgagctgtac gaggcggccg agatcgacgg   12720
cgcgaaccgc tggcagcagt tccggcacat catcgcgccc ggcatcagac ccgtgctgag   12780
cctgagcgtg atcctctcgg tctccggctc gctgtcggtc ttcgagatcc cgtacatcat   12840
gaccggcggc gccaccggca cggagacctt cgtgatccag accgtgaagc tggcgttcca   12900
gttcaacaag acgggactcg cctcggccgc cgccgtcgtc ctgctgctga tcgtcctggc   12960
ggtcacctgg gtgcagcggc gcatcgtccc cgacgagaag gtggacctcg tatgacccgc   13020
cgtaccgcgg cacgcgccct ggtcctgacg tccctgatcc tggcgacgct ggtggtgctg   13080
ctgccgctcg ccgtggtctt cctgacctcg ctgaagtcct ccgaggagat ggcgaacggc   13140
agcggagcgc tgacgccgcc cgacgacccg ctgaacttcg gcaactacgt gacggcgttc   13200
cgggacggcc agatgctgtc cgcgttcggg aacacggccg tcatcctggt cgtggccgtc   13260
ggcggaacga tcctgatcgg ctcgatgacg gcgtacgcga tcgaccgctt ccggttccgc   13320
ttcaagaagc tggtcgtggc gctgttcctg ctggccgcgc tggtccccgg ggtgaccacc   13380
caggtggcga ccttccagat cgtcaacagc ttcggcatgt tcgacagcct gtgggcgccg   13440
atcgccctct acatgggcac ggacatcgtc tcgatctacg tcttcctgca gttcatccgc   13500
tccatccccg tctccctgga cgaggcggcg cgcctggacg gcgccaacgc gttcaccgtc   13560
taccgcaagg tgatcttccc gctgctcaag ccggcgatcg cgacggtggt gatcgtaaag   13620
gggatcaacg tctacaacga cttctacatc cccttcctct acatgccctc gaggacctg   13680
ggggtcatct cgacgtccct gttccgcttc aagggccct tcggcgcgca ctgggagacg   13740
atctcggcgg gcgcggtcct ggtcatcctg cccaccttga tcgtcttcct gttcctccag   13800
cgcttcatct acaacgggtt catgcggggg gcgacgaagt agccagcgcg gccaccagca   13860
cgggagtgac ctggtcgacc tgccacgcgc gtgcccgtg cgccgtcagc gccgcggcga   13920
cggaccgctc gtcgggcccc ggcggctccc agcagaccct gcgcaccgtg tccggggtga   13980
tcaggttctc cggcggcatg ttcagccgct cggcgagttc ggcgacccc gcgcgggccg   14040
ccgacagccg ggccgcggca acggggtcct tgtccgccca ggcgcgcggc ggcggagggc   14100
```

```
cggtcaccgg ctggccgggc tgcggcagct gggcctcgct cagcgccttc gcgcggtcga   14160
cggccgcctg ccactgctcc agctggcgcc gccccacccg ctgcccgaac ccgttgagcg   14220
cggccatggc gtgcaggttg cgggcagcg cgagcgcggc ctccacgatc gccgcgtcgg    14280
aaagcacctt gccgggggag acgtcacggc gccgggcgat ccggtcgcgg gtctcccaca   14340
gctcccgcac caccgccatc tggcggcgcc ggcgcacctt gtgcatgccg gaggtgcggc   14400
gccaggggtc cttgcgggc tccggcgcg gggccgaggc gatcgcgtcg aactcctgcc     14460
gggcccagtc cagcttgccc tggcggtcca gctccttctc cagggcgtcc cgcagatcga   14520
ccagcagttc gacgtcgagg gcggcgtacc gcagccaggg ctcggcagc ggacgggtgg    14580 accagtcgac ggcggagtgg cccttctcca ggacgaagcc gagcacgttc tcgaccatcg   14640
cgccgagccc gacgcggggg aacccggcaa ggcggccggc cagctcggtg tcgaagaggc   14700
gggagggcac catgcctatc tcgcgcagac agggcaggtc ctgggtggcg gcgtgcagca   14760
cccactcgac gccggacagc gcctcgccga gggcggacag gtcggggcag gccacggggt   14820
cgatcagcgc ggtacccgca ccctcgcggc gcagctggac gaggtaggcg cgctggccgt   14880
agcggtaccc ggaggcgcgc tcggcgtcca cggcgacggg tccgctgccg gccgcgaagg   14940
cggcgaccgc ctcggcgagg gcggcctcgt ccgctatcac gggcggaatg ccctcgcggg   15000
gttccagcaa gggggtcggc gcctccgtaa cagaagatcc gccgtcgtcc ggaggagcgc   15060
ctccggtggt gcgcagtgaa ctgtctgctg cggtgtcgtg ggcgtcggtc acctgtcaag   15120
ggtatccgtg ccgcgaaggc gcccgtcgac ggttgtgctc cgtgacgggc gccggtgggt   15180
cgtattccgt tcagaagagt gaaagaacgt gttcgcttgg ccgtgggcgg gcggatcggg   15240
gacgggcgga tcggggggcgg gacggaaggg tcagtggatg atgccggtgc gcagggccac   15300
ggccaccatg ccggcgcggt cgccgtgcc gagcttgcgg gcgatccggg ccaggtggct    15360
cttgacggtc agtgcggaca ggcccatcga gacgccgatc gccttgttcg actggccttc   15420
cgccaccagc cgcagcacct ccacctcgcg gccggacagc tcgcggtagc cgcccgggtg   15480
gctcggggca cccgggggc ggcggtgcag gcgcgcggcg gcggcgccga tgggagcggc    15540
acccggccgg gtggggagcc cgaggttggt gcgggtgccg gtgacgacgt agcccttgac   15600
tccgcccgcg agggcgttgc gcacggcgcc gatgtcgtcc gccgcggaga gggcgaggcc   15660
gttgggccag cccgcggcgc gggtctcgga gaggagggtg aggccggaac catccggcag   15720
atggacttcg gcgacgcaga tgtcgcgggg gttgccgatg cggggacgag cctccgcgac   15780
ggacgaggcc tcgatgacgt cgcgtacgcc gagcgcccac aggtggcggg tgacggtcga   15840
acggacgcgg gggtcggcca cgaccaccat ggcggtcggc ttgttcgggc ggtaggcgac   15900
caggcttgcg ggctgctcga ggagaacgga caccaggcct cctggggtgc gggacgggcc   15960
ggctcgtggg ggtgaaggcg ggacgaaccg tgctttcaag gtcacagtcg tcttcggcag   16020
caaacctggt gtcctttaac gaatgatcac gaagtgatga gtaacaatcc gggcaattcg   16080
gacgcacgat cgatcattcg aagatcgaac ggtttcggtc tgcgtcgcaa cgcttccgaa   16140
agtggccgta tcgacaaaga gagatgcagg aggccggtcg tcgggacccc gcagcgggag   16200
gctcagcgcg actgcggccc cctccgctgc ggcagcgtca ccacggacgc gtccccggga   16260
gcggccggcg gcagcccgc gacctgcgcc agcagatcgg accacgcgac cagatgggcg    16320
gccgtgtccg gaaccccgcc cagacccctca gcggcgtcc acgaggcacg gatctcgatc   16380 tgggaggcg cgggccgcgc ggacagcccg ccgaagtagt gcgaactcgc ccgcgtcacc    16440
gtgccgctcg gctcgccgta cgacaggccg cgcgccgcca gcgcgccggt cagccaggac   16500
```

```
cagcacacgt ccggcagcag cggatccgcc gccatctccg gctccagctc ggcgcgcacc    16560
agcgtcacca gacggaaggt cccccgccag gcgtcgtgtc cggccgggtc gcacagcagc    16620
accagccggc cgtcggccag atcctcctcg ccgtcgacga ccgccgcctc cagcgcgtgc    16680
gcgtacgggg cgagccgttt cggcgcgggc accgtctcca cctcgatctg cggccgcagc    16740
cgggcgctct gcagcgcctc gacagcggcc cggaagggcg gcggaggcgc acctccgtgc    16800
ccgggatccc ccccgccctc cttcggttcg tccattccgc cagcgccgtc cgacagtcgt    16860
ccctgagccg cagccatgcc gggaagatta gcggaacgg ccccggcg cagggaggga     16920 cacccgcgcc gccggcgct gtccggatcc tgcaccgcgg ccccgcccgc cggacgcccc    16980
tggggtccgg ggcggcggac gggtcgtgcg agactggccg gtgtgagtgc caacacgagc    17040
ccgaagggcc agacgcctac cgcgaccccc gaccccgtca agaacgacgc cgtccgggaa    17100
tcagccttcc tcaaggcgtg ccggcgcgag ccggtgccgc acacgccggt gtggttcatg    17160
cggcaggccg ggcgctcact gccggagtac cgcaaggtgc gcgagggcat cgggatgctc    17220
gactcctgca tgcggcccga gctggtcacc gagatcaccc tccagccggt gcgccgccac    17280
cacgtcgacg cggcgatcta cttcagcgac atcgtcgtcc cgctcaaggc catcggcatc    17340
gacctcgaca tcaagcccgg catcggcccg gtcgtcgagc agccggtgcg cacccgcgcc    17400
gacctcgccc ggctgcgcga cctgacccg gaggacgtct cctacgtcac cgaggccatc    17460
ggcatgctga cccgtgagct cgggtccacc ccgctgatcg gtttcgcggg cgccccgttc    17520
acccttgcga gttacctcgt cgagggcggc ccgtcccgta cgtacgagaa cgccaaggcg    17580
atgatgtacg gcgaccccga gctctgggcc gacctgctcg accgcctcgc cgacatcacg    17640
gcggccttcc tcgacgtcca gatccggggcc ggcgcctcgg ccgtgcagct cttcgactcc    17700
tgggccggcg cgctcgcccc ctccgactac cggcgttcgg tgctgcccgc ctcggcgaag    17760
gtgttccgcg cggtggccgg ccacggcgtc ccgcgcatcc acttcggcgt cggcaccggc    17820
gagctgctgg ggctcatggg cgaggccggc gcggacatcg tcggcgtcga ctggcgcgtc    17880
ccgatggacg aggccgcccg ccgcgtcggc cccggcaagg cgctccaggg caacctggac    17940
ccgaccgtgc tgttcgccgg ccggggaggcc gtcgagacga aggcgcgcga ggtcctggac    18000
accgccgcgg gcctggaggg ccacatcttc aacctcggtc acggagtgat gccctccacc    18060
gacccggacg ccctcacccg tctcgtggag tacgtccaca cgcagacggc gcgctgaccc    18120
accgctcacg cgccggacgc gagtcggaat ccggggcgg ggtactgggc acgggtgccc    18180
accacgttca cccccgggta cgggcaggtg gaggcccat gaggctcgag atgttcgacc    18240
ccgccccgat cggcgtcgtg ttcacccagg ggccggagca ccggctcgcg tacaccaacg    18300
ccgtctaccg ggagaccttc ggcgaccgcc cgctggggcg gacgatccgc gaggccttcc    18360
ccgacctcgc gcagtccggc tacttcgaca tcttcgaccg ggtcctcacc acgggcgcgg    18420
ccgaggtggt caccgcggtg cccctcgacc tgatctaccc cggctccacg ggcgagggca    18480
ggcgctactt cacgttcagc atctcccgcg ccacgatgag cgacggccgg ccgggagtgc    18540
tcggcgtgat cgtggaggtg accgcgcagg tgaccgccgc ggaacggatc cgtgtgctgg    18600
ccgaggagcg ccgccgcgcg ctgcagcgct accgcagcct ggtgaacgcc ggaacgcaga    18660
tggtgtgggt ggcggacgcc aagggccgga tcaccgagcc gagcccggc tgggaacgcg    18720 tgaccgggca gacctgggag gagttccgcg gcgaggctg gatgaacgcc gtccacccg    18780 acgaccgcgc cgcctcggtc gaggcgtggc ggcgggcgac gaccgaacag gtgccgcgct    18840
```

```
ggatccacac ctaccggctg cggctggccg ccggcgggta ccggcacttc gtcgtcgacg   18900
ccgcgcccgt gcgcgacggg aacacggtga tcgaatgggt gggcacctgc acggacatcg   18960
agcgggaatg gcaggagggc cgccgtacgg aactgctggc gcgggccgcc accgccacgt   19020
ccggcatcgc gcggctggac gagatgctcg ccgcccctggc cgatgtgatc gtgcccgaca   19080
tcgccgacaa ctgcaccatc cacctcctgc cgcaggccct gcaccgtctg ccgggcaccc   19140
cgctgaccac cgaacgcgtc gccgcggtca cccgcccggg gctcccggac ctgccccgc    19200
accacgagga gcacctgcgg cccggcagcc cgctggcccg cgccgccgac cgccgcagcc   19260
cgctccactt cgtcttcccg cccggcgagc cgccggccga cctcgctccg ctcgacggcg   19320
agccctggat ggccgaggac gtcaacagcg tcgtgctgct gcccgtcgtc gtcgacggca   19380
ccaccgccgc cctggtcgcc gtctccacca gcggcgcccg cccgcccctc ggccaggcgg   19440
agatcggcct gctgcagaca ctcctggaac gcgcccacac cccctcagc aacgccctgg   19500
agtaccagcg caccggcag gtggccctgg ccctgcagaa cagcctgctc accgaccgc    19560
cggacgcgcc cggcctggac atcgccgtcc gctaccggcc cagcaccgcc gccgccgagg   19620
tcggcgggga ctggtacgac gcgttcgtgc tgcgcgacgg cgccaccgtc ctcaccatcg   19680
gcgacgtctc cggccacgac ctgccggccg ccgtcaccat gagccagctg cgcaacatgc   19740
tgcgcgggct cacgctggac cgccaggaac cgaccggcac catcctgcgc cggctggaca   19800
tcgccgtgca gaccctctat acggagtgca ccgccacctg cgtgctggcc cgggtggaac   19860
gcccggactc cggcggcgtc cggctgcact actccgtcgc cggtcacccg ccgccgctgc   19920
tcgtcgaggc ggacggctcc gcgcgcttcc tgaccggggc gcggtccccg atgctcgggc   19980
tcgtccccgc gccggagtac tcgagcgcca tggaaccgct gccgcccggc tccaccctgc   20040
tgctgtacac cgacgggctg gtggagcgcc gcgacgagga tctcaccgtg ggcctggagc   20100
ggctgcggca ccacgcctcg gaggcggtca gccgcccgct gcaggacttc tgcgacacac   20160
tgctcaccgg ccagctcacc gtcgacaacg acgacgacgt ggcgatgctg gtcctgcgcc   20220
ggtaggagcg tgccgaggag cgccactctg gccgatttta cccttgcttt tccatcggga   20280
ttcgttctcc ggatttcccg atccggcgcc gacggcgaga ccgttgggat caccaatacc   20340
ccggaattcc cgcctccgcc accgttgggc agcgacggat cctgtgatat ttcgactacg   20400
cgcggtgatg aattggctcg gtgccggtcg cgccccggctg tagcagttct ggagcgcgtc   20460
tggacatcgt cacgagcgct tgtgattctt ggtcctgtac acgcaagccg gcgcaacgtc   20520
cacgttgccc atcagcggtt atcgcggtc caccggcgcg acggtgaccg cgggcgggta   20580
ctcataggg gaactgcaat gaattactca aaagcagcga gaggaatgcc gacagccgga   20640
caaggtgccg ttcgggcggc gcgcgtcgtc cgtgaaagtc cggcggaatc agaaacggtc   20700
acagttcaga tagcgtcgtt attaccgggt gagtcgctgc gctcgaaagg gatcgagcag   20760
aaccacgtcg cggcactcgc ggaggtagac gcgccgcttc cgcccatact ggtggaccgg   20820
aagacgatgc gggtcgtcga cgggatgcac cggctcctcg cggctctgct caacggacgg   20880
cagacgatcg aggccgaact gttcgacgga accgcggatg agggattcct gcgcgccgtc   20940
cgggagaacg tggtgcacgg actcccgctg tcgcaggcgg accgccgggc cgcgctgcg    21000
cgcatcatcg tgtcccaccc gcatctgtcg gacagggcga tcgcccgggc gtccgggctc   21060
ggggcgaaga ccgtcgcggc cgtcggggcg agttcaactg ccgtcgtgcc gcagttgaac   21120
acccgggtgg gccaggacgg cagggtccgg ccgctgaacg ggggcgaggg gcggcgcagg   21180
gccatggcgg tactggccga acaccccgac gcgtccctgc gcgaggtcgc ccgtctgtcc   21240
```

```
ggggtgtcgc cgcgacggt cagcgacgta cgccggcggc tggccgccgg cgagtcgccc   21300
ctgccgtcga gacgggaacc ggccgaaccg cggacgggcg ccgactccca ccgcaaccag   21360
agcttcgtgg atcccgtccc ggtgctggag aagctgctgc gcgacccctc tctgcggcac   21420
aaggagggcg gccgccagct gctccagctg ctccgccaga acgcggtcgg cgtgcaggac   21480
ctgatggagc tgtccgacgc cgtgccgtcc cactgcaggt ccctggtgat ccatctgcgc   21540
cagcagtacc gggacgcctg gcagtccttc gcggagaagc tggacgagcc cgcctgcgcc   21600
tgtcccgggt gacgaacggg cggcacggac ccgttcaccg acatgaccg gcgccgcgcc    21660
gcgttcacgg cgcgccgccg gcactccac ggcacccgga ccaccgccgc gtatccggcg    21720
gacccgggcc cgggcgggcc ggattcagcg ggcgggggcc caggtgccac ccgattccag   21780
ccaccgggag agctccgccg ccgagtcctt gcgcacgacc agttcgacga ggccgcgggt   21840
ctggtcctga ccgtgctcga tgcggacgtc ctcgatgttg acgcccaagt cgccgatcga   21900
cgtgaacagt tcgccagggg cgccgggctt gtcggagatg gtcaccgaga cggtcgcgag   21960
ctccgtccgg cgcgtaccgg gtttgcgcac gatcctggcg caccccggt tccctcccg     22020
caacagctcc tcgagctcct cctgcgcgcg cggcgcgacc agcgggtcgg cgtcggagac   22080
ggcgcgcagc gcgccgacgg cccggcccag gccggcggcg agggagtcga aacgtccgc    22140
cacgccgtg gcgttggaac gcaggatgtc cccccagagc cgggcgtcac cggccgcgat    22200
ccgggtgacg tcggcgacgc cctgccccgc cagccggacg ctgtcctccg ccgcgtgctc   22260
cagccgcgcg gcgagcaggg aggagagccg atggggcgcg tgcgagacga gggccaccgc   22320
gtggtcgtgc acaccggcgt ccatgaccac cggcatgccg tcgcacaacg acaccatctc   22380
cagggcggtt ttcagcacgt cctgcccggt cagctccgac ggggtgagca cccaggggcg   22440
cccctcgaag aggtccgccc gggcggcgag cggcccggaa cgctcggtgc cggccagcgg   22500
atggcttcct atgtagctgg ccgggtcggc ccgcatcgcg cgcacgtcgt cgtgcgggac   22560
cttcttgacg ctggcgacat cgaggtaggc tcgggccagc ccgctctcct gtgcgcgcgc   22620
gagcacgcgt ccgacctgtg ccggggcac ggccagcacc gccaggtcga cctgacggtc    22680
cggtctctcc agggatcccg cgcccatcgc ctccgccgtc ctggcggcgt tccggtcgac   22740
gtcctccagg tgcacgccga ccccgcggcg ggtcagcgcg agagcgacgg acgtgccgat   22800
ggccccggtg ccgatgactg tggtggtcct caacgcgcgc ccccaggtgc ggtgatccga   22860
aatcggctcg gacaagtgcc gtgcccggca cgggaaaagg gaattcccat ggcgccgtgc   22920
gccgccaatt taacgcttcg gcgcgcatgt tcaactgcgg cgtcgcagcg gtcgaacaca   22980
gtagcggtac accggaccat tgaggcatcg tgctcagttg gcgacaccgg gtcggataaa   23040
cgccggaatc cgaggagttg acgttgcagt cagcgctgag acacgacgac ctgcatccga   23100
tagaagaagt ggaaataagt tcgctctcca ccgacggctc cccgcggatc gacggggaga   23160
gtcccgagca cgtggaaatg ctggccgccg ccgacaccgc gcttccaccg atcatgtgtc   23220
accgccgcac cgggcgggtc atcgacggca tgcaccggct gcgcgccgcg atgctgacgg   23280
gccgtacgac gatcgcggtg aggttcttcg acggcaccga ggaggacgcc ttcgtcctcg   23340
ccgtgaagtc gaacatcgcg cacggactgc cgctgtccgc cgccgaccgc cggcgggccg   23400
ccgggcgcat catggccacc catcccggt ggtcggaccg gatgatcgcc tcggtggtcg    23460
gcacctccgc caggacggtc gccgagatcc gccgcgacgc cggcgccgcc ggggcggggg   23520
agcccacccg catcggccgg gacggcaggg tacggcccgt cgacgtgagc gagggccgca   23580
```

```
gactggccca cgacatgatc gtccgcgacc cgggcctgtc gctgcgccag gtcgcccgcg   23640
ccgccgggat ctcgccggag accgtcaggg acgtcagaca ccggatgctc cgcggtgagg   23700
acccggtgcc cgcgccgcgg ccgcggaccc tggtggagcg cggcgcggac cgccgggcgg   23760
agccggccgg gaaggccgcc gcgccgtgcg ggacggagcc gccgcccgcc gtcgtgatga   23820
agcggctgag ggccgatccg gcgctgcgtc tcaacgagaa cggacgcgac ctgctgcggc   23880
ttctggatat ccacacggtc cggctggagg actggaaccg cattatcgaa agcgtgccgc   23940
cgcaccgtct ggagacggtg gcgcagctgg cacgctcctg cgccgacaaa tggtccgaga   24000
tcgcgtcacg catcgaaagc aacgcatcac atctggccgg gtgaacgagg aaacacacga   24060
atccttcgag gagccgtcgg agaaagcggg acggcccgtc ggaacaccct tgtggagggg   24120
caatggagat acgtcgatc gatcacgtcg aattgttcgt cgaggacgcc caggacacgg   24180
ccggcaggct gtgcgactcc ttcggcttcg tccgcgtggg ccgcggcgcc gggaccaccg   24240
gactgcgcgg ctgcgagtcc gtcctgctgc gccagaacga catcgccctg ctgctgacca   24300
cggccaccga cgccgaccac cgtgccgccg agtacgtgaa gcagcacggg gacggggtcg   24360
cggtgatcgg catcggggtg gacgacgcgc gcgccgccta cgccgaggcc gtgcggcgcg   24420
gagccgtccc ggtcgccgcg cccgaggagt tcgggcccgc cggcgccgt gtcgtcttcg    24480 cctcggtggc gggattcggc gacgtggagc accgcttcgt ctcccgggag gaccccggag   24540
cgccgttcgc gcccttcatc gaggagaccg cgcccacgg ctccggggc atgctgaagc     24600 gggtcgacca cttcgcggtc tgcgtcccgg ccggcgaact cgacgggacc gtccgccgct   24660
accaggaggt gttcggcctc agccagacct tcgaggagcg gatcgtcgtc ggctcgcagg   24720
ccatggactc caaggtcgtg cagagcgacc gcggcgcggt gacgttcacc gtcatcgagc   24780
cggacaccac ccgcgcaccc ggccagatcg acgcgttcgt ggcctccac ggcggggccg    24840 gtgtgcagca cgtcgcgttc ctcactgagg acatcaccac cgcggtgcgc acctgcaccg   24900
ggcgcggggt ccgcttcctc accacgccgc cgagctacta cgagatgctg ccggggcggc   24960
tgggcccggt cggcgtaccc gtggaggagc tcagcgcgct caacatcctg ccgaccgcg    25020 acccgtccgg gatcatgctg cagatcttca ccgagtcgac gcacccgagg cggaccctgt   25080
tctgggaact gatcgaccgc cgcggcgcgc agaccttcgg cagcaacaac atccaggccc   25140
tgtacgaggc cgtggagcgc cagcaggcgg cggaggcggc cgaccaggaa tgaggaagct   25200
ccccgcagac gcgtgtggac ccggaggaca cgccctccgg gtccacacgc gtctgcgggg   25260
ccagcgtcgg ctacgccccg aggagccggc cgccgtgcag cgtctccccg tacgcgaaca   25320
catggccggc ccccacctcc acgggcgcga gcagtgccag atccgtgccc ggacggccgg   25380
agagggcgag ccggccggga ccgctccaga ccggtgagaa ctcgacgccg ctcacctccg   25440
aggcgaccag gcggggccgt ggcggggcgt cggacggcac ccaccgcgga aggacgagac   25500
tgtgcgccag cgggacgtcg tgcagcgcgg cggccgctc ggagcggcgc tcgaccgtga    25560
ccgacgcctc ggcggtgagc cggccgtgga cggagagcgc gccgtcgaag cggccccgg    25620 gagcgagccg tgagcccgcc cggccgacgg tcaccggcct ggtctggtgg atggcgccga   25680
actgcttggg catgccctgg acccagccgc gcaccatcgg cacggctgg tcgacccagg    25740 cgaacgggca gcgcgccatc ggccggccct cgaacgcgca cccgaggagg atcaggaact   25800
ccgagaaccg gcagacgcc gggtcggcca gctccgcgcc gtcctcggag caccactgcc    25860
aggtggcgaa cacggcggcc gccgcacccg gatccgctcc cgcgtccagg cccggcgggca  25920 ggaaacgccg tgcggcgtcg gggtcgacac ggtagtcgac catgaggatc tcgccggaga   25980
```

```
agtgccacgg cggaggcgtg agcatcgacg cctgccccga aggggacagg ggaaggctgt   26040
agccgatggg cccggcggcc ccggccgcgt ccggatccgt cggatgtgtg tgcccggtgg   26100
tggccgtcat gggttccctc cgatctgccg gtccggcggg ccgccggacc atgcctgggt   26160
cagccgtcga gcggcgcgtt cgagcagcgg gggcggattg aagctgtagg ccaggcgcac   26220
gctcggctcc cgtgtgccgc cgaagcgcga acccgcggtg acgcgcacac ccgcccgctc   26280
cgcacgggcg agcagttcgt cctcgccgag cccgtgccg caccggagcc agaggaagaa    26340
cccgccctcc ggacggctga tccgcaccgg gaggtccgcc gcctcccgca gcgcgtcgag   26400
gagggcgtcg cgccgcgccc tcagaccgc ccgcaacatt tccagatgcc ggtcgtagcc    26460
gccgtcggac agcagccctg cgacggcgag cgaggtgatg tggttgagcg acccgccgct   26520
gcggaacagc ccgtgcgacg cgatccgttc ggccagtgcc ggctccgtca ccagccagcc   26580
cagccggagc cccggcccca gggtcttgga gaagctgccc agccgcacca cgccccggtg   26640
tccggcgagg gccgccagtg gcggcggggc cggggaccg tccgtcaggc ccagttcgcc    26700
gtaggcgtcg tcctcgacga ccaggacgcc gtgctccgcc gccgcctcca gcagccgcag   26760
ccggcgctcc agcggcatgg tggcgcccgt cggattgtgg tgggtcgggg tgaggtacac   26820
gaacgcggtg cggccggtgc cgccttcgcc gccccgcgcg gtcccggcga gggcgcgccg   26880
gagcgcctcc ggcaccatgc ccgacgcgtc gagggcgacc cgcctcaggc gcagcgcgca   26940
gtccccgagg atgcgctgcc cgaggtcgta gccgaggccc tccacgagca ccgtgtcgcc   27000
gggcctcgcg agggtggtcg ccagcaggtg gagcgcctgg gacgtgcccg ccgtgacgac   27060
cacgtgctcc ggcccgcacg gggaccgccc ccgcacggtg gccgggcgg ccagctcggc    27120 gcgcaggggc agggcgcccg gatcgtgtcc gtagcccagt gccgccgctc cgtactcctc   27180
cagcgcgcgt gcgtaggcgt cccgcaccag ccccaccggc agcagcgccg gttcgaggta   27240
gccgggcccc aggtcgagga cgcccgcggg ggcgacctcc tgcaccacac cgcgacgcca   27300
ccgccgcgtg tgcgacaacg ggcgggccgt gccgtacggc agggtcccct cgccggcagc   27360
ggtcatcagc ggggtgtcag cacatggcgc aacgcccgta cgcactgggc cagcggggcg   27420
gacgcccggg cgagcgccag gcgcagcgtg cggtcgccgc gggcggggtc agcccagtag   27480
aaggcacggc agggcagggc gtacacatgg tgctcgcgca gcgcctccca gacctcggtc   27540
ccggtcagat gcctgatcag cacccgctcc acactggccc ggctgtccgg gtcgggcacc   27600
ccggtggtcg acaggtccgc cagcccggcg cgcaccaccg accgctgggc ggcgatgaac   27660
tcgtgcagct ccgtcagccc gccggcggcg gcgtcctcgg agaagcggcg gaccatcccg   27720
aggatcagcg gggagacgcc cagcaggatg tcggagtaga tcttctccac cggcaggccc   27780
aggttctcga gtggaccag catgccgacc ttgaggtcga gggtcggcca gagcttgccc    27840
gtgtcctcga tgacgaccca gcgcacatcg ctggcgtcga ggatctcgta gtggtcgtac   27900
tgggcgcggg tgtcgaagcc gcggaaggac gtgtcgaggg cgaggatcac gccgtgccgt   27960
gcgcactgcc cggccagccg gcgcagccgc tccgccgaca cgacccggcc cgtcgggttg   28020
ttcggcgtgg tgacgaagac acagcccacg gactcgagca gctccgcggg caggtcgtcg   28080
gcgtgcagcg gatcctcctc cagggcacc agacccagg ggttgccgcg caacaggtcg     28140
gcgatgttgt cgaaggtggg gtggaccagc gccacggagt ccgtgaccga cgccagggcg   28200
cgggagagga tctccatggc caccgacgag gagtagcagc tcagcacacg gccgggtgcg   28260
gacgggtagc ggtgctggcc gagggccttg aagaaggccg cgtgggcctc gcgttcgagc   28320
```

```
tgctcgacgg ggcgcttctc gccgtcctcg aaaagcagcg ggagatcatt gacgatcttg   28380
ctctggccgg gagtgagcgg ctgccgggca tgcccgtcgg cgatgttgaa ctcgctgttg   28440
agtgcgagga attccagttg ggtgaggttc tccgcgcctg atccggcgtg cgcagcgtgg   28500
gccttgcttt gcagtgttcc ggacacaggt atgcctctct gggatgtgag ggtttccaga   28560
agcggagcgg acgtaaatga gcggcccact ctacggcctt cgccctccgg ctgaaatgcc   28620
tcttcttttc ggcaccgtgt tcaactgcgg tggtgcggca gtcgaacgag ccgtctcgcc   28680
cgccgtatcg gccggacatc gcgttccgac ggtgacgcgc gtgcggttcc cgtgtccaac   28740
tgacctgagg gcgcagttgg acgggccacc ggcacacggc cgcccgatcc ttgtcggacg   28800
ggcccgggca cgcgaaagtg gacgtgcggg atctgtgttc cgccgccggt gtctcttcgt   28860
aagccgtgaa gtggggcctt gatggaattg tcgctcgatg aattcgcgtc gctcgcccgg   28920
gaacggctgg accggccgt ctgggatttc atcgaaggcg gcgccggaga ggaacgcacg   28980
ctcgccgcga acaccgcggc attcgaccgc gtcccgctgc ggccgtcggt gctgcgcggc   29040
gcgggcagcc cgcacaccgg caccacgatc ctcgggcgga cgtgggacgc gcccctcgcg   29100
gtcgccccgg tggcctacca cacgctcgcg gacccggccg gtgaggtcgc caccgtccgg   29160
ggaacggcgg ccgccgccgg actcccggtc gtcgtcagca ccttcgcggg ccgcacgttc   29220
gaggacatcg ccgccgaggc caccgtcccg ctctggctcc aggtgtactg cctgcgggac   29280
cgctccctca cccgaggcct catcgaacgc gccgagaacg cgggcttcga ggccctggtc   29340
ctcacggtcg acgcgccgca cctcggccgc cggctgcggg acctgcgcaa cggcttccgg   29400
ctgcccgccg gcacggtccc cgccaacctc ccggtggacg gattcgcgga ccccgcggcg   29460
cactcccgcg ccgacttcga ccccggcctg gactggtcgg tggtggagtg gctgcgctcg   29520
gtctccgaac tgccgttgct cgtcaagggg atcctcaccg cgccgacgc ggtgcgcgcg   29580 gccgaggccg gggtggacgg cgtcatggtc tccaaccacg ggggccgcca gctcgacgga   29640
gtgccggcca ccctcgacgt cctgcccgag gtcgccgagg cggtcggcgg acgcctcccc   29700
gtcctcctcg acggcggggt ccgccggggg cggacatcc tggcggcgct cgcgctcggc   29760
gccgacgcgg ccctcgtcgg ccgcccgtg ctgcacggcc tcgcggccgg cggggccggc   29820
ggggtgaccg gcgtcctctc cgtcctcctg gaggagctga cggacgcgat gtcccttgcg   29880
ggcctgagga ccctcgccga catcggcccc tcactcgtcg gccgggctcc tgaccacccc   29940
cgccgaagca ccgtggacgc cgggaagggc gcggggagcg accggcgcac cgccgccggg   30000 ggagggggccg ggctgcgcct cgcggacctg cacccgagtg tcgccgaccc ggtcatggac   30060
accatgaact tcctcaacga ggtgacactg cgctacccg aggcggtgtc cttcgccccc   30120 ggacggcccct acgcggagtt cttcgagacc gagcaggtct tccgccatct gcgccgctac   30180
ctcgaccacc tggccgagca gggccgttcg cccgcgcagg tgcgcgacgc gctgttccag   30240
tacggtccgt ccgccggtgt gatccgcgag ctgatcgccc actcgctgcg ggtggacgag   30300
ggcatcgacg tgtcgcccga gtcgatcgtg gtgacggtcg gctgccagga ggcgatgttc   30360
ctgacgctgc gcgcgctcat gtccggcccg gacgacgtgc tgctcgtctc cagcccctgc   30420
tacgtgggga tcaccggggc cgcccggctg ctggacgtcg cggtgaccgc cgtcgaggag   30480
ggcgaggacg gcctgtcgtg cgacgccctc gaggccgccg tctcggcgga gcgggcgcgc   30540
ggcaggcggc cgcgggccgt ctacgtggtc ccggaccact cgaacccgtc cggcgcgacc   30600
atgccgctcg aggcccggaa gtccctcctg gagctgcgc agcggctcga cgtcctcgtc   30660
ctggaggaca gcccgtaccg gcacgtcagc ccgggcacgc aggtggcgtc cctgaaggcc   30720
```

```
ctcgaccgga cacggcgagt gatccacctc ggttcctacg ccaagaccgt cttccccggg   30780
gcacgcctcg ggttcgcggt cgccgaccag ccggtgctgg cgccggacgg cggcacgagt   30840
ctgctggcgg acgaactcgc caagatcaag agcatggtca cggtcaacac ctcgccgctc   30900
agccaggccg cggtggcggg cgcgctgctg gagtcgggcg gccgtgtctc ggagctcaac   30960
gcccgcaacg ccgcccacta cggggaggcc atgcgcttca ccctgcagtg cctggagcgg   31020
gagttcccgg ccgcgcggcg gacccggctc ggcgtccgct ggaacgcgcc cagcggcggg   31080
ttcttcctca ccctccaggt gccgttccgc gcggacaact ccgcgctggc ccggtccgcg   31140
caggacttcg gggtcatctg gacgccgatg tcgtacttct atccgcaggg cggcggcctg   31200
cacaccctca ggctctccac cagctacctg acccacgccg acatcgagaa gggcatctcc   31260
cggctggccg ggttcatcga gttcgagtgc ggggacccgg tggcctgaac cgccgcgacg   31320
acgaagggcc ccggccgcgc cggcggggcc cttcgtcggt cgcgacgctc aggacggatg   31380
cggctcctcc cagaacatgc tgtcggacga ggcgacgaga ccgccgtcga agagcgggac   31440
gtcctcgccg gcgtactctc ccagctgcgc ccgggtctgc acctgcgagc cctcctgcat   31500
cgcccggctc accgccgacg accggaacag cggggccatg ttctcctcct gccgcccggc   31560
catgtcgtcg acggcgtcgg cgaactccgc cgactgctgc ttgagccgca ggacgctcga   31620
ctcggcgtcg gagaggtcga agtccgtgct ggacatgccc gccaccagct ccacgaacga   31680
ctccagctcg gcgtggctgc tccgggtgac cttcttcgcc gtccagaagt aggagtcctc   31740
gtcgacgtgc atgtcgtaga acgaggtcag gaactcgtag aagacgccgt actcccgccg   31800
gtaccgggcc tcgaactcgt cgaaggcccg ccgctcgtcg atccgccccg ccagcacgct   31860
gttgagggag cgggcggcca gcagcgcgct gtaggtggcc agatggaccc cggaggagaa   31920
gacggggtcg acgaagcacg ccgcgtcacc gacgagcacc atccccggcc gccagaaggt   31980
cgtgtggtgg tacgagtagt ccttgcgcac ccgcagctgc ccgtactgac cggtcgtgac   32040
ccgggtggcg tccgccaggt actccttgat catcgggcat tcgtcgatga ggccgcgcag   32100
cgcgctctcc gggtcgccct gcaccttggc cgcgtcctcc cggcggacga ccgcgccgac   32160
gctggtcagc gtggagctga gcgggatgta ccagaaccag ccgctgccga acgccacaca   32220
gaggatgttg ccggcgtagg gcgccggcat ccgcttgccg ttctcgaagt agccgaacag   32280
cgccaggctc ttgaagaagt ccgagtacgt gcgcgagccg ccgacccgct tgtggatgcg   32340
gctggtgttg cccgaggcgt ccaccacgta ccgggccgac acctcgtgct ccgtgccgtc   32400
cgggtcggtg taccgcagcc cgcggggccc ccgtcggcg tcgtccacga catcggtgac   32460
cgtgcggtcc tggcggacca cgacacccctt gcgggccgcg ttgtccagca ggatcttgtc   32520
gaatttgctc cgctccacct gataggcgaa cgaggtcggt ccggagacct ggacgagac   32580
ggagaaggag aaattccacg gcttggggct cgcacccac cggaacgtcc caccgcgctt   32640
gtgcggaaaa ccggcggcgg cgagttcgtc ggtgacaccg agcagatggc agatgccgtg   32700
aatggtcgac ggcagaagcg actcgcctat ctggtacctg gggaaggtct ccttttcgag   32760
cagcagcaca ctgtgcccct gcatggccac caggtcgag agcgtcgacc ccgaagggcc   32820
gccgcccacg accacgacgt cgaattcctc gtgctgtcct gtactcattc ggcctcccgg   32880
cacgcactga tgcggtcatc gcgctggtga ctcttttgtc agggttccac aggactcaaa   32940
ggggccaaag ggtggacgac attccgtgaa tggacagccg ggcccgggcg cgcgcacgca   33000
aaggcgccgc cggggaattc ccggcggcgc ccggaccggc gtcgggtgag acgggggtca   33060
```

```
actcacccgg cgccggatcc gccacacccc gaacaccgtg aggattccgc tgagtgccac   33120
atagatcgcg gtctccagcc actggaacgc ccagtagcgg ctgctggggt ggtacaggac   33180
gtcgacgtgc aggtcgtgtt cggcgaggca caccgcggtg tcgccgaacg tgcccccgc    33240
gccggtcttg ggcgggtcgt cgaggcagcc gttgaactcg ctggaggcga gggtcctgcc   33300
gtccgcggtg cgcagcggac tggtctcggc gatccacgcg tccggcgcgt ccgggatccg   33360
caccccgccg atgacggatc cgccgccgat actgcccagg ttctgcgccg agttgatcgc   33420
ctcggccgtc atcgccagcg tcgtcctgtc cggcggcatc aggctgggcc gcaccacgtt   33480
cgggaagaag aactggaagg cgatgaagac caccagcgtc accgccatcg cgggcagggg   33540
ccgccgcagc aggagcccga cgacggtgcc gaacgtgaag gccagcgcgg cgtagccgat   33600
cggggcgatg ttgcgcgcac cgaacacgaa ggtgtcgaac tgctccttga cgacgtcgtc   33660
gaagggccgg gccgcccagg tgagcagggc gcggccgca ccggtcacga tcaccgaggc    33720
cgcgccgatg agcaggatct tgctgagcag ccagcgcggc cgggtgacgc tctggttcca   33780
caccagccga tgggtgccgt tctcgagttc cctggcgatc aggggagcgc cccagaaggt   33840
gccgatgagc gcggggatca gggcaggcc ggtcgccagg aacagcaggg tgttctggaa    33900
ggtgctgcgg aactggctcc tggcctgggc gcagttggcc gagttgtcgc agttggcctg   33960
gtagacgtca tgggcgtcac ggatgtcccc gcccaggtag agcaggtaga cggcgatcac   34020
ggccagcgcg ccggcgccga acagggcctg gacgcggaac tgccgccagc tgagccacat   34080
catcgggtgg ccccccaggc tgcggcctcg gtgcgggcgg cgggaacggc ggccgcccgg   34140
gtcatgtagg cgagcacgag ttcctcgagg gtgaccggct cggaccggta gggcagtgcc   34200
tcggtcgcgg cgccggtgcg gacgaccgcg ctgctgtgct tgccgctgtg ctcgaccgag   34260
atcacctcga tccggcggg cggctggtcg aactcgccgc gggccgcgac cagccgggcg    34320
tgcccggcca gcagctcccg ggtgtcgccg gcgacctgca cccgggcgtc gcacagcacg   34380
atgagatagt cgcagacctg ctccacgtca ccgaggaggt gcgaggagag gacggcgctg   34440
gcgccgagct ccagcacgaa ctccatcagg ttctgcagga accccggcg cgccaggggg    34500
tccagggccg ccgccggctc gtcgaagatc agcagctccg gccgcttggc cgccgcgatg   34560
gtcagcgcaa gctgcgcgcg ctggccaccc gagagctgcc cggccttctg cccggcgctg   34620
agccccacct ggctgatgcg ccgctctgcc aggacccggt cccagcccgg gttcatcttc   34680
gcgccgaact tcaggtgctc cgccacggtg aacgcgccgt acaccggcgt gttctgcgcg   34740
acgaacccca cccgggccag gtgcgacgcg ttggccgccg gacgcgagcc gaggacgctc   34800
agtgagccgg acgtcggttc ggtcagcccg caggccaggt gcaggagggt cgatttgccg   34860
gccccgttcg ggccgaccag tccgatgaca cggccggcgg ggacgctgag gtgcacgtcg   34920
ctcagggcga gcttgccgcg gcggccgtac ttcttcgtca gccctccgc gtgaagcacg    34980
ggaggggagt ctgcgtgtgg catgactcca tcctcgaatt ccgccccgtt cacggcatca   35040
gtccaaagca cggttcccgt tgccggcggc cgtactttcg gccggtcggc cacggccctg   35100
ctggtgggcg aactgggtgc ggtacagctc ggagtagaga ccgccgccgg ccagcagctg   35160
gtcgtgggtg ccccgctcct ggatccgccc gtcgtcgatg acgaggatct ggtcggcgtc   35220
ctggatggtg gacagccggt gcgcgatgac gagcgaggtg cgcccggtca gggcggtctt   35280
gagggcccgc tggatggcca gctcggactc ggagtccagg tgcgccgtcg cctcgtccag   35340
gacgacgatc ggaggcgact tgagcaggag ccgggcgatg ccagccgct gcttctcacc    35400
gccggacagc cggtagccgc ggtcgccgac gaccgtgtcg agaccgtccg ggagctggga   35460
```

```
gatcgtcggc cagatccgcg ccgcctcgca cgcctggacg atctcgggct cggaggcgtc    35520
cgggcgggcg tacagcaggt tggcccggat ggtgtcgtgg aacaggtgcg cgtcctgggt    35580
gaccacgccg accgtgttct gcagcgagcc gagggtcagg tcgcggacgt cgtggccgcc    35640
gatccgcacc gttcccgagg tggcgtcgta gagccgtggc accaggtggg tgatcgtggt    35700
cttgcccgcg ccggacgggc cgaccagcgc cgtgagccgg ccggccgggg cgtggaagct    35760
cacgtcgttg aggaccagcg cgccggggcc ctgctcgctc ttgcgctgcg gcatcaactc    35820
cagtgagggc agggacactt cctcggcgct ggggtagcgg aaggcgacct ggtcgaactc    35880
gacgggggga gcggtgccgt cgccgttcgc cgaggcgcgg gccggcaggg ggcgggcgcc    35940
gggacgctcg gtgatcagcg gcttcaggtc cagcacctcg aagacgcggt cgaagctgac    36000
cagcgcggtc atgacgtcgc tctggatgtt cgtcagctgg ttgacggggc cgtacagcat    36060
cagcagcagg gcgaccatgg ccaccagcgt gccgatctgc agcgagccgt cgatgacgaa    36120
ccagccgccg aagccgtaca ccatcgccgt ggtgacggtg gtgagcaggg tgacgaggat    36180
gaacagcagc cgtgcgtgca cgtccatcga gatcgcgatg tcccggacga ggcccgcctt    36240
cttggagaac tcggcggact cgtcctccgg acggccgtag agcttgacga gcatcgcgcc    36300
ggagatgttg aaccgctcgg tcatcatcga gcccagcttg gcgtcgttct gcatgccggc    36360
gcgggccagc ttctccagcc gctgggcgat gatcttcccg gggatgaaga acagcgggat    36420
catgatcagc gccgccacgg tgatcggcca cgagaggtag agcatcgccg cgagcaccag    36480
gaccagcgtc agcagcgtcg acagcgactg cgacagcagc gaggtgaggg cctgttgggc    36540
gcccacgatg tcggtgttga tccggctgac cagcgacccg gtctgggtgc gggtgaagaa    36600
cgccaccggc tgccgctgga tgtgggagaa caccgcggtc cgcaggtcga agatgaggcc    36660
ctggccgacc cttccggaga accacgtctg cgtgtagacc gccacgacgt tcagcagggc    36720
cagtccggcg acgagcccgg cgaggccgaa cacgacggac gtcttcccgg ggatgatgcc    36780
gtcatcgatg atcattttga gggtcagcgg gatcgacacc gtgatcaggg agtcgacgat    36840
cgtcgccacc atgaccatcg ccatggcccg gcggtagcgc atggcgtagg gaatgatccg    36900
cttgaacgtg ccggacctga ccggctgcgg gtccaccagt ccttcgaccc gcagtccgat    36960
cgtgcccatc gtcgggtcgt gtcccacggt cacggagact ctcctcagtg tgtgtcgcgt    37020
cgctatgtgt cgcgtcgctg tgtggcgcgt cgctgtgtgt cgtcgggcg tcgcgtcagt    37080 gcttgtcgag gaactcgacg atcgccgcgt tgaccgcgtc gggccgctcg aagtacccga    37140
ggtgcccgca gtccgggatc tccacgagat cgcagtcggg aacggcctcg cgacctcca    37200 cgcccaggtg cggcggggtg atgaggtcgt cggcgaaggt cacgacgcga caggggggcgg    37260 ccacccggcg cagcgccggg cggcggtcgt ccatgatgtc ggcccaggcg tgccgggcct    37320
gcgcctcccc gccccggac agctcgaaga cgtccagcca ggcggtcacc gcctggtcgt    37380
cgttgagcgt cgcgggcgag aacatccgga acaccgtcga cgcggcgtcg tacgcggccg    37440
gcagccgcac cccgctctcc accagtgccg tctccgcccg cgtctgggcc cgccgcgcgg    37500
cgtccgcacg ggcccgggtg gcgatgagca ccgcgcaccg cacgagttcg ggatgcccga    37560
tcgccagctc ctgcgcgatc atcgcccca gggaggtgcc cacgatccgg cacggcgcca    37620
gatccagggc ctcgatcagg cccttggcgt cggcggtcat gtccagcagc gagtacctgc    37680
ccggcggcgc gtcggacggc gggacacccc ggtggtcgaa gacgaccgtg gagtagcccg    37740
ccgtgtgcag cgccggcgtc tggtgcaggg tccaggcatg gccggccgag cccgagccca    37800
```

```
tgatcatgag caccggttcg ccccggcccg cacgctggta ggcgatgcgg acgcccccca   37860
cggtgacgaa gtgcggggcg cgccggcccg cggtgtggtc catgccgcct ctccctcctc   37920
gtcgtcgcgg gggccgcccg gtggtaccgg ccggccccgg gggcggctca ctatcgcacg   37980
cggccacggg gcggggcagt gtgcgcgggg cacgtccatg gacacccccc ggcccgcgtc   38040
caactgcggt gatgccctca gttggacacc ggccggccgc gtccaagcag gcccggccga   38100
cggttgatcc gctgtgtgga gctgagccat attgggccgc cgtgagccac tgacgcccac   38160
caagtccccg cgcttcttcc gcaccggccg cctggcgcgc ccgtcgcgcc gagggaggga   38220
ccaccttgtc agcttccgac cttccagcca cccggctgac acccgagaag atccggtcct   38280
ggctcgtcga ccgggtcgcc tactacgcca ggctgcccgc cgaggagatc ggcgccgacg   38340
tcccgctcgc gcactacgga ctggactcgg tgtacgcctt cgccctgtgc ggagacatcg   38400
aggacggcct cggcctcgtc gtcgagcccg tcctgctctg gacgtcgac accatcaccg    38460
agctcaccga ccatctcgcc gaactgcacg ccgactgagg ccttcgagg gggaggacga    38520
tgcgtcgaaa ggacctggag aggctgacgt ccggtcagct cggcgtctgg tacgcgcagc   38580
agctcgaacc cctgagcccc gtgtacaaca tcgccgagta cgtggagatc gcgggcgacg   38640
tggacgtcgg gcttctggtg tcggcgctgc ggtctgccct cgacgaggcc cagacctacc   38700
ggctccgctt ccggcaggag gacgccggcc ccggacagta cgtcgacgac tcgctggagc   38760
ttcccgtcca cgtcgccgac ctcggctccg caggggaccc gcgcgccgcg gccgtggagt   38820
ggatgaccgc cgacctggac cgccccgcgg acccctcac cggcccgctg ccgcccacg    38880
ccgtgttccg gctgggaccc ggccatgtcc tctggtacca gcgtgcccac cacctcgtcc   38940
tcgacgggac cagcctctcc gtgttcgccg gtgggatccc cgggtaccga gctcgaattc   39000
gccctatagt gagtcgtatt acaattcact ggccgtcgtt ttacaacgtc gtgactggga   39060
aaaccctggc gttacccaac ttaatcgcct tgcagcacat ccccctttcg ccagctggcg   39120
taatagcgaa gaggcccgca ccgatcgccc ttcccaacag ttgcgcagct gaatggcgaa   39180
tggcgcctga tgcggtattt tctccttacg catctgtgcg gtatttcaca ccgcatatgg   39240
tgcactctca gtacaatctg ctctgatgcc gcatagttaa gccagccccg acacccgcca   39300
acacccgctg acgcgaaccc cttgcggccg c                                  39331
```

<210> SEQ ID NO 40
<211> LENGTH: 40551
<212> TYPE: DNA
<213> ORGANISM: Artificial sequence
<220> FEATURE:
<223> OTHER INFORMATION: Synthetic fosmid pXYF24

<400> SEQUENCE: 40

```
atcgaatata acttcgtata atgtatgcta tacgaagtta ttagcgatga gctcggactt     60
ccattgttca ttccacggac aaaaacagag aaaggaaacg acagaggcca aaagctcgc    120
tttcagcacc tgtcgtttcc tttcttttca gagggtattt taaataaaaa cattaagtta   180
tgacgaagaa gaacggaaac gccttaaacc ggaaaatttt cataaatagc gaaaacccgc   240
gaggtcgccg ccccgtaacc tgtcggatca ccggaaagga cccgtaaagt gataatgatt   300
atcatctaca tatcacaacg tgcgtggagg ccatcaaacc acgtcaaata atcaattatg   360
acgcaggtat cgtattaatt gatctgcatc aacttaacgt aaaaacaact tcagacaata   420
caaatcagcg acactgaata cggggcaacc tcatgtccga gctcgcgagc tcgtcgacag   480
cgacacactt gcatcggatg cagcccggtt aacgtgccgg cacggcctgg gtaaccaggt   540
```

```
attttgtcca cataaccgtg cgcaaaatgt tgtggataag caggacacag cagcaatcca    600
cagcaggcat acaaccgcac accgaggtta ctccgttcta caggttacga cgacatgtca    660
atacttgccc ttgacaggca ttgatggaat cgtagtctca cgctgatagt ctgatcgaca    720
atacaagtgg gaccgtggtc ccagaccgat aatcagaccg acaacacgag tgggatcgtg    780
gtcccagact aataatcaga ccgacgatac gagtgggacc gtggtcccag actaataatc    840
agaccgacga tacgagtggg accgtggttc cagactaata atcagaccga cgatacgagt    900
gggaccgtgg tcccagacta ataatcagac cgacgatacg agtgggacca tggtcccaga    960
ctaataatca gaccgacgat acgagtggga ccgtggtccc agtctgatta tcagaccgac   1020
gatacgagtg gaccgtggt cccagactaa taatcagacc gacgatacga gtgggaccgt   1080
ggtcccagac taataatcag accgacgata cgagtgggac cgtggtccca gtctgattat   1140
cagaccgacg atacaagtgg aacagtgggc ccagagagaa tattcaggcc agttatgctt   1200
tctggcctgt aacaaaggac attaagtaaa gacagataaa cgtagactaa acgtggtcg   1260
catcagggtg ctggcttttc aagttcctta agaatggcct caattttctc tatacactca   1320
gttggaacac gagacctgtc caggttaagc accattttat cgcccttata caatactgtc   1380
gctccaggag caaactgatg tcgtgagctt aaactagttc ttgatgcaga tgacgtttta   1440
agcacagaag ttaaaagagt gataacttct tcagcttcaa atatcacccc agcttttttc   1500
tgctcatgaa ggttagatgc ctgctgctta agtaattcct ctttatctgt aaaggctttt   1560
tgaagtgcat cacctgaccg ggcagatagt tcaccggggt gagaaaaaag agcaacaact   1620
gatttaggca atttggcggt gttgatacag cgggtaataa tcttacgtga aatattttcc   1680
gcatcagcca gcgcagaaat atttccagca aattcattct gcaatcggct tgcataacgc   1740
tgaccacgtt cataagcact tgttgggcga taatcgttac ccaatctgga taatgcagcc   1800
atctgctcat catccagctc gccaaccaga acacgataat cactttcggt aagtgcagca   1860
gctttacgac ggcgactccc atcggcaatt tctatgacac cagatactct tcgaccgaac   1920
gccggtgtct gttgaccagt cagtagaaaa gaagggatga gatcatccag tgcgtcctca   1980
gtaagcagct cctggtcacg ttcattacct gaccataccc gagaggtctt ctcaacacta   2040
tcacccccgga gcacttcaag agtaaacttc acatcccgac cacatacagg caaagtaatg   2100
gcattaccgc gagccattac tcctacgcgc gcaattaacg aatccaccat cggggcagct   2160
ggtgtcgata acgaagtatc ttcaaccggt tgagtattga gcgtatgttt tggaataaca   2220
ggcgcacgct tcattatcta atctcccagc gtggtttaat cagacgatcg aaaatttcat   2280
tgcagacagg ttcccaaata gaaagagcat ttctccaggc accagttgaa gagcgttgat   2340
caatggcctg ttcaaaaaca gttctcatcc ggatctgacc tttaccaact tcatccgttt   2400
cacgtacaac attttttaga accatgcttc cccaggcatc ccgaatttgc tcctccatcc   2460
acggggactg agagccatta ctattgctgt atttggtaag caaatacgt acatcaggct   2520
cgaaccctt aagatcaacg ttcttgagca gatcacgaag catatcgaaa actgcagtg   2580
cggaggtgta gtcaaacaac tcagcaggcg tgggaacaat cagcacatca gcagcacata   2640
cgacattaat cgtgccgata cccaggttag gcgcgctgtc aataactatg acatcatagt   2700
catgagcaac agtttcaatg gccagtcgga gcatcaggtg tggatcggtg gcagtttac   2760
cttcatcaaa tttgcccatt aactcagttt caatacggtg cagagccaga caggaaggaa   2820
taatgtcaag ccccggccag caagtgggct ttattgcata agtgacatcg tcctttcccc   2880
```

```
caagatagaa aggcaggaga gtgtcttctg catgaatatg aagatctggt acccatccgt    2940
gatacattga ggctgttccc tggggtcgt taccttccac gagcaaaaca cgtagcccct    3000
tcagagccag atcctgagca agatgaacag aaactgaggt tttgtaaacg ccacctttat    3060
gggcagcaac cccgatcacc ggtggaaata cgtcttcagc acgtcgcaat cgcgtaccaa    3120
acacatcacg catatgatta atttgttcaa ttgtataacc aacacgttgc tcaacccgtc    3180
ctcgaatttc catatccggg tgcggtagtc gccctgcttt ctcggcatct ctgatagcct    3240
gagaagaaac cccaactaaa tccgctgctt cacctattct ccagcgccgg gttattttcc    3300
tcgcttccgg gctgtcatca ttaaactgtg caatggcgat agccttcgtc atttcatgac    3360
cagcgtttat gcactggtta agtgtttcca tgagtttcat tctgaacatc ctttaatcat    3420
tgctttgcgt ttttttatta aatcttgcaa tttactgcaa agcaacaaca aaatcgcaaa    3480
gtcatcaaaa aaccgcaaag ttgtttaaaa taagagcaac actacaaaag gagataagaa    3540
gagcacatac ctcagtcact tattatcact agcgctcgcc gcagccgtgt aaccgagcat    3600
agcgagcgaa ctggcgagga agcaaagaag aactgttctg tcagatagct cttacgctca    3660
gcgcaagaag aaatatccac cgtgggaaaa actccaggta gaggtacaca cgcggatagc    3720
caattcagag taataaactg tgataatcaa ccctcatcaa tgatgacgaa ctaaccccccg    3780 atatcaggtc acatgacgaa gggaagagaa aggaaatcaa ctgtgacaaa ctgccctcaa    3840
atttggcttc cttaaaaatt acagttcaaa aagtatgaga aaatccatgc aggctgaagg    3900
aaacagcaaa actgtgacaa attaccctca gtaggtcaga acaaatgtga cgaaccaccc    3960
tcaaatctgt gacagataac cctcagacta tcctgtcgtc atggaagtga tatcgcggaa    4020
ggaaaatacg atatgagtcg tctggcggcc tttcttttc tcaatgtatg agaggcgcat    4080
tggagttctg ctgttgatct cattaacaca gacctgcagg aagcggcggc ggaagtcagg    4140
catacgctgg taactttgag gcagctggta acgctctatg atccagtcga ttttcagaga    4200
gacgatgcct gagccatccg gcttacgata ctgacacagg gattcgtata aacgcatggc    4260
atacggattg gtgatttctt ttgtttcact aagccgaaac tgcgtaaacc ggttctgtaa    4320
cccgataaag aagggaatga gatatgggtt gatatgtaca ctgtaaagcc ctctggatgg    4380
actgtgcgca cgtttgataa accaaggaaa agattcatag cctttttcat cgccggcatc    4440
ctcttcaggg cgataaaaaa ccacttcctt ccccgcgaaa ctcttcaatg cctgccgtat    4500
atccttactg gcttccgcag aggtcaatcc gaatatttca gcatatttag caacatggat    4560
ctcgcagata ccgtcatgtt cctgtagggt gccatcagat tttctgatct ggtcaacgaa    4620
cagatacagc atacgttttt gatcccggga gagactatat gccgcctcag tgaggtcgtt    4680
tgactggacg attcgcgggc tattttacg tttcttgtga ttgataaccg ctgtttccgc    4740
catgacagat ccatgtgaag tgtgacaagt ttttagattg tcacactaaa taaaaaagag    4800
tcaataagca gggataactt tgtgaaaaaa cagcttcttc tgagggcaat tgtcacagg     4860 gttaagggca atttgtcaca gacaggactg tcatttgagg gtgatttgtc acactgaaag    4920
ggcaatttgt cacaacacct tctctagaac cagcatggat aaaggcctac aaggcgctct    4980 aaaaagaag atctaaaaac tataaaaaaa ataattataa aaatatcccc gtggataagt    5040
ggataacccc aagggaagtt ttttcaggca tcgtgtgtaa gcagaatata aagtgctgt     5100 tccctggtgc ttcctcgctc actcgaccgg gagggttcga gaaggggggg caccccctt     5160 cggcgtgcgc ggtcacgcgc acagggcgca gccctggtta aaaacaaggt ttataaatat    5220
tggtttaaaa gcaggttaaa agacaggtta gcggtggccg aaaaacgggc ggaaaccctt    5280
```

```
gcaaatgctg gattttctgc ctgtggacag cccctcaaat gtcaataggt gcgcccctca    5340
tctgtcagca ctctgcccct caagtgtcaa ggatcgcgcc cctcatctgt cagtagtcgc    5400
gcccctcaag tgtcaatacc gcagggcact tatccccagg cttgtccaca tcatctgtgg    5460
gaaactcgcg taaaatcagg cgttttcgcc gatttgcgag gctggccagc tccacgtcgc    5520
cggccgaaat cgagcctgcc cctcatctgt caacgccgcg ccgggtgagt cggcccctca    5580
agtgtcaacg tccgcccctc atctgtcagt gagggccaag ttttccgcga ggtatccaca    5640
acgccggcgg ccggccgcgg tgtctcgcac acggcttcga cggcgtttct ggcgcgtttg    5700
cagggccata cacggccgcc agcccagcgg cgagggcaac cagccgaggg cttcgccctg    5760
tcgctcgact gcggcgagca ctactggctg taaaaggaca gaccacatca tggttctgtg    5820
ttcattaggt tgttctgtcc attgctgaca taatccgctc cacttcaacg taacaccgca    5880
cgaagatttc tattgttcct gaaggcatat tcaaatcgtt ttcgttaccg cttgcaggca    5940
tcatgacaga acactacttc ctataaacgc tacacaggct cctgagatta ataatgcgga    6000
tctctacgat aatgggagat tttcccgact gtttcgttcg cttctcagtg ataacagcc    6060 agcttctctg tttaacagac aaaaacagca tatccactca gttccacatt tccatataaa    6120
ggccaaggca tttattctca ggataattgt ttcagcatcg caaccgcatc agactccggc    6180
atcgcaaact gcaccggtg ccgggcagcc acatccagcg caaaaacctt cgtgtagact    6240
tccgttgaac tgatggactt atgtcccatc aggctttgca gaactttcag cggtataccg    6300
gcatacagca tgtgcatcgc ataggaatgg cggaacgtat gtggtgtgac cggaacagag    6360
aacgtcacac cgtcagcagc agcggcggca accgcctccc caatccaggt cctgaccgtt    6420
ctgtccgtca cttcccagat ccgcgctttc tctgtccttc ctgtgcgacg gttacgccgc    6480
tccatgagct tatcgcgaat aaatacctgt gacggaagat cacttcgcag aataaataaa    6540
tcctggtgtc cctgttgata ccgggaagcc ctgggccaac ttttggcgaa atgagacgt    6600 tgatcggcac gtaagaggtt ccaactttca ccataatgaa ataagatcac taccgggcgt    6660 atttttttgag ttatcgagat tttcaggagc taaggaagct aaaatggaga aaaaaatcac    6720
tggatatacc accgttgata tatcccaatg gcatcgtaaa gaacattttg aggcatttca    6780
gtcagttgct caatgtacct ataaccagac cgttcagctg gatattacgg ccttttttaaa    6840 gaccgtaaag aaaaataagc acaagtttta tccggccttt attcacattc ttgcccgcct    6900
gatgaatgct catccggaat ttcgtatggc aatgaaagac ggtgagctgg tgatatggga    6960
tagtgttcac ccttgttaca ccgttttcca tgagcaaact gaaacgtttt catcgctctg    7020
gagtgaatac cacgacgatt tccggcagtt tctacacata tattcgcaag atgtggcgtg    7080
ttacggtgaa aacctggcct atttccctaa agggtttatt gagaatatgt ttttcgtctc    7140
agccaatccc tgggtgagtt tcaccagttt tgatttaaac gtggccaata tggacaactt    7200
cttcgccccc gttttcacca tgggcaaata ttatacgcaa ggcgacaagg tgctgatgcc    7260
gctggcgatt caggttcatc atgccgtttg tgatggcttc catgtcggca gaatgcttaa    7320
tgaattacaa cagtactgcg atgagtggca gggcggggcg taatttttttt aaggcagtta    7380 ttggtgccct taaacgcctg gttgctacgc ctgaataagt gataataagc ggatgaatgg    7440
cagaaattcg atgataagct gtcaaacatg agaattggtc gacggcccgg cggccgcaa    7500 ggggttcgcg ttgccgatt cattaatgca gctggcacga caggtttccc gactggaaag    7560
cgggcagtga gcgcaacgca attaatgtga gttagctcac tcattaggca ccccaggctt    7620
```

```
tacactttat gcttccggct cgtatgttgt gtggaattgt gagcggataa caatttcaca    7680
caggaaacag ctatgaccat gattacgcca agctatttag gtgagactat agaatactca    7740
agcttgcatg cctgcaggtc gactctagag gatcccacgg ttcttctccc gggtccaccc    7800
ccggttccgg acgccgtacc ggccgacgat cctgctcggc gtcgccatcg cgatcctcgc    7860
cggcttcacc ccgctgaacg agctcgcggc gctggtgaac atcggcaccc tgttcgcctt    7920
cgtgatcgtc gcgatcagcg tgatcatcct ccgcaggacc cggcccgacc tgccccgcgc    7980
cttccgcacg ccctgggtgc ccgtgctgcc gatcgtctcg gtcgccgcgt ccctgtggct    8040
gatgctgaac ctgccggccg agacctgggt ccgcttcggc atctggatgg cggtcggcgt    8100
cgtcgtctac ttcctgtaca gccgcaaaca cagccgtctg gccgaggagc gcggcgggga    8160
acggacgtcg tcctgaggcc ggcgcctccc ggcgctaccc gtcccgccgc ggcgcccagg    8220
cgccgcccgc gggccgcacc gcgcgcgggc cggtgacgtc agcgcccagg acgtcaccc    8280 ggcggcgcag ctcgcggtcg gccgtgacca ccaggaccgg gcggtcgccc gcctccgcca    8340
ccaggtcgac catgcggtcg tcgccgctgc ccggggccgg gtccaccgg acaccgggga    8400 ccgactccac cccgcgggcc gccccctcgg tcaccaggac gatctccacc gggcccgggt    8460
gacccggcac gccctccgcg gccagccggt cgcgcagccg ttccgcggcg ccccggcggt    8520
cccgccacca tccgtcgggc accgacccga ccacgttggc ggcgtcgacg atcacgagca    8580
ggccggtgtc atccatggcg tcagggtccc acgcggcgcc ccggccgtcc gggtcgcggg    8640
ggtgcgaccg cgcgcggggg aggacgcccg ggaacacatg aacgatcgac atatgatgtg    8700
tcgagtttca gcgttcccgc gtcggtgacg cggcgggccg caggaagggg cacctggcga    8760
tgcggagaag gtcggcgggc cccgtgggcg cctccgtcaa ggacggacgt gccgccgggg    8820
agcaccggga ggccgcgtcc ggggccgccc acggtgactg gctcacccgc ggcaaggacg    8880
gccggctgac gctgtacgtc cccaccgacg gcggtctgct gcgctggacg gagaccgccg    8940
tgggtggccc cggctggagc ggtccgcact tcgtcccggt ggccgggctg acgcacctgg    9000
cggtggctca gggagccaac ggctacgtcc acttcctcgg ccgcagggag cgcgagggcg    9060
ccgactccac gccgggcgtg gacatcgtgc acgcgatcca gtaccagacc ggactcgcct    9120
tcagcgactg gcggtccctc ggcaacccgc accgggtccc ggaggagccc ggaccgctcg    9180
ccgtgccggt cggggcggtc gcccgggacg gcaccgtgca cgtgttcgtg cggggcgcgc    9240
acggagggct gatgctgcgg cgcgaggccc cgaacggcaa gtggaaggcg tgggaggacc    9300
tgggcggcgg cggcgccggc gcccagcccg gcgcgtcgc gctcaccgac gggcggatcg    9360
aggtctgcgt ggccgccgag acgggcgtgc tggcgtggag ccagtccaag cccggcggcg    9420
acttcaccgg gccccggggt ttctcgctgc gccccgtgcc gggcacggtc gcggccctgg    9480
agaccggtcc gggccgggcc acgttcttct ggacggacgc cgagagcggc ggtgcggcgg    9540
cctggcgggc gggggcgtgg cccgtcgcgc tgggcggtac cccggccgag cggccgtgcg    9600
cggtgctccg cacgtcgctg gacggctacg actgtgtcgt cctcgcctac cgtgaccagg    9660
acggcacggc cgtgctcggc atgggcggca cggagaacga ggccgccggc ttctggtggt    9720
acgcgctgac cgagtcctgc cagggcgctc cggccctggc cctggacggg cggggccgcg    9780
tggtgatggc gctgatcggc gccgacgca ggcccagggt cgcccgccag gaggacggcg    9840
acggcctctc gctcacccgg tgggacgtcc tcggggggctg agcgcgccgt cgccgtgccg    9900
gaggtcagcc gcccgtcgcg ggcgacttct tcgcggactc ggggatctcc gcgtcggagc    9960
ggatcgcctt ccacagctgg tcggcctgcg ggtgcgcggc caccacccgg ttcgggtcgg   10020
```

```
tcttgtcgta cgccacgggg agcatgacgg tctccatgga cgccgggtcg accccgttca   10080
tgctgcgcgc gaagtccgcc aggctggtca gcgaggccag ctcggagtcg gtggtcaggg   10140
ccgaggtcag ggtgtcggcg atcttgtacg tcttggtggg gctgccgaac aggtcctgct   10200
tcttcacctc gctcagcagg gcgatcatga actgctgctg gaggcctatg cggcccaggt   10260
cgctgccgtc gccgacgccg tgccgggtcc ggacgaacgc cagggagtcg gtgccgtcca   10320
gcttgtgcgt cccggcgctc aggtccaggc cgctcgtgct gtccttgatg ggctcgtcga   10380
cggtgaccgt gacgccgccg atcgcgtcga ccagccccct gaagccggcg aagtcgatct   10440
ccatgtagtg gtccatgcgg acgccggaca tcttctccac ggtcttgacc acgcaggcc   10500
ggccggccgt cgagtacacg gagttgaaca tgacgcgctc ggcctgcgga agggcggagc   10560
cgtccgcctt ggtgcactcc gggcgggtga cgagggtgtc gcgcgggatg ctcacggcga   10620
cggcctgccg gcggccctcc gggatgtgca tgaccagcgc ggtgtccgac cgggcgcccg   10680
ccaccttgcc ggtgcccagg ccggcgttgt ctccggcacg cgagtccgag ccgaggacca   10740
gcacgttctg tccggaggtc ggcagcttct cggggcggtc ctcgccgagg gcctcgtcca   10800
ggtcgacccc gtcgatgttc ccgttcaggt cgctgtagag ccagtagccg gtgccccccg   10860
cggcgagcac gacggccagc agggacagca ggacgatgcg tccccagcgc cggcgcttcg   10920
gccggcggcg tccgccgccg gactcgggct gcgcacgccg ggactccgtg gtggcgctgt   10980
gcgtcatggt tcttgggttc ctctcctcac gggctccgcg cggcggagtg gggcccgggt   11040
gggggggagac cggtccacag atgcgttcac gtcagtggga gaactatagg cagcggtcca   11100
cggcacatcc tgcacgggtg gaattagcac ggctcagcga tgaatgccac atgaaccgac   11160
cttgaccact cttaaggctg gaataagatg tgtcgggcct gtgaccgtcg tggagggggg   11220
ctttcacgag gtcggaggtg ctggtggggc ggagcggccg gaagccgcga agcctcacat   11280
aaggggtggg cgtccggtgt ggacgatttg gtgtcccggc gggcgaaatg tcttggtagg   11340
agtacgagtt ggtggttcag ccgcgtctga gtattgtcgt gcccttccag gacgtcgagg   11400
tgtacctcgc cgagtgtctg gaatcgatcc cgcggcagtc gttccgcgac ttcgaggtca   11460
tcctggtcga cgacggctcc accgacgggt ccgtgcggat cgcggcggac ttctgcgccg   11520
ccgaccgccg tttccggctg gtccgccagc acgcccacgg accgggccac gcgcgcaaca   11580
ccggactgcg gaacacgcac cccgcggcgg agttcctcgc cttcgtggac ggtgacgacg   11640
tcatccccga gtacgcctac gaactcctgg tgcgcacgct cgaggagtcc gagtcggact   11700
tcgtctcggg caacgtgcag atgatgaact ccaccaagaa gtggcagtca ccgctgcaca   11760
agggccccat gcagaagaac cggcgcggga cgcacatcac gaagttcgac gcgctgatct   11820
acgaccgcac cgtctggaac aaactcttcc ggcgctcctt ctggaaccag aactccatca   11880
ggttccccga aggcgtgctg tacgaggact cgtgggtcaa catgtacgcc cacttccgcg   11940
ccgccaaggt cgacgtcatc acggacgtcg tctatttctg gcgccgccgg gacggcggag   12000
cggcgccctc catcacccag cgccactccg aactgtcgaa cctccgggac cgggtcgcgg   12060
ccgtgcagtc ggtgagccgc ttcctcggcg accggcgctc gcgtgagtac gcggacagca   12120
agcggaagta cgatctcgcc tgcctgaagt ccgacctcct gctccatctg aaggtgctcc   12180
cggacgcgga cgaggagtac cagcacgcct tcatgaagtg ggccaacgag ttcctcgacg   12240
agacggatct caccatcatc gacgagctgc ccgcggactc ccgcgtcaag tggctcctgg   12300
tgcgcgagga gcggctggcc gaactgctcg aggtcatcga gttcgagcgc cgcggcggtc   12360
```

```
ccatgcccgt gcagcggcgt ttccggcgct acctgaacta cccgtacctc ggggaccggg   12420
gggtgggcct cgacaagaag gcctaccggc tggacaagga gctctcgctg cacggctcgc   12480
tgtccggagc ccgctggagc accggctccg acctgctcac cctcaccgga acggcgtacg   12540
tccgcttcat caacgtgcac aagaagcaca tgtcggtgaa ggcgatcgcc ctgcggaaca   12600
agaagcaggg gcgcatgcag atcacgacgg cgaagaccgt ctacgcgccg caggcgaccg   12660
aggacagtaa gcagaatcgt tactgctatg actgggccgg cttcgaggcg cgcatcgaca   12720
ccacccgcct caagcgcaag ggccagtggg tcgagggcac ctgggacgtg gccgccggtg   12780
tcctcagccg gggactgttc cgctaccggg gcatcgaccg gggcggcgcg ggcagcgccg   12840
ccaacccgcc ctaccgctac gtcgacaaga acacccgcat cctcccggtc ttcctccagg   12900
gcaaactcaa gctgcgcgtc gagatcgtgc gctgccggat caccaagcac cgtgtcgtcg   12960
gcgaccagct ggagctgcgc ggcgtctacc tcggccccaa ggtcccggag tggggcaagc   13020
tccgcgtcac cagcatgagc ggcgcgggac gccacgacgc acgcgtccac ttcaccccgg   13080
gcggtgaggg ctggtgcacc ttctccgcca agctcccccct gagccgtctg gtgcccaagt   13140
cccgcgtcca gcggaacc gacgcggacg tcccgcagtc ctggggcatg ggcagcaacg   13200
gctggaagac caccttccac gtcgagggcc gcaagtcggc catctatccc gtgatggcgg   13260
aggagacccc ggacgggcac tactccatgc cgtcctccct gcagacccccg gagcgcgacc   13320
gggagatcgt cgtgcaccgc aacggctccg gctatctcgt gctcttcgaa cgagcgaccc   13380
tgccctggc gacccggtgc gactggcagg aggacggctc gctgtggatc cagggccgtt   13440
acctggccgc ggaccagctg accccggagc agtaccgctc cgcccacctc gtggtgcgct   13500
cgcgcgccca cggcgcggaa cgctccgtac cgctcacctg ggacgggcac gagttccgct   13560
gcgtcctggc cccgccgcg atgcggaccc tggccgggga catcccgctg gcggccggac   13620
ggtgggactt cttcctgcgc cgccaggacc tgtcggccgt ggcccgcgag accggctcg   13680
aagacctcat ggtgaagatc gagcaggatc tcatcgaggc gttcccgcag gagtacgaga   13740
gaaacgaacg ccgctacgag acgcaggccg aggcctacga ccggctgtcg ctgctcgtcc   13800
actcggcgat gcccgaccac gcccgcgcc cctaccggca gaagctcctg aggaccaagg   13860
cctaccccga cgcccggcgc cggccggtgc gtgacgccgt gctgttcgac gccttcaagg   13920
gcacccagta ctcggacagc ccccgcgccc tgcacgagga actcgtgcgc cgccgcaccg   13980
gcctggaaca cctctgggtg gtgcgcgacg accaggtgca ggtgccgccc acggcgacgc   14040
ccgtccgcat gtggtcgccg gagtggtacg aggcctcgc caccagccgc tacgtcgtcg   14100
ccaacaacca cctcccggac tggttcaaga agcgggacgg acaggtcgtc gtgcagacct   14160
ggcacggcac gccgctgaag aagatcggcc acgacatcga gtccatccac ttcgccgacc   14220
agcgctatct ggaacgcgtc gagaaggagg tgcagaactg ggacatgctg gtgtcgccca   14280
acagcttctc caccccgatc ctcaagcgcg ccttcggctt ccccggcgag atggtggaga   14340
gcggctaccc gcgcaacgac atcctgcgcc ggccggacac cggggccggg agcaggaga   14400
tccgccgcag catcgggctg ccggagggca gcgggtggt gctgtacgcg ccgacctggc   14460
gcgacgacca gttctacgcg cccggcaagt acaagctgga cttccggatc gacctggccg   14520
ccgcgcgtgc gcagctcggc cccgaccacg tcctcatggt gcgccgccac cccaacgtcg   14580
tggacccggt gccgggcgcc ggcgacggat tcgtcttcga cgtgtccgac tacccggaca   14640
tggccgacct ctcgctgatc accgacgtga tgatcaccga ctactcctcc ctgatgttcg   14700
actacgtgaa caccgggcgg cccatcctgt tcttcaccta cgacctggac cactaccggg   14760
```

```
acaccctgcg cgggttctac ttcgacttcg agggcagcgc gccgggcccc ctcctctaca   14820
cgtccgagga actggtggcg gcgatccgtg acatcgacgc catccaggac ctctacgccg   14880
agcggtaccg ctggttccag cgggagttct gcgacctgga cgacggttac gccgcggccc   14940
ggctcgccga ccggatgctg gtcgcggggc gcgacctcgc ccccgggcag gcgcacgcgc   15000
cggccgtcgg cgcggtcgac acccggcaca ccggaaggcc gatgaccccc ctccagtggg   15060
ggaactcgga gtggttcgcc ggccccgcc cgccggcggg tctcgtcgac gccgtgcccg    15120
cccagcccgc cccggcgtac gacgccgtac cgcagcacca ggcgggtccg ttcggccata   15180
ccccgcccgc cggcgaccgc agctacgaag gcgtgatcgc gtgacgccgc cgaccccgcc   15240
cggcgcgagg tccccggcgt gccgcgcggt gccggaaggc cccggccccc gatgaccgcc   15300
gtgccgttcg ccacgcgggc gccggccgcc gctgccggtc cgtcgtccgg cggccgcccg   15360
ggcgcgtcct cagccggtgc cggtgtccac ccggatcagc agcgcgcggt ggtcggagac   15420
cccggtgtcg ctcacccggc acccgagcac gggcagcccg gtgaagaggt agtccagctt   15480
gtggtgcgag acgtgcgtcg gccgggccgg ccggagggga ccgggcgtcc cgtcgcactc   15540
ccggtgcgtg ccgtaaggct ggtcgggcca gacccgggag agcgggttgc gctctcccgg   15600
cggatccacg ttgaggtcgc cgccgtagac ggtgcgccgc tcgggcaccg cgtccaccag   15660
ggccttcagc tgtccggcgc ggaactcgcg gtccggatgc gccagatcgc cgccgcgcgg   15720
ggtcagatgc gcggtgcaca ccgtgaggtc gtgcgccgcg acgaacgcgc agagtattcc   15780
gcgctgcacc ccgaccgcgg gctggggcgc gggcaccgcg cgcacggacg acagcggata   15840
cgccgacagc agggcgtagc ccgcggagcc ccggccgggc gccccgcagc gcaccgcggt   15900
gcggcgcccg tcacgccgc gccaggtgta ggccctgaac tccgcgtgcc acgacgcccc    15960
gagggaggcg cgcaccgcct cgacgtccgc cgcgcaggtc tcctgcagga acagcacccg   16020 ggcccccggat tccgcggcga ggcgttccgt ccggccgcgc ttggcgtcct cgccgcccgt   16080
gccctcgcag ttccattccc tgaccccgca catgttccag gtcgccacgg tcagtgtccg   16140
gtccccggtg gcggagcggt ccgctccatt gccgctccgc tcgtgggtca ccacggcggc   16200
gagccccgcg agggcggcgg ccgccgtgac ggcggcgagc aggcgccgtc cgcgcgggcg   16260
gggcgaccgg gttcggttcc tgagcacccg gccatcatga ccgatccgcc gctgaccagc   16320
caaaaccacc cggcgccagg cgccttccgg caggtgtcct ccccctgccc gcgcacccgc   16380
ccgtcgtcca agtacctctg agagtggagt ccgtacatgt ccaaggcacc ctcgaacggg   16440
cggcagctgc tcaacggcat cgaagcctcg ggaacgttcc cggtggagta ccggttcacc   16500
cacgccaaga gcggcaaccg gcacctcgtg gtggtcttcg ccaacttctc ggcacccgag   16560 gactacgget ggtcgaacgg cgtcttcgac aacgtccgtg ccaacatcct gtggatccgt   16620
gaccggttcg acgggatgaa cgcctactac ctgtgccgga acatggactt cggtctggcg   16680
gactcggtgc agaccctgat cgcgaacgtc accggggcgc tcgggctgac gccggaccaa   16740
gtcacgctct ggggcggctc caagggcggc agcgccgcgc tgtacttcgg cctgcggtac   16800
ggctaccgga acatcgtcgc catcgtcccg cagttcctca tcggcgacgc cctggagaag   16860
cggcacccga aggtctccgc gtacatgctc ggcgaagggg cgcaggcgca caacgcgcgg   16920
atcctggacg cgctcctgcc cgacctggtg cgcgccaagg ccaacccggg cgccaacatc   16980
tacgtgctct cctccccgca ggacgagcat tacgccgtgc aggtcgagcc gttcctcggc   17040
atgttccacg gctacgagaa cttcaatttc ctgtacagcg agtcgccgac catcacgggg   17100
```

```
cacgccacgg cgacccggcg gaacgtcccg gcgctggtcg gcctgctcaa cctgctcgcc   17160
gacggctacg ccccccggct gggcttcacc cgccacgccg ccgaggactt cgaccacgac   17220
cggtcggaca tcaacgccta cctcgcctcg acctccaagg tccagggcgc cgacgcgttc   17280
gcgccgccgg tggtgaccac cccgggcttc aacagcgagg tcccgcgcac cggaccgtgg   17340
ttcaccggga cggcccacgg agcggtgcgg gtgagcatgt ggcgcaacgg caagttcgtg   17400
gcgtcgcccc aggtcgcggc cgacggcacc tggtcctggc agccgaccgg gccgtgggag   17460
gccgggaagc acatcgtcaa gatcttcgcg gtggacccgg cgggcttcca ctccgcccgg   17520
gtcgagatcc ccttcaccgt ggtcgaccgg gatcccgtcc ctgccccgcc ggtcgtctcc   17580
gcaccggtgt ccgggcagca gaccggagcg gcggtcgggt tccacggcag cgcgccggga   17640
gcgtcacagg tcggcttccg ggagaacggc gtgctcctcg gcgcggtggc cgtcgcgccc   17700
gacggcacct ggggctggga ccccggccgg ccctggcccg aggggcagca cctggtcgag   17760
atcgtcgcgg tcgacgcgta cggcatggag tccgcgcccg ccgccgccgg cttcaccgtg   17820
ctcggccacg cggtgcccgc cggacacttc acgccgcggt actgaccgac ggcccaggac   17880
gacgacacac cacgagtggg aagcagacat gccgaaagaa gcgccgacaa cacgcgagct   17940
gatcaccggg atcgacacct ccggcgcgta tcccgtcgag taccggttca cgcacgccaa   18000 gggggggcaac cggcacctcg tcgtcgtgtt cgccaacttc gcggtcaagg acgactacgg   18060
ctggtccaac ggcgtcctca acccggtgcg ggccaacatc ctgtggatcc gtgaccggtt   18120
ccgcgacatg aacagctact acctgtgcga ggggatggac ttctcccctgg agcagtccgt   18180 gatcgggctc atctccaagg tgatgaacgc cctggaactc accccggagc aggtcacgat   18240
gtggggcggc tcgaagggcg gcagcgccgc gctctacttc ggcatgcgct acggcttcgg   18300
caacatcgtc tccatcgtgc cgcagttcct cgtcggcacc tatgtgaagc gggtgcaccc   18360
caaggttgcc cggttcatgc tgggcgaggc ggtgccggag gagaacgtcc gcgcggtcga   18420
cgcgctcatc ccggacctgg cccgttcggg cgtcgcccgg cactccaaca tctatctgct   18480
ctcctcgccg caggacgagc agtaccagga gcaggtcgag cctttcctcg gactgttcca   18540
ggggtacgac aacttcaact tcgtgttcag cgagtccccc cacatcaccc gtcactcgga   18600
cgtcacccgg cgcaacgtcc ccttcctgat gggcctcgtg aacatgctcg ccgacgggat   18660
gtccccgcgc ctgggcctgg tgcgcaacgg gtacgaggag ccggaccgcg acaggtccgc   18720
catcgagggc ttcctggcgg ccacttcggc ggagcggccc agcgccatcc cgatgcccgt   18780
ggtgacgcat ccgcttccgc acatggaact gcccacggac ggcgtgtact tcacagggac   18840
gggccccggc gcggtgcggg tgagcctgtg ggagcacggc aagttcctgg gttcgccgtc   18900
ggtggcgccg gacggcacct ggtcctggaa gcgggacaag ccgtggagca agggcgacca   18960
tctggtcaag gccgtcggct gggacgcgga gaagcgccgc accaagggca ccgtggtccc   19020
gttcaccacg gtcgccggcg cgaacgccgc cgcgcccggg gcaccggccg ccgcgcccct   19080
ggcgcccggg cagccgctgc cggcgccgac ggtccacacg ccggggggcgt acgagcagat   19140 caccggcacg gccgtgcgct tcagcggctt cgccccgggc gccgccagg tgggattcag   19200 ggcgggggcc accctccttg gcacgagccg ggtcgcggcc gacggaacgt gggcctggga   19260
ctccggctgg ccctggcagg cgggcatgca caccgtggag gtgttcgccg tggacgccgc   19320
gggatccgag tcgcccgtgg cgccggtgcc cttcgacgtc atgcacgcca cggcggggcgc   19380 ctcgccgttc gcctactgac cggtcgccac gcgcggaagg gctcctggag atcgccggcg   19440
atctccagga gcccttccgc ggtctacggg gactaggcgg gcacgctcgc cgtgcccggc   19500
```

```
tccaggaacc gcttcccgtt cacccgctcg gagacgccct cgcggtccag gtacggcgtg   19560
atgccgccca ggtggaaggg ccagccggcg ccggtgatca ggcacaggtc gatgtcctgg   19620
gcctcggcga cgacgccctc gtcgagcatg agcccgatct cctgggccac cgcgtccagg   19680
acgcgggcgc ggacctgctc ctcggtgagg acggtgtcgc cctgcttcag gagcgcggcg   19740
acctccgggt ccagctcggg cttgccgctg tcgtagaggt agaagccacg cttgccggcc   19800
tcgacgaccg ccctgaggtt cggggagacc gtgaagcgct ccgggaacgc cctgttgagg   19860
gtctcggaca cgtgcagacc gatcgcgggg ccgaccagct ccagcagcac cagcggggac   19920
atcggcaggc cgagcggctc gacggccttc tccgcgacct cgaccggggt gccctcgtcg   19980
atgacgttct ggatctcgcc catgaagcgg gtcaggatgc ggttcacgac gaacgccggg   20040
gcgtccttga ccaggaccgc ggtcttcttc agcttcttgg cgacaccgaa cgccgtggcc   20100
agcgccgcgt cgtcggtccg ctcgccgcgg acgatctcca ggagcggcag gatcgcgacc   20160
gggttgaaga agtggaagcc gacgacccgc tcggggtgct tcagcttcga cgccatctcg   20220
gagacggaga gcgaggaggt gttggtggcg aggatcgcgt gcgccggggc gaccgcctcg   20280
acctccgcga acacctgctg cttgacgccc atctcctcga agacggcctc gatcacgaag   20340
tcggcgtccg cgaagccctc ggccttgtcc agcacaccgg tgaccagggc cttgaggcgg   20400
ttggccttgt cctggttgat ccggcccttg ccgagcagct tgtcgatctc ggcgtggacg   20460
tagcccacac ccttgtcgat gcgcgcctgg tcgatgtcgg tcagcacgac cggcacctcg   20520
aggcggcgca ggaacagcag cgcgagctgg gaggccatca gaccggcgcc gaccacgccc   20580
accttggtga ccgggcgggc cagcgacttg tccggggcgc cggccggccg cttgccgcgc   20640
ttctgcacca ggttgaacgc gtagatgccg gagcgcagtt caccgcccat gatcaggtcg   20700
gcgagcgcct ggtcctcggc gtcgtagccc tgctggaggt cgccgttctt ggcggcggcg   20760
atgatgtcca gggcgcggta ggcggccggg gcggcgccgt gcaccttgga gtcggcgatg   20820
aagcggccct tggcgacggc ctggtcccag gcctcgccgc ggtcgatcac cgggcgctcg   20880
atccggatct cgtccttgag gacggccgcg gtccagatca gcgactgctc caggaagtcc   20940
gcgccctcga agatcgcgtc cgcgatgccg agttcgaaga cctgcgcgcc cttgagctgc   21000
ttgttctggt tgaggctgtt ctcgatgatg accgagacgg ccttctcggc gccgatcagg   21060 tcggcagca gcgtgcagcc gccccagccg ggacgagac cgaggaagac ctcggggagc   21120
gagaacgccg ggagggcggc cgacaccgtg cggtaggtgc agtgcagacc gacctcgacg   21180
ccaccgccca tcgccgcgcc gttgtagtac gcgaaggtcg gcacggccag cgtcgacagc   21240
cgcttgaaga cgtcgtggcc gcccttgccg atggccagcg cgtcctcgtg ccgcttcagc   21300
agctcgacgc ccttgaggtc ggcgccgacg gcgaagatga acggcttgcc ggtgacgccg   21360
acgccgacga tctcgccgtc gcggcctcc ttctcgaccc ggtcgatcgc ggcgtcgatg   21420
ttcgccagcg actgcgggcc gagcgtggtc ggcttggtgt ggtcgtggcc gttgtccagg   21480
gtgatgagcg cgaagcgccc ggcgcccagg gggaggtcga agtggcgcac gtgcgcgctg   21540
gtgacgacct cgccggggaa cagctcggcc gcacccttca gaagtctgc ggtggtgctc   21600 acttgtcccc ctcgaagtgc gggttctccc agatgaccgt cgcgcccatg ccgaagccga   21660
cgcacatggt ggtgaggccg taacggacct gcggctgctc ctcgaactgg cgggccagct   21720
gcgtcatcag acgacgccg gaggaggcca cgggtggcc gaacgcgatg gcgccgccgt   21780
actggttgac gcgcgcgtcg tcgtcggcga tgccgtagtg ctccaggaag gccagcacct   21840
```

```
ggacggcgaa ggcctcgttg atctcgaaca gaccgatgtc ggagatggac agccccgcct   21900
gggcgagggc cttctccgtg gccgggatcg ggccgtagcc catgacctcg ggctccacgc   21960
cggcgaagga gtaggagacc aggcgcatct tgaccgggag gccgttctcg cgggcgaagt   22020
cctcgctcgc gatgaccgag gcggtggcgc cgtcgttcag accggccgcg ttgccggcgg   22080
tgacccggcc gtggacgcgg aaggggtct tcaggccggc caggttctcc agggtggtgc   22140
ccgggcgcat cggctcgtcg gcggtgacca ggccccagcc ggtctcaccg gcctcctcgt   22200
tggtgcggcg caccgagacc gggaccaggt cggcctggat cttgccgttg gcgtaggcct   22260
tggcggcctt ctcctgggag cgcacggcgt actcgtcggc gcgctgcttg gtgatcgagg   22320
ggtagcggtc gtgcaggttc tccgcggtca tgcccatgaa cagggcggac tcgtcgacca   22380
gcttctcgga gacgaagcgc gggttggggt cgacgccctc gcccatcggg tggcggccca   22440
tgtgctcgac gccgcccgcg atggcgacgt cgtacgcgcc gaaggcgacg gagccggcga   22500
ccgtggtgac ggcggtcagg gcgccggcgc acatgcggtc gatggagtag cccgggaccg   22560
aggtgggcag gcccgcgagg atgccggccg tgcggccgat ggtcaggccc tggtcgccga   22620
tctgcgtggt cgcggcgacg gcgacctcgt cgatcttctt cgggtcgaga ccggggttgc   22680
ggcgcagcag ctcccggatc gccttcacga ccaggtcgtc ggcgcgggtc tcgtggtaga   22740
tgcccttcgg gcccgccttg ccgaacgggg tacggacgcc gtcgacgaag acgacgtccc   22800
tgacggtacg aggcacgatg gctctcctcc caggggtgcgg gacgctgagc gcttgcttac   22860
gccatgctac ttatgagtaa cgtgactgcc cagtcccggc ccccgagcg gcgaacatca   22920 cacgtacggc ggcgcccgcc aaacgccgga ggggctggaa tcagccccct ccggcgtttg   22980
aggagcggga acccctcacg gtggagccgt ggagcctcgc ggggtcagga ccggggtcgg   23040
taccgggtgc gaccccggct gctcctcccc ggtgatgacg ccgaacagcg tgcgcgccac   23100
ctccgccccg aacccgtgca catcgtgact catcgcggac agcgtcggat cgtcagccg   23160 gcacagctgc gagtcgtccc acgccagcag cgacacgtcg tccggcaccc gcagccccat   23220
ctccgccgcc accgacagcc ccgccaccgc catgatgtcg ttgtcgtaca cgatcgccgt   23280
gggccgttcc cccggcgcgg ccgccagcag cgaacgcgtc gcccgcgccc ccgcgtcccc   23340
cgagaagtcc gtggccgtct gccacgcccg cgcgggcggc tccagcgccc ggaccgcctc   23400
gtcgaacgcc gccgtgcgga tcgaggtgtg cccgagcgcc gccgcgccgc caccccgggc   23460
gatccgccgg tgcccgagcg ccgccagata ccgcacggcc tccgtcacgg ccgtggcgtc   23520
gtccgtccac acggaggtga gcccgcccgt cagcgccggg tgcccgacgg ccaccgccgg   23580
cagcccgagc cgctccgcca ccgccggacg ggggtcgccg gccgggaagt ccaccaggat   23640
cgagccgccg atctgccgcc cgcgccacca cgactccatc agcccgacct cctcctccgg   23700
gctgcgcacc agccgcagca gcagcgagca ggaccgctcc accaggacgc tctccacccc   23760
ggagatgaac tccatgtaga acggctccag gccgagcagc cggcgggcc ggcagaccgc   23820 gagacccacc acgtccaccc gcgacccggc cagcgtgcgc gcggttcggc tcggcgccca   23880
ccccagctcc cgcgccgccc ggaagatgcg gtcccgggtc gcctccgaca gcccgggctt   23940
ccggttgaag gcgagggaca cggcgcccctt ggacacgccg gcgcgcgcgg cgacgtccct   24000
gatggtgacg cgaggggtcg gcgttgccgt catcgagtgg gctccacgca gtacagggcg   24060
gaacgggcgg tgtccgggtc cggagtcttc caccccgca cccgatggt cacctgttcc   24120 ccggggagca gggtcaccag ccccgggtcg gcccgcgccc cggggtccag ccggtcggcc   24180
tggagcagca ggtcccgtac gagggtgcgg gccgtgaccg tgatcccgtc cggcgcgagg   24240
```

```
gcgacctcga actccggcgg ggggtagggg atctcccggt ccggcgccgg gaagtgccac   24300
gcccgcaccc cgtccgcgtc ggcgaccagg aactccccgg ggccgtccgg cagcagttcg   24360
accgggacct cgaccacggc caccgtccgc cccccggcgt ccagcgccgg ggccgcctcc   24420
gcgatcgggg cgccgtcgac ggacatccgg cgcagccgca gcgttcsccg ccagtcctcc   24480
gcggactggt tgaccgccgc caccaccaga ccgtcaccgt ccgcgcgcac ggtcagcagc   24540
cggtccgcgt acagccggcg cagctcgtgg tagagcggct tctcccgccc gtccccgtcg   24600
atcgcggccc acgacgtcac cggccagcag tcgttgagct gccagaccac cgtgcccgcg   24660
cacaccggcc agtgcgagcg ccagtgctcg acaccggccg ccaccgcacg cgcctggttg   24720
acctgcgtca gatagtgcca gcggtcgaag tcgccctccg gcacggcgaa gtggcgggcg   24780
aggccgcgct ccagcttgcc gttgccgtcc tccgccttct ggtggtgcag catgccgggg   24840
gagtccggcg cggggtcctc cccgggcagc gcccgccgca gcgtggcgtg cgcgggaggc   24900
gcctgccagc cgaactcggc cacgaagcgc gggacgtcgc gccggtagtc ggcgtagtcg   24960
gcgcggttcc acacctccca ggagtggtgg gtgccgtgcg ccggatcgtt ggggtggtgc   25020
cgccaggaac cggaccaggg actgcccgcc gtgtacggcc gcgtcgggtc cagctccgcg   25080
accacccgcg gcaggacgcc gaggtagtag ccctcgcccc aggagtcccc ggcgagcccc   25140
tgctcccagt cccagtcccg gaaccccccac aggttctcgt tgttgccgtt ccacagcacc   25200
agggaggggt gcggcatcag ccgtacgacg ttctcccggg cctccgcctc cacctccccg   25260
cgcagcggct gctcctcggg gtaggcggcg cacgcgaacg ggaagtcctg ccagaccagc   25320
agccccaact cgtcgcaggc gtcgtagaag tcctcgtcct cgtagatccc gccgcccag    25380 acccggacca ggtccacccc cgcgccggcc gcctgctcca gccggtgccg gtagcgctcc   25440
cgggtgatcc gggacgggaa cacgtcgtcc gggatccagt tgacgccccg cgcgaacagc   25500
cgctcaccgt tgacgaccag ggtgaacccg gtgccgtgcg cgtcggccga ggtgtccagc   25560
tcaaccgtcc ggaacccggt cctgcgccgc caggcgtcca gcgcctcgtc accgtgggac   25620
aacgtcagct cgacgtcgta cagcggctgt tcgccgtatc cgcgcggcca ccacaggcgg   25680
acgtccggca cccggagccg cacggtcccg gccgtcccat cgaccccgcgc ccgggcgcgc   25740 acgcccccgg cgctcgcctc cagggtgagc ggtgcctcga cccggagcg ctccacgtcg    25800 accgccagct cgatctgccc caccccgtcc tcgacggtga ccagcgggcg cacccggggc   25860
atccgcgccg tcgaccagcg ctccagccgc accggccgcc agatcccggc cgtcaccagc   25920
gtcggccccc agtcccagcc gaacgagcag gccatcttcc gcaggtactg gtacggctcg   25980
gcgtacgctc cggggcgctc gcccagcctg ccgcgcaccg cctccgcctc ggcgtacgcg   26040
gaggcgaacc gcaccgtgag ccggccgctc agtcccgtca cgtcgaagcg gtacgagcgg   26100
tgcatgttcc gcgtccggcc cagtggccgg ccgtcgagca ggatctcggc gacggtgtcg   26160
agaccgtcga agacgaggtc cgtctgctcg tgcgggcccg tcccggcggt cagctccgtc   26220
tcgtacgtcc actcccgccg gcccacccag gccacctcgg tctcgttgcg gccgaggaac   26280
ggatcgggga tcagcccggc cgccagcaga tcggtgtgca cacacccgg caccgaggcg    26340 gggagggcgt ccccgtgcc gtccgggtgt cgcaggatcc atccctcggt gagcggtgtg    26400
acctgacgca tgcacactcc ctaaaccggt tgagccttct ctgaagagtg gtctggcatc   26460
gttggcgcga ttgcgacttt accggttcag ttcagggctg ccagagtgcc gaatcagcca   26520
tcccactcgt gctcgtccgt cccgtgaacg gagccgtgat gcatctgaac cgccgtacga   26580
```

```
cactcaccgg atcgctcgcc ctgctcgccc tcctggcctc cgcctgcacg ggcacggggg   26640
gttcctcgaa gggcgcggac gccaaggctc ccgacgaccc gtcaaaggtc aaggggtccc   26700
tcacggtcct cacccaccgg accgatctgg tgcaggacga gacgatgaag aagtacgccg   26760
ccgagttcaa cgagacctat cccgggtga aggtggagtt cgacggcctc accgactacg   26820
agggcgaggt caagatccgt atgaacacgg agaactacg cgacgtcctc atgatcccgg    26880
cggtcgtcga agaaggac tacccgaagt tcttcgcctc cctgggcacc aaggccgaac     26940
gcgccgccaa gtaccggttc accgactact ccaccgtcga cggcaaggtc tacgggcaga   27000
gccccgtcgg cgtcgtcccc gggttcatct acaacaagcg ggtgtggagc gaggccggcg   27060
tcaccgactg gcccaccacc cccgccgagt tcctggacga cctgaaggcg atccggtcga   27120
agaccgacgc ggtgccgtac tacaccaact caaggacat gtggccgctg acccagtgga    27180
ccaacgtcaa cggctccgtc ggctgcgacc cgcacgccac cacgaagctc gccgagggcg   27240
acccgtgggc cgaggggcc gacctgcgcg tgggcgacac cctgctccac gacatcgtgc    27300
gcggcggact cgccgagaag gacccgacca ccaccaactg ggagggctcc aagcccaagc   27360
tggccaaggg cgagatcgcc accatgtggc tgggctcctg ggccgtcgtg cagatgcggg   27420
acgcggcgaa gcaggccggc gccgaccccg ccgacatcgg cttcatgccc ttccccgcac   27480
agcgggacgg cacgttctgc gcggtgacct ccccggacta ccagcaggcg gtcaacgtca   27540
actccgacaa caaggaggcc gcccgcgcct ggatcgactg gttcaccgac aagtccggct   27600
acgccgaggc caacctcgcc ctatccccc tgaaggacgc cccgctgccc gccgtcctcg    27660
agccctacga gaaggccggc gtgaagctcc tggacctcga ggacagcaag ggcgccgagg   27720
tgaagtccct cgacaaccgc tccgaggtcg gcatctacaa gcccgactac cgccaggaac   27780
tcgtcgacct cgcccgcggc gcccgcaagg cggcctgga cgactacctc ggcggcctcg    27840
gcgagcgctg ggccgaggcg cgcagcgcgc tggggggcctg atgacggaca ccacccgcaa   27900
ggcggcgcgc ccggttcccc cggccgcgcc cgccggggcg ggccgcgcgg cgccggcccc   27960
gcgccgcacc cggctgtcgc gccgcctcac cccgtggctg ttcctggccg caccgctggc   28020
cctgctcctg accttcacct acgcgcccga tcgccaacat ggtcgcgtac agcttcaccg   28080
actgggacgg cgtgagcccg gagctgaact ggacgggcac cgggaactac accgaactcc   28140
tcacccgctc cgagctgttc gaggtcttct cgtcagcgg ctactacctc gtcgcctccg    28200
cggtgcagat cgtgctcgcc ctctacttcg ccacggtcct cagcttcgac gtccgcttcc   28260
ggaacttctt caagggcgtg ctgttcttcc cgtacctcat caacggggtg gccatcggct   28320
tcgtcttcct ctacttcttc caggacggcg gcaccctcga ctccgtactg ggcctgctcg   28380
gcgtcgagac cgaccacgcc tggctgggca cgccgttctc cgcgaacacc tcgctggccg   28440
gcgtctccgt ctggcgctac ctcggactga acttcgtcct cttcctcggc gcgatccagt   28500
ccatcccggg cgagctgtac gaggcggccg agatcgacgg cgcgaaccgc tggcagcagt   28560
tccggcacat catcgcgccc ggcatcagac ccgtgctgag cctgagcgtg atcctctcgg   28620
tctccggctc gctgtcggtc ttcgagatcc cgtacatcat gaccggcggc gccaccggca   28680
cggagacctt cgtgatccag accgtgaagc tggcgttcca gttcaacaag acgggactcg   28740
cctcggccgc cgccgtcgtc ctgctgctga tcgtcctggc ggtcacctgg gtgcagcggc   28800
gcatcgtccc cgacgagaag gtggacctcg tatgacccgc cgtaccgcgg cacgcgccct   28860
ggtcctgacg tccctgatcc tggcgacgct ggtggtgctg ctgccgctcg ccgtggtctt   28920
cctgacctcg ctgaagtcct ccgaggagat ggcgaacggc agcggagcgc tgacgccgcc   28980
```

```
cgacgacccg ctgaacttcg gcaactacgt gacggcgttc cgggacggcc agatgctgtc   29040
cgcgttcggg aacacggccg tcatcctggt cgtggccgtc ggcggaacga tcctgatcgg   29100
ctcgatgacg gcgtacgcga tcgaccgctt ccggttccgc ttcaagaagc tggtcgtggc   29160
gctgttcctg ctggccgcgc tggtcccegg ggtgaccacc caggtggcga ccttccagat   29220
cgtcaacagc ttcggcatgt tcgacagcct gtgggcgccg atcgccctct acatgggcac   29280
ggacatcgtc tcgatctacg tcttcctgca gttcatccgc tccatccccg tctccctgga   29340
cgaggcggcg cgcctggacg gcgccaacgc gttcaccgtc taccgcaagg tgatcttccc   29400
gctgctcaag ccggcgatcg cgacggtggt gatcgtaaag gggatcaacg tctacaacga   29460
cttctacatc cccttcctct acatgccctc cgaggacctg ggggtcatct cgacgtccct   29520
gttccgcttc aagggcccct tcggcgcgca ctggagacg atctcggcgg gcgcggtcct   29580
ggtcatcctg cccaccttga tcgtcttcct gttcctccag cgcttcatct acaacgggtt   29640
catgcggggg gcgacgaagt agccagcgcg gccaccagca cggagtgac ctggtcgacc   29700 tgccacgcgc gtgccccgtg cgccgtcagc gccgcggcga cggaccgctc gtcgggcccc   29760
ggcggctccc agcagaccct gcgcaccgtg tccggggtga tcaggttctc cggcggcatg   29820
ttcagccgct cggcgagttc ggcgaccccc gcgcgggccg ccgacagccg ggccgcggca   29880
acggggtcct tgtccgccca ggcgcgcggc ggcggagggc cggtcaccgg ctggccgggc   29940
tgcggcagct gggcctcgct cagcgccttc gcgcggtcga cggccgcctg ccactgctcc   30000
agctggcgcc gccccacccg ctgcccgaac ccgttgagcg cggccatggc gtgcaggttg   30060
gcgggcagcg cgagcgcggc ctccacgatc gccgcgtcgg aaagcacctt gccggggggag   30120 acgtcacggc gccgggcgat ccggtcgcgg gtctcccaca gctcccgcac caccgccatc   30180
tggcggcgcc ggcgcacctt gtgcatgccg gaggtgcggc gccaggggtc cttgcggggc   30240
tccggcggcg gggccgaggc gatcgcgtcg aactcctgcc gggcccagtc cagcttgccc   30300
tggcggtcca gctccttctc cagggcgtcc cgcagatcga ccagcagttc gacgtcgagg   30360
gcggcgtacc gcagccaggg ctcgggcagc ggacgggtgg accagtcgac ggcggagtgg   30420
cccttctcca ggacgaagcc gagcacgttc tcgaccatcg cgccgagccc gacgcggggg   30480
aacccggcaa ggcggccggc cagctcggtg tcgaagaggc gggagggcac catgcctatc   30540
tcgcgcagac agggcaggtc ctgggtggcg gcgtgcagca cccactcgac gccggacagc   30600
gcctcgccga gggcggacag gtcggggcag gccacgggt cgatcagcgc ggtacccgca   30660
ccctcgcggc gcagctggac gaggtaggcg cgctggccgt agcggtaccc ggaggcgcgc   30720
tcggcgtcca cggcgacggg tccgctgccg gccgcgaagg cggcgaccgc ctcggcgagg   30780
gcggcctcgt ccgctatcac gggcggaatg ccctcgcggg gttccagcaa gggggtcggc   30840
gcctccgtaa cagaagatcc gccgtcgtcc ggaggagcgc ctccggtggt gcgcagtgaa   30900
ctgtctgctg cggtgtcgtg ggcgtcggtc acctgtcaag ggtatccgtg ccgcgaaggc   30960
gcccgtcgac ggttgtgctc cgtgacgggc gccgtgggt cgtattccgg tcagaagagt   31020
gaaagaacgt gttcgcttgg ccgtgggcgg gcggatcggg gacgggcgga tcggggcgg   31080 gacgaaggg tcagtggatg atgccggtgc gcagggccac ggccaccatg ccggcgcggt   31140
cgcccgtgcc gagcttgcgg gcgatccggg ccaggtggct cttgacggtc agtgcggaca   31200
ggcccatcga gacgccgatc gccttgttcg actggccttc cgccaccagc cgcagcacct   31260
ccacctcgcg gccggacagc tcgcggtagc cgcccgggtg gctcggggca cccggggggc   31320
```

```
ggcggtgcag gcgcgcggcg gcggcgccga tgggagcggc acccggccgg gtggggagcc    31380
cgaggttggt gcgggtgccg gtgacgacgt agcccttgac tccgcccgcg agggcgttgc    31440
gcacggcgcc gatgtcgtcc gccgcggaga gggcgaggcc gttgggccag cccgcggcgc    31500
gggtctcgga gaggagggtg aggcggaac catccggcag atggacttcg gcgacgcaga    31560
tgtcgcgggg gttgccgatg cggggacgag cctccgcgac ggacgaggcc tcgatgacgt    31620
cgcgtacgcc gagcgcccac aggtggcggg tgacggtcga acggacgcgg gggtcggcca    31680
cgaccaccat ggcggtcggc ttgttcgggc ggtaggcgac caggcttgcg ggctgctcga    31740
ggagaacgga caccaggcct cctggggtgc gggacgggcc ggctcgtggg ggtgaaggcg    31800
ggacgaaccg tgctttcaag gtcacagtcg tcttcggcag caaacctggt gtcctttaac    31860
gaatgatcac gaagtgatga gtaacaatcc gggcaattcg gacgcacgat cgatcattcg    31920
aagatcgaac ggtttcggtc tgcgtcgcaa cgcttccgaa agtggccgta tcgacaaaga    31980
gagatgcagg aggccggtcg tcgggacccc gcagcgggag gctcagcgcg actgcggccc    32040
cctccgctgc ggcagcgtca ccacgacgcg gtccccggga gcggcggcg gcagcccgc    32100
gacctgcgcc agcagatcgg accacgcgac cagatgggcg gccgtgtccg gaaccccgcc    32160
cagaccctca cgcggcgtcc acgaggcacg gatctcgatc tgggaggcgg cgggccgcgc    32220
ggacagcccg ccgaagtagt gcgaactcgc ccgcgtcacc gtgccgctcg gctcgccgta    32280
cgacaggccg cgcgccgcca gcgccggt cagccaggac cagcacacgt ccggcagcag    32340
cggatccgcc gccatctccg gctccagctc ggcgcgcacc agcgtcacca gacggaaggt    32400
cccccgccag gcgtcgtgtc cggccgggtc gcacagcagc accagccggc cgtcggccag    32460
atcctcctcg ccgtcgacga ccgccgcctc cagcgcgtgc gcgtacgggg cgagccgttt    32520
cggcgcgggc accgtctcca cctcgatctg cggccgcagc cggggcgctct gcagcgcctc    32580
gacagcggcc cggaagggcg gcggaggcgc acctccgtgc ccgggatccc ccccgccctc    32640
cttcggttcg tccattccgc cagcgccgtc cgacagtcgt ccctgagccg cagccatgcc    32700
gggaagatta agcggaacgg gccccccggcg cagggaggga caccccgcgcc gccccggcgct    32760
gtccggatcc tgcaccgcgg ccccgcccgc cggacgcccc tgggggtccgg ggcggcggac    32820
gggtcgtgcg agactggccg gtgtgagtgc caacacgagc ccgaagggcc agacgcctac    32880
cgcgaccccc gacccccgtca gaacgacgcg cgtccgggaa tcagccttcc tcaaggcgtg    32940
ccggcgcgag ccggtgccgc acacgccggt gtggttcatg cggcaggccg ggcgctcact    33000
gccgagtac cgcaaggtgc gcgagggcat cgggatgctc gactcctgca tgcggcccga    33060
gctggtcacc gagatcaccc tccagccggt gcgccgccac cacgtcgacg cggcgatcta    33120
cttcagcgac atcgtcgtcc cgctcaaggc catcggcatc gacctcgaca tcaagcccgg    33180
catcggcccg gtcgtcgagc agccggtgcg caccccgcgcc gacctcgccc ggctgcgcga    33240
cctgaccccg gaggacgtct cctacgtcac cgaggccatc ggcatgctga cccgtgagct    33300
cgggtccacc ccgctgatcg gtttcgcggg cgccccgttc acccttgcga gttacctcgt    33360
cgagggcggc ccgtcccgta cgtacgagaa cgccaaggcg atgatgtacg cgaccccgga    33420
gctctgggcc gacctgctcg accgcctcgc cgacatcacg cgggccttcc tcgacgtcca    33480
gatccgggcc ggcgcctcgg ccgtgcagct cttcgactcc tgggccggcg cgctcgcccc    33540
ctccgactac cggcgttcgg tgctgccccgc ctcggcgaag gtgttccgcg cggtggccgg    33600
ccacggcgtc ccgcgcatcc acttcggcgt cggcaccggc gagctgctgg ggctcatggg    33660
cgaggccggc gcggacatcg tcggcgtcga ctggcgcgtc ccgatggacg aggccgcccg    33720
```

```
ccgcgtcggc cccggcaagg cgctccaggg caacctggac ccgaccgtgc tgttcgccgg    33780
ccgggaggcc gtcgagacga aggcgcgcga ggtcctggac accgccgcgg gcctggaggg    33840
ccacatcttc aacctcggtc acggagtgat gccctccacc gacccggacg ccctcacccg    33900
tctcgtggag tacgtccaca cgcagacggc gcgctgaccc accgctcacg cgccggacgc    33960
gagtcggaat ccggggggcgg ggtactgggc acgggtgccc accacgttca cccccgggta    34020
cgggcaggtg gaggccccat gaggctcgag atgttcgacc ccgccccgat cggcgtcgtg    34080
ttcacccagg ggccggagca ccggctcgcg tacaccaacg ccgtctaccg ggagaccttc    34140
ggcgaccgcc cgctggggcg gacgatccgc gaggccttcc ccgacctcgc gcagtccggc    34200
tacttcgaca tcttcgaccg ggtcctcacc acgggcgcgg ccgaggtggt caccgcggtg    34260
cccctcgacc tgatctaccc cggctccacg ggcgagggca ggcgctactt cacgttcagc    34320
atctcccgcg ccacgatgag cgacggccgg ccgggagtgc tcggcgtgat cgtggaggtg    34380
accgcgcagg tgaccgccgc ggaacggatc cgtgtgctgg ccgaggagcg ccgccgcgcg    34440
ctgcagcgct accgcagcct ggtgaacgcc ggaacgcaga tggtgtgggt ggcggacgcc    34500
aagggccgga tcaccgagcc gagccccggc tgggaacgcg tgaccgggca gacctgggag    34560
gagttccgcg gcgagggctg gatgaacgcc gtccaccccg acgaccgcgc cgcctcggtc    34620
gaggcgtggc ggcgggcgac gaccgaacag gtgccgcgct ggatccacac ctaccggctg    34680
cggctggccg ccggcgggta ccggcacttc gtcgtcgacg ccgcgcccgt gcgcgacggg    34740
aacacggtga tcgaatgggt gggcacctgc acggacatcg agcgggaatg gcaggagggc    34800
cgccgtacgg aactgctggc gcgggccgcc accgccacgt ccggcatcgc gcggctggac    34860
gagatgctcg ccgccctggc cgatgtgatc gtgcccgaca tcgccgacaa ctgcaccatc    34920
cacctcctgc cgcaggccct gcaccgtctg ccgggcaccc cgctgaccac cgaacgcgtc    34980
gccgcggtca cccgcccggg gctcccggac ctgccccccgc accacgagga gcacctgcgg    35040
cccggcagcc cgctggcccg cgccgccgac cgccgcagcc cgctccactt cgtcttcccg    35100
cccggcgagc cgccggccga cctcgctccg ctcgacggcg agccctggat ggccgaggac    35160
gtcaacagcg tcgtgctgct gccgtcgtc gtcgacggca ccaccgccgc cctggtcgcc    35220
gtctccacca gcggcgcccg cccgccccct ggccaggcgg agatcggcct gctgcagaca    35280
ctcctggaac gcgcccacac cccccctcagc aacgccctgg agtaccagcg cacccggcag    35340
gtggccctgg ccctgcagaa cagcctgctc accgacccgc cggacgcgcc cggcctggac    35400
atcgccgtcc gctaccggcc cagcaccgcc gccgccgagg tcggcgggga ctggtacgac    35460
gcgttcgtgc tgcgcgacgg cgccaccgtc ctcaccatcg gcgacgtctc cggccacgac    35520
ctgccggccg ccgtcaccat gagccagctg cgcaacatgc tgcgcgggct cacgctggac    35580
cgccaggaac cgaccggcac catcctgcgc cggctggaca tcgccgtgca gaccctctat    35640
acggagtgca ccgccacctg cgtgctggcc cgggtggaac gcccggactc cggcggcgtc    35700
cggctgcact actccgtcgc cggtcacccg ccgccgctgc tcgtcgaggc ggacggctcc    35760
gcgcgcttcc tgaccggggc gcggtccccg atgctcgggc tcgtcccccgc gccggagtac    35820 tcgagcgcca tggaaccgct gccgcccggc tccaccctgc tgctgtacac cgacgggctg    35880
gtggagcgcc gcgacgagga tctcaccgtg ggcctggagc ggctgcggca ccacgcctcg    35940
gaggcggtca gccgcccgct gcaggacttc tgcgacacac tgctcaccgg ccagctcacc    36000
gtcgacaacg acgacgacgt ggcgatgctg gtcctgcgcc ggtaggagcg tgccgaggag    36060
```

```
cgccactctg gccgatttta cccttgcttt tccatcggga ttcgttctcc ggatttcccg    36120
atccggcgcc gacggcgaga ccgttgggat caccaatacc ccggaattcc cgcctccgcc    36180
accgttgggc agcgacggat cctgtgatat ttcgactacg cgcggtgatg aattggctcg    36240
gtgccggtcg cgcccggctg tagcagttct ggagcgcgtc tggacatcgt cacgagcgct    36300
tgtgattctt ggtcctgtac acgcaagccg gcgcaacgtc cacgttgccc atcagcggtt    36360
atcggcggtc caccggcgcg acggtgaccg cgggcgggta ctcataggg gaactgcaat    36420 gaattactca aaagcagcga gaggaatgcc gacagccgga caaggtgccg ttcgggcggc    36480
gcgcgtcgtc cgtgaaagtc cggcggaatc agaaacggtc acagttcaga tagcgtcgtt    36540
attaccgggt gagtcgctgc gctcgaaagg gatcgagcag aaccacgtcg cggcactcgc    36600
ggaggtagac gcgccgcttc cgcccatact ggtggaccgg aagacgatgc gggtcgtcga    36660
cgggatgcac cggctcctcg cggctctgct caacggacgg cagacgatcg aggccgaact    36720
gttcgacgga accgcggatg agggattcct gcgcgccgtc cgggagaacg tggtgcacgg    36780
actcccgctg tcgcaggcgg accgccgggc cgccgctgcg cgcatcatcg tgtcccaccc    36840
gcatctgtcg gacagggcga tcgcccgggc gtccgggctc ggggcgaaga ccgtcgcggc    36900
cgtgcggcgc agttcaactg ccgtcgtgcc gcagttgaac acccgggtgg ccaggacgg    36960 cagggtccgg ccgctgaacg ggggcgaggg gcggcgcagg gccatggcgg tactggccga    37020
acaccccgac gcgtccctgc gcgaggtcgc ccgtctgtcc ggggtgtcgc ccgcgacggt    37080
cagcgacgta cgccggcggc tggccgccgg cgagtcgccc ctgccgtcga cgggaacc    37140 ggccgaaccg cggacgggcg ccgactccca ccgcaaccag agcttcgtgg atcccgtccc    37200
ggtgctggag aagctgctgc gcgacccctc tctgcggcac aaggagggcg gccgccagct    37260
gctccagctg ctccgccaga acgcggtcgg cgtgcaggac ctgatggagc tgtccgacgc    37320
cgtgccgtcc cactgcaggt ccctggtgat ccatctcgcg cagcagtacc gggacgcctg    37380
gcagtccttc gcggagaagc tggacgagcc cgcctgcgcc tgtcccgggt gacgaacggg    37440
cggcacggac ccgttcaccg gacatgaccg gcgccgcgcc gcgttcacgg cgcgccgccg    37500
gcactcccac ggcaccccgga ccaccgccgc gtatccggcg gacccgggcc cgggcgggcc    37560
ggattcagcg ggcggggggcc caggtgccac ccgattccag ccaccgggag agctccgccg    37620
ccgagtcctt gcgcacgacc agttcgacga ggccgcgggt ctggtcctga ccgtgctcga    37680
tgcggacgtc ctcgatgttg acgcccaagt cgccgatcga cgtgaacagt tcggccaggg    37740
cgccgggctt gtcggagatg gtcaccgaga cggtcgcgag ctccgtccgg cgcgtaccgg    37800
gtttgcgcac gatcctggcg cacccccggt tccccctccg caacagctcc tcgagctcct    37860
cctgcgcgcg gcggcggacc agcgggtcgg cgtcggagac ggcgcgcagc gcgccgacgg    37920
cccggcccag gccggcggcg agggagtcga gaacgtccgc cacggccgtg gcgttggaac    37980
gcaggatgtc cccccagagc cgggcgtcac cggccgcgat ccgggtgacg tcggcgacgc    38040
cctgccccgc cagccggacg ctgtcctccg ccgcgtgctc cagccgcgcg gcgagcaggg    38100
aggagagccg atgggcgcg tgcgagacga gggccaccgc gtggtcgtgc acaccggcgt    38160
ccatgaccac cggcatgccg tcgcacaacg acaccatctc cagggcggtg ttcagcacgt    38220
cctgcccggt cagctccgac ggggtgagca cccaggggcg cccctcgaag aggtccgccc    38280
gggcggcgag cggcccggaa cgctcggtgc cggccagcgg atggcttcct atgtagctgg    38340
ccgggtcggc ccgcatcgcg cgcacgtcgt cgtgcggac cttcttgacg ctggcgacat    38400
cgaggtaggc tcgggccagc ccgctctcct gtgcgcgcgc gagcacgcgt ccgacctgtg    38460
```

```
ccgggggcac ggccagcacc gccaggtcga cctgacggtc cggtctctcc agggatcccg  38520
cgcccatcgc ctccgccgtc ctggcggcgt tccggtcgac gtcctccagg tgcacgccga  38580
ccccgcggcg ggtcagcgcg agagcgacgg acgtgccgat ggccccggtg ccgatgactg  38640
tggtggtcct caacgcgcgc ccccaggtgc ggtgatccga aatcggctcg gacaagtgcc  38700
gtgcccggca cgggaaaagg gaattcccat ggcgccgtgc gccgccaatt taacgcttcg  38760
gcgcgcatgt tcaactgcgg cgtcgcagcg gtcgaacaca gtagcggtac accgaccat   38820
tgaggcatcg tgctcagttg gcgacaccgg gtcggataaa cgccggaatc cgaggagttg  38880
acgttgcagt cagcgctgag acacgacgac ctgcatccga tagaagaagt ggaaataagt  38940
tcgctctcca ccgacggctc cccgcggatc gacggggaga gtcccgagca cgtggaaatg  39000
ctggccgccg ccgacaccgc gcttccaccg atcatggtgc accgccgcac cgggcgggtc  39060
atcgacggca tgcaccggct gcgcgccgcg atgctgacgg gccgtacgac gatcgcggtg  39120
aggttcttcg acggcaccga ggaggacgcc ttcgtcctcg ccgtgaagtc gaacatcgcg  39180
cacggactgc cgctgtccgc cgccgaccgc cggcgggccg ccgggcgcat catggccacc  39240
catccccggt ggtcggaccg gatgatcgcc tcggtggtcg gcacctccgc caggacggtc  39300
gccgagatcc gccgcgacgc cggcgccgcc ggggcggggg agcccacccg catcggccgg  39360
gacggcaggg tacggcccgt cgacgtgagc gagggccgca gactggccca cgacatgatc  39420
gtccgcgacc cgggcctgtc gctgcgccag gtcgcccgcg ccgccgggat ctcgccggag  39480
accgtcaggg acgtcagaca ccggatgctc cgcggtgagg accggtgcc cgcgccgcg   39540
ccgcggaccc tggtggagcg cggcgcggac cgccgggcgg agcggccgg gaaggccgcc   39600
gcgccgtgcg ggacggagcc gccgcccgcc gtcgtgatga agcggctgag ggccgatccg  39660
gcgctgcgtc tcaacgagaa cggacgcgac ctgctgcggc ttctggatat ccacacggtc  39720
cggctggagg actggaaccg cattatcgaa agcgtgccgc cgcaccgtct ggagacggtg  39780
gcgcagctgg cacgctcctg cgccgacaaa tggtccgaga tcgcgtcacg catcgaaagc  39840
aacgcatcac atctggccgg gtgaacgagg aaacacacga atccttcgag gagccgtcgg  39900
agaaagcggg acggcccgtc ggaacaccct tgtggagggg caatggagat acggtcgatc  39960
gatcacgtcg aattgttcgt cgaggacgcc caggacacgg ccggcaggct gtgcgactcc  40020
ttcggcttcg tccgcgtggg ccgcggcgcc gggaccaccg gactgcgcgg ctgcgagtcc  40080
gtcctgctgc gccagaacga catcgccctg ctgctgacca cggccaccga cgccgaccac  40140
cgtgccgccg agtacgtgaa gcagcacggg gacggggtcg cggtgatcgg gtgggatccc  40200
cgggtaccga gctcgaattc gccctatagt gagtcgtatt acaattcact ggccgtcgtt  40260
ttacaacgtc gtgactggga aaaccctggc gttacccaac ttaatcgcct tgcagcacat  40320
ccccctttcg ccagctggcg taatagcgaa gaggcccgca ccgatcgccc ttcccaacag  40380
ttgcgcagct gaatggcgaa tggcgcctga tgcggtattt tctccttacg catctgtgcg  40440
gtatttcaca ccgcatatgg tgcactctca gtacaatctg ctctgatgcc gcatagttaa  40500
gccagccccg acaccgcca acaccgctg acgcgaaccc cttgcggccg c             40551
```